(12) United States Patent
Shah et al.

(10) Patent No.: US 12,577,594 B2
(45) Date of Patent: Mar. 17, 2026

(54) ENGINEERED MICROORGANISMS AND METHODS FOR IMPROVED ALDEHYDE DEHYDROGENASE ACTIVITY

(71) Applicant: Genomatica, Inc., San Diego, CA (US)

(72) Inventors: Amit M. Shah, San Diego, CA (US); Harish Nagarajan, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 803 days.

(21) Appl. No.: 17/605,196

(22) PCT Filed: Apr. 24, 2020

(86) PCT No.: PCT/US2020/029793
§ 371 (c)(1),
(2) Date: Oct. 20, 2021

(87) PCT Pub. No.: WO2020/219863
PCT Pub. Date: Oct. 29, 2020

(65) Prior Publication Data
US 2022/0235385 A1      Jul. 28, 2022

Related U.S. Application Data

(60) Provisional application No. 62/860,160, filed on Jun. 11, 2019, provisional application No. 62/860,123, filed on Jun. 11, 2019, provisional application No. 62/837,888, filed on Apr. 24, 2019.

(51) Int. Cl.
| | |
|---|---|
| *C12P 13/00* | (2006.01) |
| *C12N 1/20* | (2006.01) |
| *C12N 9/02* | (2006.01) |
| *C12N 9/10* | (2006.01) |
| *C12N 15/52* | (2006.01) |
| *C12N 15/70* | (2006.01) |
| *C12P 7/18* | (2006.01) |
| *C12P 7/40* | (2006.01) |
| *C12P 7/44* | (2006.01) |
| *C12P 7/62* | (2022.01) |
| *C12P 17/08* | (2006.01) |
| *C12P 17/10* | (2006.01) |

(52) U.S. Cl.
CPC .............. *C12P 13/001* (2013.01); *C12N 1/20* (2013.01); *C12N 9/0008* (2013.01); *C12N 9/001* (2013.01); *C12N 9/1096* (2013.01); *C12N 15/52* (2013.01); *C12N 15/70* (2013.01); *C12P 7/18* (2013.01); *C12P 7/40* (2013.01); *C12P 7/44* (2013.01); *C12P 7/62* (2013.01); *C12P 13/005* (2013.01); *C12P 17/08* (2013.01); *C12P 17/10* (2013.01); *C12Y 103/01044* (2013.01); *C12Y 206/01* (2013.01); *C12Y 103/01038* (2013.01)

(58) Field of Classification Search
CPC .. C12P 13/001; C12P 7/18; C12P 7/40; C12P 7/44; C12P 7/62; C12P 13/005; C12P 17/10; C12N 1/20; C12N 9/0008; C12N 9/001; C12N 9/1096; C12N 15/52; C12N 15/70; C12Y 103/01044; C12Y 206/01; C12Y 103/01038
See application file for complete search history.

(56) References Cited

U.S. PATENT DOCUMENTS

| | | | |
|---|---|---|---|
| 9,458,480 | B2 | 10/2016 | Burk et al. |
| 9,719,118 | B2 | 8/2017 | Burgard et al. |
| 10,150,977 | B2 | 12/2018 | Burk et al. |
| 10,704,064 | B2 | 7/2020 | Park et al. |
| 2019/0284592 | A1 | 9/2019 | Burgard et al. |
| 2019/0300918 | A1 | 10/2019 | Osterhout et al. |

FOREIGN PATENT DOCUMENTS

WO      WO-2010129936 A1 * 11/2010 ............... C12N 1/00

OTHER PUBLICATIONS

ABSS Sequence-to-sequence Alignment of SucD from Clostridium kluyveri and SEQ ID No. 1, downloaded Mar. 28, 2024"SucD alignment and SEQ ID No. 1". (Year: 1996).*

ABSS Sequence-to-sequence Alignment of SucD from Porphyromonas gingivalis and SEQ ID No. 1, downloaded Mar. 28, 2024"SucD alignment and SEQ ID No. 2". (Year: 2003).*

Takehara et al. (2018) "Metabolic pathway of 6-aminohexanoate in the nylon oligomer-degrading *Bacterium arthrobacter* sp. KI72: identification of the enzymes responsible for the conversion of 6-aminohexanoate to adipate" Applied Microbiology and Biotechnology, 102:801-814.

Notice of Reasons for Rejection and English Translation for Chinese application No. 2021-563375 mailed Feb. 4, 2025, (11 pages).

GenBank Protein Accession No. AUU91822.1: aldehyde dehydrogenase EutE [Enterobacteriaceae bacterium ENNIH3] (463 aa), Jan. 29, 2018, 2 pages.

Chinese Second Office Action for Chinese application No. 2020800468015 mailed Dec. 23, 2024, (13 pages).

Sohling, B., et al. (1996) "Molecular Analysis of the Anaerobic Succinate Degradation Pathway in Clostridium kluyveri", Journal of Bacteriology, 178(3):871-880.

Reiser, S., et al. (1997) "Isolation of Mutants of Acinetobacter calcoaceticus Deficient in Wax Ester Synthesis and Complementation of One Mutation with a Gene Encoding a Fatty Acyl Coenzyme A Reductase", Journal of Bacteriology, 179(9):2969-2975.

Ishige, T., et al. (2002) "Wax Ester Production from n-Alkanes by *Acinetobacter* sp. Strain M-1: Ultrastructure of Cellular Inclusions and Role of Acyl Coenzyme A Reductase", Applied and Environmental Microbiology, 68 (3);1192-1195.

* cited by examiner

*Primary Examiner* — Suzanne M Noakes
*Assistant Examiner* — Ciara A Mcknight
(74) *Attorney, Agent, or Firm* — Kagan Binder, PLLC

(57) ABSTRACT

Disclosed are biosynthetic methods and engineered microorganism that enhance or improve the biosynthesis of hexamethylenediamine, caproic acid or caprolactam. The engineered microorganisms include selected aldehyde dehydrogenase activity.

13 Claims, 10 Drawing Sheets

Specification includes a Sequence Listing.

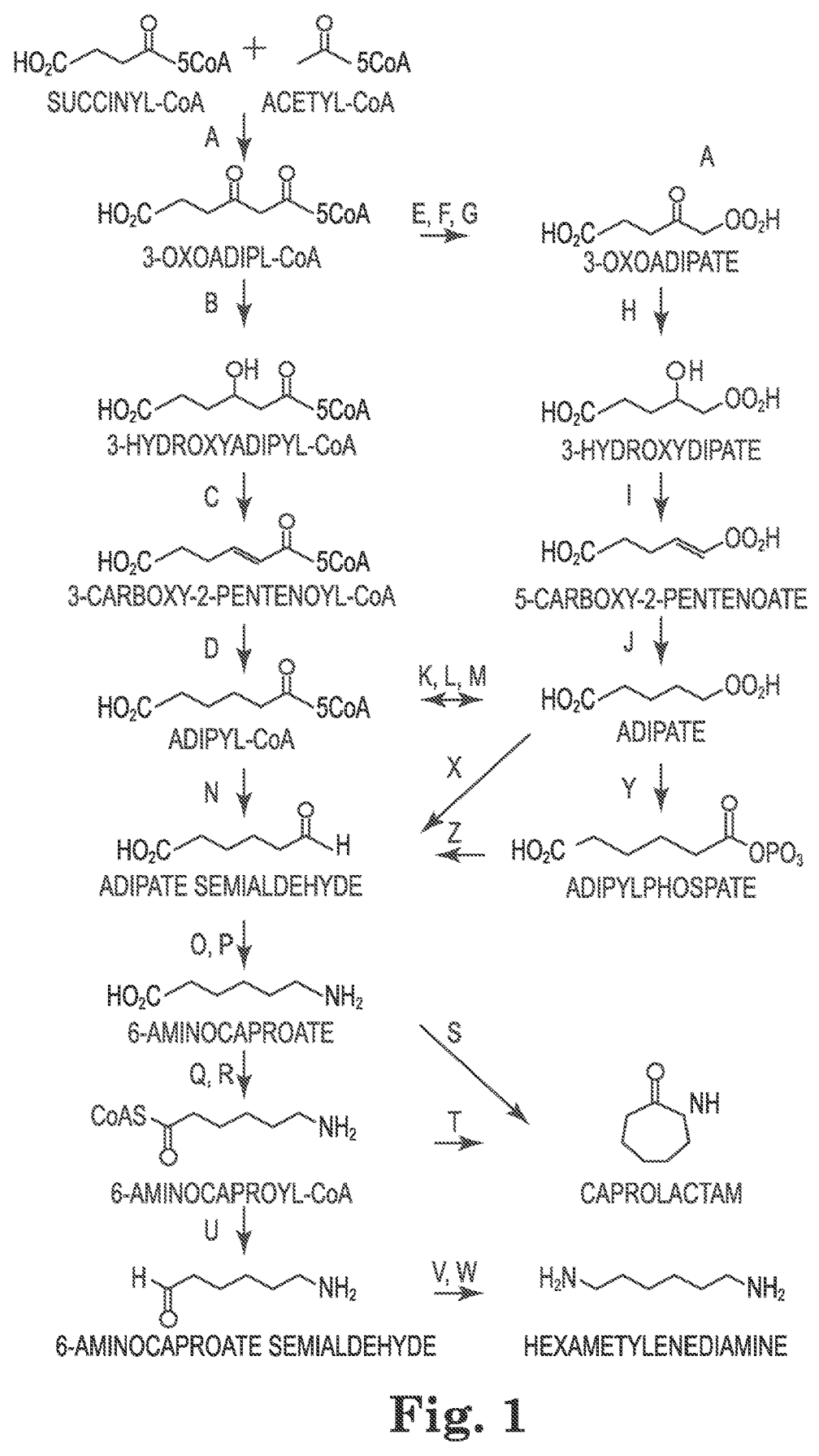

HO₂C ⎯⎯ 5CoA  +  ⎯⎯ 5CoA
SUCCINYL-CoA        ACETYL-CoA

A ↓

HO₂C ⎯⎯ 5CoA          E, F, G →          HO₂C ⎯⎯ OO₂H
3-OXOADIPL-CoA                                    3-OXOADIPATE

B ↓                                                      H ↓

HO₂C ⎯⎯ 5CoA                              HO₂C ⎯⎯ OO₂H
3-HYDROXYADIPYL-CoA                       3-HYDROXYDIPATE

C ↓                                                      I ↓

HO₂C ⎯⎯ 5CoA                              HO₂C ⎯⎯ OO₂H
3-CARBOXY-2-PENTENOYL-CoA                5-CARBOXY-2-PENTENOATE

D ↓                                                      J ↓

HO₂C ⎯⎯ 5CoA          K, L, M ↔          HO₂C ⎯⎯ OO₂H
ADIPYL-CoA                                        ADIPATE

N ↓                          X                          Y ↓

HO₂C ⎯⎯ H          Z ←          HO₂C ⎯⎯ OPO₃
ADIPATE SEMIALDEHYDE                      ADIPYLPHOSPATE

O, P ↓

HO₂C ⎯⎯ NH₂
6-AMINOCAPROATE                              S

Q, R ↓                          T →

CoAS ⎯⎯ NH₂                                              ⎯NH
6-AMINOCAPROYL-CoA                              CAPROLACTAM

U ↓

H ⎯⎯ NH₂          V, W →          H₂N ⎯⎯ NH₂
6-AMINOCAPROATE SEMIALDEHYDE      HEXAMETYLENEDIAMINE

Fig. 1

Kinetic data showing purified Alds with high adipyl-CoA preference over acetyl-CoA & succinyl-CoA

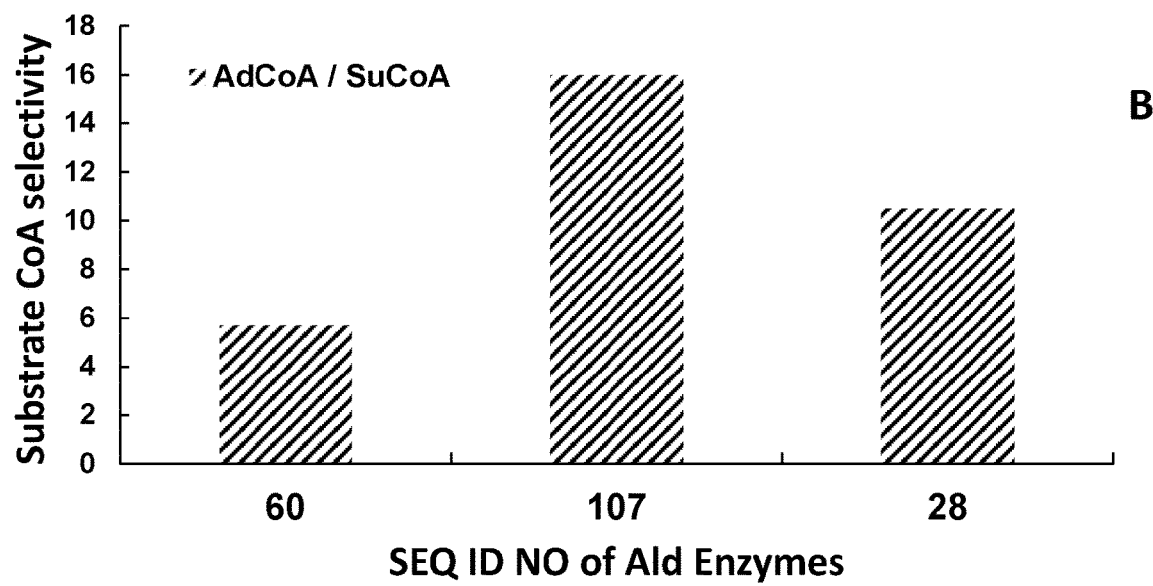
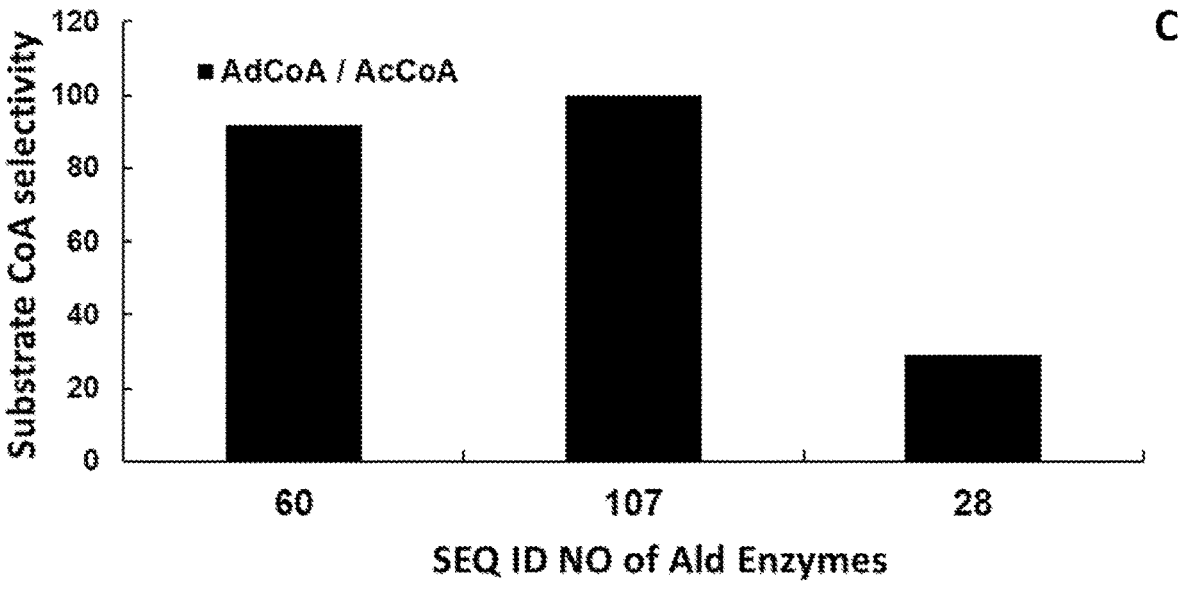
FIG. 3 (cont.)

ENGINEERED MICROORGANISMS AND METHODS FOR IMPROVED ALDEHYDE DEHYDROGENASE ACTIVITY

CROSS REFERENCE TO RELATED APPLICATIONS

This application claims priority to International Application No. PCT/US2020/029793, filed Apr. 24, 2020, which claims the benefit of U.S. Provisional Patent Application Ser. Nos. 62/837,888, filed Apr. 24, 2019; 62/860,123, filed Jun. 11, 2019; and 62/860,160, filed Jun. 11, 2019, the disclosures of which are incorporated by reference herein in their entirety.

INCORPORATION OF SEQUENCE LISTING

This application contains a sequence listing titled "GNO0099WO Sequence Listing2.txt," which was created Apr. 23, 2020 and is 319 kilobytes in size. The sequence listing is incorporated herein by reference.

BACKGROUND

Nylons are polyamides that can be synthesized by the condensation polymerization of a diamine with a dicarboxylic acid or the condensation polymerization of lactams. Nylon 6,6 is produced by reaction of hexamethylenediamine (HMD) and adipic acid, while nylon 6 is produced by a ring opening polymerization of caprolactam. Therefore, adipic acid, hexamethylenediamine, and caprolactam are important intermediates in nylon production.

Microorganisms have been engineered to produce some of the nylon intermediates. However, engineered microorganisms can produce undesirable byproducts as a result of undesired enzymatic activity on pathway intermediates and final products. Such byproducts and impurities therefore increase, cost, and complexity of biosynthesizing compounds and can decrease efficiency or yield of the desired products.

SUMMARY

Provided herein are non-naturally occurring microbial organisms having a 6-aminocaproic acid pathway, caprolactam pathway, hexamethylenediamine pathway, caprolactone pathway, 1,6-heaxanediol pathway, or a combination of one or more of these pathways. The microbial organisms comprise at least one exogenous nucleic acid encoding an aldehyde dehydrogenase enzyme that reacts with adipyl-CoA to form adipate-semialdehyde. The aldehyde dehydrogenase enzyme has greater turnover number, greater catalytic efficiency, or a combination thereof for adipyl-CoA substrate as compared to succinyl CoA, acetyl CoA, or both succinyl CoA and acetyl CoA substrates. The non-naturally occurring microbial organisms may further comprise additional exogenous nucleic acids encoding enzymes necessary for producing 6-aminocaproic acid, 1,6-hexanediol, caprolactone, caprolactam, hexamethylenediamine in a sufficient amount to produce the respective product. In some cases, one or more of these exogenous nucleic acids may be heterologous to the microbial organisms.

Also disclosed are methods for producing 6-aminocaproic acid, 1,6-hexanediol, caprolactone, caprolactam, hexamethylenediamine. The methods can include culturing a 6-aminocaproic acid, 1,6-hexanediol, caprolactone, caprolactam, and/or hexamethylenediamine producing non-naturally occurring microbial organisms, where the microbial organisms express at least one exogenous nucleic acid encoding an aldehyde dehydrogenase enzyme that reacts with adipyl-CoA to form adipate-semialdehyde. The methods include culturing the non-naturally occurring microbial organisms under conditions and for a sufficient period of time to produce 6-aminocaproic acid, 1,6-hexanediol, caprolactone, caprolactam, hexamethylenediamine.

In one aspect provided are a non-naturally occurring microbial organism comprising at least one exogenous nucleic acid encoding an aldehyde dehydrogenase enzyme that reacts with adipyl-CoA to form adipate-semialdehyde, wherein the aldehyde dehydrogenase has greater catalytic efficiency for adipyl-CoA substrate as compared to succinyl-CoA, acetyl-CoA, or both succinyl-CoA and acetyl-CoA substrates, and/or the aldehyde dehydrogenase has higher turnover number for adipyl-CoA substrate as compared to succinyl-CoA, acetyl-CoA, or both succinyl-CoA and acetyl-CoA substrates.

In one aspect, provided are methods of producing adipate-semialdehyde comprising culturing a non-naturally occurring microorganism of any one of the above aspects and embodiments for a sufficient time period and conditions for producing adipate-semialdehyde.

In one aspect, provided are methods of producing 6-aminocaproic acid (6ACA) comprising culturing a non-naturally occurring microbial organism of any one the above aspect and embodiments for a sufficient time period and conditions for producing 6ACA. In some embodiments, the methods further include recovering 6ACA from the microbial organism, fermentation broth, or both.

In one aspect provided are methods of producing hexamethylene diamine comprising culturing a non-naturally occurring microbial organism of any one of the above aspects and embodiments for a sufficient time period and conditions for producing hexamethylene diamine. In some embodiments, the methods further include recovering hexamethylene diamine from the microbial organism, fermentation broth, or both. In some embodiments, the non-naturally occurring microbial organism comprises two, three, four, five, six or seven exogenous nucleic acid sequences each encoding a hexamethylene diamine pathway enzyme.

In one aspect, provided are methods of producing 6-aminocaproic acid, 1,6-hexanediol, caprolactone, caprolactam, hexamethylenediamine comprising culturing a non-naturally occurring microbial organism of any one of the above aspects and embodiments for a sufficient time period and conditions for producing 6-aminocaproic acid, 1,6-hexanediol, caprolactone, caprolactam, and hexamethylenediamine. In some embodiments, the methods further include recovering 6-aminocaproic acid, 1,6-hexanediol, caprolactone, caprolactam, and hexamethylenediamine from the microbial organism, fermentation broth, or both. In some embodiments, the non-naturally occurring microbial organism comprises two, three, four, five, six or seven exogenous nucleic acid sequences each encoding 6-aminocaproic acid, 1,6-hexanediol, caprolactone, caprolactam, hexamethylenediamine pathway enzymes.

In one aspect, provided are bioderived 6-aminocaproic acid, hexamethylenediamine, or caprolactam synthesized using the disclosed methods.

In some embodiments, the aldehyde dehydrogenase enzyme of the non-naturally occurring microbial organism does not comprise the amino acid sequence of SEQ ID NO:1, SEQ ID NO:2, or SEQ ID NO:3.

In some embodiments, the aldehyde dehydrogenase enzyme of the non-naturally occurring microbial organism comprises an amino acid sequence having at least about 60% amino acid sequence identity to at least 25, 50, 75, 100, 150, 200, 250, 300, or more contiguous amino acids of any of SEQ ID NOs: 4, 7, 11, 15, 17, 19, 24, 25, 27, 28, 31-33, 36, 38, 40-42, 44, 45, 47, 53, 58-60, 63, 65-67, 74, 75, 77, 80, 82, 84, 86-88, 90, 91, 94, 95, 97, 100, 101, 103, 107, 109, 111, 112, 117, 134, 135, 137, 145, 146, 148-150, 152, 157-159, 164-167, 176, 187, and 188.

In some embodiments, the aldehyde dehydrogenase enzyme of the non-naturally occurring microbial organism comprises an amino acid sequence having at least about 65%, 70%, 75%, 80%, 85%, 90%, 95%, 99%, or 100% amino acid sequence identity to at least 25, 50, 75, 100, 150, 200, 250, 300, or more contiguous amino acids of any of SEQ ID NOs: 4, 7, 11, 15, 17, 19, 24, 25, 27, 28, 31-33, 36, 38, 40-42, 44, 45, 47, 53, 58-60, 63, 65-67, 74, 75, 77, 80, 82, 84, 86-88, 90, 91, 94, 95, 97, 100, 101, 103, 107, 109, 111, 112, 117, 134, 135, 137, 145, 146, 148-150, 152, 157-159, 164-167, 176, 187, and 188. In some embodiments, the aldehyde dehydrogenase enzyme uses NADH as a cofactor.

In some embodiments, the aldehyde dehydrogenase enzyme of the non-naturally occurring microbial organism comprises an amino acid sequence having at least about 60% amino acid sequence identity to at least 25, 50, 75, 100, 150, 200, 250, 300, or more contiguous amino acids of any of SEQ ID NOs: 7, 28, 60, and 107. In some embodiments, the aldehyde dehydrogenase comprises an amino acid sequence having at least about 65%, 70%, 75%, 80%, 85%, 90%, 95%, 99%, or 100% amino acid sequence identity to at least 50, 75, 100, 150, 200, 250, 300, or more contiguous amino acids of any of SEQ ID NOs: 7, 28, 60, and 188. In some embodiments, the aldehyde dehydrogenase enzyme uses NADH as a cofactor.

In some embodiments, the aldehyde dehydrogenase enzyme of the non-naturally occurring microbial organism comprises an amino acid sequence having at least about 60% amino acid sequence identity to at least 25, 50, 75, 100, 150, 200, 250, 300, or more contiguous amino acids of any of SEQ ID NOs: 53, 77, 82, 94, and 152. In some embodiments, the aldehyde dehydrogenase enzyme uses NADH, NADPH, or both as a cofactor.

In some embodiments, the aldehyde dehydrogenase enzyme of the non-naturally occurring microbial organism has higher catalytic efficiency for adipyl-CoA substrate compared to succinyl-CoA substrate. In some embodiments, the catalytic efficiency of the aldehyde dehydrogenase enzyme for adipyl-CoA substrate is at least twice as high as the catalytic efficiency for succinyl-CoA substrate.

In some embodiments, the aldehyde dehydrogenase enzyme of the non-naturally occurring microbial organism has greater catalytic efficiency for adipyl-CoA substrate compared to acetyl-CoA substrate. In some embodiments, the catalytic efficiency of the aldehyde dehydrogenase enzyme for adipyl-CoA substrate is at least five times as high as the catalytic efficiency for acetyl-CoA substrate. In some embodiments, the aldehyde dehydrogenase enzyme has higher turnover number for adipyl-CoA substrate as compared to acetyl-CoA substrate.

In some embodiments, the aldehyde dehydrogenase enzyme of the non-naturally occurring microbial organism further reacts with 6-aminocaproyl-CoA to form 6-aminocaproate semialdehyde.

In some embodiments, the non-naturally occurring microbial organism comprising at least one exogenous nucleic acid encoding an aldehyde dehydrogenase enzyme converts more adipyl-CoA to adipate semialdehyde than a control microbial organism substantially identical to the non-naturally occurring microbial organism, with the exception that the control microbial organism does not comprise the exogenous nucleic acid encoding an aldehyde dehydrogenase enzyme.

In some embodiments, at least one exogenous nucleic acid encoding an aldehyde dehydrogenase enzyme that reacts with adipyl-CoA to form adipate-semialdehyde is heterologous to the microbial organism.

In some embodiments, the non-naturally occurring microbial organism comprises a 6-aminocaproic acid pathway. In some embodiments, the 6-aminocaproic acid pathway comprises: (i) transaminase, (ii) 6-aminocaproate dehydrogenase, or both (iii) transaminase and 6-aminocaproate dehydrogenase enzymes. In some embodiments, the non-naturally occurring microbial organism further comprises one or more additional exogenous nucleic acids encoding one or more of the 6-aminocaproic acid pathway enzymes. In some embodiments, the exogenous nucleic acids encoding one or more of the 6-aminocaproic acid pathway enzymes is heterologous to the microbial organism.

In some embodiments, the non-naturally occurring microbial organism comprises a hexamethylenediamine pathway. In some embodiments, the hexamethylenediamine pathway comprises (i) 6-aminoacaproyl CoA transferase, (ii) 6-amino caproyl CoA synthase, (iii) 6-amino caproyl CoA reductase, (iv) hexamethylenediamine transaminase, (v) hexamethylenediamine dehydrogenase, (v) or a combination of one or more of the enzymes (i)-(v). In some embodiments, the microbial organism further comprises one or more additional exogenous nucleic acids encoding one or more of the hexamethylenediamine pathway enzymes such as carboxylic acid reductase (CAR) that converts 6-aminocaproate to 6-aminocaproate semialdehyde. The 6-aminocaproate semialdehyde can subsequently be converted to hexamethylene diamine. In some embodiments, the exogenous nucleic acids encoding one or more of the hexamethylenediamine pathway enzymes is heterologous to the microbial organism.

In some embodiments, the non-naturally occurring microbial organism comprises a caprolactam pathway. In some embodiments, the caprolactam pathway comprises aminohydrolase enzyme. In some embodiments, the microbial organism further comprises one or more additional exogenous nucleic acids encoding aminohydrolase enzyme. In some embodiments, the exogenous nucleic acids encoding aminohydrolase enzyme is heterologous to the microbial organism.

In some embodiments, the non-naturally occurring microbial organism comprises a 1,6-hexanediol pathway. In some embodiments, the 1,6-hexanediol pathway comprises the following enzymes: a 6-aminocaproyl-CoA transferase or synthetase catalyzing conversion of 6ACA to 6-aminocaproyl-CoA; a 6-aminocaproyl-CoA reductase catalyzing conversion of 6-aminocaproyl-CoA to 6-aminocaproate semialdehyde; a 6-aminocaproate semialdehyde reductase catalyzing conversion of 6-aminocaproate semialdehyde to 6-aminohexanol; a 6-aminocaproate reductase catalyzing conversion of 6ACA to 6-aminocaproate semialdehyde; an adipyl-CoA reductase adipyl-CoA to adipate semialdehyde; an adipate semialdehyde reductase catalyzing conversion of adipate semialdehyde to 6-hydroxyhexanoate; a 6-hydroxyhexanoyl-CoA transferase or synthetase catalyzing conversion of 6-hydroxyhexanoate to 6-hydroxyhexanoyl-CoA; a 6-hydroxyhexanoyl-CoA reductase catalyzing conversion of 6-hydroxyhexanoyl-CoA to 6-hydroxyhexanal; a 6-hydroxyhexanal reductase catalyzing conversion of 6-hydroxyhexanal to HDO; a 6-aminohexanol aminotransferase or oxidoreductases catalyzing conversion of 6-aminohexanol to 6-hydroxyhexanal; a 6-hydroxyhexanoate reductase catalyzing conversion of 6-hydroxyhexanoate to 6-hydroxyhexanal; an adipate reductase catalyzing conversion of ADA to adipate semialdehyde; and an adipyl-CoA transferase, hydrolase or synthase catalyzing conversion of adipyl-CoA to ADA.

In some embodiments, the non-naturally occurring microbial organism comprises pathways from adipate or adipyl-CoA to caprolactone. In some embodiments, the pathways from adipate or adipyl-CoA to caprolactone comprises the following enzymes: adipyl-CoA reductase, adipate semialdehyde reductase, 6-hydroxyhexanoyl-CoA transferase or synthetase, 6-hydroxyhexanoyl-CoA cyclase or spontaneous cyclization, adipate reductase, adipyl-CoA transferase, synthetase or hydrolase, 6-hydroxyhexanoate cyclase, 6-hydroxyhexanoate kinase, 6-hydroxyhexanoyl phosphate cyclase or spontaneous cyclization, phosphotrans-6-hydroxyhexanoylase.

In some embodiments, the aldehyde dehydrogenase of the non-naturally occurring microbial organism is derived from a prokaryotic species. In some embodiments, the aldehyde dehydrogenase enzyme is derived from *Acidaminococcus, Collinsella*, Peptostreptococcaceae, or Romboustsia.

In some embodiments, the non-naturally occurring microbial organism comprises a species of *Acinetobacter, Actinobacillus, Anaerobiospirillum, Aspergillus, Bacillus, Clostridium, Corynebacterium, Escherichia, Gluconobacter, Klebsiella, Kluyveromyces, Lactococcus, Lactobacillus, Mannheimia, Pichia, Pseudomonas, Rhizobium, Rhizopus, Saccharomyces, Schizosaccharomyces, Streptomyces*, and *Zymomonas*. In some embodiments, the non-naturally occurring microbial organism is a strain of *Escherichia. coli*.

In some embodiments, the culturing is performed in a fermentation broth comprising a sugar.

BRIEF DESCRIPTION OF THE DRAWINGS

FIG. 1 shows exemplary pathways from succinyl-CoA and acetyl-CoA to 6-aminocaproate, hexamethylenediamine (HMDA), caprolactam. The enzymes are designated as follows: A) 3-oxoadipyl-CoA thiolase, B) 3-oxoadipyl-CoA reductase, C) 3-hydroxyadipyl-CoA dehydratase, D) 5-carboxy-2-pentenoyl-CoA reductase, E) 3-oxoadipyl-CoA/ acyl-CoA transferase, F) 3-oxoadipyl-CoA synthase, G) 3-oxoadipyl-CoA hydrolase, H) 3-oxoadipate reductase, I) 3-hydroxyadipate dehydratase, J) 5-carboxy-2-pentenoate reductase, K) adipyl-CoA/acyl-CoA transferase, L) adipyl-CoA synthase, M) adipyl-CoA hydrolase, N) adipyl-CoA reductase (aldehyde forming), O) 6-aminocaproate transaminase, P) 6-aminocaproate dehydrogenase, Q) 6-aminocaproyl-CoA/acyl-CoA transferase, R) 6-aminocaproyl-CoA synthase, S) amidohydrolase, T) spontaneous cyclization, U) 6-aminocaproyl-CoA reductase (aldehyde forming), V) HMDA transaminase, W) HMDA dehydrogenase, X) adipate reductase, Y) adipate kinase, Z) adipylphosphate reductase.

FIG. 3A shows the catalytic efficiency of the various aldehyde dehydrogenases indicated by their SEQ ID Nos for Succinyl-CoA, Acetyl Co-A, and Adipyl-CoA substrates.

FIG. 3B shows the ratio of the catalytic efficiencies for adipyl-CoA over Succinyl-CoA substrates of the various aldehyde dehydrogenases indicated by their SEQ ID Nos. FIG. 3C shows the ratio of the catalytic efficiencies for adipyl-CoA over acetyl-CoA substrates of the various aldehyde dehydrogenases indicated by their SEQ ID NOs.

DETAILED DESCRIPTION

Figure 2:
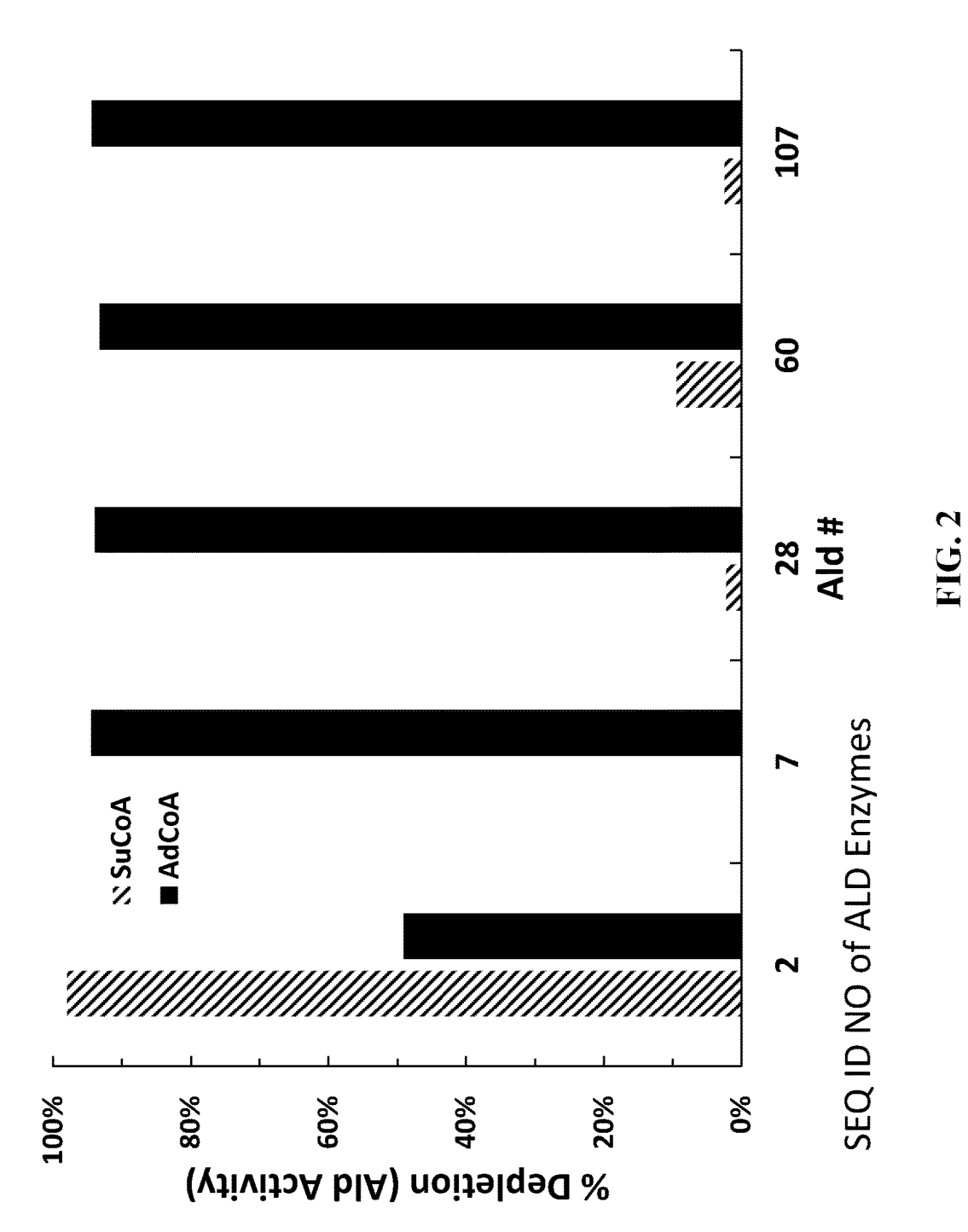
FIG. 2 is a graphical representation of aldehyde dehydrogenase enzyme lysate data showing activity with adipyl-CoA over succinyl-CoA.
Figure 3:
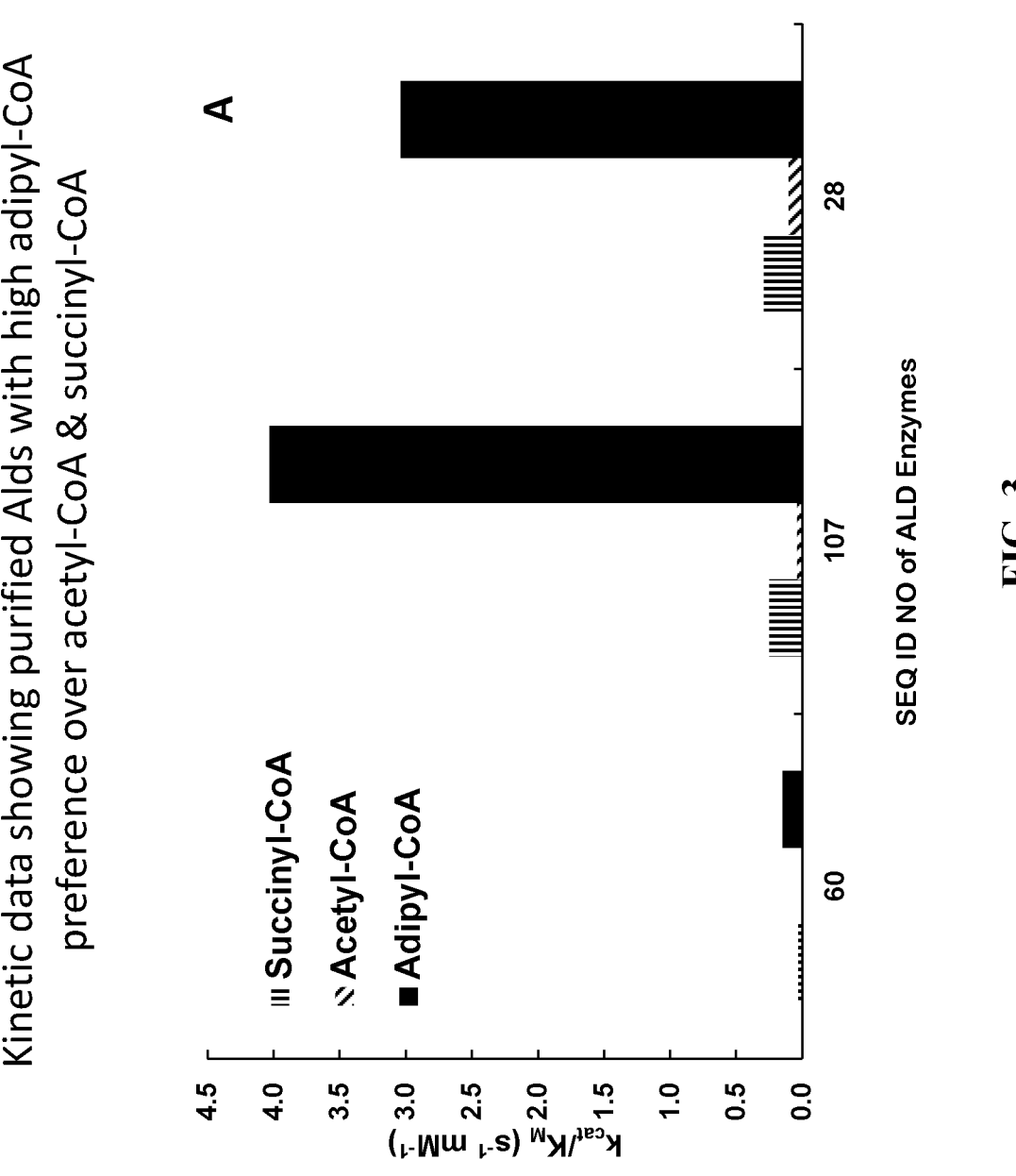
FIG. 3A-C is a graphical representation of kinetic data showing purified aldehyde dehydrogenase enzyme with higher adipyl-CoA preference over acetyl-CoA & succinyl-CoA.
Figure 4:
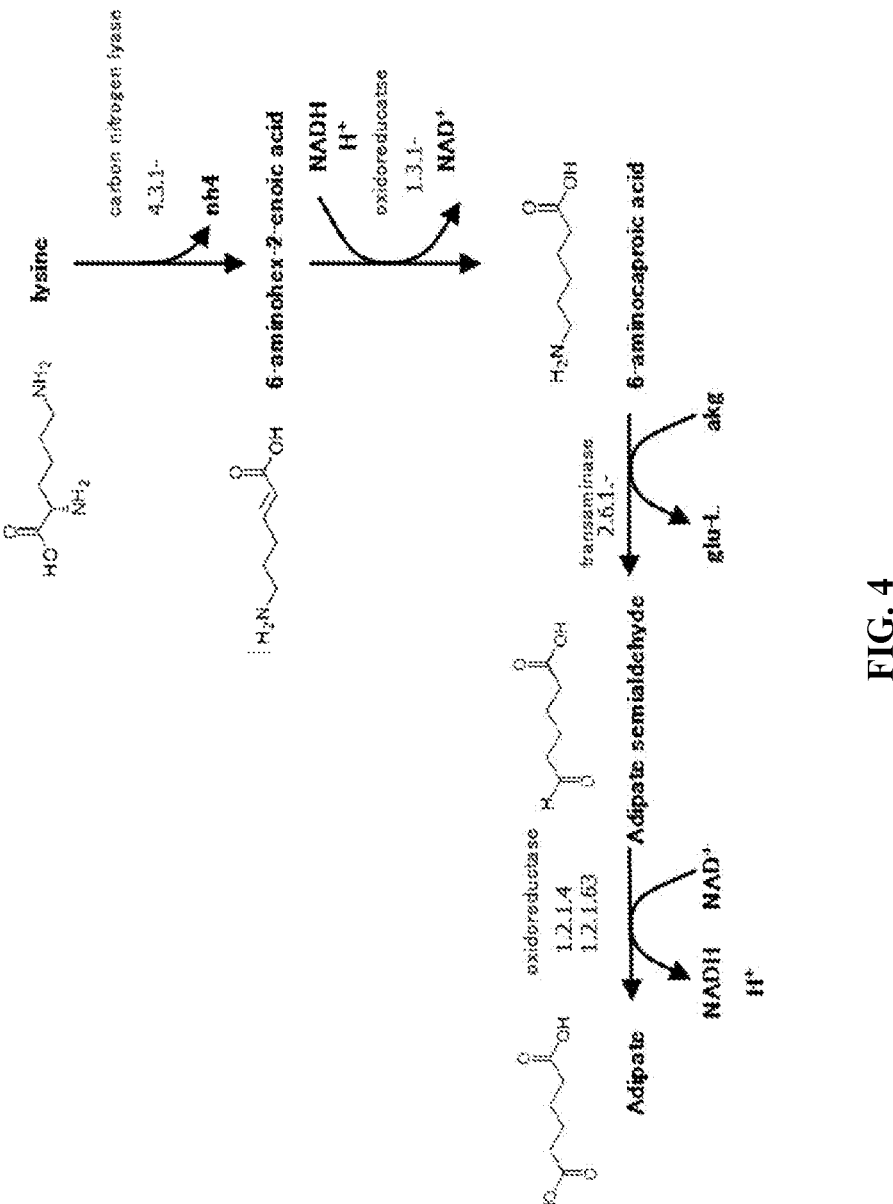
FIG. 4 shows an exemplary pathway for synthesis of 6-amino caproic acid and adipate using lysine as a starting point.
Figure 5:
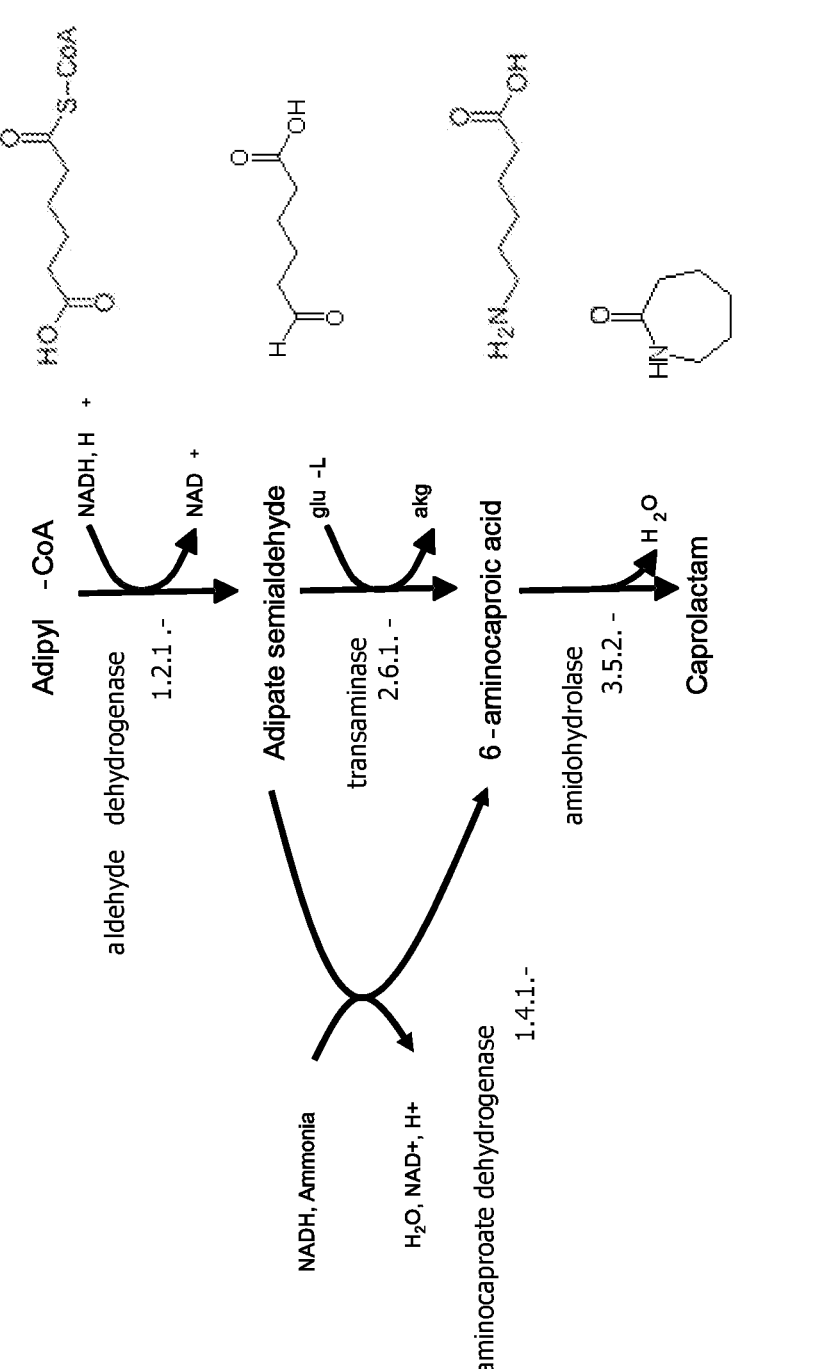
FIG. 5 shows an exemplary caprolactam synthesis pathway using adipyl-CoA as a starting point.
Figure 6:
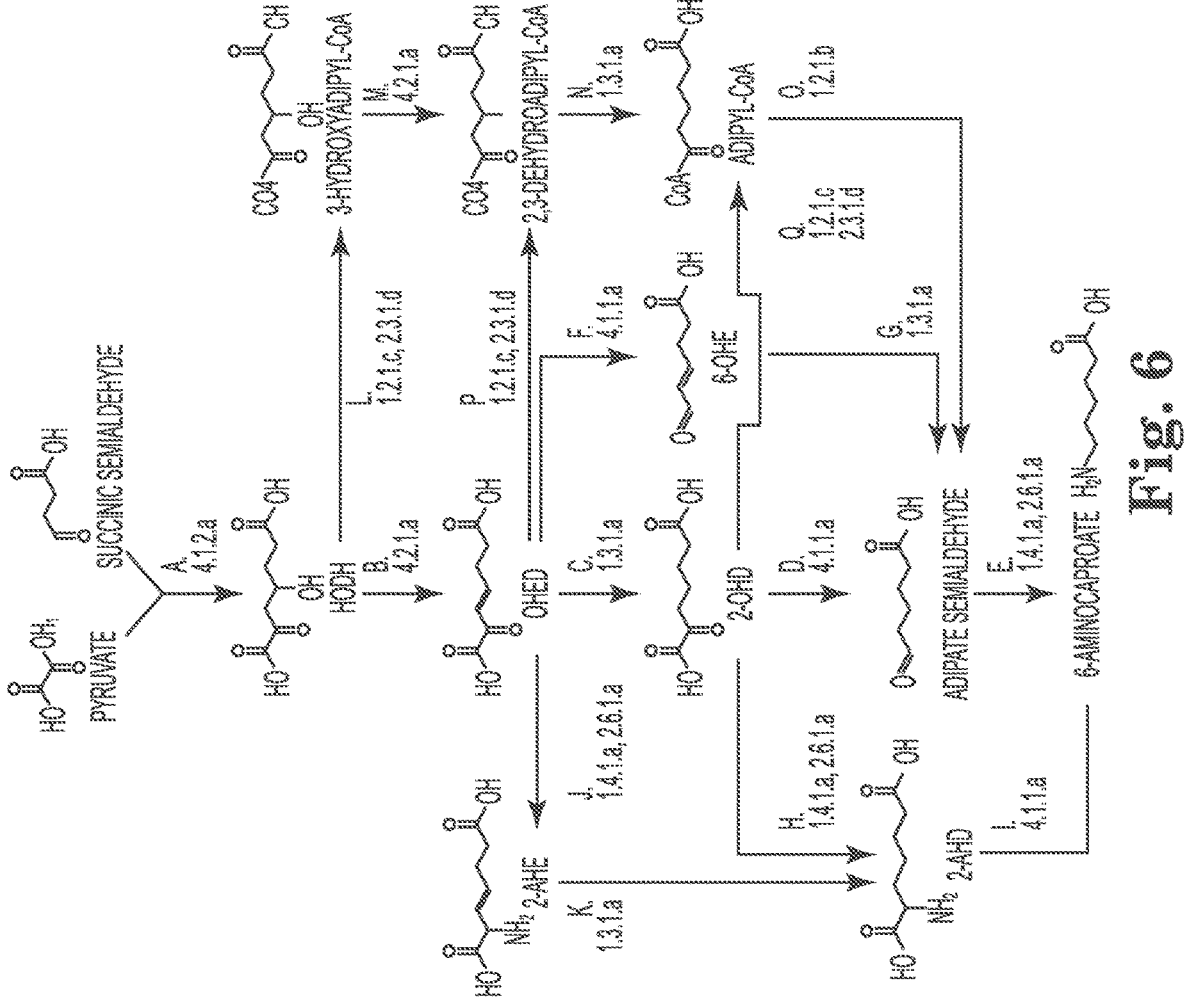
FIG. 6 shows exemplary pathways to 6-aminocaproate from pyruvate and succinic semialdehyde. Enzymes are A) HODH aldolase, B) OHED hydratase, C) OHED reductase, D) 2-OHD decarboxylase, E) adipate semialdehyde aminotransferase and/or adipate semialdehyde oxidoreductase (aminating), F) OHED decarboxylase, G) 6-OHE reductase, H) 2-OHD aminotransferase and/or 2-OHD oxidoreductase (aminating), I) 2-AHD decarboxylase, J) OHED aminotransferase and/or OHED oxidoreductase (aminating), K) 2-AHE reductase, L) HODH formate-lyase and/or HODH dehydrogenase, M) 3-hydroxyadipyl-CoA dehydratase, N) 2,3-dehydroadipyl-CoA reductase, O) adipyl-CoA dehydrogenase, P) OHED formate-lyase and/or OHED dehydrogenase, Q) 2-OHD formate-lyase and/or 2-OHD dehydrogenase. Abbreviations are: HODH=4-hydroxy-2-oxoheptane-1,7-dioate, OHED=2-oxohept-4-ene-1,7-dioate, 2-OHD=2-oxoheptane-1,7-dioate, 2-AHE=2-aminohept-4-ene-1,7-dioate, 2-AHD=2-aminoheptane-1,7-dioate, and 6-OHE=6-oxohex-4-enoate.
Figure 7:
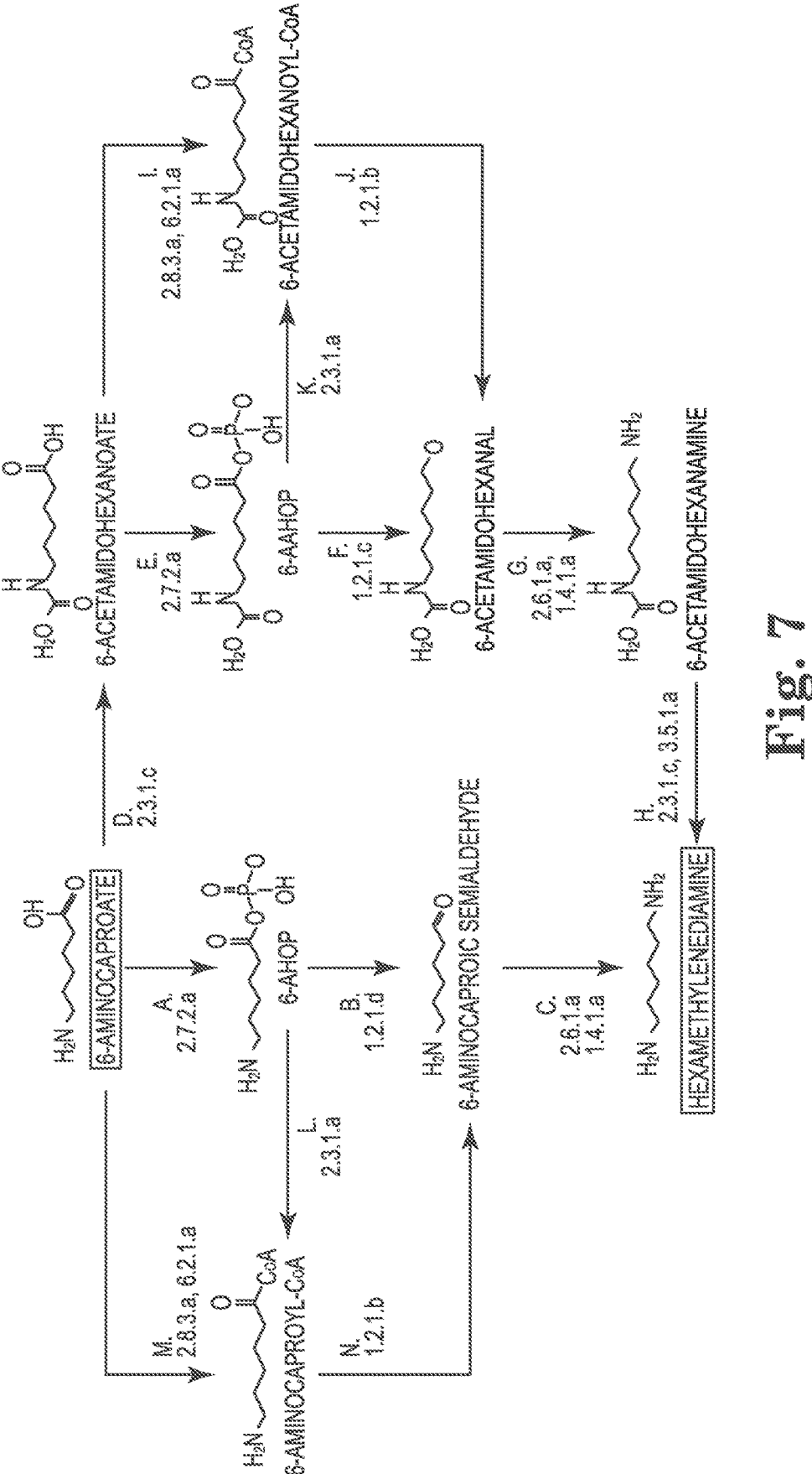
FIG. 7 shows exemplary pathways to hexamethylenediamine from 6-aminocapropate. Enzymes are A) 6-aminocaproate kinase, B) 6-AHOP oxidoreductase, C) 6-aminocaproic semialdehyde aminotransferase and/or 6-aminocaproic semialdehyde oxidoreductase (aminating), D) 6-aminocaproate N-acetyltransferase, E) 6-acetamidohexanoate kinase, F) 6-AAHOP oxidoreductase, G) 6-acetamidohexanal aminotransferase and/or 6-acetamidohexanal oxidoreductase (aminating), H) 6-acetamidohexanamine N-acetyltransferase and/or 6-acetamidohexanamine hydrolase (amide), I) 6-acetamidohexanoate CoA transferase and/ or 6-acetamidohexanoate CoA ligase, J) 6-acetamidohexanoyl-CoA oxidoreductase, K) 6-AAHOP acyltransferase, L) 6-AHOP acyltransferase, M) 6-aminocaproate CoA transferase and/or 6-aminocaproate CoA ligase, N) 6-aminocaproyl-CoA oxidoreductase. Abbreviations are: 6-AAHOP=[(6-acetamidohexanoyl)oxy]phosphonate and 6-AHOP=[(6-aminohexanoyl)oxy]phosphonate.
Figure 8:
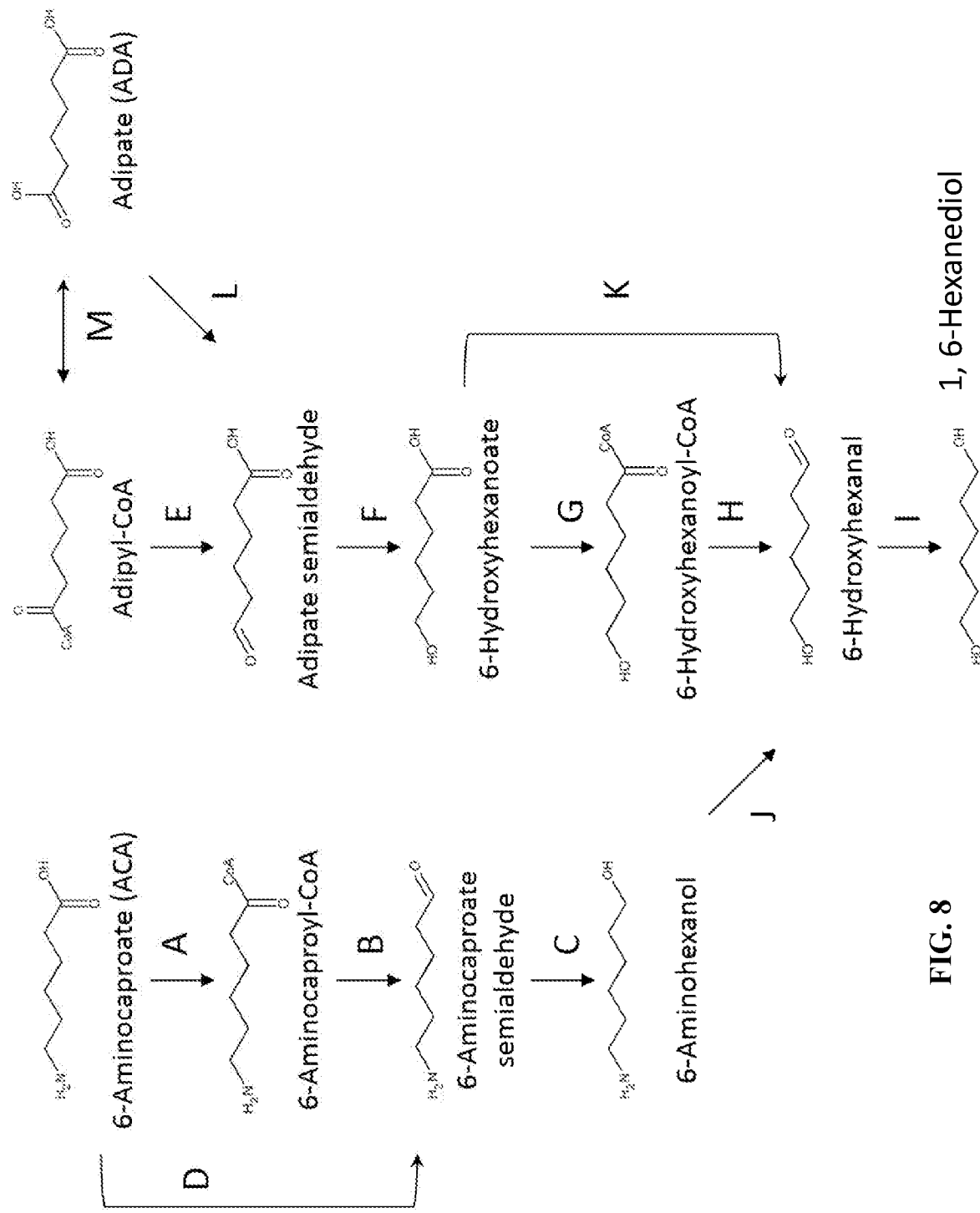
FIG. 8 shows exemplary biosynthetic pathways leading to 1,6-hexanediol. A) is a 6-aminocaproyl-CoA transferase or synthetase catalyzing conversion of 6ACA to 6-aminocaproyl-CoA; B) is a 6-aminocaproyl-CoA reductase catalyzing conversion of 6-aminocaproyl-CoA to 6-aminocaproate semialdehyde; C) is a 6-aminocaproate semialdehyde reductase catalyzing conversion of 6-aminocaproate semialdehyde to 6-aminohexanol; D) is a 6-aminocaproate reductase catalyzing conversion of 6ACA to 6-aminocaproate semialdehyde; E) is an adipyl-CoA reductase adipyl-CoA to adipate semialdehyde; F) is an adipate semialdehyde reductase catalyzing conversion of adipate semialdehyde to 6-hydroxyhexanoate; G) is a 6-hydroxyhexanoyl-CoA transferase or synthetase catalyzing conversion of 6-hydroxyhexanoate to 6-hydroxyhexanoyl-CoA; H) is a 6-hydroxyhexanoyl-CoA reductase catalyzing conversion of 6-hydroxyhexanoyl-CoA to 6-hydroxyhexanal; I) is a 6-hydroxyhexanal reductase catalyzing conversion of 6-hydroxyhexanal to HDO; J) is a 6-aminohexanol aminotransferase or oxidoreductases catalyzing conversion of 6-aminohexanol to 6-hydroxyhexanal; K) is a 6-hydroxyhexanoate reductase catalyzing conversion of 6-hydroxyhexanoate to 6-hydroxyhexanal; L) is an adipate reductase catalyzing conversion of ADA to adipate semialdehyde; and M) is an adipyl-CoA transferase, hydrolase or synthase catalyzing conversion of adipyl-CoA to ADA.
Figure 9:
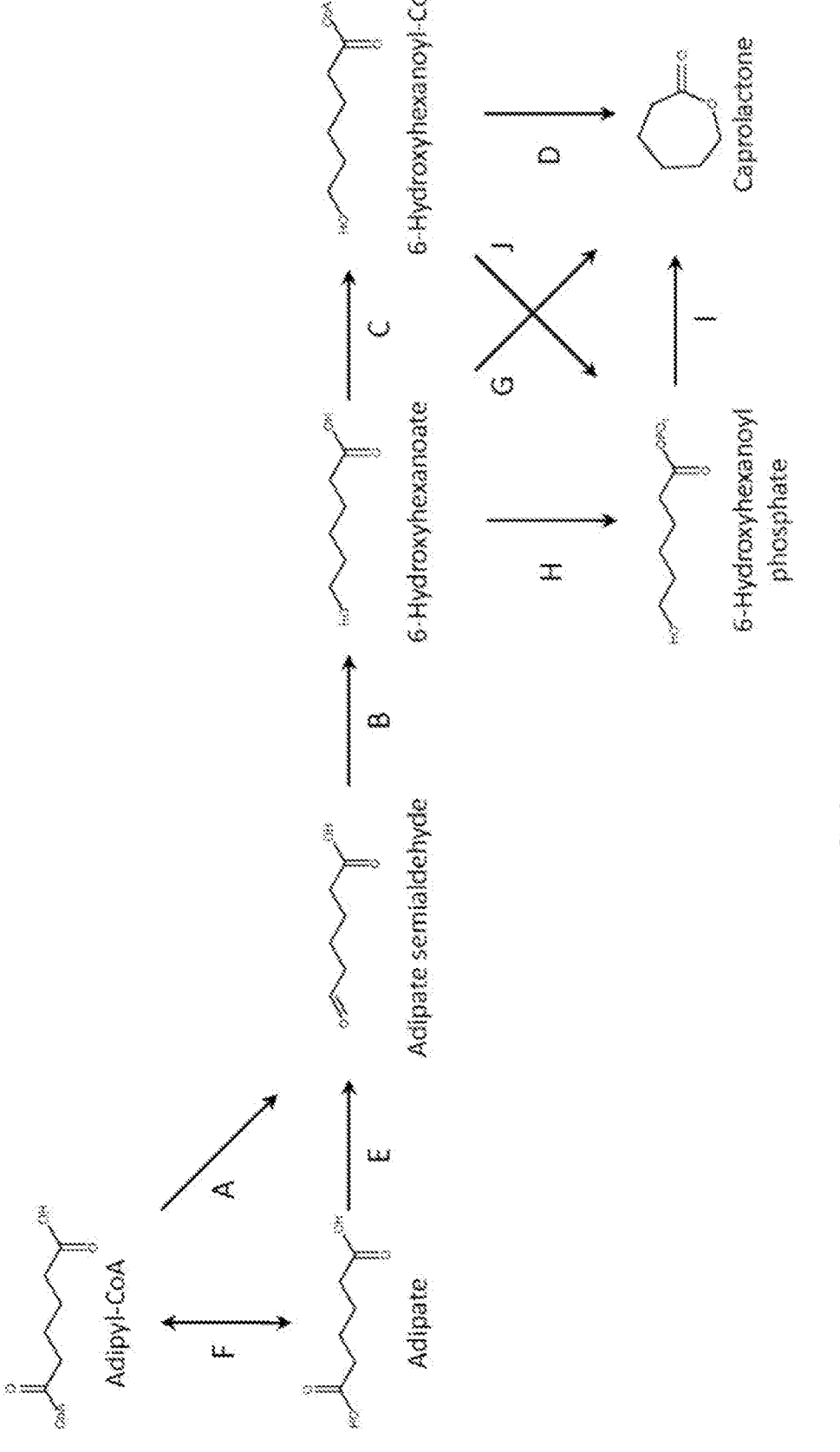
FIG. 9 shows exemplary pathways from adipate or adipyl-CoA to caprolactone. Enzymes are A. adipyl-CoA reductase, B. adipate semialdehyde reductase, C. 6-hydroxyhexanoyl-CoA transferase or synthetase, D. 6-hydroxyhexanoyl-CoA cyclase or spontaneous cyclization, E. adipate reductase, F. adipyl-CoA transferase, synthetase or hydrolase, G. 6-hydroxyhexanoate cyclase, H. 6-hydroxyhexanoate kinase, I. 6-hydroxyhexanoyl phosphate cyclase or spontaneous cyclization, J. phosphotrans-6-hydroxyhexanoylase.

Unless defined otherwise, all technical and scientific terms used herein have the same meaning as commonly understood by those of ordinary skill in the art to which the invention belongs. Any methods, devices and materials similar or equivalent to those described herein can be used in the practice of this invention. The following definitions are provided to facilitate understanding of certain terms used frequently herein and are not meant to limit the scope of the present disclosure. All references referred to herein are incorporated by reference in their entirety.

Disclosed herein are non-naturally occurring microbial organisms engineered to express exogenous aldehyde dehydrogenase (ALD) enzymes having greater catalytic efficiency and turnover number for the adipyl CoA substrate as compared to succinyl-CoA, or acetyl-CoA, or both substrates. Adipyl CoA is an intermediate in pathways leading to the biosynthetic production of 6-aminocaproic acid, caprolactam, and hexamethylenediamine (referred herein as the nylon intermediates). A number of different pathways may be used for the production of these nylon intermediates. In some embodiments, the nylon intermediates can be produced from pathways as shown in FIG. 1. Details for other pathways to the nylon intermediates via adipyl CoA can be found, for example, in U.S. Pat. No. 8,377,680 and incorporated herein by reference in its entirety.

In the various pathways leading to the nylon intermediates an acyl-CoA dehydrogenase capable of reducing an acyl-CoA to its corresponding aldehyde can transform adipyl-CoA to adipate semialdehyde (Step N, FIG. 1). However, some acyl-CoA dehydrogenases can also react with succinyl CoA and acetyl CoA. In some embodiments is disclosed an acyl CoA dehydrogenase (aldehyde producing) that has higher catalytic efficiency, higher turnover number, or both for adipyl CoA substrate than for succinyl-CoA, acetyl CoA, or both substrates. This improves the efficiency and in turn the production of the nylon intermediates.

To identify enzymes with greater catalytic efficiency, greater turnover number or both for adipyl CoA substrate than for succinyl-CoA, acetyl CoA, or both substrates, an exemplary sequence of *Clostridium kluyveri* DSM555, encoded by the gene adh (SEQ ID NO:1) was used to identify other aldehyde dehydrogenase enzymes. Homologous enzymes were identified as set forth in Table 1 (with amino acid sequences shown in the sequence listing).

In some embodiments, aldehyde dehydrogenase enzymes or sequences are identified by BLAST. In some embodiments, the aldehyde dehydrogenase share at least about 40%, 45%, 50%, 55%, 60%, 65%, 70%, 75%, 80%, 85%, 90%, 95%, 96%, 97%, 98%, 99% or 100% sequence identity, to at least 50, 75, 100, 150, 200, 250, 300, or more contiguous amino acids of the amino acid sequences of the ALDs of Table 1.

These aldehyde dehydrogenase enzymes with greater catalytic efficiency, greater turnover number or both for adipyl CoA substrate than for succinyl-CoA, acetyl CoA, or both substrates are derived from very genetically diverse organisms. Often a simple amino acid sequence identity between the sequences is not indicative of their common function. For example, the pairwise sequence alignment results of some exemplary aldehyde dehydrogenases disclosed in Table 1 are shown below.

TABLE 1

| | % Sequence Identity | | | |
| --- | --- | --- | --- | --- |
| | SEQ ID NO: 7 | SEQ ID NO: 28 | SEQ ID NO: 60 | SEQ ID NO: 107 |
| SEQ ID NO: 7 | | 50% | 56% | 60% |
| SEQ ID NO: 28 | 50% | | 53% | 57% |
| SEQ ID NO: 60 | 56% | 53% | | 60% |
| SEQ ID NO: 107 | 60% | 67% | 60% | |

These aldehyde dehydrogenase enzymes have multiple conserved domains, for example, N-terminal domain, C-terminal domain, and a cysteine residue at its active site. The aldehyde dehydrogenases comprise a cofactor binding domain with a Rossmann-fold type nucleotide binding architecture. The Rossmann fold, also called βαβ fold, is a super-secondary structure that is characterized by an alternating motif of beta-strand-alpha helix-beta strand secondary structures. The β-strands participate in the formation of a β-sheet. The βαβ fold structure is commonly observed in enzymes that have dinucleotide coenzymes, such as FAD, NAD and NADP. The βαβ fold structure was associated with a specific Gly-rich sequence of (GxGxxG) at the region of the tight loop between the first β-strand the α-helix. In addition, the cofactor binding domain is also the same domain that binds the substrate CoA. It is typical feature of Alds, where the substrate CoA binds first, forms the intermediate, then the cofactor binds and completes the chemistry and performs the hydride transfer.

Based on the multiple sequence alignments and hidden Markov models (HMMs), the aldehyde dehydrogenase enzymes are grouped into Pfam PF00171, Clan CL0099 of the Pfam database from the European Bioinformatics Institute (pfam.xfam.org). These enzymes are classified as EC 1.2.1 according to the Enzyme Commission nomenclature.

In some embodiments, the ALD enzymes have greater catalytic efficiency, and/or turnover rate when adipyl-CoA is the substrate as compared to succinyl-CoA, acetyl Co-A, or both. In some embodiments, the aldehyde dehydrogenase enzyme comprises an amino acid sequence having at least about 60% amino acid sequence identity to at least 50, 75, 100, 150, 200, 250, 300, or more contiguous amino acids of any of SEQ ID NOs: 4, 7, 11, 15, 17, 19, 24, 25, 27, 28, 31-33, 36, 38, 40-42, 44, 45, 47, 53, 58-60, 63, 65-67, 74, 75; 77, 80, 82, 84, 86-88, 90, 91, 94, 95, 97, 100, 101, 103, 107, 109, 111, 112, 117, 134, 135, 137, 145, 146, 148-150, 152, 157-159, 164-167, 176, 187, or 188. In some embodiments the amino acid sequence of the aldehyde dehydrogenase enzyme that reacts with adipyl-CoA to form adipate-semialdehyde are selected from the amino acid sequences of SEQ ID NOs: 1-4, 7, 11, 15, 17, 19, 24, 25, 27, 28, 31-33, 36, 38; 40-42, 44, 45, 47, 53, 58-60, 63, 65-67, 74, 75, 77, 80, 82, 84, 86-88, 90, 91, 94, 95, 97, 100, 101, 103, 107, 109, 111, 112, 117, 134, 135, 137, 145, 146, 148-150, 152, 157-159, 164-167, 176, 187, and 188.

In some embodiments, the amino acid sequence of aldehyde dehydrogenase that has greater catalytic efficiency, greater turnover rate or a combination thereof for adipyl-CoA substrate as compared to succinyl-CoA, acetyl-CoA, or both substrates is at least about 60% amino acid sequence identity to at least 50, 75, 100, 150, 200, 250, 300, or more contiguous amino acids of any of SEQ ID NOs:7, 28, 60 and 107. In some embodiments, the amino acid sequence of aldehyde dehydrogenase that has greater catalytic efficiency, greater turnover rate or a combination thereof for adipyl-CoA substrate as compared to succinyl-CoA, acetyl-CoA, or both substrates is at least about 65%, 70%, 75%, 80%, 85%, 90%, 95%, 96%, 97%, 98%, 99% or 100% sequence identity to at least 50, 75, 100, 150, 200, 250, 300, or more contiguous amino acids of amino acid sequence of any of SEQ ID NOs:7, 28, 60 and 107.

In some embodiments, the ALD enzyme has at least a catalytic efficiency for adipyl-CoA substrate that is at least 5×, at least 10×, at least 25×, or 5-25× as compared to succinyl-CoA, acetyl-CoA, or both as substrates.

In some embodiments, the enzymatic conversion of the indicated substrate(s) (e.g. adipyl-CoA) to indicated product(s) (e.g. adipate semialdehyde) under known standard conditions for that enzyme is at least 10, at least 20, at least 30, at least 40, at least 50, at least 60, at least 70, at least 80, or at least 90 percent more than the enzymatic activity for the an enzyme that has no specificity for only adipyl-CoA.

In some embodiments, the aldehyde dehydrogenase enzyme further reacts with 6-aminocaproyl-CoA to form 6-aminocaproate semialdehyde.

A cell having reduced enzymatic activity can be identified using any method known in the art. For example, enzyme activity assays can be used to identify cells having reduced enzyme activity, see, for example, Enzyme Nomenclature, Academic Press, Inc., New York 2007. Other assays that may be used to determine the reduction in ADH include GC/MS analysis. In other examples, levels of NADH/NADPH may be monitored. For example, the NADH/NADPH may be monitored colorimetrically or spectroscopically using NADP/NADPH assay kits (e.g. ab65349 available from ABCAM™.)

The disclosed ALD enzyme can be used in pathways for the production of the nylon intermediates. In some embodiments, a non-naturally occurring microorganism may be used in the production of adipate semialdehyde or other nylon intermediates that are produced using the adipate semialdehyde as an intermediate.

In some embodiments, genetically modified cells (e.g. non-naturally occurring microorganisms) are capable of producing the nylon intermediates such as 6-aminocaproic acid, caprolactam; and hexamethylenediamine.

In some embodiments, the nylon intermediates are bio-synthesized using the pathway described in FIG. 1. In some embodiments, FIG. 1 pathway is provided in genetically modified cell described herein (e.g., a non-naturally occurring microorganism) where the pathway includes at least one exogenous nucleic acid encoding a pathway enzyme expressed in a sufficient amount to produce 6-aminocaproic acid, caprolactam, and hexamethylenediamine.

In some embodiments the pathway is an HMD pathway as set forth in FIG. 1. The HMI) pathway is provided in genetically modified cell described herein (e.g., a non-naturally occurring microorganism) where the HMD pathway includes at least one exogenous nucleic acid encoding a HMD pathway enzyme expressed in a sufficient amount to produce HMD. The enzymes are 1A is a 3-oxoadipyl-CoA thiolase; 1B is a 3-oxoadipyl-CoA reductase; 1C is a 3-hydroxyadipyl-CoA dehydratase; 1D is a 5-carboxy-2-pentenoyl-CoA reductase; 1E is a 3-oxoadipyl-CoA/acyl-CoA transferase; 1F is a 3-oxoadipyl-CoA synthase; 1G is a 3-oxoadipyl-CoA hydrolase; 1H is a 3-oxoadipate reductase; 1I is a 3-hydroxyadipate dehydratase; 1J is a 5-carboxy-2-pentenoate reductase; 1K is an adipyl-CoA/acyl-CoA transferase; 1L is an adipyl-CoA synthase; 1M is an adipyl-CoA hydrolase; 1N is an adipyl-CoA reductase (aldehyde forming); 1O is a 6-aminocaproate transaminase; 1P is a 6-aminocaproate dehydrogenase; 1Q is a 6-aminocaproyl-CoA/acyl-CoA transferase; 1R is a 6-aminocaproyl-CoA synthase; 1S is an amidohydrolase; 1T is spontaneous cyclization; 1U is a 6-aminocaproyl-CoA reductase (aldehyde forming); 1V is a HMDA transaminase; and 1W is a HMDA dehydrogenase.

With reference to FIG. 1, in some embodiments, the non-naturally occurring microorganism has one or more of the following pathways: ABCDNOPQRUVW; ABCD-NOPQRT; or: ABCDNOPS. Other exemplary pathways that include the ALD enzyme to produce adipate semialdehyde include those described in U.S. Pat. No. 8,377,680 incorporated herein by reference in their entireties.

FIG. 1 also shows a pathway from 6-aminocaproate to 6-aminocaproyl-CoA by a transferase or synthase enzyme (FIG. 1, Step Q or R) followed by the spontaneous cyclization of 6-aminocaproyl-CoA to form caprolactam (FIG. 1, Step T). In other embodiments, 6-aminocaproate is activated to 6-aminocaproyl-CoA (FIG. 1, Step Q or R), followed by a reduction (FIG. 1, Step U) and amination (FIG. 1, Step V or W) to form HMDA. 6-Aminocaproic acid can also be activated to 6-aminocaproyl-phosphate instead of 6-aminocaproyl-CoA. 6-Aminocaproyl-phosphate can spontaneously cyclize to form caprolactam. In some embodiments, 6-aminocaproyl-phosphate can be reduced to 6-aminocaproate semialdehyde, which can be then converted to HMDA as depicted in FIG. 1. In some embodiments, a 6-aminocaproic acid is converted to 6-aminocaproate semialdehyde by an aminocaproate reductase (CAR). While not shown in FIG. 1, the aminocaproate reductase can catalyze the conversion of aminocaproic acid as shown in FIG. 1 to 6-aminocaproate semialdehyde.

In some embodiments the non-naturally occurring microbial organism has a hexamethylenediameine pathway that includes (i) 6-aminoacaproyl CoA transferase, (ii) 6-amino caproyl CoA synthase, (iii) 6-amino caproyl CoA reductase, (iv) hexamethylenediamine transaminase, (v) hexamethylenediamine dehydrogenase, (v) or a combination of one or more of the enzymes (i)-(v). In other embodiments, the non-naturally occurring microbial organism has a hexam-ethylenediameine pathway that includes a 3-oxoadipyl-CoA thiolase (Thl), a 3-oxoadipyl-CoA dehydrogenase (Hbd), and a 3-oxoadipyl-CoA dehydratase ("crotonase" or Crt), a 5-carboxy-2-pentenoyl-CoA reductase (Ter), a transaminase (HMD TA) and a carboxylic acid reductase (CAR).

As used herein, the term "non-naturally occurring" when used in reference to a microbial organism or microorganism is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes within a 6-aminocaproic acid, caprolactam, hexamethylenediamine or levulinic acid biosynthetic pathway.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the terms "microbial," "microbial organism" or "microorganism" has been used interchangeably and is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, "adipate," having the chemical formula —OOC—(CH2)4-COO— (see FIG. 1) (IUPAC name hexanedioate), is the ionized form of adipic acid (IUPAC name hexanedioic acid), and it is understood that adipate and adipic acid can be used interchangeably throughout to refer to the compound in any of its neutral or ionized forms, including any salt forms thereof. It is understood by those skilled understand that the specific form will depend on the pH.

As used herein, "6-aminocaproate," having the chemical formula —OOC—(CH2)5-NH2 (see FIG. 1, and abbreviated as 6-ACA), is the ionized form of 6-aminocaproic acid (IUPAC name 6-aminohexanoic acid), and it is understood that 6-aminocaproate and 6-aminocaproic acid can be used interchangeably throughout to refer to the compound in any of its neutral or ionized forms, including any salt forms thereof. It is understood by those skilled understand that the specific form will depend on the pH.

As used herein, "caprolactam" (IUPAC name azepan-2-one) is a lactam of 6-aminohexanoic acid (see FIG. 1, and abbreviated as CPO).

As used herein, "hexamethylenediamine," also referred to as 1,6-diaminohexane or 1,6-hexanediamine, has the chemical formula H2N(CH2)6NH2 (see FIG. 1 and abbreviated as HMD).

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

As used herein, the term "osmoprotectant" when used in reference to a culture or growth condition is intended to mean a compound that acts as an osmolyte and helps a microbial organism as described herein survive osmotic stress. Osmoprotectants include, for example, betaines, amino acids, and the sugar trehalose. Non-limiting examples of such are glycine betaine, praline betaine, dimethylthetin, dimethylslfonioproprionate, 3-dimethylsulfonio-2-methyl-proprionate, pipecolie acid, dimethylsulfonioacetate, choline, L-carnitine and ectoine.

As used herein, the term "growth-coupled" when used in reference to the production of a biochemical is intended to mean that the biosynthesis of the referenced biochemical is produced during the growth phase of a microorganism. In a particular embodiment, the growth-coupled production can be obligatory, meaning that the biosynthesis of the referenced biochemical is an obligatory product produced during the growth phase of a microorganism.

As used herein, "metabolic modification" is intended to refer to a biochemical reaction that is altered from its naturally occurring state. Metabolic modifications can include, for example, elimination of a biochemical reaction activity by functional disruptions of one or more genes encoding an enzyme participating in the reaction.

As used herein, the term "gene disruption," or grammatical equivalents thereof, is intended to mean a genetic alteration that renders the encoded gene product inactive. The genetic alteration can be, for example, deletion of the entire gene, deletion of a regulatory sequence required for transcription or translation, deletion of a portion of the gene which results in a truncated gene product, or by any of various mutation strategies that inactivate the encoded gene product. One particularly useful method of gene disruption is complete gene deletion because it reduces or eliminates the occurrence of genetic reversions in the non-naturally occurring microorganisms.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism.

The term "heterologous" refers to a molecule or activity derived from a source other than the referenced species whereas "homologous" refers to a molecule or activity derived from the host microbial organism. Accordingly, exogenous expression of an encoding nucleic acid can utilize either or both a heterologous or homologous encoding nucleic acid.

As used herein the term "about" means±10% of the stated value. The term "about" can mean rounded to the nearest significant digit Thus, about 5% means 4.5% to 5.5%. Additionally, about in reference to a specific number also includes that exact number. For example, about 5% also includes exact 5%.

A used herein, the term turnover number (also termed as $k_{cat}$) is defined as the maximum number of chemical conversions of substrate molecules per second that a single catalytic site will execute for a given enzyme concentration $[E_T]$. It can be calculated from the maximum reaction rate Vmax and catalyst site concentration $[E_T]$ as follows:

$$Kcat=Vmax/[E_T]. \text{ The unit is } s^{-1}.$$

As used herein the term "catalytic efficiency" is a measure of how efficiently an enzyme converts substrates into products. A comparison of catalytic efficiencies can also be used as a measure of the preference of an enzyme for different substrates (i.e., substrate specificity). The higher the catalytic efficiency, the more the enzyme "prefers" that substrate. It can be calculated from the formula: $k_{cat}/K_M$, where $k_{cat}$ is the turnover number and $K_M$ is the Michaelis constant, $K_M$ is the substrate concentration at which the reaction rate is half of Vmax. The unit of catalytic efficiency can be expressed as $s^{-1}M^{-1}$.

As used herein the term "bioderived" in the context of 6-aminocaproic acid, 1,6-hexanediol, caprolactone, caprolactam, or hexamethylenediamine means that these compounds are synthesized in a microbial organism.

It is understood that when more than one exogenous nucleic acid is included in a microbial organism, the exogenous nucleic acids refer to the referenced encoding nucleic acid or biosynthetic activity, as discussed above. It is further understood, as disclosed herein, that such exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, which are not integrated into the host chromosome, and the plasmids remain as extra-chromosomal elements, and still be considered as two or more exogenous nucleic acids. The number of referenced exogenous nucleic acids or biosynthetic activities refers to the number of encoding nucleic acids or the number of biosynthetic activities, not the number of separate nucleic acids introduced into the host organism.

The non-naturally occurring microbial organisms can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

In the case of gene disruptions, a particularly useful stable genetic alteration is a gene deletion. The use of a gene deletion to introduce a stable genetic alteration is particularly useful to reduce the likelihood of a reversion to a phenotype prior to the genetic alteration. For example, stable growth-coupled production of a biochemical can be achieved, for example, by deletion of a gene encoding an enzyme catalyzing one or more reactions within a set of metabolic modifications. The stability of growth-coupled production of a biochemical can be further enhanced through multiple deletions, significantly reducing the likelihood of multiple compensatory reversions occurring for each disrupted activity.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less than 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms having 6-aminocaproic acid, caprolactam, hexamethylenediamine or levulinic acid biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes. In gene disruption strategies, evolutionarily related genes can also be disrupted or deleted in a host microbial organism, paralogs or orthologs, to reduce or eliminate activities to ensure that any functional redundancy in enzymatic activities targeted for disruption do not short circuit the designed metabolic modifications.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well-known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.2.29+ (Jan. 14, 2014) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

It is understood that any of the pathways disclosed herein, including those as described in the Figures can be used to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a 6-aminocaproic acid, caprolactam, hexamethylenediamine or levulinic acid pathway intermediate can be utilized to produce the intermediate as a desired product.

Described herein with general reference to the metabolic reaction, reactant or product thereof, or with specific reference to one or more nucleic acids or genes encoding an enzyme associated with or catalyzing the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze the referenced reaction, reactant or product. Likewise, given the well-known fields of metabolic biochemistry, enzymology and genomics, reference herein to a gene or encoding nucleic acid also constitutes a reference to the corresponding encoded enzyme and the reaction it catalyzes as well as the reactants and products of the reaction.

The non-naturally occurring microbial organisms can be produced by introducing expressible nucleic acids encoding one or more of the enzymes participating in one or more 6-aminocaproic acid, caprolactam, hexamethylenediamine or levulinic acid biosynthetic pathways. Depending on the host microbial organism chosen for biosynthesis, nucleic acids for some or all of a particular 6-aminocaproic acid, caprolactam, hexamethylenediamine or levulinic acid biosynthetic pathway can be expressed. For example, if a chosen host is deficient in one or more enzymes for a desired biosynthetic pathway, then expressible nucleic acids for the deficient enzyme(s) are introduced into the host for subsequent exogenous expression. Alternatively, if the chosen host exhibits endogenous expression of some pathway genes, but is deficient in others, then an encoding nucleic acid is needed for the deficient enzyme(s) to achieve 6-aminocaproic acid, caprolactam, hexamethylenediamine or levulinic acid biosynthesis. Thus, a non-naturally occurring microbial organism can be produced by introducing exogenous enzyme activities to obtain a desired biosynthetic pathway or a desired biosynthetic pathway can be obtained by introducing one or more exogenous enzyme activities that, together with one or more endogenous enzymes, produce a desired product such as 6-aminocaproic acid, caprolactam, hexamethylenediamine or levulinic acid.

Depending on the 6-aminocaproic acid, caprolactam, hexamethylenediamine or levulinic acid biosynthetic pathway constituents of a selected host microbial organism, the non-naturally occurring microbial organisms will include at least one exogenously expressed 6-aminocaproic acid, caprolactam, hexamethylenediamine or levulinic acid pathway-encoding nucleic acid and up to all encoding nucleic acids for one or more adipate, 6-aminocaproic acid or caprolactam biosynthetic pathways. For example, 6-aminocaproic acid, caprolactam, hexamethylenediamine or levulinic acid biosynthesis can be established in a host deficient in a pathway enzyme through exogenous expression of the corresponding encoding nucleic acid. In a host deficient in all enzymes of a 6-aminocaproic acid, caprolactam, hexamethylenediamine or levulinic acid pathway, exogenous expression of all enzymes in the pathway can be included, although it is understood that all enzymes of a pathway can be expressed even if the host contains at least one of the pathway enzymes.

Given the teachings and guidance provided herein, those skilled in the art will understand that the number of encoding nucleic acids to introduce in an expressible form will, at least, parallel the adipate, 6-aminocaproic acid, caprolactam, hexamethylenediamine or levulinic acid pathway deficiencies of the selected host microbial organism. Therefore, a non-naturally occurring microbial organism can have at least one, two, three, four, five, six, seven, eight, nine, ten, eleven or twelve, up to all nucleic acids encoding the above enzymes constituting a 6-aminocaproic acid, caprolactam, hexamethylenediamine or levulinic acid biosynthetic pathway. In some embodiments, the non-naturally occurring microbial organisms also can include other genetic modifications that facilitate or optimize 6-aminocaproic acid, caprolactam, hexamethylenediamine or levulinic acid biosynthesis or that confer other useful functions onto the host microbial organism. One such other functionality can include, for example, augmentation of the synthesis of one or more of the 6-aminocaproic acid, caprolactam, hexamethylenediamine or levulinic acid pathway precursors such as succinyl-CoA and/or acetyl-CoA in the case of adipate synthesis, or adipyl-CoA or adipate in the case of 6-aminocaproic acid or caprolactam synthesis, including the adipate pathway enzymes disclosed herein, or pyruvate and succinic semialdehyde, glutamate, glutaryl-CoA, homolysine or 2-amino-7-oxosubarate in the case of 6-aminocaproate synthesis, or 6-aminocaproate, glutamate, glutaryl-CoA, pyruvate and 4-aminobutanal, or 2-amino-7-oxosubarate in the case of hexamethylenediamine synthesis.

In some embodiments, a non-naturally occurring microbial organism has at least one exogenous nucleic acid encoding an aldehyde dehydrogenase that reacts with adipyl-CoA to form adipate-semialdehyde and selected from aldehyde dehydrogenases comprising the amino acid sequences having at least about 60% amino acid sequence identity to at least 50, 75, 100, 150, 200, 250, 300, or more contiguous amino acids of any of any of SEQ ID NOs:1-4, 7, 11, 15, 17, 19, 24, 25, 27, 28, 31-33, 36, 38, 40-42, 44, 45, 47, 53, 58-60, 63, 65-67, 74, 75, 77, 80, 82, 84, 86-88, 90, 91, 94, 95, 97, 100, 101, 103, 107, 109, 111, 112, 117, 134, 135, 137, 145, 146, 148-150, 152, 157-159, 164-167, 176, 187, or 188. In some embodiments, a non-naturally occurring microbial organism has at least one exogenous nucleic acid encoding an aldehyde dehydrogenase that reacts with adipyl-CoA to form adipate-semialdehyde and selected from aldehyde dehydrogenases comprising the amino acid sequences having at least about 65%, 70%, 75%, 80%, 85%, 90%, 95%, or 100% amino acid sequence identity to at least 50, 75, 100, 150, 200, 250, 300, or more contiguous amino acids of any of any of SEQ ID NOs:1-4, 7, 11, 15, 17, 19, 24, 25, 27, 28, 31-33, 36, 38, 40-42, 44, 45, 47, 53, 58-60, 63, 65-67, 74, 75, 77, 80, 82, 84, 86-88, 90, 91, 94, 95, 97, 100, 101, 103, 107, 109, 111, 112, 117, 134, 135, 137, 145, 146, 148-150, 152, 157-159, 164-167, 176, 187, or 188.

In other embodiments, the non-naturally occurring microbial organism has at least one exogenous nucleic acid encoding an aldehyde dehydrogenase that reacts with adipyl-CoA to form adipate-semialdehyde comprising the amino acid sequences having at least 60% amino acid sequence identity to at least 50, 75, 100, 150, 200, 250, 300, or more contiguous amino acids of any of the amino acid sequence of SEQ ID NO:7, 28, 60, or 107. In other embodiments, the non-naturally occurring microbial organism has at least one exogenous nucleic acid encoding an aldehyde dehydrogenase that reacts with adipyl-CoA to form adipate-semialdehyde comprising the amino acid sequences having at least about 65%, 70%, 75%, 80%, 85%, 90%, 95%, or 100% amino acid sequence identity to at least 50, 75, 100, 150, 200, 250, 300, or more contiguous amino acids of any of the amino acid sequence of SEQ ID NO:7, 28, 60, or 107.

Generally, a host microbial organism is selected such that it produces the precursor of a 6-aminocaproic acid, caprolactam, or hexamethylenediamine pathway, either as a naturally produced molecule or as an engineered product that either provides de novo production of a desired precursor or increased production of a precursor naturally produced by the host microbial organism. A host organism can be engineered to increase production of a precursor, as disclosed herein. In addition, a microbial organism that has been engineered to produce a desired precursor can be used as a host organism and further engineered to express enzymes or proteins of a 6-aminocaproic acid, caprolactam, hexamethylenediamine or levulinic acid pathway.

In some embodiments, a non-naturally occurring microbial organism is generated from a host that contains the enzymatic capability to synthesize 6-aminocaproic acid, caprolactam, hexamethylenediamine or levulinic acid. In this specific embodiment it can be useful to increase the synthesis or accumulation of a 6-aminocaproic acid, caprolactam, hexamethylenediamine or levulinic acid pathway product to, for example, drive 6-aminocaproic acid, caprolactam, hexamethylenediamine or levulinic acid pathway reactions toward 6-aminocaproic acid, caprolactam, hexamethylenediamine or levulinic acid production. Increased synthesis or accumulation can be accomplished by, for example, overexpression of nucleic acids encoding one or more of the above-described 6-aminocaproic acid, caprolactam, hexamethylenediamine or levulinic acid pathway enzymes. Over expression of the 6-aminocaproic acid, caprolactam, hexamethylenediamine or levulinic acid pathway enzyme or enzymes can occur, for example, through exogenous expression of the endogenous gene or genes, or through exogenous expression of the heterologous gene or genes. Therefore, naturally occurring organisms can be readily generated to be non-naturally occurring microbial organisms, for example, producing 6-aminocaproic acid, caprolactam, hexamethylenediamine or levulinic acid, through overexpression of at least one, two, three, four, five, six, seven, eight, nine, ten, eleven, twelve, thirteen, fourteen, that is, up to all nucleic acids encoding 6-aminocaproic acid, caprolactam, hexamethylenediamine or levulinic acid biosynthetic pathway enzymes. In addition, a non-naturally occurring organism can be generated by mutagenesis of an endogenous gene that results in an increase in activity of an enzyme in the 6-aminocaproic acid, caprolactam, hexamethylenediamine or levulinic acid biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

In some embodiments, a non-naturally occurring microbial organism includes one or more gene disruptions, where the organism produces a 6-ACA, adipate and/or HMDA. The disruptions occur in genes encoding an enzyme that couples production of adipate, 6-ACA and/or HMDA to growth of the organism when the gene disruption reduces the activity of the enzyme, such that the gene disruptions confer increased production of adipate, 6-ACA and/or HMDA onto the non-naturally occurring organism. Thus, in some embodiments is provided a non-naturally occurring microbial organism, comprising one or more gene disruptions, the one or more gene disruptions occurring in genes encoding proteins or enzymes wherein the one or more gene disruptions confer increased production of adipate, 6-ACA and/or HMDA in the organism. As disclosed herein, such an organism contains a pathway for production of adipate, 6-ACA and/or HMDA.

It is understood that, in methods, any of the one or more exogenous nucleic acids can be introduced into a microbial organism to produce a non-naturally occurring microbial organism. The nucleic acids can be introduced so as to confer, for example, a 6-aminocaproic acid, caprolactam, hexamethylenediamine or levulinic acid biosynthetic pathway onto the microbial organism. Alternatively, encoding nucleic acids can be introduced to produce an intermediate microbial organism having the biosynthetic capability to catalyze some of the required reactions to confer 6-aminocaproic acid, caprolactam, hexamethylenediamine or levulinic acid biosynthetic capability. For example, a non-naturally occurring microbial organism having a 6-aminocaproic acid, caprolactam, hexamethylenediamine or levulinic acid biosynthetic pathway can comprise at least two exogenous nucleic acids encoding desired enzymes. In the case of adipate production, at least two exogenous nucleic acids can encode the enzymes such as the combination of succinyl-CoA: acetyl-CoA acyl transferase and 3-hydroxyacyl-CoA dehydrogenase, or succinyl-CoA: acetyl-CoA acyl transferase and 3-hydroxyadipyl-CoA dehydratase, or 3-hydroxyadipyl-CoA and 5-carboxy-2-pentenoyl-CoA reductase, or 3-hydroxyacyl-CoA and adipyl-CoA synthetase, and the like. In the case of caprolactam production, at least two exogenous nucleic acids can encode the enzymes such as the combination of CoA-dependent aldehyde dehydrogenase and transaminase, or CoA-dependent aldehyde dehydrogenase and amidohydrolase, or transaminase and amidohydrolase. In the case of 6-aminocaproic acid production, at least two exogenous nucleic acids can encode the enzymes such as the combination of an 4-hydroxy-2-oxoheptane-1,7-dioate (HODH) aldolase and a 2-oxohept-4-ene-1,7-dioate (OHED) hydratase, or a 2-oxohept-4-ene-1,7-dioate (OHED) hydratase and a 2-aminoheptane-1,7-dioate (2-AHD) decarboxylase, a 3-hydroxyadipyl-CoA dehydratase and a adipyl-CoA dehydrogenase, a glutamyl-CoA transferase and a 6-aminopimeloyl-CoA hydrolase, or a glutaryl-CoA beta-ketothiolase and a 3-aminopimelate 2,3-aminomutase. In the case of hexamethylenediamine production, at least two exogenous nucleic acids can encode the enzymes such as the combination of 6-aminocaproate kinase and [(6-aminohexanoyl)oxy]phosphonate (6-AHOP) oxidoreductase, or a 6-acetamidohexanoate kinase and an [(6-acetamidohexanoyl)oxy]phosphonate (6-AAHOP) oxidoreductase, 6-aminocaproate N-acetyltransferase and 6-acetamidohexanoyl-CoA oxidoreductase, a 3-hydroxy-6-aminopimeloyl-CoA dehydratase and a 2-amino-7-oxoheptanoate aminotransferase, or a 3-oxopimeloyl-CoA ligase and a homolysine decarboxylase. Thus, it is understood that any combination of two or more enzymes of a biosynthetic pathway can be included in a non-naturally occurring microbial organism.

Similarly, it is understood that any combination of three or more enzymes of a biosynthetic pathway can be included in a non-naturally occurring microbial organism, for example, in the case of adipate production, the combination of enzymes succinyl-CoA: acetyl-CoA acyl transferase, 3-hydroxyacyl-CoA dehydrogenase, and 3-hydroxyadipyl-CoA dehydratase; or succinyl-CoA: acetyl-CoA acyl transferase, 3-hydroxyacyl-CoA dehydrogenase and 5-carboxy-2-pentenoyl-CoA reductase; or succinyl-CoA: acetyl-CoA acyl transferase, 3-hydroxyacyl-CoA dehydrogenase and adipyl-CoA synthetase; or 3-hydroxyacyl-CoA dehydrogenase, 3-hydroxyadipyl-CoA dehydratase and adipyl-CoA: acetyl-CoA transferase, and so forth, as desired, so long as the combination of enzymes of the desired biosynthetic pathway results in production of the corresponding desired product. In the case of 6-aminocaproic acid production, the at least three exogenous nucleic acids can encode the enzymes such as the combination of an 4-hydroxy-2-oxoheptane-1,7-dioate (HODH) aldolase, a 2-oxohept-4-ene-1, 7-dioate (OHED) hydratase and a 2-oxoheptane-1,7-dioate (2-OHD) decarboxylase, or a 2-oxohept-4-ene-1,7-dioate (OHED) hydratase, a 2-aminohept-4-ene-1,7-dioate (2-AHE) reductase and a 2-aminoheptane-1,7-dioate (2-AHD) decarboxylase, or a 3-hydroxyadipyl-CoA dehydratase, 2,3-dehydroadipyl-CoA reductase and a adipyl-CoA dehydrogenase, or a 6-amino-7-carboxyhept-2-enoyl-CoA reductase, a 6-aminopimeloyl-CoA hydrolase and a 2-aminopimelate decarboxylase, or a glutaryl-CoA beta-ketothiolase, a 3-aminating oxidoreductase and a 2-aminopimelate decarboxylase, or a 3-oxoadipyl-CoA thiolase, a 5-carboxy-2-pentenoate reductase and a adipate reductase. In the case of hexamethylenediamine production, at least three exogenous nucleic acids can encode the enzymes such as the combination of 6-aminocaproate kinase, [(6-amino-hexanoyl)oxy]phosphonate (6-AHOP) oxidoreductase and 6-aminocaproic semialdehyde aminotransferase, or a 6-aminocaproate N-acetyltransferase, a 6-acetamidohexanoate kinase and an [(6-acetamidohexanoyl)oxy]phosphonate (6-AAHOP) oxidoreductase, or 6-aminocaproate N-acetyltransferase, a [(6-acetamidohexanoyl)oxy]phosphonate (6-AAHOP) acyltransferase and 6-acetamidohexanoyl-CoA oxidoreductase, or a 3-oxo-6-aminopimeloyl-CoA oxidoreductase, a 3-hydroxy-6-aminopimeloyl-CoA dehydratase and a homolysine decarboxylase, or a 2-oxo-4-hydroxy-7-aminoheptanoate aldolase, a 2-oxo-7-aminohept-3-enoate reductase and a homolysine decarboxylase, or a 6-acetamidohexanoate reductase, a 6-acetamidohexanal aminotransferase and a 6-acetamidohexanamine N-acetyltransferase. Similarly, any combination of four or more enzymes of a biosynthetic pathway as disclosed herein can be included in a non-naturally occurring microbial organism, as desired, so long as the combination of enzymes of the desired biosynthetic pathway results in production of the corresponding desired product.

In addition to the biosynthesis of 6-aminocaproic acid, caprolactam, hexamethylenediamine or levulinic acid as described herein, the non-naturally occurring microbial organisms and methods also can be utilized in various combinations with each other and with other microbial organisms and methods well known in the art to achieve product biosynthesis by other routes. For example, one alternative to produce 6-aminocaproic acid, caprolactam, hexamethylenediamine or levulinic acid other than use of the 6-aminocaproic acid, caprolactam, hexamethylenediamine or levulinic acid producers is through addition of another microbial organism capable of converting an adipate, 6-aminocaproic acid or caprolactam pathway intermediate to 6-aminocaproic acid, caprolactam, hexamethylenediamine or levulinic acid. One such procedure includes, for example, the fermentation of a microbial organism that produces a 6-aminocaproic acid, caprolactam, hexamethylenediamine or levulinic acid pathway intermediate. The 6-aminocaproic acid, caprolactam, hexamethylenediamine or levulinic acid pathway intermediate can then be used as a substrate for a second microbial organism that converts the 6-aminocaproic acid, caprolactam, hexamethylenediamine or levulinic acid pathway intermediate to 6-aminocaproic acid, caprolactam, hexamethylenediamine or levulinic acid. The 6-aminocaproic acid, caprolactam, hexamethylenediamine or levulinic acid pathway intermediate can be added directly to another culture of the second organism or the original culture of 6-aminocaproic acid, caprolactam, hexamethylenediamine or levulinic acid pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods can be assembled in a wide variety of sub pathways to achieve biosynthesis of, for example, 6-aminocaproic acid, caprolactam, hexamethylenediamine or levulinic acid. In these embodiments, biosynthetic pathways for a desired product can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of 6-aminocaproic acid, caprolactam, hexamethylenediamine or levulinic acid can be accomplished by constructing a microbial organism that contains biosynthetic pathways for conversion of one pathway intermediate to another pathway intermediate or the product. Alternatively, 6-aminocaproic acid, caprolactam, hexamethylenediamine or levulinic acid also can be biosynthetically produced from microbial organisms through co-culture or co-fermentation using two organisms in the same vessel, where the first microbial organism produces a 6-aminocaproic acid, caprolactam, hexamethylenediamine or levulinic acid intermediate and the second microbial organism converts the intermediate to 6-aminocaproic acid, caprolactam, hexamethylenediamine or levulinic acid.

Given the teachings and guidance provided herein, those skilled in the art will understand that a wide variety of combinations and permutations exist for the non-naturally occurring microbial organisms and methods together with other microbial organisms, with the co-culture of other non-naturally occurring microbial organisms having sub pathways and with combinations of other chemical and/or biochemical procedures well known in the art to produce 6-aminocaproic acid, caprolactam, hexamethylenediamine or levulinic acid.

Similarly, it is understood by those skilled in the art that a host organism can be selected based on desired characteristics for introduction of one or more gene disruptions to increase production of 6-aminocaproic acid, caprolactam, hexamethylenediamine or levulinic acid. Thus, it is understood that, if a genetic modification is to be introduced into a host organism to disrupt a gene, any homologs, orthologs or paralogs that catalyze similar, yet non-identical metabolic reactions can similarly be disrupted to ensure that a desired metabolic reaction is sufficiently disrupted. Because certain differences exist among metabolic networks between different organisms, those skilled in the art will understand that the actual genes disrupted in a given organism may differ between organisms. However, given the teachings and guidance provided herein, those skilled in the art also will understand that the methods can be applied to any suitable host microorganism to identify the cognate metabolic alterations needed to construct an organism in a species of interest that will increase 6-aminocaproic acid, caprolactam, hexamethylenediamine or levulinic acid biosynthesis. In a particular embodiment, the increased production couples bio-synthesis of 6-aminocaproic acid, caprolactam, hexamethylenediamine or levulinic acid to growth of the organism, and can obligatorily couple production of 6-aminocaproic acid, caprolactam, hexamethylenediamine or levulinic acid to growth of the organism if desired and as disclosed herein.

Sources of encoding nucleic acids for a 6-aminocaproic acid, caprolactam, hexamethylenediamine or levulinic acid pathway enzyme can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. In some embodiments, the source of the encoding nucleic acids for a 6-aminocaproic acid, caprolactam, hexamethylenediamine or levulinic acid pathway enzyme is shown in Table 1. In some embodiments, the source of the encoding nucleic acids for aldehyde dehydrogenase enzyme is shown in Table 1. In other embodiments, the source of the encoding nucleic acids for aldehyde dehydrogenase enzyme is *Acidaminococcus, Collinsella, Peptostreptococcaceae*, or *Romboustsia*. In some embodiments, the source of the encoding nucleic acids for a 6-aminocaproic acid, caprolactam, hexamethylenediamine or levulinic acid pathway enzyme are species such as, *Escherichia coli, Escherichia coli* str. K12, *Escherichia coli* C, *Escherichia coli* W, *Pseudomonas* sp, *Pseudomonas knackmussii, Pseudomonas* sp. Strain B13, *Pseudomonas putida, Pseudomonas fluorescens, Pseudomonas stutzeri, Pseudomonas mendocina, Rhodopseudomonas palustris, Mycobacterium tuberculosis, Vibrio cholera, Helicobacter pylori, Klebsiella pneumoniae, Serratia proteamaculans, Streptomyces* sp. 2065, *Pseudomonas aeruginosa, Pseudomonas aeruginosa* PAO1, *Ralstonia eutropha, Ralstonia eutropha* H16, *Clostridium acetobutylicum, Euglena gracilis, Treponema denticola, Clostridium kluyveri, Homo sapiens, Rattus norvegicus, Acinetobacter* sp. ADP1, *Acinetobacter* sp; Strain M-1, *Streptomyces coelicolor, Eubacterium barkeri, Peptostreptococcus asaccharolyticus, Clostridium botulinum, Clostridium botulinum* A3 str, *Clostridium tyrobutyricum, Clostridium pasteurianum, Clostridium thermoaceticum* (*Moorella thermoaceticum*), *Moorella thermoacetica Acinetobacter calcoaceticus, Mus musculus, Sus scrofa, Flavobacterium* sp, *Arthrobacter aurescens, Penicillium chrysogenum, Aspergillus niger, Aspergillus nidulans, Bacillus subtilis, Saccharomyces cerevisiae, Zymomonas mobilis, Mannheimia succiniciproducens, Clostridium ljungdahlii, Clostridium carboxydivorans, Geobacillus stearothermophilus, Agrobacterium tumefaciens, Achromobacter denitrificans, Arabidopsis thaliana, Haemophilus influenzae, Acidaminococcus fermentans, Clostridium* sp. M62/1, *Fusobacterium nucleatum, Bos taurus, Zoogloea ramigera, Rhodobacter sphaeroides, Clostridium beijerinckii, Metallosphaera sedula, Thermoanaerobacter species, Thermoanaerobacter brockii, Acinetobacter baylyi, Porphyromonas gingivalis, Leuconostoc mesenteroides, Sulfolobus tokodaii, Sulfolobus tokodaii 7, Sulfolobus solfataricus, Sulfolobus solfataricus, Sulfolobus acidocaldarius, Salmonella typhimurium, Salmonella enterica, Thermotoga maritima, Halobacterium salinarum, Bacillus cereus, Clostridium difficile, Alkalophilus metalliredigenes, Thermoanaerobacter tengcongensis, Saccharomyces kluyveri, Helicobacter pylori, Corynebacterium glutamicum, Clostridium saccharoperbutylacetonicum, Pseudomonas chlororaphis, Streptomyces clavuligerus, Campylobacter jejuni, Thermus thermophilus, Pelotomaculum thermopropionicum, Bacteroides capillosus, Anaerotruncus colihominis, Natranaerobius thermophilius, Archaeoglobus fulgidus, Archaeoglobus fulgidus* DSM 4304, *Haloarcula marismortui, Pyrobaculum aerophilum, Pyrobaculum aerophilum* str. IM2, *Nicotiana tabacum, Menthe piperita, Pinus taeda, Hordeum vulgare, Zea mays, Rhodococcus opacus, Cupriavidus necator, Bradyrhizobium japonicum, Bradyrhizobium japonicum* USDA110, *Ascarius suum*, butyrate-producing bacterium L2-50, *Bacillus megaterium, Methanococcus maripaludis, Methanosarcina mazei, Methanosarcina mazei, Methanocarcina barkeri, Methanocaldococcus jannaschii, Caenorhabditis elegans, Leishmania major, Methylomicrobium alcaliphilum* 20Z, *Chromohalobacter salexigens, Archaeglubus fulgidus, Chlamydomonas reinhardtii, Trichomonas vaginalis* G3, *Trypanosoma brucei, Mycoplana ramose, Micrococcus luteas, Acetobacter pasteurians, Kluyveromyces lactis, Mesorhizobium loti, Lactococcus lactis, Lysinibacillus sphaericus, Candida boidinii, Candida albicans* SC5314, *Burkholderia ambifaria* AMMD, *Ascaris suun, Acinetobacter baumanii, Acinetobacter calcoaceticus, Burkholderia phymatum, Candida albicans, Clostridium subterminale, Cupriavidus taiwanensis, Flavobacterium lutescens, Lachancea kluyveri, Lactobacillus* sp. 30a, *Leptospira interrogans, Moorella thermoacetica, Myxococcus xanthus, Nicotiana glutinosa, Nocardia iowensis* (sp. NRRL 5646), *Pseudomonas reinekei* MT1, *Ralstonia eutropha* JMP134, *Ralstonia metallidurans, Rhodococcus jostii, Schizosaccharomyces pombe, Selenomonas ruminantium, Streptomyces clavuligenus, Syntrophus aciditrophicus, Vibrio parahaemolyticus, Vibrio vulnificus*, as well as other exemplary species disclosed herein or available as source organisms for corresponding genes (see Examples). However, with the complete genome sequence available for now more than 550 species (with more than half of these available on public databases such as the NCBI), including 395 microorganism genomes and a variety of yeast, fungi, plant, and mammalian genomes, the identification of genes encoding the requisite 6-aminocaproic acid, caprolactam, hexamethylenediamine or levulinic acid biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of 6-aminocaproic acid, caprolactam, hexamethylenediamine or levulinic acid described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when a 6-aminocaproic acid, caprolactam, hexamethylenediamine or levulinic acid biosynthetic pathway exists in an unrelated species, 6-aminocaproic acid, caprolactam, hexamethylenediamine or levulinic acid biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods can be applied to all microbial organisms using the cognate metabolic alterations to those exemplified herein to construct a microbial organism in a species of interest that will synthesize 6-aminocaproic acid, caprolactam, hexamethylenediamine or levulinic acid.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida.* Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae,* and the like. For example, *E. coli* is a particularly useful host organism since it is a well characterized microbial organism suitable for genetic engineering. Other particularly useful host organisms include yeast such as *Saccharomyces cerevisiae.* It is understood that any suitable microbial host organism can be used to introduce metabolic and/or genetic modifications to produce a desired product.

Methods for constructing and testing the expression levels of a non-naturally occurring 6-aminocaproic acid, caprolactam, hexamethylenediamine or levulinic acid-producing host can be performed, for example, by recombinant and detection methods well known in the art. Such methods can be found described in, for example, Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, Md. (1999).

Exogenous nucleic acid sequences involved in a pathway for production of 6-aminocaproic acid, caprolactam, hexamethylenediamine or levulinic acid can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., J. Biol. Chem. 280:4329-4338 (2005). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more 6-aminocaproic acid, caprolactam, hexamethylenediamine or levulinic acid biosynthetic pathway encoding nucleic acids as exemplified herein operably linked to expression control sequences functional in the host organism. Expression vectors applicable for use in the microbial host organisms include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In some embodiments are methods for producing a desired intermediate or product such as adipate, 6-aminocaproic acid, caprolactam, hexamethylenediamine or levulinic acid. For example, a method for producing adipate can involve culturing a non-naturally occurring microbial organism having an adipate pathway, the pathway including at least one exogenous nucleic acid encoding an adipate pathway enzyme expressed in a sufficient amount to produce adipate, under conditions and for a sufficient period of time to produce adipate, the adipate pathway including succinyl-CoA: acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA synthetase or phosphotransadipylase/adipate kinase or adipyl-CoA: acetyl-CoA transferase or adipyl-CoA hydrolase. Additionally, a method for producing adipate can involve culturing a non-naturally occurring microbial organism having an adipate pathway, the pathway including at least one exogenous nucleic acid encoding an adipate pathway enzyme expressed in a sufficient amount to produce adipate, under conditions and for a sufficient period of time to produce adipate, the adipate pathway including succinyl-CoA: acetyl-CoA acyl transferase, 3-oxoadipyl-CoA transferase, 3-oxoadipate reductase, 3-hydroxyadipate dehydratase, and 2-enoate reductase.

Further, a method for producing 6-aminocaproic acid can involve culturing a non-naturally occurring microbial organism having a 6-aminocaproic acid pathway, the pathway including at least one exogenous nucleic acid encoding a 6-aminocaproic acid pathway enzyme expressed in a sufficient amount to produce 6-aminocaproic acid, under conditions and for a sufficient period of time to produce 6-aminocaproic acid, the 6-aminocaproic acid pathway including CoA-dependent aldehyde dehydrogenase and transaminase or 6-aminocaproate dehydrogenase. Additionally, a method for producing caprolactam can involve culturing a non-naturally occurring microbial organism having a caprolactam pathway, the pathway including at least one exogenous nucleic acid encoding a caprolactam pathway enzyme expressed in a sufficient amount to produce caprolactam, under conditions and for a sufficient period of time to produce caprolactam, the caprolactam pathway including CoA-dependent aldehyde dehydrogenase, transaminase or 6-aminocaproate dehydrogenase, and amidohydrolase.

Suitable purification and/or assays to test for the production of 6-aminocaproic acid, caprolactam, hexamethylenediamine or levulinic acid can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art. The individual enzyme activities from the exogenous DNA sequences can also be assayed using methods well known in the art.

The 6-aminocaproic acid, caprolactam, hexamethylenediamine or levulinic acid can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products. For example, the 6-aminocaproic acid, caprolactam, hexamethylenediamine or levulinic acid producers can be cultured for the biosynthetic production of 6-aminocaproic acid, caprolactam, hexamethylenediamine or levulinic acid.

For the production of 6-aminocaproic acid, caprolactam, hexamethylenediamine or levulinic acid, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in U.S. Pat. No. 7,947,483 issued May 24, 2011. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms for the production of 6-aminocaproic acid, caprolactam, hexamethylenediamine or levulinic acid.

In addition to renewable feedstocks such as those exemplified above, the 6-aminocaproic acid, caprolactam, hexamethylenediamine, or levulinic acid microbial organisms also can be modified for growth on syngas as its source of carbon. In this specific embodiment, one or more proteins or enzymes are expressed in the 6-aminocaproic acid, caprolactam, hexamethylenediamine or levulinic acid producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, Acetogenesis, pp. 3-60 Chapman and Hall, New York, (1994)). This can be summarized by the following equation:

$$2CO2+4H2+n \text{ ADP}+n \text{ Pi} \rightarrow CH3COOH+2H_2O+n \text{ ATP}$$

Hence, non-naturally occurring microorganisms possessing the Wood-Ljungdahl pathway can utilize CO2 and H2 mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: cobalamide corrinoid/iron-sulfur protein, methyltransferase, carbon monoxide dehydrogenase, acetyl-CoA synthase, acetyl-CoA synthase disulfide reductase and hydrogenase, and these enzymes can also be referred to as methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a 6-aminocaproic acid, caprolactam, hexamethylenediamine or levulinic acid pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, CO2 and/or H2 to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate: ferredoxin oxidoreductase, succinyl-CoA synthetase, succinyl-CoA transferase, fumarate reductase, fumarase, malate dehydrogenase, NAD(P)Ferredoxin oxidoreductase, carbon monoxide dehydrogenase, and hydrogenase. Specifically, the reducing equivalents extracted from CO and/or H2 by carbon monoxide dehydrogenase and hydrogenase are utilized to fix CO2 via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl- CoA can be converted to the p-toluate, terepathalate, or (2-hydroxy-3-methyl-4-oxobutoxy) phosphonate precursors, glyceraldehyde-3-phosphate, phosphoenolpyruvate, and pyruvate, by pyruvate: ferredoxin oxidoreductase and the enzymes of gluconeogenesis. Following the teachings and guidance provided herein for introducing a sufficient number of encoding nucleic acids to generate a p-toluate, terephthalate or (2-hydroxy-3-methyl-4-oxobutoxy) phosphonate pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms such that the modified organism contains the complete reductive TCA pathway will confer syngas utilization ability.

Given the teachings and guidance provided herein, those skilled in the art will understand that a non-naturally occurring microbial organism can be produced that secretes the biosynthesized compounds when grown on a carbon source such as a carbohydrate. Such compounds include, for example, 6-aminocaproic acid, caprolactam, hexamethylenediamine or levulinic acid and any of the intermediate metabolites in the 6-aminocaproic acid, caprolactam, hexamethylenediamine or levulinic acid pathway. All that is required is to engineer in one or more of the required enzyme activities to achieve biosynthesis of the desired compound or intermediate including, for example, inclusion of some or all of the 6-aminocaproic acid, caprolactam, hexamethylenediamine or levulinic acid biosynthetic pathways.

Accordingly, some embodiments provide a non-naturally occurring microbial organism that produces and/or secretes 6-aminocaproic acid, caprolactam, hexamethylenediamine or levulinic acid when grown on a carbohydrate and produces and/or secretes any of the intermediate metabolites shown in the 6-aminocaproic acid, caprolactam, hexamethylenediamine or levulinic acid pathway when grown on a carbohydrate. For example, an adipate producing microbial organisms can initiate synthesis from an intermediate, for example, 3-oxoadipyl-CoA, 3-hydroxyadipyl-CoA, 5-carboxy-2-pentenoyl-CoA, or adipyl-CoA (see FIG. 1), as desired. In addition, an adipate producing microbial organism can initiate synthesis from an intermediate, for example, 3-oxoadipyl-CoA, 3-oxoadipate, 3-hydroxyadipate, or hexa-2-enedioate. The 6-aminocaproic acid producing microbial organism can initiate synthesis from an intermediate, for example, adipate semialdehyde. The caprolactam producing microbial organism can initiate synthesis from an intermediate, for example, adipate semialdehyde or 6-aminocaproic acid (see FIG. 1), as desired.

In some embodiments, the non-naturally occurring microbial organisms further include an exogenously expressed nucleic acid encoding a trans-enoyl CoA reductase (TER). The TER reacts with 5-carboxy-2-pentenoyl-CoA to produce adipyl-CoA. In some embodiments, the TER can be known Tears and in other embodiments, the TER enzyme is engineered. In some embodiments, the engineered trans-enoyl CoA reductase has an amino acid sequence having at least 50% identity to the amino acid sequence of SEQ ID NO: 189, wherein the engineered trans-enoyl CoA reductase comprises any of the amino acid sequence alterations of the variants shown in Table 2.

TABLE 2

| # | Mutations to Homolog 1 (SEQ ID NO: 189) | Active - CPCoA | Active - CrCoA | Cofactor pref |
|---|---|---|---|---|
| 1 | None | + | + | NADPH |
| 2 | V105G V149I V301R | +++ | ND | NADPH |
| 3 | V105N V149I V301R | +++ | ND | NADPH |
| 4 | V105R V149I V301R | +++ | ND | NADPH |
| 5 | V105K V149S V301V | ++ | ND | NADPH |
| 6 | V105R V301K | ++ | ND | NADPH |
| 7 | V149A V301K | ++ | ND | NADPH |
| 8 | V105K V149I V301R | ++ | ND | NADPH |
| 9 | V105K V149I V301L | +++ | ND | NADPH |
| 10 | V105R V149I V301K | ++ | ND | NADPH |
| 11 | Q52H | ++ | ND | NADPH |
| 12 | V105N | ++ | ND | NADPH |
| 13 | V105R | ++ | ND | NADPH |
| 14 | V105A | ++ | ND | NADPH |
| 15 | V105C | ++ | ND | NADPH |
| 16 | V149C | ++ | ND | NADPH |
| 17 | V149S | ++ | ND | NADPH |
| 18 | T153S S148R | ++ | ND | NADPH |
| 19 | T302R | +++ | ND | NADPH |
| 20 | V301M N307K | ++ | ND | NADPH |
| 21 | V301L | ++ | ND | NADPH |
| 22 | V105G V149I V301L T302R | +++ | ND | NADPH |
| 23 | V105G V149I V301K T302R | +++ | ND | NADPH |
| 24 | V105G V149I T302R | ++ | ND | NADPH |
| 25 | V105K V301I T302R | ++ | ND | NADPH |
| 26 | V105R V301L T302R | ++ | ND | NADPH |
| 27 | V105K V301L T302R | ++ | ND | NADPH |
| 28 | V105A V149I V301L T302R | ++ | ND | NADPH |
| 29 | V105G V149I V301I T302R | ++ | ND | NADPH |
| 30 | V105K V149I V301R T302R | ++ | ND | NADPH |
| 31 | V105C V149I V301R T302R | ++ | ND | NADPH |
| 32 | V105G V149I V301R T302R | +++ | ND | NADPH |
| 33 | V105G V149I T153S V301K T302R | ++ | ND | NADPH |
| 34 | V105K S148R V149S T153S V301L | ++ | ND | NADPH |
| 35 | V105G S148R V149I T153S T302R | ++ | ND | NADPH |
| 36 | V105A S148R V149S T153S | ++ | ND | NADPH |
| 37 | V105G T302R | +++ | ND | NADPH |
| 38 | V105N S148R V149S V301L N307K | +++ | ND | NADPH |
| 39 | V105K V149S V301L N307K | +++ | ND | NADPH |
| 40 | V105A S148R V149S V301L N307K | +++ | ND | NADPH |
| 41 | V105G S148R V149S T153S V301K T302R | ++ | + | NADPH |
| 42 | V105G V149I T153S T302R N307K | ++ | + | NADPH |
| 43 | V105G V149I V301L T302R N307K | ++ | + | NADPH |
| 44 | V105G S148R V149I T153S V301L T302R | ++ | + | NADPH |
| 45 | A32E V105G V149I V301R T302R | ++ | + | NADPH |
| 46 | S59C S48I V105G V149I V301R T302R | +++ | + | NADPH |
| 47 | G97R V105G N106C V149I V301R T302R | ++ | + | NADPH |
| 48 | V105G F107M V149I V301R T302R | +++ | + | NADPH |
| 49 | V105G I147V V149I V301R T302R | ++ | + | NADPH |
| 50 | V105G S148F V149I V301R T302R | ++ | + | NADPH |
| 51 | V105G V149I L152A V301R T302R | +++ | + | NADPH |
| 52 | V105G V149I L152M V301R T302R | ++ | + | NADPH |
| 53 | V105G V149I L156Y V301R T302R | +++ | + | NADPH |
| 54 | V105G V149I L156W V301R T302R | ++ | + | NADPH |
| 55 | V105G V149I V301R T302R E303N | ++ | + | NADPH |
| 56 | V105G V149I V301R T302R K306D | ++ | + | NADPH |
| 57 | S59V V105A S148R V149S V301L N307K | ++ | + | NADPH |
| 58 | S59Q V105A S148R V149S V301L N307K | ++ | + | NADPH |
| 59 | H104L V105A S148R V149S V301L N307K | ++ | + | NADPH |
| 60 | S103A V105A S148R V149S V301L N307K | ++ | + | NADPH |
| 61 | V105A S148R V149S V301L N307K L316T | ++ | + | NADPH |
| 62 | V105A S148R V149S L156F V301L N307K | ++ | + | NADPH |
| 63 | V105A S148R V149S V301L K306V N307K | ++ | + | NADPH |
| 64 | Q11H V105A S148R V149S V301L N307P | ++ | + | NADPH |
| 65 | V105A S148R V149S V301L N307V | ++ | + | NADPH |
| 66 | V105A S148R V149S V301L N307E | ++ | + | NADPH |
| 67 | V105A S148R V149S V301L N307Y | ++ | + | NADPH |
| 68 | V105A S148R V149S V301L N307L | ++ | + | NADPH |
| 69 | V105A S148R V149S V301L N307K N308D | ++ | + | NADPH |
| 70 | V105G F107M V149I R200D D201I R202D V301R T302R | ND | + | NADH |
| 71 | V105G F107M V149I R200G D201I R202D V301R T302R | ND | – | ND |
| 72 | V105G F107M V149I R200L D201I R202D V301R T302R | ND | – | ND |
| 73 | V105G F107M V149I R200D D201L R202D V301R T302R | ND | – | ND |

TABLE 2-continued

| # | Mutations to Homolog 1 (SEQ ID NO: 189) | Active - CPCoA | Active - CrCoA | Cofactor pref |
|---|---|---|---|---|
| 74 | V105G F107M V149I R200G D201L R202D V301R T302R | ND | – | ND |
| 75 | V105G F107M V149I R200L D201L R202D V301R T302R | ND | – | ND |
| 76 | V105G F107M V149I R200D D201V R202D V301R T302R | ND | + | NADH |
| 77 | V105G F107M V149I R200G D201V R202D V301R T302R | ND | + | NADH |
| 78 | V105G F107M V149I R200L D201V R202D V301R T302R | ND | – | ND |
| 79 | V105G F107M V149I R200D D201I R202G V301R T302R | ND | + | NADH |
| 80 | V105G F107M V149I R200G D201I R202G V301R T302R | ND | – | ND |
| 81 | V105G F107M V149I R200L D201I R202G V301R T302R | ND | – | ND |
| 82 | V105G F107M V149I R200D D201L R202G V301R T302R | ND | + | NADH |
| 83 | V105G F107M V149I R200G D201L R202G V301R T302R | ND | – | ND |
| 84 | V105G F107M V149I R200L D201L R202G V301R T302R | ND | + | NADH |
| 85 | V105G F107M V149I R200D D201V R202G V301R T302R | +++ | + | NADH |
| 86 | V105G F107M V149I R200G D201V R202G V301R T302R | ND | – | ND |
| 87 | V105G F107M V149I R200L D201V R202G V301R T302R | ND | – | ND |
| 88 | V105G F107M V149I R200D D201I R202L V301R T302R | ND | – | ND |
| 89 | V105G F107M V149I R200G D201I R202L V301R T302R | ND | – | ND |
| 90 | V105G F107M V149I R200L D201I R202L V301R T302R | ND | – | ND |
| 91 | V105G F107M V149I R200D D201L R202L V301R T302R | ND | + | NADH |
| 92 | V105G F107M V149I R200G D201L R202L V301R T302R | ND | – | ND |
| 93 | V105G F107M V149I R200L D201L R202L V301R T302R | ND | – | ND |
| 94 | V105G F107M V149I R200D D201V R202L V301R T302R | ND | + | NADH |
| 95 | V105G F107M V149I R200G D201V R202L V301R T302R | ND | – | ND |
| 96 | V105G F107M V149I R200L D201V R202L V301R T302R | ND | – | ND |
| 97 | V105G F107M V149I R200D R202D V301R T302R | ND | + | NADH |
| 98 | V105G F107M V149I R200G R202D V301R T302R | ND | + | NADH |
| 99 | V105G F107M V149I R200L R202D V301R T302R | ND | + | NADH |
| 100 | V105G F107M V149I R200D R202G V301R T302R | +++ | + | NADH |
| 101 | V105G F107M V149I R200G R202G V301R T302R | +++ | + | NADH |
| 102 | V105G F107M V149I R200L R202G V301R T302R | +++ | + | NADH |
| 103 | V105G F107M V149I R200D R202L V301R T302R | +++ | + | NADH |
| 104 | V105G F107M V149I R200G R202L V301R T302R | ND | + | NADH |
| 105 | V105G F107M V149I R200L R202L V301R T302R | ND | + | NADH |
| 106 | V105G F107M V149I R200D V301R T302R | +++ | + | NADPH |
| 107 | V105G F107M V149I R200D R202H V301R T302R | +++ | + | NADH |
| 108 | V105G F107M V149I R200D R202S V301R T302R | +++ | + | NADH |
| 109 | V105G F107M V149I R200D R202K V301R T302R | +++ | + | NADPH |
| 110 | V105G F107M V149I R200D R202Q V301R T302R | +++ | + | |
| 111 | V105G F107M V149I R200D R202A V301R T302R | +++ | + | NADPH |
| 112 | V105G F107M V149I R200D R202C V301R T302R | ND | + | NADH |
| 113 | V105G F107M V149I R200D R202V V301R T302R | ND | + | NADH |

In some embodiments the non-naturally occurring microbial organism has a hexamethylenediameine pathway that includes (i) 6-aminoacaproyl CoA transferase, (ii) 6-amino caproyl CoA synthase, (iii) 6-amino caproyl CoA reductase, (iv) hexamethylenediamine transaminase, (v) hexamethyl-enediamine dehydrogenase, (v) or a combination of one or more of the enzymes (i)-(v). In other embodiments, the non-naturally occurring microbial organism has a hexam-ethylenediameine pathway that includes a 3-oxoadipyl-CoA thiolase (Thl), a 3-oxoadipyl-CoA dehydrogenase (Hbd), and a 3-oxoadipyl-CoA dehydratase ("crotonase" or Crt), a 5-carboxy-2-pentenoyl-CoA reductase (Ter), a transaminase (HMD TA) and a carboxylic acid reductase (CAR).

The non-naturally occurring microbial organisms are con-structed using methods well known in the art as exemplified herein to exogenously express at least one nucleic acid encoding a 6-aminocaproic acid, caprolactam, hexamethyl-enediamine or levulinic acid pathway enzyme in sufficient amounts to produce 6-aminocaproic acid, caprolactam, hex-amethylenediamine or levulinic acid. It is understood that the microbial organisms are cultured under conditions sufficient to produce 6-aminocaproic acid, caprolactam, hexamethylenediamine or levulinic acid. Following the teachings and guidance provided herein, the non-naturally occurring microbial organisms can achieve biosynthesis of 6-aminocaproic acid, caprolactam, hexamethylenediamine or levulinic acid resulting in intracellular concentrations between about 0.1-200 mM or more. Generally, the intracellular concentration of 6-aminocaproic acid, caprolactam, hexamethylenediamine or levulinic acid is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. Pat. No. 7,947,483, issued May 24, 2011. Any of these conditions can be employed with the non-naturally occurring microbial organisms as well as other anaerobic conditions well known in the art. Under such anaerobic conditions, the 6-aminocaproic acid, caprolactam, hexamethylenediamine or levulinic acid producers can synthesize 6-aminocaproic acid, caprolactam, hexamethylenediamine or levulinic acid at intracellular concentrations of 5-10 mM or more as well as all other concentrations exemplified herein. It is understood that, even though the above description refers to intracellular concentrations, 6-aminocaproic acid, caprolactam, hexamethylenediamine or levulinic acid producing microbial organisms can produce 6-aminocaproic acid, caprolactam, hexamethylenediamine or levulinic acid intracellularly and/or secrete the product into the culture medium.

The culture conditions can include, for example, liquid culture procedures as well as fermentation and other large scale culture procedures. As described herein, particularly useful yields of the biosynthetic products can be obtained under anaerobic or substantially anaerobic culture conditions.

As described herein, one exemplary growth condition for achieving biosynthesis of 6-aminocaproic acid, caprolactam, hexamethylenediamine or levulinic acid includes anaerobic culture or fermentation conditions. In certain embodiments, the non-naturally occurring microbial organisms can be sustained, cultured or fermented under anaerobic or substantially anaerobic conditions. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also include growing or resting cells in liquid medium or on solid agar inside a sealed chamber maintained with an atmosphere of less than 1% oxygen. The percent of oxygen can be maintained by, for example, sparging the culture with an N2/CO2 mixture or other suitable non-oxygen gas or gases.

The culture conditions described herein can be scaled up and grown continuously for manufacturing of 6-aminocaproic acid, caprolactam, hexamethylenediamine or levulinic acid. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of 6-aminocaproic acid, caprolactam, hexamethylenediamine or levulinic acid. Generally, and as with non-continuous culture procedures, the continuous and/or near-continuous production of 6-aminocaproic acid, caprolactam, hexamethylenediamine or levulinic acid will include culturing anon-naturally occurring 6-aminocaproic acid, caprolactam, hexamethylenediamine or levulinic acid producing organism in sufficient nutrients and medium to sustain and/or nearly sustain growth in an exponential phase. Continuous culture under such conditions can include, for example, 1 day, 2, 3, 4, 5, 6 or 7 days or more. Additionally, continuous culture can include 1 week, 2, 3, 4 or 5 or more weeks and up to several months. Alternatively, organisms can be cultured for hours, if suitable for a particular application. It is to be understood that the continuous and/or near-continuous culture conditions also can include all time intervals in between these exemplary periods. It is further understood that the time of culturing the microbial organism is for a sufficient period of time to produce a sufficient amount of product for a desired purpose.

Fermentation procedures are well known in the art. Briefly, fermentation for the biosynthetic production of 6-aminocaproic acid, caprolactam, hexamethylenediamine or levulinic acid can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the 6-aminocaproic acid, caprolactam, hexamethylenediamine or levulinic acid producers for continuous production of substantial quantities of 6-aminocaproic acid, caprolactam, hexamethylenediamine or levulinic acid, the 6-aminocaproic acid, caprolactam, hexamethylenediamine or levulinic acid producers also can be, for example, simultaneously subjected to chemical synthesis procedures to convert the product to other compounds or the product can be separated from the fermentation culture and sequentially subjected to chemical conversion to convert the product to other compounds, if desired. As described herein, an intermediate in the adipate pathway utilizing 3-oxoadipate, hexa-2-enedioate, can be converted to adipate, for example, by chemical hydrogenation over a platinum catalyst.

As described herein, exemplary growth conditions for achieving biosynthesis of 6-aminocaproic acid, caprolactam, hexamethylenediamine or levulinic acid includes the addition of an osmoprotectant to the culturing conditions. In certain embodiments, the non-naturally occurring microbial organisms can be sustained, cultured or fermented as described above in the presence of an osmoprotectant. Briefly, an osmoprotectant means a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfonioproprionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. For example, as described in Example XXII, *Escherichia coli* in the presence of varying amounts of 6-aminocaproic acid is suitably grown in the presence of 2 mM glycine betaine. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

Successfully engineering a pathway involves identifying an appropriate set of enzymes with sufficient activity and specificity. This entails identifying an appropriate set of enzymes, cloning their corresponding genes into a production host, optimizing fermentation conditions, and assaying for product formation following fermentation. To engineer a production host for the production of 6-aminocaproic acid or caprolactam, one or more exogenous DNA sequence(s) can be expressed in a host microorganism. In addition, the microorganism can have endogenous gene(s) functionally deleted. These modifications will allow the production of 6-aminocaproate or caprolactam using renewable feedstock.

In some embodiments minimizing or even eliminating the formation of the cyclic imine or caprolactam during the conversion of 6-aminocaproic acid to HMDA entails adding a functional group (for example, acetyl, succinyl) to the amine group of 6-aminocaproic acid to protect it from cyclization. This is analogous to ornithine formation from L-glutamate in *Escherichia coli*. Specifically, glutamate is first converted to N-acetyl-L-glutamate by N-acetylglutamate synthase. N-Acetyl-L-glutamate is then activated to N-acetylglutamyl-phosphate, which is reduced and transaminated to form N-acetyl-L-ornithine. The acetyl group is then removed from N-acetyl-L-ornithine by N-acetyl-L-ornithine deacetylase forming L-ornithine. Such a route is necessary because formation of glutamate-5-phosphate from glutamate followed by reduction to glutamate-5-semialdehyde leads to the formation of (S)-1-pyrroline-5-carboxylate, a cyclic imine formed spontaneously from glutamate-5-semialdehyde. In the case of forming HMDA from 6-aminocaproic acid, the steps can involve acetylating 6-aminocaproic acid to acetyl-6-aminocaproic acid, activating the carboxylic acid group with a CoA or phosphate group, reducing, aminating, and deacetylating.

EXPERIMENTS

Example 1. Screening of Candidate Aldehyde Dehydrogenases for Activity on Adipyl-CoA Genes encoding candidate aldehyde dehydrogenases (Ald) were identified bioinformatically in the genomes of multiple species (Table 1). Genes encoding each of the aldehyde dehydrogenases were synthesized, expressed in *E. coli*, and evaluated for Ald activity.

The genes encoding the Ald enzyme candidates of Table 1 were cloned into a low-copy vector under a constitutive promoter and the constructs were transformed into *E. coli* using standard techniques. Transformants were cultured in LB medium in the presence of antibiotic overnight at 35° C., after which the cells were harvested at 15,000 rpm at room temperature. To prepare lysates, cells were resuspended in a chemical lysis solution containing lysozyme, nuclease, and 10 mM DTT and incubated at room temperature for at least 30 min. The resulting lysate was used to test aldehyde dehydrogenase activity.

The lysates (5 µl) were added to an assay mixture to result in a total volume of 20 µL with final concentrations of 0.1 M Tris-HCl, pH 7.5, 2.5 mM adipyl-CoA (AdCoA), and either 0.5 mM NADH or 0.5 mM NADPH. This assay was used to screen all of the Ald enzyme candidates. Some Ald candidates were also assayed using succinyl-CoA (SuCoA) or acetyl-CoA (AcCoA) as substrates. AdCoA, SuCoA, and AcCoA were obtained from commercial suppliers. Activity was monitored by a linear decrease in fluorescence of NADH or NADPH in the presence of the CoA substrate. Alds that were significantly active on adipyl-CoA using either the NADH or NADPH were designated as positive (+) in Table 3 and those with little to no activity were designated with a minus (−).

TABLE 3

| | Activity of Aldehyde Dehydrogenases on Adipyl-CoA | | | |
|---|---|---|---|---|
| SEQ ID NO. | Organism | accession | Activity - NADH | Activity - NADPH |
| 1 | *Clostridium kluyveri* DSM555 | | − | + |
| 2 | *Porphyromonas gingivalis* W83 | | + | − |
| 3 | *Clostridium difficile* 630 | | − | + |
| 4 | *Kluyvera intestini* | WP_071196317.1 | + | − |
| 5 | *Clostridium neonatale* | WP_058295546.1 | − | − |
| 6 | *Aerococcus* sp. HMSC062B07 | WP_070558456.1 | − | − |
| 7 | *Peptostreptococcaceae bacterium* oral | WP_021676458.1 | + | − |
| 8 | *Dasania marina* | WP_026244399.1 | − | − |
| 9 | *Porphyromonadaceae bacterium* COT-184 | WP_036830068.1 | − | − |
| 10 | *Clostridium lundense* | WP_027623222.1 | − | − |
| 11 | *Anaerocolumna jejuensis* | WP_073279774.1 | + | − |
| 12 | *Clostridium homopropionicum* | WP_052222510.1 | − | − |
| 13 | *Geosporobacter ferrireducens* | WP_069981616.1 | − | − |
| 14 | *Listeria ivanovii* | WP_038407128.1 | − | − |
| 15 | *Bacillus soli* | WP_066062455.1 | + | − |
| 16 | *Enterococcus rivorum* | WP_069697141.1 | − | − |
| 17 | *Desnuesiella massiliensis* | WP_055665162.1 | + | − |
| 18 | *Bacteroidales bacterium* KA00251 | WP_066041885.1 | − | − |
| 19 | *Caldanaerobius polysaccharolyticus* | WP_026487268.1 | + | − |
| 20 | *Clostridium* sp. ASF356 | WP_004036483.1 | − | − |

TABLE 3-continued

Activity of Aldehyde Dehydrogenases on Adipyl-CoA

| SEQ ID NO. | Organism | accession | Activity - NADH | Activity - NADPH |
|---|---|---|---|---|
| 21 | *Clostridiales bacterium* DRI-13 | WP_034420506.1 | – | – |
| 22 | *Fusobacterium ulcerans* ATCC 49185 | WP_005981617.1 | – | – |
| 23 | *Anaerocolumna jejuensis* | WP_073279351.1 | – | – |
| 24 | *Cellulosilyticum* sp. I15G10I2 | WP_070001026.1 | + | – |
| 25 | *Geosporobacter ferrireducens* | WP_083273866.1 | + | – |
| 26 | *Pelosinus* sp. UFO1 | WP_038668911.1 | – | – |
| 27 | *Bacillus korlensis* | WP_084362095.1 | + | – |
| 28 | *Acidaminococcus massiliensis* | WP_075579339.1 | + | – |
| 29 | *Eubacterium* sp. SB2 | WP_050640767.1 | – | – |
| 30 | *Erwinia teleogrylli* | WP_058911295.1 | + | – |
| 31 | *Lachnospiraceae bacterium* 32 | WP_016223553.1 | + | – |
| 32 | *Eubacterium plexicaudatum* | WP_004061597.1 | + | – |
| 33 | *Clostridium* sp. KNHs205 | WP_033166114.1 | + | – |
| 34 | *Butyricimonas virosa* | WP_027200274.1 | – | – |
| 35 | *Malonomonas rubra* | WP_072908980.1 | – | – |
| 36 | *Robinsoniella peoriensis* | WP_044292972.1 | + | – |
| 37 | *Clostridium taeniosporum* | WP_069679818.1 | – | – |
| 38 | *Caldithrix abyssi* | WP_006928331.1 | + | – |
| 39 | *Piscicoccus intestinalis* | WP_084343789.1 | – | – |
| 40 | *Sporomusa sphaeroides* | WP_075753933.1 | + | – |
| 41 | *Bacillus* sp. FJAT-25547 | WP_057762439.1 | + | – |
| 42 | *Dorea* sp. D27 | WP_049729435.1 | + | – |
| 43 | *Oscillibacter* sp. 13 | WP_081646270.1 | – | – |
| 44 | *Enterococcus phoeniculicola* | WP_010767571.1 | + | – |
| 45 | *Blautia schinkii* | WP_044941637.1 | + | – |
| 46 | *Shuttleworthia satelles* DSM14600 | WP_006905683.1 | – | – |
| 47 | *Clostridium intestinale* | WP_073018444.1 | + | – |
| 48 | *Massilioclostridium coli* | WP_069989048.1 | – | – |
| 49 | *Cloacibacillus porcorum* | WP_066745012.1 | – | – |
| 50 | *Clostridium* sp. CL-2 | WP_032120205.1 | – | – |
| 51 | *Clostridia bacterium* UC5.1-1D10 | WP_054330586.1 | – | – |
| 52 | *Methylobacterium* sp. CCH5-D2 | WP_082772960.1 | – | – |
| 53 | *Sporosarcina globispora* | WP_053435653.1 | + | + |
| 54 | *Lachnospiraceae bacterium* AC3007 | WP_031546337.1 | – | – |
| 55 | *Lachnospiraceae bacterium* 28-4 | WP_016290199.1 | – | – |
| 56 | *Enterococcus avium* | WP_034875865.1 | – | – |
| 57 | *Desulfotomaculum thermocisternum* | WP_027356260.1 | – | – |
| 58 | *Rhodobacter aestuarii* | WP_076486054.1 | + | – |
| 59 | *Clostridium grantii* | WP_073337420.1 | + | – |
| 60 | *Collinsella* sp. GD7 | WP_066830323.1 | + | – |
| 61 | *Clostridium estertheticum* | WP_071611886.1 | – | – |
| 62 | *bacterium* MS4 | WP_038325413.1 | – | – |
| 63 | *Clostridium glycyrrhizinilyticum* | WP_009268007.1 | + | – |
| 64 | *Bacillus horikoshii* | WP_082892049.1 | – | – |
| 65 | *Thermincola ferriacetica* | WP_052218568.1 | + | – |
| 66 | *Lachnospiraceae bacterium* AC3007 | WP_035653923.1 | + | – |
| 67 | *Eubacterium* sp. 14-2 | WP_016216571.1 | + | – |
| 68 | *Candidatus Marispirochaeta associata* | WP_069895590.1 | – | – |
| 69 | *Clostridium drakei* | WP_032078293.1 | – | – |
| 70 | *Halanaerobium kushneri* | WP_076543773.1 | – | – |
| 71 | *Clostridium fallax* | WP_072896506.1 | – | – |
| 72 | *Flavonifractor plautii* | WP_009261118.1 | – | – |
| 73 | *Clostridium propionicum* | WP_066049640.1 | – | – |
| 74 | *Anaerosalibacter massiliensis* | WP_042682918.1 | + | – |
| 75 | *Clostridium indolis* DSM 755 | WP_024295710.1 | + | – |
| 76 | *Gabonibacter massiliensis* | WP_059027034.1 | – | – |
| 77 | *Catabacter hongkongensis* | WP_046444791.1 | + | + |
| 78 | *Desulfitibacter alkalitolerans* | WP_028307735.1 | – | – |
| 79 | *Porphyromonas levii* | WP_018357742.1 | – | – |
| 80 | *Bacillus thermotolerans* | WP_039235348.1 | + | – |
| 81 | *Desulfitibacter alkalitolerans* | WP_028307055.1 | – | – |
| 82 | *Gracilibacillus kekensis* | WP_073203236.1 | + | + |
| 83 | *Lactonifactor longoviformis* | WP_072848455.1 | – | – |
| 84 | *Propionispora* sp. 2/2-37 | WP_054258533.1 | + | – |
| 85 | *Erysipelothrix larvae* | WP_067632640.1 | – | – |
| 86 | *Clostridium chauvoei* | WP_021875658.1 | + | – |
| 87 | *Thermoanaerobacterium aotearoense* | WP_014757178.1 | + | – |
| 88 | *Ruminococcus* sp. AT10 | WP_059066688.1 | + | – |
| 89 | *Porphyromonas* sp. HMSC077F02 | WP_070707924.1 | – | – |

TABLE 3-continued

Activity of Aldehyde Dehydrogenases on Adipyl-CoA

| SEQ ID NO. | Organism | accession | Activity - NADH | Activity - NADPH |
|---|---|---|---|---|
| 90 | *Acetobacterium dehalogenans* | WP_026396046.1 | + | – |
| 91 | *Spirochaeta alkalica* | WP_018526526.1 | + | – |
| 92 | *Alistipes* sp. ZOR0009 | WP_047449305.1 | – | – |
| 93 | *Clostridiisalibacter paucivorans* | WP_026895448.1 | – | – |
| 94 | *Clostridium caminithermale* DSM 15212 | WP_073149471.1 | + | + |
| 95 | *Caldanaerobius fijiensis* | WP_073341480.1 | + | – |
| 96 | *Clostridium kluyveri* | WP_073539833.1 | – | – |
| 97 | *Pelosinus fermentans* | WP_007958399.1 | + | – |
| 98 | *Halanaerobium saccharolyticum* subsp. *saccharolyticum* DSM 6643 | WP_005487288.1 | – | – |
| 99 | *Anaeroarcus burkinensis* DSM 6283 | WP_018702299.1 | – | – |
| 100 | *Blautia wexlerae* | WP_026648408.1 | + | – |
| 101 | *Paenibacillus* sp. OSY-SE | WP_019424162.1 | + | – |
| 102 | *Brachyspira intermedia* PWSA | WP_014488056.1 | – | – |
| 103 | *Spirochaetes bacterium* GWC2_52_13 | OHD32879.1 | + | – |
| 104 | *Thermoanaerobacterales bacterium* 50_218 | KUK31085.1 | – | – |
| 105 | *Cohaesibacter marisflavi* | WP_090072157.1 | – | – |
| 106 | *Gracilibacillus ureilyticus* | WP_089739945.1 | – | – |
| 107 | *Romboutsia lituseburensis* DSM | WP_092724914.1 | + | – |
| 108 | uncultured *Clostridium* sp. | SCJ29526.1 | – | – |
| 109 | *Clostridium* sp. CAG: 448 | CDC62685.1 | + | – |
| 110 | *Clostridium ultunense* Esp | CCQ95129.1 | – | – |
| 111 | *Yersinia bercovieri* ATCC 43970 | WP_005274635.1 | + | – |
| 112 | *Proteocatella sphenisci* | WP_028829945.1 | + | – |
| 113 | *Clostridium* sp. MSTE9 | WP_009063988.1 | – | – |
| 114 | *Spirochaeta africana* | WP_014454236.1 | – | – |
| 115 | *Deltaproteobacteria bacterium* RIFCSPHIGHO2_02_FULL_40_11 | OGQ13386.1 | – | – |
| 116 | *Clostridiales bacterium* PH28_bin88 | KKM11466.1 | – | – |
| 117 | *Pelosinus propionicus* DSM | WP_090932308.1 | + | – |
| 118 | *Propionispora vibrioides* | WP_091747803.1 | – | – |
| 119 | *Natronincola ferrireducens* | WP_090549432.1 | – | – |
| 120 | uncultured *Ruminococcus* sp. | WP_112331601.1 | – | – |
| 121 | *Firmicutes bacterium* CAG: 41 | WP_022229858.1 | – | – |
| 122 | *Tannerella* sp. oral | ETK11816.1 | – | – |
| 123 | *Clostridium* sp. DL-VIII | WP_009171375.1 | – | – |
| 124 | *Desulfobulbus japonicus* | WP_028581706.1 | – | – |
| 125 | *Veillonella* sp. oral | WP_009353657.1 | – | – |
| 126 | *Bacillus selenitireducens* | WP_013174003.1 | – | – |
| 127 | *Deltaproteobacteria bacterium* GWA2_38_16 | OGP02283.1 | – | – |
| 128 | *Clostridiaceae bacterium* BRH | KJS20094.1 | – | – |
| 129 | *Clostridium cadaveris* | WP_035770223.1 | – | – |
| 130 | *Vibrio hangzhouensis* | WP_103880502.1 | – | – |
| 131 | *Halanaerobium congolense* | SDI24694.1 | – | – |
| 132 | uncultured *Eubacterium* sp. | SCH28733.1 | – | – |
| 133 | *Oscillibacter* sp. CAG: 241 | CDB26907.1 | – | – |
| 134 | *Clostridium* sp. KLE | ERI68946.1 | + | – |
| 135 | *Caldalkalibacillus thermarum* TA2.A1 | WP_007505383.1 | + | – |
| 136 | *Budvicia aquatica* | WP_029095874.1 | – | – |
| 137 | *Caldalkalibacillus thermarum* TA2.A1 | WP_007505383.1 | + | – |
| 138 | *Rhodospirillum rubrum* ATCC 11170 | WP_011388669.1 | – | – |
| 139 | *Bacteroidetes bacterium* GWE2_39_28 | OFX78235.1 | – | – |
| 140 | *Desulfosporosinus* sp. BICA1 | KJS46946.1 | – | – |
| 141 | *Clostridium uliginosum* | WP_090094411.1 | – | – |
| 142 | *Pseudobutyrivibrio* sp. ACV-2 | WP_090301343.1 | – | – |
| 143 | *Sporolituus thermophilus* DSM | WP_093690468.1 | – | – |
| 144 | *Eubacteriaceae bacterium* CHKCI004 | WP_087275421.1 | – | – |
| 145 | *Blautia* sp. CAG: 257 | CDA04862.1 | + | – |
| 146 | *Listeria marthii* FSL | EFR88049.1 | + | – |
| 147 | *Desulfosporosinus* sp. OT | WP_009624792.1 | – | – |
| 148 | *Clostridium methoxybenzovorans* | WP_024346771.1 | + | – |
| 149 | *Bacillus* sp. m3-13 | WP_010197697.1 | + | – |
| 150 | *bacterium* CG2_30_54 10 | OIP28307.1 | + | – |
| 151 | *Halanaerobium* sp. 4-GBenrich | ODS50009.1 | – | – |

TABLE 3-continued

Activity of Aldehyde Dehydrogenases on Adipyl-CoA

| SEQ ID NO. | Organism | accession | Activity - NADH | Activity - NADPH |
|---|---|---|---|---|
| 152 | Candidatus Izimaplasma sp. | KFZ26741.1 | + | + |
| 153 | Desulfotomaculum guttoideum | WP_092244224.1 | – | – |
| 154 | Bacillus daliensis | WP_090843272.1 | – | – |
| 155 | Sporomusa acidovorans | WP_093796665.1 | – | – |
| 156 | Clostridium sp. C105KSO15 | WP_089994985.1 | – | – |
| 157 | Firmicutes bacterium CAG: 41 | CCZ36420.1 | + | – |
| 158 | Fusobacterium nucleatum subsp. | WP_085057258.1 | + | – |
| 159 | Thermoanaerobacterium xylanolyticum LX-11 | WP_013788835.1 | + | – |
| 160 | Enterococcus pallens | WP_010758150.1 | – | – |
| 161 | Porphyromonas uenonis | WP_007364879.1 | – | – |
| 162 | Tenericutes bacterium GWD2_38_27 | OHE32257.1 | – | – |
| 163 | Clostridia bacterium BRH_c25 | KUO67763.1 | – | – |
| 164 | Listeria monocytogenes | WP_012951491.1 | + | – |
| 165 | Clostridium lavalense | WP_092361844.1 | + | – |
| 166 | Acetanaerobacterium elongatum | WP_092640331.1 | + | – |
| 167 | Alkaliphilus peptidifermentans DSM | WP_091539210.1 | + | – |
| 168 | Clostridium sp. C105KSO15 | WP_089983798.1 | – | – |
| 169 | Ruminococcus sp. CAG: 17 | CCY97458.1 | – | – |
| 170 | Clostridium hylemonae DSM 15053 | EEG72288.1 | – | – |
| 171 | Acetonema longum DSM 6540 | EGO64744.1 | – | – |
| 172 | Brachyspira innocens | WP_020003501.1 | – | – |
| 173 | Clostridium saccharobutylicum | WP_022747467.1 | – | – |
| 174 | Tenericutes bacterium GWD2_38_27 | OHE28831.1 | – | – |
| 175 | Bacillus sp. FJAT-25547 | WP_053476394.1 | – | – |
| 176 | Clostridium populeti | WP_092561044.1 | + | – |
| 177 | Natronincola peptidivorans | WP_090442614.1 | – | – |
| 178 | Megasphaera paucivorans | WP_091652222.1 | – | – |
| 179 | Anaerobium acetethylicum | WP_091232027.1 | – | – |
| 180 | Eubacterium limosum | ALU13318.1 | – | – |
| 181 | Porphyromonas sp. CAG: 1061 | CCY08492.1 | – | – |
| 182 | Clostridium beijerinckii strain NRRL B593 | AAD31841.1 | – | – |
| 183 | Clostridium sticklandii DSM 519 | WP_013360893.1 | – | – |
| 184 | Bacillus oryziterrae | WP_017754440.1 | – | – |
| 185 | Yersinia enterocolitica | WP_005157703.1 | – | – |
| 186 | Syntrophobacterales bacterium GWC2_56_13 | OHE18777.1 | – | – |
| 187 | Candidates Bacteroides periocalifornicus | KQM08700.1 | + | – |
| 188 | Anaerocolumna aminovalerica | WP_091689178.1 | + | – |
| 189 | Natronincola peptidivorans | WP_090439673.1 | – | – |
| 190 | Dendrosporobacter quercicolus | WP_092070189.1 | – | – |
| 191 | uncultured Flavonifractor sp. | SCJ32847.1 | – | – |
| 192 | Geobacillus sp. Y4.1MC1 | OUM85091.1 | – | – |
| 193 | Clostridium bolteae CAG: 59 | CCX97030.1 | – | – |
| 194 | Roseburia inulinivorans A2-194 | WP_118109132.1 | – | – |

Example 2. Aldehyde Dehydrogenases Assays to Determine Substrate Specificity To determine substrate preference of several aldehyde dehydrogenase enzymes, a substrate CoA depletion assay was used using succinyl CoA and adipyl CoA substrates. In this assay, the substrate solution contained 0.1 M Tris-HCl, pH 7.5, 1 mM adipyl-CoA, 0.2 mM Succinyl-CoA, and 0.2 mM Acetyl-CoA with an excess amount of the NADH or NADPH cofactor at 1.5 mM. The reaction was initiated by addition of the lysate to the assay buffer and was incubated for 2 hours at room temperature. The reactions were quenched with 1% formic acid and then evaluated by LC/MS analytical methods to quantitate each of the residual substrate CoAs. Ald activity was measured as % depletion of each CoA substrate. Higher % depletion of a particular CoA substrate with respect to another CoA substrate present in the assay indicated a preference for the particular substrate CoA. FIG. 2 shows that the Peptostreptococcaceae bacterium oral aldehyde dehydrogenase (SEQ ID NO:7), the Acidaminococcus massiliensis aldehyde dehydrogenase (SEQ ID NO:28), the Collinsella sp. GD7 aldehyde dehydrogenase (SEQ ID NO:60), and the Romboutsia litusebu-rensis DSM aldehyde dehydrogenase (SEQ ID NO:107) depleted much more adipyl-CoA than Succinyl-CoA from the assay mixture and were therefore designated as adipyl-CoA preferring. Aldehyde dehydrogenase from Porphyromonas gingivalis W83 (SEQ ID NO: 2) was found to be succinyl-CoA preferring.

Example 3. In Vivo Assays of Aldehyde Dehydrogenases

Aldehyde dehydrogenases demonstrated to have an adipyl-CoA substrate preference were also tested in an in vivo assay, in which an E. coli strain that expressed genes encoding a 3-oxoadipyl-CoA thiolase (Thl), a 3-oxoadipyl- CoA dehydrogenase (Hbd), and a 3-oxoadipyl-CoA dehydratase ("crotonase" or Crt), a 5-carboxy-2-pentenoyl-CoA reductase (Ter), and a transaminase (TA) was transformed with a construct that included an aldehyde dehydrogenase (Ald) gene. The Thl, Hbd, Crt, Ter, TA E. coli strain included all of the pathway enzymes necessary for producing 6-aminocaproate (6ACA), with the exception of the Ald enzyme. Genes encoding the Porphyromonas gingivalis W83 Ald (SEQ ID NO:2), the Peptostreptococcaceae bacterium oral Ald (SEQ ID NO:7), the Acidaminococcus massiliensis Ald (SEQ ID NO:28), the Collinsella sp. GD7 Ald (SEQ ID NO:60), and the Romboutsia lituseburensis DSM Ald (SEQ ID NO:107) were separately cloned in a low copy number ever, in this case purified protein was used instead of cell lysates. Each of the Acidaminococcus massiliensis Ald (SEQ ID NO:28), the Collinsella sp. GD7 Ald (SEQ ID NO:60), and the Romboutsia lituseburensis DSM Ald (SEQ ID NO:107) was purified using affinity chromatography. In these assays, the concentration each of the substrate CoAs was varied to determine the turnover number ($k_{cat}$), the affinity of the enzyme for the substrate ($K_M$) of the enzyme, the catalytic efficiency ($k_{cat}/K_M$) of each selected Ald enzyme for each substrate were determined and shown in the Table 5 below.

TABLE 5

| Kinetic parameters of the aldehyde dehydrogenase enzymes with various substrates | | | | | | | | |
|---|---|---|---|---|---|---|---|---|
| | | | | Substrates | | | | |
| Succinyl-CoA | | | Acetyl-CoA SEQ ID Nos: | | | Adipyl-CoA | | |
| 60 | 107 | 28 | 60 | 107 | 28 | 60 | 107 | 28 |
| $K_M$ (mM) 0.40 | 0.22 | 0.79 | >2 | 0.31 | 0.38 | 0.10 | 0.24 | 0.81 |
| Turnover number $k_{cat}$ (s$^{-1}$) 0.010 | 0.056 | 0.23 | ND | 0.013 | 0.040 | 0.015 | 1.0 | 2.5 |
| Catalytic efficiency $k_{cat}/K_M$ (s$^{-1}$ mM$^{-1}$) 0.026 | 0.25 | 0.29 | 0.0016 | 0.04 | 0.10 | 0.15 | 4.0 | 3.0 | plasmid vector under a constitutive promoter. The plasmids for expressing the Ald genes were transformed into the Thl/Hbd/Crt/Ter/TA strain using standard techniques. Transformants that included any one of the Ald genes were then tested for 6-aminocaproate (6ACA) production. The engineered E. coli cells were fed 2% glucose in minimal media, and after 18 hours incubation at 35° C., the cells were harvested, and the supernatants were evaluated by analytical HPLC or standard LS/MS analytical methods for 6ACA. As shown in Table 4, expression of genes encoding Ald enzymes in E. coli that included Thl, Hbd, Crt, Ter, and TA genes resulted in 6ACA production by these strains.

TABLE 4

| In vivo activity of Aldehyde Dehydrogenases in an ACA Pathway. | | | |
|---|---|---|---|
| Homolog # | Species | Amino acid sequence | In vivo ACA production |
| 2 | Porphyromonas gingivalis W83 | SEQ ID NO: 2 | + |
| 7 | Peptostreptococcaceae bacterium oral | SEQ ID NO: 7 | ++ |
| 28 | Acidaminococcus massiliensis | SEQ ID NO: 28 | ++ |
| 60 | Collinsella sp. GD7 | SEQ ID NO: 60 | ++ |
| 107 | Romboutsia lituseburensis DSM | SEQ ID NO: 107 | ++ |
| [no Ald gene] | — | | – |

Example 4. Kinetic Characterization of Aldehyde Dehydrogenases

Kinetic characterization was done under similar conditions as the lysate screening described in Example 1; how- Catalytic efficiency ($k_{cat}/K_M$) of the various aldehyde dehydrogenases using various substrates were plotted in a bar graph for comparison (FIG. 3A). Catalytic efficiency ($k_{cat}/K_M$ of the Ald homolog for adipyl-CoA over succinyl-CoA was calculated as the ratio of $k_{cat}/K_M$ of adipyl-CoA over $k_{cat}/K_M$ of succinyl-CoA. FIG. 3B shows that all three Ald enzymes that were assayed had higher catalytic efficiency for adipyl-CoA over succinyl-CoA. FIG. 3C shows that all three Ald enzymes that were assayed also had higher catalytic efficiency for adipyl-CoA over acetyl-CoA.

Example 5 In Vivo Assays of Aldehyde Dehydrogenases

Aldehyde dehydrogenases demonstrated to have an adipyl-CoA substrate preference were tested in vivo assay in an E. coli strain that expressed genes encoding a 3-oxoadipyl-CoA thiolase (Thl), a 3-oxoadipyl-CoA dehydrogenase (Hbd), and a 3-oxoadipyl-CoA dehydratase ("crotonase" or Crt), a 5-carboxy-2-pentenoyl-CoA reductase (Ter), and a transaminase (TA) as described in Example 3 was also transformed with a construct that included two additional genes, carboxylic acid reductase (CAR), CAR-WP_003872682.1), and another TA gene (HMD-TA WP 001301395.1), along with the Ald gene integrated in E. coli chromosome. Genes encoding the Porphyromonas gingivalis W83 Ald (SEQ ID NO:2), the Peptostreptococcaceae bacterium oral Ald (SEQ ID NO:7), the Acidaminococcus massiliensis Ald (SEQ ID NO:28), the Collinsella sp. GD7 Ald (SEQ ID NO:60), and the Romboutsia lituseburensis DSM Ald (SEQ ID NO:107) were separately cloned in a low copy number plasmid vector under a constitutive promoter. The plasmids for expressing the Ald genes were transformed into the Thl/Hbd/Crt/Ter/TA/CAR strain using standard techniques. These constructs were subject to the same conditions and testing as described for 6ACA production in Example 3. The construct was shown to produce HMD as detected by LC/MS analytical methods described in Example 3.

What is claimed is:

1. A method of producing adipate-semialdehyde comprising culturing a non-naturally occurring microorganism comprising at least one exogenous nucleic acid encoding an aldehyde dehydrogenase enzyme that reacts with adipyl-CoA to form adipate-semialdehyde, wherein the aldehyde dehydrogenase has greater catalytic efficiency for adipyl-CoA as a substrate as compared to succinyl-CoA, acetyl-CoA, or both as substrates, and/or the aldehyde dehydrogenase has higher turnover number for adipyl-CoA substrate as compared to succinyl-CoA, acetyl-CoA, or both succinyl-CoA and acetyl-CoA substrates and wherein the aldehyde dehydrogenase has at least 80%, at least 85%, at least 90%, at least 95%, at least 99%, or 100% amino acid sequence identity to any one of SEQ ID NOs: 4, 7, 11, 15, 17, 19, 24, 25, 27, 28, 31-33, 36, 38, 40-42, 44, 45, 47, 53, 58-60, 63, 65-67, 74, 75, 77, 80, 82, 84, 86-88, 90, 91, 94, 95, 97, 100, 101, 103, 107, 109, 111, 112, 117, 134, 135, 137, 145, 146, 148-150, 152, 157-159, 164-167, 176, 187, and 188.

2. The method of claim 1, wherein the aldehyde dehydrogenase enzyme comprises an amino acid sequence selected from the group consisting of SEQ ID NOs: SEQ ID NO: 7, 28, 60, or 107.

3. The method of claim 1, wherein the non-naturally occurring microbial organism comprises a 6-aminocaproic acid pathway.

4. The method of claim 3, wherein the 6-aminocaproic acid pathway comprises: (i) transaminase, (ii) 6-aminocaproate dehydrogenase, or both (iii) transaminase and 6-aminocaproate dehydrogenase enzymes.

5. The method of claim 1, wherein the non-naturally occurring microbial organism comprises two, three, four, five, six, or seven exogenous nucleic acids each encoding an enzyme for a 6-aminocaproic acid pathway, hexamethylenediamine pathway, caprolactam pathway, 1, 6-hexanediol pathway, caprolactone pathway, or a combination of two or more pathways.

6. The method of claim 5, wherein the hexamethylenediamine pathway comprises (i) 6-amino caproyl CoA transferase, (ii) 6-amino caproyl CoA synthase, (iii) 6-amino caproyl CoA reductase, (iv) hexamethylenediamine transaminase, (v) hexamethylenediamine dehydrogenase, (v) or a combination of one or more of the enzymes (i)-(v); and the caprolactam pathway comprises amidohydrolase enzyme.

7. The method of claim 1, wherein the non-naturally occurring microbial organism comprises a species of *Aci-netobacter, Actinobacillus, Anaerobiospirillum, Aspergillus, Bacillus, Clostridium, Corynebacterium, Escherichia, Gluconobacter, Klebsiella, Kluyveromyces, Lactococcus, Lactobacillus, Mannheimia, Pichia, Pseudomonas, Rhizobium, Rhizopus, Saccharomyces, Schizosaccharomyces, Streptomyces*, and *Zymomonas*.

8. A method of producing adipate-semialdehyde comprising culturing a non-naturally occurring microorganism comprising at least one exogenous nucleic acid encoding an aldehyde dehydrogenase enzyme that reacts with adipyl-CoA to form adipate-semialdehyde, wherein the aldehyde dehydrogenase has at least 80%, at least 85%, at least 90%, at least 95%, at least 99%, or 100% amino acid sequence identity to any one of SEQ ID NOs: 4, 7, 11, 15, 17, 19, 24, 25, 27, 28, 31-33, 36, 38, 40-42, 44, 45, 47, 53, 58-60, 63, 65-67, 74, 75, 77, 80, 82, 84, 86-88, 90, 91, 94, 95, 97, 100, 101, 103, 107, 109, 111, 112, 117, 134, 135, 137, 145, 146, 148-150, 152, 157-159, 164-167, 176, 187, and 188.

9. The method of claim 8, wherein the non-naturally occurring microbial organism comprises a 6-aminocaproic acid pathway.

10. The method of claim 9, wherein the 6-aminocaproic acid pathway comprises: (i) transaminase, (ii) 6-aminocaproate dehydrogenase, or both (iii) transaminase and 6-aminocaproate dehydrogenase enzymes.

11. The method of claim 8, wherein the non-naturally occurring microbial organism comprises two, three, four, five, six, or seven exogenous nucleic acids each encoding an enzyme for a 6-aminocaproic acid pathway, a hexamethylenediamine pathway, a caprolactam pathway, a 1,6-hexanediol pathway, a caprolactone pathway, or a combination of two or more said pathways.

12. The method of claim 11, wherein the hexamethylenediamine pathway comprises (i) 6-amino caproyl CoA transferase, (ii) 6-amino caproyl CoA synthase, (iii) 6-amino caproyl CoA reductase, (iv) hexamethylenediamine transaminase, (v) hexamethylenediamine dehydrogenase, (v) or a combination of one or more of the enzymes (i)-(v); and the caprolactam pathway comprises aminohydrolase enzyme.

13. The method of claim 8, wherein the non-naturally occurring microbial organism comprises a species of *Acinetobacter, Actinobacillus, Anaerobiospirillum, Aspergillus, Bacillus, Clostridium, Corynebacterium, Escherichia, Gluconobacter, Klebsiella, Kluyveromyces, Lactococcus, Lactobacillus, Mannheimia, Pichia, Pseudomonas, Rhizobium, Rhizopus, Saccharomyces, Schizosaccharomyces, Streptomyces*, and *Zymomonas*.

* * * * *

SEQUENCE LISTING

<160> NUMBER OF SEQ ID NOS: 190

<210> SEQ ID NO 1
<211> LENGTH: 453
<212> TYPE: PRT
<213> ORGANISM: Clostridium kluyveri DSM555

<400> SEQUENCE: 1

```
Met Ser Asn Glu Val Ser Ile Lys Glu Leu Ile Glu Lys Ala Lys Val
1               5                   10                  15

Ala Gln Lys Lys Leu Glu Ala Tyr Ser Gln Glu Gln Val Asp Val Leu
            20                  25                  30

Val Lys Ala Leu Gly Lys Val Val Tyr Asp Asn Ala Glu Met Phe Ala
        35                  40                  45

Lys Glu Ala Val Glu Glu Thr Glu Met Gly Val Tyr Glu Asp Lys Val
        50                  55                  60

Ala Lys Cys His Leu Lys Ser Gly Ala Ile Trp Asn His Ile Lys Asp
65                  70                  75                  80

Lys Lys Thr Val Gly Ile Ile Lys Glu Glu Pro Glu Arg Ala Leu Val
                85                  90                  95

Tyr Val Ala Lys Pro Lys Gly Val Val Ala Ala Thr Thr Pro Ile Thr
            100                 105                 110

Asn Pro Val Val Thr Pro Met Cys Asn Ala Met Ala Ala Ile Lys Gly
            115                 120                 125

Arg Asn Thr Ile Ile Val Ala Pro His Pro Lys Ala Lys Lys Val Ser
    130                 135                 140

Ala His Thr Val Glu Leu Met Asn Ala Glu Leu Lys Lys Leu Gly Ala
145                 150                 155                 160

Pro Glu Asn Ile Ile Gln Ile Val Glu Ala Pro Ser Arg Glu Ala Ala
                165                 170                 175

Lys Glu Leu Met Glu Ser Ala Asp Val Val Ile Ala Thr Gly Gly Ala
            180                 185                 190

Gly Arg Val Lys Ala Ala Tyr Ser Ser Gly Arg Pro Ala Tyr Gly Val
            195                 200                 205

Gly Pro Gly Asn Ser Gln Val Ile Val Asp Lys Gly Tyr Asp Tyr Asn
    210                 215                 220

Lys Ala Ala Gln Asp Ile Ile Thr Gly Arg Lys Tyr Asp Asn Gly Ile
225                 230                 235                 240

Ile Cys Ser Ser Glu Gln Ser Val Ile Ala Pro Ala Glu Asp Tyr Asp
                245                 250                 255

Lys Val Ile Ala Ala Phe Val Glu Asn Gly Ala Phe Tyr Val Glu Asp
            260                 265                 270

Glu Glu Thr Val Glu Lys Phe Arg Ser Thr Leu Phe Lys Asp Gly Lys
            275                 280                 285

Ile Asn Ser Lys Ile Ile Gly Lys Ser Val Gln Ile Ile Ala Asp Leu
    290                 295                 300

Ala Gly Val Lys Val Pro Glu Gly Thr Lys Val Ile Val Leu Lys Gly
305                 310                 315                 320

Lys Gly Ala Gly Glu Lys Asp Val Leu Cys Lys Glu Lys Met Cys Pro
            325                 330                 335

Val Leu Val Ala Leu Lys Tyr Asp Thr Phe Glu Glu Ala Val Glu Ile
            340                 345                 350

Ala Met Ala Asn Tyr Met Tyr Glu Gly Ala Gly His Thr Ala Gly Ile
            355                 360                 365
```

-continued

```
His Ser Asp Asn Asp Glu Asn Ile Arg Tyr Ala Gly Thr Val Leu Pro
    370             375                 380

Ile Ser Arg Leu Val Val Asn Gln Pro Ala Thr Thr Ala Gly Gly Ser
385                 390                 395                 400

Phe Asn Asn Gly Phe Asn Pro Thr Thr Thr Leu Gly Cys Gly Ser Trp
                405                 410                 415

Gly Arg Asn Ser Ile Ser Glu Asn Leu Thr Tyr Glu His Leu Ile Asn
                420                 425                 430

Val Ser Arg Ile Gly Tyr Phe Asn Lys Glu Ala Lys Val Pro Ser Tyr
                435                 440                 445

Glu Glu Ile Trp Gly
    450
```

```
<210> SEQ ID NO 2
<211> LENGTH: 451
<212> TYPE: PRT
<213> ORGANISM: Porphyromonas gingivalis W83

<400> SEQUENCE: 2
```

```
Met Glu Ile Lys Glu Met Val Ser Leu Ala Arg Lys Ala Gln Lys Glu
1               5                   10                  15

Tyr Gln Ala Thr His Asn Gln Glu Ala Val Asp Asn Ile Cys Arg Ala
            20                  25                  30

Ala Ala Lys Val Ile Tyr Glu Asn Ala Ala Ile Leu Ala Arg Glu Ala
            35                  40                  45

Val Asp Glu Thr Gly Met Gly Val Tyr Glu His Lys Val Ala Lys Asn
    50                  55                  60

Gln Gly Lys Ser Lys Gly Val Trp Tyr Asn Leu His Asn Lys Lys Ser
65                  70                  75                  80

Ile Gly Ile Leu Asn Ile Asp Glu Arg Thr Gly Met Ile Glu Ile Ala
                85                  90                  95

Lys Pro Ile Gly Val Val Gly Ala Val Thr Pro Thr Thr Asn Pro Ile
                100                 105                 110

Val Thr Pro Met Ser Asn Ile Ile Phe Ala Leu Lys Thr Cys Asn Ala
            115                 120                 125

Ile Ile Ile Ala Pro His Pro Arg Ser Lys Lys Cys Ser Ala His Ala
        130                 135                 140

Val Arg Leu Ile Lys Glu Ala Ile Ala Pro Phe Asn Val Pro Glu Gly
145                 150                 155                 160

Met Val Gln Ile Ile Glu Glu Pro Ser Ile Glu Lys Thr Gln Glu Leu
                165                 170                 175

Met Gly Ala Val Asp Val Val Val Ala Thr Gly Gly Met Gly Met Val
            180                 185                 190

Lys Ser Ala Tyr Ser Ser Gly Lys Pro Ser Phe Gly Val Gly Ala Gly
            195                 200                 205

Asn Val Gln Val Ile Val Asp Ser Asn Ile Asp Phe Glu Ala Ala Ala
    210                 215                 220

Glu Lys Ile Ile Thr Gly Arg Ala Phe Asp Asn Gly Ile Ile Cys Ser
225                 230                 235                 240

Gly Glu Gln Ser Ile Ile Tyr Asn Glu Ala Asp Lys Glu Ala Val Phe
                245                 250                 255

Thr Ala Phe Arg Asn His Gly Ala Tyr Phe Cys Asp Glu Ala Glu Gly
            260                 265                 270

Asp Arg Ala Arg Ala Ala Ile Phe Glu Asn Gly Ala Ile Ala Lys Asp
    275                 280                 285
```

-continued

```
Val Val Gly Gln Ser Val Ala Phe Ile Ala Lys Lys Ala Asn Ile Asn
    290             295             300

Ile Pro Glu Gly Thr Arg Ile Leu Val Val Glu Ala Arg Gly Val Gly
305             310             315             320

Ala Glu Asp Val Ile Cys Lys Glu Lys Met Cys Pro Val Met Cys Ala
            325             330             335

Leu Ser Tyr Lys His Phe Glu Glu Gly Val Glu Ile Ala Arg Thr Asn
            340             345             350

Leu Ala Asn Glu Gly Asn Gly His Thr Cys Ala Ile His Ser Asn Asn
            355             360             365

Gln Ala His Ile Ile Leu Ala Gly Ser Glu Leu Thr Val Ser Arg Ile
    370             375             380

Val Val Asn Ala Pro Ser Ala Thr Thr Ala Gly Gly His Ile Gln Asn
385             390             395             400

Gly Leu Ala Val Thr Asn Thr Leu Gly Cys Gly Ser Trp Gly Asn Asn
            405             410             415

Ser Ile Ser Glu Asn Phe Thr Tyr Lys His Leu Leu Asn Ile Ser Arg
            420             425             430

Ile Ala Pro Leu Asn Ser Ser Ile His Ile Pro Asp Asp Lys Glu Ile
            435             440             445

Trp Glu Leu
    450

<210> SEQ ID NO 3
<211> LENGTH: 463
<212> TYPE: PRT
<213> ORGANISM: Clostridium difficile  630

<400> SEQUENCE: 3

Met Glu Lys Ala Val Glu Asn Phe Glu Asp Leu Ser Lys Glu Tyr Ile
1               5               10              15

Asn Gly Tyr Ile Glu Arg Ala Arg Lys Ala Gln Arg Glu Phe Glu Cys
            20              25              30

Tyr Thr Gln Glu Gln Val Asp Lys Ile Val Lys Ile Val Gly Lys Val
        35              40              45

Val Tyr Tyr Asn Ala Glu Tyr Leu Ala Lys Leu Ala Val Glu Glu Thr
    50              55              60

Gly Met Gly Val Tyr Glu Asp Lys Val Ala Lys Asn Lys Ser Lys Ala
65              70              75              80

Lys Val Ile Tyr Asn Asn Leu Lys Asp Lys Lys Ser Val Gly Ile Ile
            85              90              95

Asp Ile Asp Arg Glu Thr Gly Ile Thr Lys Val Ala Lys Pro Val Gly
            100             105             110

Val Val Ala Ala Ile Thr Pro Cys Thr Asn Pro Ile Val Thr Pro Met
        115             120             125

Ser Asn Ala Met Phe Ala Leu Lys Gly Arg Asn Ala Ile Ile Ile Thr
    130             135             140

Pro His His Lys Ala Ile Gly Cys Ser Thr Lys Thr Val Glu Met Ile
145             150             155             160

Asn Glu Glu Leu Glu Lys Ile Gly Ala Pro Glu Asn Leu Ile Gln Ile
            165             170             175

Leu Asp Gln Gln Ser Arg Glu Asn Thr Arg Asn Leu Ile Ser Ser Ala
        180             185             190

Asp Val Val Ile Ala Thr Gly Gly Met Gly Met Val Lys Ala Ala Tyr
```

-continued

```
                195                 200                 205

Ser Ser Gly Lys Pro Ala Leu Gly Val Gly Ala Gly Asn Val Gln Cys
    210                 215                 220

Ile Ile Asp Arg Asp Val Asp Ile Lys Glu Ala Val Pro Lys Ile Ile
225                 230                 235                 240

Ala Gly Arg Ile Phe Asp Asn Gly Ile Ile Cys Ser Gly Glu Gln Ser
                245                 250                 255

Val Ile Val Ala Glu Glu Met Phe Asp Lys Ile Met Asp Glu Phe Lys
                260                 265                 270

Asn Asn Lys Gly Phe Ile Val Arg Asp Lys Val Gln Lys Glu Ala Phe
                275                 280                 285

Arg Asn Ala Met Phe Val Asn Lys Ser Met Asn Lys Asp Ala Val Gly
    290                 295                 300

Gln Ser Val His Thr Ile Ala Lys Ile Ala Gly Val Glu Ile Pro Glu
305                 310                 315                 320

Asp Thr Lys Ile Ile Val Ile Glu Ala Asp Gly Pro Gly Glu Glu Asp
                325                 330                 335

Ile Ile Ala Lys Glu Lys Met Cys Pro Val Ile Ser Ala Tyr Lys Tyr
                340                 345                 350

Lys Ser Phe Glu Glu Gly Val Ala Ile Ala Lys Ala Asn Leu Asn Val
                355                 360                 365

Glu Gly Lys Gly His Ser Val Ser Ile His Ser Asn Thr Val Lys Asn
    370                 375                 380

Ile Glu Tyr Ala Gly Glu Asn Ile Glu Val Ser Arg Phe Val Ile Asn
385                 390                 395                 400

Gln Cys Cys Ala Thr Ser Ala Gly Gly Ser Phe Phe Asn Gly Leu Ala
                405                 410                 415

Pro Thr Asn Thr Leu Gly Cys Gly Ser Trp Gly Asn Asn Ser Ile Ser
                420                 425                 430

Glu Asn Leu Asp Tyr Lys His Leu Ile Asn Ile Ser Arg Ile Ala Tyr
                435                 440                 445

Tyr Met Pro Glu Asn Glu Val Pro Thr Asp Glu Glu Leu Trp Gly
    450                 455                 460

<210> SEQ ID NO 4
<211> LENGTH: 463
<212> TYPE: PRT
<213> ORGANISM: Kluyvera intestini

<400> SEQUENCE: 4

Met Asn Thr Thr Glu Leu Glu Thr Leu Ile Arg Thr Ile Leu Ser Glu
1               5                   10                  15

Gln Leu Thr Pro Thr Gln Glu Lys Lys Glu Ser Cys Thr Lys Gly Val
                20                  25                  30

Phe Ala Thr Pro Ala Glu Ala Ile Asp Ala Ala His Gln Ala Phe Leu
            35                  40                  45

Arg Tyr Gln Gln Cys Pro Leu Lys Thr Arg Gly Ala Ile Ile Gly Gly
    50                  55                  60

Ile Arg Asp Glu Leu Ala Pro Tyr Leu Ala Glu Leu Ala Asp Glu Ser
65                  70                  75                  80

Ala Thr Glu Thr Gly Met Gly Asn Lys Glu Asp Lys Phe Leu Lys Asn
                85                  90                  95

Lys Ala Ala Leu Glu Asn Thr Pro Gly Ile Glu Asp Leu Thr Thr Thr
                100                 105                 110
```

-continued

```
Ala Leu Thr Gly Asp Gly Gly Met Val Leu Phe Glu Tyr Ser Pro Phe
        115                 120                 125

Gly Val Ile Gly Ser Val Ala Pro Ser Thr Asn Pro Thr Glu Thr Ile
        130                 135                 140

Ile Asn Asn Ser Ile Ser Met Leu Ala Ala Gly Asn Thr Ile Tyr Phe
145                 150                 155                 160

Ser Pro His Pro Gly Ala Lys Lys Val Ser Leu Lys Leu Ile Arg Ile
                165                 170                 175

Ile Glu Asp Ile Ala Phe Arg His Thr Gly Ile Arg Asn Leu Val Val
                180                 185                 190

Thr Val Ala Glu Pro Thr Phe Glu Ala Thr Gln Gln Met Met Ala His
                195                 200                 205

Pro Lys Ile Ala Leu Leu Ala Ile Thr Gly Gly Pro Gly Ile Val Leu
        210                 215                 220

Met Gly Leu Lys Ser Gly Lys Lys Val Ile Gly Ala Gly Ala Gly Asn
225                 230                 235                 240

Pro Pro Cys Ile Val Asp Glu Thr Ala Asp Leu Val Lys Ala Ala Glu
                245                 250                 255

Asp Ile Ile Asn Gly Ala Ser Phe Asp Tyr Asn Leu Pro Cys Ile Ala
                260                 265                 270

Glu Lys Ser Leu Ile Val Val Asp Cys Val Ala Asp Arg Leu Met Gln
        275                 280                 285

Gln Met Gln Ala Phe Gly Ala Leu Arg Ile Thr Gly Ala Asp Ile Asp
        290                 295                 300

Lys Leu Arg Ala Val Cys Ile Gln Asp Gly Val Ala Asn Lys Lys Leu
305                 310                 315                 320

Val Gly Lys Ser Pro Ser His Ile Leu Gln Ala Ala Gly Leu Ser Val
                325                 330                 335

Pro Pro Lys Ala Pro Arg Leu Leu Ile Ala Glu Val Gln Gly Asn Asp
        340                 345                 350

Pro Leu Val Thr Ala Glu Gln Leu Met Pro Val Leu Pro Val Val Arg
        355                 360                 365

Val Asn Asp Phe Asp Ala Ala Leu Ala Leu Ala Leu Val Val Glu Glu
        370                 375                 380

Gly Leu His His Thr Ala Val Met His Ser Gln Asn Val Ser Arg Leu
385                 390                 395                 400

Asn Leu Ala Ala Arg Ser Leu Gln Thr Ser Ile Phe Val Lys Asn Gly
                405                 410                 415

Pro Ser Tyr Ala Gly Ile Gly Val Gly Gly Glu Gly Phe Thr Thr Phe
                420                 425                 430

Thr Ile Ala Thr Pro Thr Gly Glu Gly Thr Thr Ser Ala Lys Thr Phe
                435                 440                 445

Ala Arg Ser Arg Arg Cys Val Leu Thr Asn Gly Phe Ser Ile Arg
        450                 455                 460
```

<210> SEQ ID NO 5

<400> SEQUENCE: 5

000

<210> SEQ ID NO 6

<400> SEQUENCE: 6

000

-continued

<210> SEQ ID NO 7
<211> LENGTH: 455
<212> TYPE: PRT
<213> ORGANISM: Peptostreptococcaceae bacterium oral

<400> SEQUENCE: 7

Met Leu Asp Pro Asn Ser Met Val Asn Glu Leu Ile Arg Arg Ala Arg
1               5                   10                  15

Thr Ala Gln Thr Glu Phe Glu Thr Tyr Ser Gln Glu Arg Val Asp Lys
            20                  25                  30

Ala Val Arg Ala Ile Gly Lys Ser Ile Tyr Asp His Gly Asp Glu Leu
        35                  40                  45

Ala Lys Met Gly Ala Glu Glu Ser Gly Met Gly Arg Tyr Glu Asp Lys
    50                  55                  60

Ile Val Lys Asn Gln Gly Lys Ser Lys Met Thr Trp Trp Arg Leu Lys
65                  70                  75                  80

Gly Val Lys Ser Arg Gly Ile Ile Asn Ile Asp Arg Glu Lys Gln Ile
                85                  90                  95

Tyr Glu Ile Ala Lys Pro Ile Gly Val Leu Gly Val Val Thr Pro Ala
            100                 105                 110

Thr Asn Pro Thr Met Thr Pro Val His Asn Ala Met Ile Ala Leu Lys
            115                 120                 125

Gly Ala Asn Ala Val Ile Ile Cys Pro His Pro Lys Thr Arg Lys Thr
    130                 135                 140

Thr Ser Lys Thr Val Glu Tyr Met Arg Leu Ala Leu Lys Asp Ile Ser
145                 150                 155                 160

Val Pro Glu Asp Leu Ile Gln Ile Val Asp Asp Pro Ser Ile Glu Val
            165                 170                 175

Ser Gln Ala Leu Met Ala Phe Cys Asp Thr Thr Ile Ser Thr Gly Gly
            180                 185                 190

Pro Gly Met Val Lys Ser Ala Tyr Ser Ser Gly Lys Pro Ala Ile Gly
            195                 200                 205

Val Gly Pro Gly Asn Val Gln Cys Leu Val Gly Asp Asp Ala Asp Ile
    210                 215                 220

Asp Ala Ile Val Pro Lys Ile Met Lys Gly Arg Thr Tyr Asp Asn Gly
225                 230                 235                 240

Val Leu Cys Thr Cys Glu Gln Ser Ile Ile Cys Ala Glu Asn Leu Tyr
            245                 250                 255

Asp Arg Leu Val Lys Gly Leu Val Asp Asn Gly Ala Tyr Phe Val Lys
            260                 265                 270

Glu Asp Glu Val Glu Lys Leu Arg Asn Gly Phe Phe Pro Gly Gly Val
            275                 280                 285

Met Asn Lys Asn Leu Val Gly Ser Ser Pro Phe Glu Ile Ala Lys Ala
    290                 295                 300

Ser Gly Phe Glu Val Gln Glu Glu Ser Lys Ile Leu Leu Val Pro Val
305                 310                 315                 320

Ser Lys Thr Gly Lys Asp Glu Phe Leu Ala Lys Glu Lys Leu Ala Pro
            325                 330                 335

Ile Leu Ala Leu Tyr Lys Tyr Ser Glu Trp Lys Glu Ala Val Asp Ile
            340                 345                 350

Ala Leu Lys Asn Leu Leu Asn Glu Gly Arg Gly His Ser Val Val Ile
    355                 360                 365

His Ser Ala Asn Lys Thr Asn Ile Glu Tyr Ala Ala Asn Ile Leu Pro

-continued

```
          370              375              380
Val Ser Arg Val Gly Val Gly Met Val Gly Ser Ser Gly Leu Gly Gly
385              390              395              400

Gly Phe Asp Asn Gly Phe Met Pro Thr Ala Thr Leu Gly Cys Gly Ser
                 405              410              415

Trp Gly Asn Asn Ser Ile Ala Gly Asn Val Trp Trp Asn His Leu Val
                 420              425              430

Asn Ile Thr Lys Leu Ala Tyr Val Leu Asn Asp Val Ser Ile Pro Thr
                 435              440              445

Asp Glu Glu Ile Trp Ala Glu
    450              455
```

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 452
<212> TYPE: PRT
<213> ORGANISM: Anaerocolumna jejuensis

<400> SEQUENCE: 11

```
Met Asn Gln Ile Ile Gln Ser Leu Val Glu Arg Ser Arg Lys Ala Gln
1               5               10              15

Gln Ile Leu Tyr Thr Tyr Asn Gln Glu Lys Thr Asp Glu Ile Val Glu
                20              25              30

Met Phe Ala Ser Val Val Phe Asn His Ala Glu Pro Leu Ala Arg Met
        35              40              45

Ala Val Glu Glu Ser Arg Met Gly Val Tyr Glu Asp Lys Ile Thr Lys
    50              55              60

Asn Lys Glu Lys Ala Lys Thr Ile Trp Asn Ser Leu Lys Gly Lys Lys
65              70              75              80

Ser Ile Gly Ile Ile Gly Arg Glu Glu Glu Ala Gly Leu Ile Glu Ile
                85              90              95

Ala Lys Pro Met Gly Val Ile Ala Ala Ala Met Pro Cys Thr Asn Pro
            100             105             110

Ile Ile Thr Pro Met Cys Asn Ala Met Phe Ala Val Lys Cys Gln Asn
            115             120             125

Thr Ile Ile Val Ala Pro His Pro Arg Gly Lys Lys Cys Ala Met Ala
        130             135             140

Leu Ala Glu Leu Tyr Tyr Lys Glu Leu Asp Gly Met Gly Val Pro Arg
145             150             155             160

Asp Ile Phe Leu Val Val Glu Glu Pro Thr Ile Asp Leu Thr Thr Glu
                165             170             175
```

-continued

```
Leu Met Ser Ala Cys Asp Thr Val Ile Ala Thr Gly Gly Met Gly Val
            180                 185                 190

Val Lys Ser Ala Tyr Ser Ser Gly Lys Pro Ser Tyr Gly Val Gly Pro
        195                 200                 205

Gly Asn Val Gln Gly Leu Ile Asp Glu Gly Ile Asp Tyr Arg Ala Ala
    210                 215                 220

Ala Gly Arg Met Ile Ala Ser Arg Ile Phe Asp Asn Gly Ile Leu Cys
225                 230                 235                 240

Thr Ser Thr Gln Ser Ile Ile Ala Pro Glu Lys Asp Tyr Glu Ser Val
                245                 250                 255

Ile Lys Glu Phe Val Ala Gln Gly Ala Tyr Tyr Ile Asp Asp Pro Ala
            260                 265                 270

Val Ile Ala Ser Leu Ser Glu Val Val Phe Pro Gly Gly Val Ile Asn
        275                 280                 285

Lys Asn Val Val Gly Gln Ser Val Lys Thr Ile Ala Gly Leu Ala Gly
    290                 295                 300

Ile Ser Ile Pro Glu Gly Thr Lys Val Ile Ile Val Lys Pro Glu Arg
305                 310                 315                 320

His Gly Ala Gly Val Val Trp Ser Arg Glu Lys Met Cys Pro Met Met
                325                 330                 335

Thr Ala Tyr Ser Tyr Lys Thr Trp Glu Glu Ala Val Gln Ile Ala Tyr
                340                 345                 350

Asp Asn Leu Leu Val Glu Gly Glu Gly His Thr Ala Asp Ile Gln Ser
            355                 360                 365

Asp Asn Gln Ala His Ile Glu Tyr Ala Gly Val Lys Leu Pro Val Ser
    370                 375                 380

Arg Val Val Val Asn Gln Ser Cys Ser Val Met Ala Gly Gly Ala Phe
385                 390                 395                 400

Gly Asn Ala Leu Asn Pro Ser Ala Thr Leu Gly Cys Gly Ser Trp Gly
                405                 410                 415

Asn Asn Ala Ile Ser Glu Asn Leu Phe Tyr Thr His Leu Met Asn Lys
                420                 425                 430

Ser Arg Ile Ala Phe Val Arg Lys Asn Trp Lys Gln Pro Ser Asp Glu
            435                 440                 445

Glu Ile Phe Ala
    450
```

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15
<211> LENGTH: 475
<212> TYPE: PRT

-continued

```
<213> ORGANISM: Bacillus soli

<400> SEQUENCE: 15

Met Gln Ile Asn Glu Thr Asp Ile Lys Lys Met Val Glu Gln Val Leu
1               5                   10                  15

Lys Gln Leu Gly Glu Ser Gln Pro Ala Ser Ala Pro Ala Ala Ser Leu
            20                  25                  30

Lys Asp Val Ser Tyr Gly Asp Gly Val Phe Ala Thr Val Asp Glu Ala
        35                  40                  45

Ala Glu Ala Ala Arg Leu Ala Trp Glu Lys Leu Arg Lys Leu Pro Leu
    50                  55                  60

Ala Ala Arg Arg Gln Met Ile Glu Asn Met Arg Glu Val Ser Arg Gln
65                  70                  75                  80

His Val Asn Glu Leu Ala Thr Leu Ala Val Glu Glu Thr Lys Leu Gly
                85                  90                  95

Arg Val Glu Asp Lys Val Ala Lys Ile Leu Leu Ala Val Asn Lys Thr
            100                 105                 110

Pro Gly Val Glu Asp Leu Val Ser Thr Ala Phe Ser Gly Asp Asp Gly
            115                 120                 125

Leu Thr Leu Val Glu Tyr Ala Pro Ile Gly Val Phe Gly Ser Ile Thr
    130                 135                 140

Pro Ser Thr Asn Pro Ala Ala Thr Ile Ile Asn Asn Ser Ile Ser Leu
145                 150                 155                 160

Val Ala Ala Gly Asn Thr Val Val Tyr Asn Pro His Pro Ser Ala Lys
                165                 170                 175

Arg Val Ser Ile Lys Thr Leu Gln Leu Leu Asn Gln Ala Ile Val Ala
            180                 185                 190

Ala Gly Gly Pro Glu Asn Thr Leu Thr Ser Val Ala Ala Pro Asn Leu
            195                 200                 205

Glu Thr Ser Ala Gln Val Met Asn His Pro Lys Val His Ala Leu Val
    210                 215                 220

Val Thr Gly Gly Gly Pro Val Val Lys Ala Ala Met Ala Val Gly Lys
225                 230                 235                 240

Lys Val Ile Ala Ala Gly Pro Gly Asn Pro Pro Val Val Val Asp Glu
                245                 250                 255

Thr Ala Ile Ile Ser Lys Ala Ala Ala Asp Ile Val Gln Gly Ala Ser
            260                 265                 270

Phe Asp Asn Asn Val Leu Cys Thr Ala Glu Lys Glu Val Phe Val Val
            275                 280                 285

Asp Lys Val Ala Asn Ala Leu Lys Ala Glu Met Val Lys Ser Gly Ala
    290                 295                 300

Met Glu Leu Lys Gly Phe Gln Leu Glu Lys Leu Leu Glu Lys Val Leu
305                 310                 315                 320

Val Lys Lys Asn Asp Lys Phe Tyr Pro Asn Arg Asp Leu Ile Gly Lys
                325                 330                 335

Asp Ala Ala Val Ile Leu Gln Ala Ala Gly Ile Gln Ala Ser Pro Ser
            340                 345                 350

Val Lys Leu Ile Ile Ala Glu Thr Thr Lys Asp His Pro Leu Val Met
            355                 360                 365

Thr Glu Met Leu Met Pro Ile Leu Pro Ile Val Arg Val Ser Asn Val
    370                 375                 380

Asp Gln Ala Ile Glu Leu Ala Val Ile Ala Glu Lys Gly Asn Arg His
385                 390                 395                 400
```

-continued

```
Thr Ala Val Met His Ser Gln Asn Ile Thr Asn Leu Thr Lys Met Ala
            405                 410                 415

Gln Glu Ile Gln Ala Thr Ile Phe Val Lys Asn Gly Pro Ser Val Ala
            420                 425                 430

Gly Leu Gly Phe Glu Ser Glu Gly Phe Thr Thr Leu Thr Ile Ala Gly
            435                 440                 445

Pro Thr Gly Glu Gly Leu Thr Ser Ala Lys Thr Phe Thr Arg Gln Arg
    450                 455                 460

Arg Cys Val Leu Val Asp Gly Leu Arg Ile Ile
465                 470                 475

<210> SEQ ID NO 16

<400> SEQUENCE: 16

000

<210> SEQ ID NO 17
<211> LENGTH: 496
<212> TYPE: PRT
<213> ORGANISM: Desnuesiella massiliensis

<400> SEQUENCE: 17

Met Asn Ile Thr Glu Asn Asp Ile Glu Lys Ile Ile Gln Gln Val Leu
1               5                   10                  15

Val Asn Ile Thr Ser Lys Pro Ser Glu Asp Val Lys Lys Asp Ala Thr
            20                  25                  30

Pro Glu Val Lys Ala Glu Ala Thr Pro Leu Arg Lys Lys Tyr Leu Gly
            35                  40                  45

Val Phe Glu Lys Ala Glu Asp Ala Ile Glu Ala Ala Ser Lys Ala Gln
    50                  55                  60

Lys Lys Leu Leu Lys Glu Phe Lys Ile Glu Asp Arg Glu Arg Phe Ile
65                  70                  75                  80

Ile Ser Ile Lys Lys Ala Thr Val Ala Asn Ala Glu Ile Leu Ala Arg
                85                  90                  95

Met Ile Ile Asp Glu Thr Gly Met Gly Lys Tyr Glu Asp Lys Val Leu
            100                 105                 110

Lys His Lys Leu Val Ser Glu Lys Thr Pro Gly Thr Asp Ile Leu Thr
            115                 120                 125

Thr Glu Ala Trp Ser Gly Asp Asn Gly Leu Thr Ile Val Glu Met Ala
            130                 135                 140

Pro Tyr Gly Val Ile Gly Ala Val Thr Pro Ser Thr Asn Pro Ser Glu
145                 150                 155                 160

Thr Ala Ile Cys Asn Ser Ile Gly Met Ile Gly Ala Gly Asn Ser Val
                165                 170                 175

Val Phe Asn Ala His Pro Gly Ala Lys Glu Cys Val Ala Tyr Ala Val
            180                 185                 190

Asp Met Met Asn Lys Ala Ile Val Glu Ala Gly Gly Pro Glu Asn Leu
            195                 200                 205

Ile Thr Met Val Ala Glu Pro Thr Met Glu Ser Leu Glu Ala Ile Met
            210                 215                 220

Lys His Pro Glu Ile Arg Leu Leu Cys Gly Thr Gly Gly Pro Gly Leu
225                 230                 235                 240

Val Lys Thr Leu Leu Ser Ser Gly Lys Lys Ala Ile Gly Ala Gly Ala
            245                 250                 255

Gly Asn Pro Pro Val Ile Val Asp Asp Thr Ala Asn Val Lys Lys Ala
```

-continued

```
                 260                 265                 270

Gly Lys Asp Ile Ile Glu Gly Cys Ser Phe Asp Asn Asn Leu Pro Cys
        275                 280                 285

Ile Ala Glu Lys Glu Val Phe Val Phe Glu Asn Val Ala Asp Asp Leu
        290                 295                 300

Ile Tyr His Met Leu Gln Asn Lys Ala Tyr Met Leu Thr Lys Asn Gln
305                 310                 315                 320

Val Glu Glu Leu Val Lys Ile Val Leu His Glu Asn Ile Glu Glu Lys
                325                 330                 335

Ala Val Gly Cys Ser Leu Asp Arg Lys Arg His Tyr Val Ile Asn Lys
                340                 345                 350

Lys Trp Val Gly Lys Asp Ala Ala Leu Tyr Leu Lys Ala Leu Gly Ile
        355                 360                 365

Glu Gly Lys Asp Asp Ile Gln Cys Leu Ile Cys Glu Val Asp Leu Asp
        370                 375                 380

His Pro Phe Val Met Thr Glu Leu Met Met Pro Ile Leu Pro Ile Val
385                 390                 395                 400

Arg Val Lys Gly Ile Asp Gln Ala Ile Ala Tyr Ala Lys Lys Ala Glu
                405                 410                 415

His Gly Asn Arg His Ser Ala His Met His Ser Lys Asn Val Asp Asn
                420                 425                 430

Leu Thr Arg Phe Ala Arg Glu Ile Glu Thr Thr Ile Phe Val Lys Asn
                435                 440                 445

Ala Lys Ser Phe Ala Gly Val Gly Phe Gly Gly Glu Gly Phe Thr Thr
        450                 455                 460

Phe Thr Ile Ala Gly Pro Thr Gly Glu Gly Ile Thr Ser Ala Arg Thr
465                 470                 475                 480

Phe Thr Arg Gln Arg Arg Cys Val Leu Ala Glu Gly Phe Ser Ile Ile
                485                 490                 495
```

<210> SEQ ID NO 18

<400> SEQUENCE: 18

000

<210> SEQ ID NO 19
<211> LENGTH: 469
<212> TYPE: PRT
<213> ORGANISM: Caldanaerobius polysaccharolyticus

<400> SEQUENCE: 19

```
Met Ala Gly Ile Arg Glu Glu Asp Ile Glu Leu Ile Val Arg Arg Val
1                   5                   10                  15

Leu Ser Asn Leu Asp Leu Lys Asn Leu Lys Ala Ala Val Lys Lys Asp
                20                  25                  30

Ile Gly Val Phe Glu Asp Met Lys Gln Ala Ile Ser Ala Ala Lys Lys
        35                  40                  45

Ala Gln Lys Glu Leu Lys Ser Met Ser Ile Glu Phe Arg Glu Lys Ile
        50                  55                  60

Ile Gln Asn Ile Arg Lys Lys Thr Leu Glu Asn Ala Arg Ile Met Ala
65                  70                  75                  80

Glu Met Gly Val Gln Glu Thr Gly Met Gly Lys Val Glu His Lys Val
                85                  90                  95

Leu Lys His Glu Leu Val Ala Arg Lys Thr Pro Gly Thr Glu Asp Ile
                100                 105                 110
```

-continued

```
Ile Thr Thr Ala Trp Ser Gly Asp Lys Gly Leu Thr Leu Val Glu Met
        115                 120                 125

Gly Pro Trp Gly Val Ile Gly Ala Ile Thr Pro Ser Thr Asn Pro Ser
        130                 135                 140

Glu Thr Val Ile Cys Asn Ser Ile Gly Met Ile Ala Ala Gly Asn Ser
145                 150                 155                 160

Val Val Phe Asn Pro His Pro Gly Ala Val Gly Val Ser Asn Tyr Ala
                165                 170                 175

Val Arg Leu Ile Asn Glu Ala Val Val Glu Ala Gly Gly Pro Pro Asn
                180                 185                 190

Leu Ala Val Ser Val Ala Lys Pro Thr Leu Glu Thr Ala Glu Ile Met
                195                 200                 205

Phe Lys His Pro Asp Ile Asn Leu Leu Val Ala Thr Gly Gly Pro Gly
        210                 215                 220

Val Val Thr Ala Val Leu Ser Thr Gly Lys Arg Ala Ile Gly Ala Gly
225                 230                 235                 240

Ala Gly Asn Pro Pro Val Val Asp Glu Thr Ala Asp Ile Arg Lys
                245                 250                 255

Ala Ala Lys Asp Ile Val Asp Gly Ala Thr Phe Asp Asn Asn Leu Pro
                260                 265                 270

Cys Ile Ala Glu Lys Glu Val Ile Ala Val Asn Lys Val Ala Asp Glu
        275                 280                 285

Leu Ile Tyr Tyr Met Lys Gln Asn Gly Cys Tyr Met Ala Ser Lys Glu
        290                 295                 300

Glu Ile Glu Glu Leu Lys Ala Met Val Leu Gln Thr Arg Asp Gly Lys
305                 310                 315                 320

Tyr Tyr Leu Asn Arg Lys Trp Val Gly Lys Asp Ala Ser Thr Leu Leu
                325                 330                 335

Lys Gly Ile Gly Val Asp Val Asp Asp Lys Val Arg Cys Ile Ile Phe
                340                 345                 350

Glu Ala Thr Lys Asp His Pro Phe Val Val Glu Glu Leu Met Met Pro
        355                 360                 365

Ile Leu Gly Ile Ile Arg Ala Glu Asn Val Asp Glu Ala Ile Ala Ile
        370                 375                 380

Ala Val Glu Leu Glu His Gly Phe Arg His Ser Ala His Met His Ser
385                 390                 395                 400

Lys Asn Val Asp Asn Leu Thr Lys Phe Ala Arg Ala Ile Asp Thr Ala
                405                 410                 415

Ile Phe Val Lys Asn Ala Pro Ser Tyr Ala Ala Ile Gly Phe Gly Gly
                420                 425                 430

Glu Gly Tyr Cys Thr Phe Thr Ile Ala Ser Arg Thr Gly Glu Gly Leu
                435                 440                 445

Thr Ser Ala Arg Thr Phe Thr Lys Ser Arg Arg Cys Val Leu Ala Asp
        450                 455                 460

Gly Leu Ser Ile Arg
465
```

<210> SEQ ID NO 20

<400> SEQUENCE: 20

000

<210> SEQ ID NO 21

-continued

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24
<211> LENGTH: 472
<212> TYPE: PRT
<213> ORGANISM: Cellulosilyticum sp. I15G10I2

<400> SEQUENCE: 24

```
Met Asn Glu Ile Glu Leu Lys Gln Val Val Glu Glu Val Val Arg Lys
1               5                   10                  15

Leu Gly Val Pro Ser Ala Thr Ala Pro Lys Thr Ala Pro Thr Ile Gly
            20                  25                  30

Leu Gly Gln Gly Val Phe Glu Ser Met Asp Glu Ala Ile Thr Ala Ala
            35                  40                  45

Lys Ala Ala Gln Glu Asp Leu His Met Met Pro Leu Glu Phe Arg Glu
        50                  55                  60

Lys Ile Ile Ala Arg Ile Arg Glu Lys Ile Met Ala Asn Lys Glu Thr
65                  70                  75                  80

Leu Ala Lys Met Ala Val His Glu Thr Gly Met Gly Lys Ile Gly His
                85                  90                  95

Lys Ile Leu Lys His Glu Leu Thr Ala Lys Lys Thr Pro Gly Thr Glu
            100                 105                 110

Cys Ile Lys Thr Arg Ala Trp Ser Gly Asp Gln Gly Leu Thr Val Ile
            115                 120                 125

Glu Ser Gly Pro Phe Gly Val Val Gly Ala Ile Thr Pro Ser Thr Asn
        130                 135                 140

Pro Ser Glu Thr Val Phe Cys Asn Ala Ile Gly Met Ile Ala Ala Gly
145                 150                 155                 160

Asn Thr Val Val Phe Asn Ser His Pro Asn Ala Ala Arg Thr Ser Asn
                165                 170                 175

Phe Ala Val Gln Leu Val Asn Glu Ala Ala Val Glu Val Gly Gly Phe
            180                 185                 190

Glu Asn Leu Ala Thr Ser Val Leu Lys Pro Thr Val Glu Ser Gly Asn
            195                 200                 205

Thr Leu Phe Lys His Pro Asp Ile Gln Leu Leu Val Ala Thr Gly Gly
        210                 215                 220

Pro Gly Val Val Lys Ala Ile Leu Gln Ser Gly Lys Arg Gly Ile Ala
225                 230                 235                 240

Ala Gly Ala Gly Asn Pro Pro Val Leu Val Asp Glu Thr Ala Asn Ile
                245                 250                 255

Lys Lys Ala Ala Ala Asp Ile Ile Asn Gly Ala Thr Phe Asp Asn Asn
            260                 265                 270

Leu Pro Cys Ile Ala Glu Lys Glu Val Ile Val Val Asn Glu Val Ala
```

-continued

```
              275                280                285

Asp Glu Leu Ile His Tyr Met Thr Ser Glu Asn Asp Cys Tyr Met Leu
    290                295                300

Lys Gly Glu Gln Ile Glu Lys Leu Ala Gln Thr Ile Leu Val Glu Lys
305                310                315                320

Asn Gly His Tyr Ile Val Asn Arg Asp Tyr Val Gly Arg Asp Ala His
                325                330                335

Val Ile Leu Lys Gly Ile Gly Ile Glu Ala Pro Glu Ser Ile Arg Cys
        340                345                350

Ile Ile Phe Glu Ala Ser Lys Glu His Ile Leu Val Val Glu Glu Leu
        355                360                365

Met Met Pro Val Leu Gly Ile Val Arg Val Ala Asn Val Asp Glu Gly
    370                375                380

Ile Ala Val Ala Lys Val Leu Glu Gly Gly Asn Arg His Ser Ala His
385                390                395                400

Met His Ser Ser Asn Val Tyr Asn Leu Thr Lys Tyr Gly Arg Ala Leu
                405                410                415

Asp Thr Ala Ile Phe Val Lys Asn Ala Pro Ser Tyr Ala Gly Ile Gly
        420                425                430

Phe Gly Gly Glu Gly Phe Ala Thr Phe Thr Ile Ala Ser Lys Thr Gly
        435                440                445

Glu Gly Leu Thr Asn Ala Ala Ser Phe Thr Lys Ser Arg Arg Cys Val
    450                455                460

Met Ala Asp Ala Leu Tyr Ile Arg
465                470

<210> SEQ ID NO 25
<211> LENGTH: 455
<212> TYPE: PRT
<213> ORGANISM: Geosporobacter ferrireducens

<400> SEQUENCE: 25

Met Ile Val Lys Lys Ile Leu Thr Glu Ile Thr Leu Lys Asn Glu Ala
1                5                10                15

Thr Asp Ser Ala Tyr Gly Ile Phe Asp His Met Glu Glu Ala Ile Glu
                20                25                30

Ala Ala Trp Ile Ala Gln Lys Glu Leu Val Lys Tyr Ser Leu Glu Cys
        35                40                45

Arg Gly Lys Phe Ile Ala Ala Met Arg Ala Ala Arg Lys Asn Ile
    50                55                60

Glu Leu Phe Ser Lys Met Ala Val Glu Glu Thr Gly Met Gly Arg Tyr
65                70                75                80

Glu His Lys Val Met Lys Asn Thr Val Ala Ile Glu Lys Thr Pro Gly
                85                90                95

Ile Glu Asp Leu Lys Pro Asp Ala Val Ser Gly Asp His Gly Leu Thr
                100                105                110

Val Phe Glu Leu Ser Pro Tyr Gly Val Ile Gly Ala Ile Thr Pro Thr
                115                120                125

Thr Asn Pro Thr Glu Thr Val Ile Cys Asn Ala Ile Gly Met Ile Ala
        130                135                140

Ala Gly Asn Ala Val Val Phe Ala Pro His Pro Arg Ala Lys Asn Thr
145                150                155                160

Ser Arg Lys Ala Ile Glu Ile Leu Asn Gln Ala Ile Ile Glu Ala Gly
                165                170                175
```

-continued

```
Gly Pro Ala Asn Leu Ile Thr Ala Ile Lys Glu Pro Thr Ile Glu Ser
            180                 185                 190

Ala Asn Ile Met Met Gln His Lys Lys Ile Lys Met Leu Val Ala Thr
            195                 200                 205

Gly Gly Pro Asp Val Val Arg Thr Val Leu Ser Ser Gly Lys Lys Ala
        210                 215                 220

Ile Gly Ala Gly Ala Gly Asn Pro Pro Ala Val Val Asp Glu Thr Ala
225                 230                 235                 240

Asp Ile Glu Lys Ala Ala Lys Asp Ile Ile Asp Gly Cys Ser Phe Asp
                245                 250                 255

Asn Asn Leu Pro Cys Val Ala Glu Lys Glu Val Ile Val Val Asp Ser
            260                 265                 270

Val Ala Asp Tyr Leu Ile Phe Asn Met Gln Lys His Asn Ala Tyr Leu
            275                 280                 285

Leu Ser Asp Glu Asn Leu Ile Lys Lys Leu Glu Lys Leu Val Phe Asn
        290                 295                 300

Asp Lys Gly His Leu Asn Arg Asp Leu Val Gly Lys Asp Ala Asp Tyr
305                 310                 315                 320

Ile Leu Arg Lys Ile Gly Val Asp Cys Asp Pro Ser Ile Arg Ala Ile
                325                 330                 335

Ile Val Glu Thr Asp Lys Asn His Asp Phe Val Gln Glu Glu Leu Met
            340                 345                 350

Met Pro Ile Leu Pro Ile Val Arg Val Lys Asp Val Asn Glu Ala Ile
            355                 360                 365

Glu Leu Ala Val Glu Val Glu His Gly Tyr Arg His Thr Ala Ile Ile
        370                 375                 380

His Ser Lys Asn Ile Asp Asn Leu Ser Lys Met Ala Lys Glu Ile Gln
385                 390                 395                 400

Thr Thr Ile Phe Val Lys Asn Gly Pro Ser Tyr Ala Gly Ile Gly Val
                405                 410                 415

Gly Gly Glu Gly Tyr Ser Thr Phe Thr Ile Ala Gly Pro Thr Gly Glu
            420                 425                 430

Gly Leu Thr Thr Ala Lys Ser Phe Thr Arg Ser Arg Arg Cys Val Leu
            435                 440                 445

Val Asp Gly Phe Ser Ile Arg
        450                 455
```

<210> SEQ ID NO 26

<400> SEQUENCE: 26

000

<210> SEQ ID NO 27
<211> LENGTH: 465
<212> TYPE: PRT
<213> ORGANISM: Bacillus korlensis

<400> SEQUENCE: 27

```
Met Ile Glu Val Lys Gln Ile Glu Asp Ile Val Met Gln Val Leu Ala
1               5                   10                  15

Gly Leu Asn Asn His Glu Asp Pro Pro Leu Asp Gly Glu Asn Gly Leu
            20                  25                  30

Tyr Ser Glu Met Asn Asp Ala Ile Asp Ala Ala Phe Val Ala Gln Lys
        35                  40                  45

Glu Leu Val Lys Leu Ser Leu Ala Glu Arg Gly Arg Ile Ile Glu Ser
```

-continued

```
        50              55              60

Ile Arg Thr Glu Phe Arg Lys His Ile Glu Leu Leu Ser Glu Met Ala
65              70              75              80

Val Glu Glu Thr Gly Met Gly Arg Val Lys Asp Lys Ile Asn Lys Asn
            85              90              95

Leu Val Ala Val Asn Asn Thr Pro Gly Ile Glu Asp Leu Thr Thr Ala
            100             105             110

Ala Cys Ser Gly Asp Asn Gly Leu Thr Val Glu Glu Leu Ser Pro Tyr
            115             120             125

Gly Val Ile Gly Ser Ile Thr Pro Thr Thr Asn Pro Ser Glu Thr Ile
        130             135             140

Ile Cys Asn Thr Ile Gly Met Leu Ala Ala Gly Asn Ala Ile Val Phe
145             150             155             160

Ser Pro His Pro Thr Ala Lys Arg Thr Ser Ile Glu Thr Ile Lys Ile
            165             170             175

Ile Ser Lys Ala Ile Ser Lys Ala Gly Gly Pro Lys Asn Leu Val Val
            180             185             190

Ser Thr Leu Gln Pro Ser Ile Glu Gln Ala Asn Ile Met Met Asn His
            195             200             205

Lys Lys Val Arg Met Leu Val Ala Thr Gly Gly Pro Ala Val Val Lys
        210             215             220

Ala Val Leu Ser Thr Gly Lys Lys Ala Ile Gly Ala Gly Ala Gly Asn
225             230             235             240

Pro Pro Ala Leu Val Asp Glu Thr Ala Asp Ile Glu Lys Ala Ala Lys
            245             250             255

Asp Ile Ile Asp Gly Cys Ser Phe Asp Asn Asn Leu Pro Cys Val Ala
            260             265             270

Glu Lys Glu Val Ile Ala Val Asp Cys Ile Ala Asp Cys Leu Ile Glu
            275             280             285

Asn Met Lys Asn Asn Gly Ala Tyr Gln Leu Thr Asp Pro Val Gln Ile
        290             295             300

Gln Arg Leu Val Asp Leu Val Val Arg Asn Gly His Ala Asn Lys Asp
305             310             315             320

Phe Val Gly Lys Asn Ala Asp Phe Ile Leu Arg Gln Leu Gly Ile Glu
            325             330             335

Val Gly Pro Glu Val Arg Val Val Ile Val Asp Val Lys Tyr Glu Gly
            340             345             350

Arg His Pro Leu Val Leu Ala Glu Leu Met Met Pro Val Leu Pro Ile
            355             360             365

Val Arg Val Asn Asn Val Asp Glu Gly Ile Asp Leu Ala Val Glu Val
        370             375             380

Glu His Gly Phe Arg His Thr Ala Ile Met His Ser Lys Asn Ile Asp
385             390             395             400

Asn Leu Thr Lys Phe Ala Lys Glu Ile Gln Thr Thr Ile Phe Val Lys
            405             410             415

Asn Gly Pro Ser Tyr Ala Gly Ile Gly Val Gly Gly Val Gly Tyr Thr
            420             425             430

Thr Phe Thr Ile Ala Gly Pro Thr Gly Glu Gly Leu Thr Ser Ala Lys
            435             440             445

His Phe Ala Arg Lys Arg Arg Cys Val Leu Val Asp Gly Leu Ser Ile
    450             455             460

Arg
465
```

-continued

<210> SEQ ID NO 28
<211> LENGTH: 459
<212> TYPE: PRT
<213> ORGANISM: Acidaminococcus massiliensis

<400> SEQUENCE: 28

Met Glu Gln Ala Val Lys Asp Tyr Leu Asp Lys Met Val Ala Ala Ser
1               5                   10                  15

Arg Ile Ala Gln Gln Glu Phe Ala Thr Tyr Pro Gln Glu Thr Val Asp
            20                  25                  30

Lys Ala Val Arg Thr Val Gly Lys Ala Ile Tyr Asp Asn Ala Glu Leu
        35                  40                  45

Leu Ala His Met Ala Val Asp Glu Thr Lys Met Gly Asn Tyr Ala Asp
    50                  55                  60

Lys Ile Ala Lys Cys Val Asn Lys Ser Lys Ser Val Trp Trp Arg Met
65                  70                  75                  80

Lys Asp Lys Lys Ser Arg Gly Ile Ile Lys Arg Ile Pro Glu Leu Gly
                85                  90                  95

Leu Val Glu Val Ala Lys Pro Ile Gly Val Ile Gly Cys Val Ala Pro
            100                 105                 110

Thr Thr Asn Pro Val Ile Asn Val Met Gln Asn Ala Met Cys Ala Leu
        115                 120                 125

Lys Cys Gly Asn Ser Met Ile Val Ser Pro His Pro Arg Ala Lys His
    130                 135                 140

Ser Ser Val Lys Thr Val Glu Val Ile Asn Glu Ala Leu Ala Ala Leu
145                 150                 155                 160

Gly Met Pro Lys Asn Leu Ile Gln Val Ile Thr Glu Pro Ser Met Glu
                165                 170                 175

Leu Ser Ala Gly Leu Met Ser Ala Val Asp Leu Cys Ile Cys Thr Gly
            180                 185                 190

Gly Pro Gly Leu Val Lys Ala Ala Tyr Ser Ser Gly Lys Pro Ala Ile
            195                 200                 205

Gly Val Gly Gln Gly Asn Val Gln Val Leu Val Asp Arg Asp Ala Asp
    210                 215                 220

Leu Asp Gln Val Ala Ala Met Val Ile Lys Gly Arg Thr Phe Asp Asn
225                 230                 235                 240

Gly Val Leu Cys Thr Cys Glu Gln Asn Val Ile Cys Pro Glu Asp Lys
                245                 250                 255

Lys Glu Glu Met Ile Ala Ala Leu Lys Lys His Gly Ala Tyr Tyr Ile
            260                 265                 270

Gly Asn Ser Glu Asp Ala Ala Lys Leu Arg Asp Thr Ala Phe Pro Asn
        275                 280                 285

Gly Gly Pro Val Ser Lys Glu Tyr Pro Gly Ala Ser Val Lys Lys Ile
    290                 295                 300

Ala Gln Leu Ser Gly Ile Gln Gly Ile Pro Glu Asp Ala Lys Val Ile
305                 310                 315                 320

Val Ser Cys Thr Arg Gly Tyr Gly Lys Asp Glu Pro Leu Ala Lys Glu
                325                 330                 335

Lys Leu Phe Pro Val Leu Ala Phe Phe Thr Tyr Asp Lys Trp Glu Asp
            340                 345                 350

Ala Ile His Ile Ala Lys Thr Asn Leu Glu Met Glu Gly Ile Gly His
        355                 360                 365

Ser Val Val Ile His Ser Asn Thr Pro Glu His Ile Glu Ala Val Ala

```
        370                 375                 380
Glu Ala Ile Pro Val Ser Arg Phe Ala Val Asn Gln Val Gly Gly Thr
385                 390                 395                 400

Asn Leu Gly Gly Ala Met Asp Asn Gly Leu Asn Pro Thr Thr Thr Leu
                405                 410                 415

Gly Cys Gly Thr Trp Gly Asn Asn Ser Ile Ser Glu Asn Phe Thr Tyr
                420                 425                 430

Tyr His Leu Met Asn Leu Thr Arg Val Ser Tyr Arg Val Pro Asp Met
                435                 440                 445

Tyr Ile Pro Thr Asp Glu Glu Ile Trp Ala Glu
        450                 455
```

<210> SEQ ID NO 29

<400> SEQUENCE: 29

000

<210> SEQ ID NO 30

<400> SEQUENCE: 30

000

<210> SEQ ID NO 31
<211> LENGTH: 462
<212> TYPE: PRT
<213> ORGANISM: Lachnospiraceae bacterium 32

<400> SEQUENCE: 31

```
Val Ser Val Asn Glu Lys Met Val Gln Asp Val Val Lys Glu Val Met
1               5                   10                  15

Ala Lys Leu Gln Leu Ala Ala Gly Ala Ser Glu Gly Lys Gly Ile Phe
                20                  25                  30

Ala Asp Met Asn Asp Ala Ile Ala Ala Ala Lys Lys Ala Gln Arg Tyr
            35                  40                  45

Ile His Arg Met Ser Met Asp Gln Arg Glu Gln Ile Ile Ser Asn Ile
        50                  55                  60

Arg Arg Lys Thr Lys Glu Asn Ala Glu Ile Leu Ala Arg Met Gly Val
65                  70                  75                  80

Glu Glu Thr Gly Met Gly Asn Val Pro His Lys Ile Leu Lys His Gln
                85                  90                  95

Leu Val Ala Glu Lys Thr Pro Gly Thr Glu Asp Ile Thr Thr Thr Ala
            100                 105                 110

Trp Ser Gly Asp Lys Gly Leu Thr Leu Ile Glu Met Gly Pro Phe Gly
        115                 120                 125

Val Ile Gly Ala Ile Thr Pro Cys Thr Asn Pro Ser Glu Thr Ile Ile
    130                 135                 140

Cys Asn Thr Ile Gly Met Leu Ala Gly Gly Asn Thr Val Val Phe Asn
145                 150                 155                 160

Pro His Pro Ala Ala Val Lys Thr Ser Gln Phe Ala Val Asn Met Leu
                165                 170                 175

Asn Glu Ala Ser Ile Glu Ala Gly Gly Pro Glu Asn Ile Ala Cys Thr
            180                 185                 190

Val Gly Lys Pro Thr Met Glu Ser Ser Asn Ile Met Met Lys His Lys
        195                 200                 205

Asp Ile Gln Leu Ile Ala Ala Thr Gly Gly Pro Gly Val Val Thr Ala
```

-continued

```
                  210                 215                 220

Val Leu Ser Ser Gly Arg Arg Gly Ile Gly Ala Gly Ala Gly Asn Pro
225                 230                 235                 240

Pro Ala Leu Val Asp Glu Thr Ala Asp Ile Arg Lys Ala Ala Gly Asp
                245                 250                 255

Ile Val Asn Gly Cys Thr Phe Asp Asn Asn Leu Pro Cys Ile Ala Glu
                260                 265                 270

Lys Glu Ile Val Ala Val Asp Ser Val Val Ser Glu Leu Met His Tyr
            275                 280                 285

Met Val Asn Glu Gln Asp Cys Tyr Leu Ala Ser Lys Glu Glu Gln Asp
        290                 295                 300

Lys Leu Thr Ala Thr Val Leu Thr Pro Lys Gly Leu Asn Arg Lys Cys
305                 310                 315                 320

Val Gly Arg Asp Ala Lys Thr Leu Leu Gly Met Ile Gly Val Thr Val
                325                 330                 335

Pro Asp Asn Ile Arg Cys Ile Val Phe Glu Gly Glu Lys Glu His Pro
                340                 345                 350

Leu Ile Ala Thr Glu Leu Met Met Pro Ile Leu Gly Val Val Arg Ala
            355                 360                 365

Lys Asp Phe Glu Asp Ala Val Glu Lys Ala Val Trp Leu Glu His Gly
        370                 375                 380

Asn Arg His Ser Ala His Ile His Ser Lys Asn Ile Asp Asn Ile Thr
385                 390                 395                 400

Arg Tyr Ala Lys Ala Ile Asp Thr Ala Ile Leu Val Lys Asn Ala Pro
                405                 410                 415

Ser Tyr Ala Ala Leu Gly Phe Gly Gly Glu Gly Phe Cys Thr Phe Thr
                420                 425                 430

Ile Ala Ser Arg Thr Gly Glu Gly Leu Thr Ser Ala Ser Thr Phe Thr
            435                 440                 445

Lys Arg Arg Arg Cys Val Met Ser Glu Ser Leu Cys Ile Arg
    450                 455                 460

<210> SEQ ID NO 32
<211> LENGTH: 462
<212> TYPE: PRT
<213> ORGANISM: Eubacterium plexicaudatum

<400> SEQUENCE: 32

Val Ser Val Asn Asp Gln Met Val Gln Asp Ile Val Arg Gln Val Leu
1                   5                   10                  15

Ala Asn Met Arg Ile Ser Ser Asp Ala Ser Gly Ser Arg Gly Val Phe
            20                  25                  30

Ser Asp Met Asn Glu Ala Val Glu Ala Ala Lys Lys Ala Gln Ala Val
            35                  40                  45

Ile Gly Lys Met Pro Met Asp His Arg Glu Lys Ile Ile Ser Ser Ile
        50                  55                  60

Arg Ala Lys Ile Met Glu Asn Ala Glu Ile Leu Ala Arg Met Gly Val
65                  70                  75                  80

Lys Glu Thr Gly Met Gly Asn Val Gly His Lys Ile Leu Lys His Gln
                85                  90                  95

Leu Val Ala Glu Lys Thr Pro Gly Thr Glu Asp Ile Thr Thr Lys Ala
            100                 105                 110

Trp Ser Gly Asp Arg Gly Leu Thr Leu Ile Glu Met Gly Pro Phe Gly
            115                 120                 125
```

-continued

```
Val Ile Gly Ala Ile Thr Pro Cys Thr Asn Pro Ser Glu Thr Ile Leu
    130                 135                 140

Cys Asn Thr Ile Gly Met Val Ala Gly Gly Asn Thr Val Val Phe Asn
145                 150                 155                 160

Pro His Pro Ala Ala Ile Lys Thr Ser Ile Phe Ala Val Asn Leu Val
                165                 170                 175

Asn Glu Ala Ser Val Glu Ala Gly Gly Pro Asp Asn Ile Ala Cys Thr
                180                 185                 190

Val Glu His Pro Thr Leu Asp Thr Ser Ala Ile Met Met Lys His Lys
            195                 200                 205

Asp Ile His Leu Ile Ala Ala Thr Gly Gly Pro Gly Val Val Thr Ala
    210                 215                 220

Val Leu Ser Ser Gly Lys Arg Gly Ile Gly Ala Gly Ala Gly Asn Pro
225                 230                 235                 240

Pro Ala Leu Val Asp Glu Thr Ala Asp Ile Arg Lys Ala Ala Glu Asp
                245                 250                 255

Ile Val Asn Gly Cys Thr Phe Asp Asn Asn Leu Pro Cys Ile Ala Glu
                260                 265                 270

Lys Glu Ile Val Ala Val Asp Ser Ile Ala Asp Glu Leu Met His Tyr
            275                 280                 285

Met Ile Ser Glu Gln Gly Cys Tyr Leu Ala Ser Ala Lys Glu Gln Glu
    290                 295                 300

Ala Leu Ile Ser Val Val Leu Lys Gly Gly Gln Leu Asn Arg Asp Cys
305                 310                 315                 320

Val Gly Arg Asp Ala Lys Thr Leu Leu Gly Met Ile Gly Val Gln Ala
                325                 330                 335

Pro Asp Asn Ile Arg Cys Ile Thr Phe Glu Gly Pro Lys Glu His Pro
                340                 345                 350

Leu Ile Thr Glu Glu Leu Met Met Pro Ile Leu Gly Val Val Arg Ala
            355                 360                 365

Asp Ser Phe Glu Asp Ala Val Glu Lys Ala Val Trp Leu Glu His Gly
    370                 375                 380

Asn Arg His Ser Ala His Ile His Ser Lys Asn Val Asp His Ile Thr
385                 390                 395                 400

Thr Tyr Ala Lys Ala Ile Asp Thr Ala Ile Leu Val Lys Asn Gly Pro
                405                 410                 415

Ser Tyr Ala Ala Ile Gly Phe Gly Gly Glu Gly Tyr Cys Thr Phe Thr
                420                 425                 430

Ile Ala Ser Arg Thr Gly Glu Gly Leu Thr Ser Ala Ser Ala Phe Thr
            435                 440                 445

Lys Arg Arg Arg Cys Val Met Cys Asp Ser Leu Cys Ile Arg
    450                 455                 460
```

```
<210> SEQ ID NO 33
<211> LENGTH: 462
<212> TYPE: PRT
<213> ORGANISM: Clostridium sp. KNHs205

<400> SEQUENCE: 33
```

```
Val Asn Leu Lys Glu Ala Gln Val Lys Asp Ile Val Arg Lys Val Leu
1                   5                   10                  15

Leu Gln Met Glu Ala Ser Asn Lys Glu Glu Gln Lys Leu Ser Gly Ile
                20                  25                  30

Phe Thr Glu Met Asn Asp Ala Ile Gly Ala Ser Ile Lys Ala Gln Lys
            35                  40                  45
```

```
Val Met Gln Gln Leu Ser Met Asp Ser Arg Glu Lys Ile Ile Ser Asn
    50              55              60

Ile Arg Lys Lys Thr Leu Glu Asn Ala Glu Leu Phe Ala Arg Met Gly
65              70              75              80

Val Glu Glu Thr Gly Met Gly Asn Val Gly His Lys Ile Leu Lys His
            85              90              95

Gln Leu Leu Ala Glu Lys Thr Pro Gly Thr Glu Asp Ile Ser Thr Val
            100             105             110

Ala Trp Ser Gly Asp Arg Gly Leu Thr Leu Val Glu Met Gly Pro Phe
            115             120             125

Gly Val Ile Gly Ala Ile Thr Pro Cys Thr Asn Pro Ser Glu Thr Ile
    130             135             140

Leu Cys Asn Ser Ile Gly Met Ile Ala Gly Gly Asn Thr Val Val Phe
145             150             155             160

Asn Pro His Pro Ala Ala Ile Gly Val Ser Asn Leu Ala Val His Met
            165             170             175

Val Asn Glu Ala Ser Arg Glu Ala Gly Gly Pro Asp Asn Ile Ala Val
            180             185             190

Ser Val Val Lys Pro Thr Leu Ala Ser Gly Asp Ile Met Met Lys His
            195             200             205

Gln Asn Ile Pro Leu Ile Val Ala Thr Gly Gly Pro Gly Val Val Thr
    210             215             220

Thr Val Leu Ser Ser Gly Lys Arg Gly Ile Gly Ala Gly Ala Gly Asn
225             230             235             240

Pro Pro Val Leu Val Asp Glu Thr Ala Asp Ile Arg Lys Ala Ala Met
            245             250             255

Asp Ile Val Asn Gly Cys Thr Phe Asp Asn Asn Leu Pro Cys Ile Ala
            260             265             270

Glu Lys Glu Val Val Ala Val Gly Lys Ile Met Asp Glu Leu Leu His
            275             280             285

Tyr Leu Ile Glu Asn Gly Cys Tyr Val Ile Ser Lys Glu Glu Gln Glu
    290             295             300

Lys Leu Thr Ala Val Val Leu Lys Asp Asn Arg Leu Asn Arg Lys Cys
305             310             315             320

Val Gly Lys Asp Ala Arg Thr Ile Leu Ser Met Ile Gly Ile Glu Thr
            325             330             335

Pro Glu Asn Ile Arg Cys Ile Ile Phe Glu Gly Glu Lys Glu His Pro
            340             345             350

Leu Ile Ala Glu Glu Leu Met Met Pro Ile Leu Gly Ile Val Arg Ala
            355             360             365

Lys Asp Ile Asp Asp Ala Ile Glu Lys Ala Val Trp Leu Glu His Gly
    370             375             380

Asn Arg His Ser Ala His Met His Ser Lys Asn Val Asp Asn Leu Thr
385             390             395             400

Arg Phe Gly Lys Ala Val Asp Thr Ala Ile Phe Val Lys Asn Ala Pro
            405             410             415

Ser Tyr Ala Ala Leu Gly Phe Gly Gly Glu Gly Phe Cys Thr Phe Thr
            420             425             430

Ile Ala Ser Arg Thr Gly Glu Gly Leu Thr Ser Ala Arg Thr Phe Thr
            435             440             445

Lys Gln Arg Arg Cys Val Met Ala Asp Ser Leu Cys Ile Arg
    450             455             460
```

<210> SEQ ID NO 34

<400> SEQUENCE: 34

000

<210> SEQ ID NO 35

<400> SEQUENCE: 35

000

<210> SEQ ID NO 36
<211> LENGTH: 470
<212> TYPE: PRT
<213> ORGANISM: Robinsoniella peoriensis

<400> SEQUENCE: 36

```
Met Ala Ile Asn Glu Gln Glu Ile Gln Asp Ile Val Arg Ser Val Leu
1               5                   10                  15

Lys Gly Met Gly Thr Thr Ala Asp Lys Pro Ala Gly Ser Ser Lys Lys
            20                  25                  30

Leu Leu Gly Val Phe Asp Asp Ile Asn Asp Ala Ile Ala Ala Ala Lys
        35                  40                  45

Glu Ala Gln Lys Glu Ile Gln Pro Met Pro Leu Glu Phe Arg Glu Lys
    50                  55                  60

Ile Ile Ser Asn Ile Arg Lys Lys Thr Leu Glu Asn Ala Lys Met Phe
65                  70                  75                  80

Ala Glu Leu Gly Val Glu Glu Thr Gly Met Gly Asn Val Gly His Lys
            85                  90                  95

Ile Leu Lys His Gln Leu Val Ala Glu Lys Thr Pro Gly Thr Glu Asp
            100                 105                 110

Leu Ser Thr Val Ala Trp Ser Gly Asp Arg Gly Leu Thr Leu Val Glu
        115                 120                 125

Met Gly Pro Phe Gly Val Ile Gly Ala Val Cys Pro Ser Thr Asn Pro
    130                 135                 140

Thr Glu Thr Val Val Cys Asn Ser Ile Gly Met Ile Ala Ala Gly Asn
145                 150                 155                 160

Thr Val Val Phe Ala Pro His Pro Ser Ala Lys Asn Val Ser Asn Leu
                165                 170                 175

Ala Ile Asp Met Ile Asn Arg Ala Ser Val Glu Val Gly Gly Pro Glu
            180                 185                 190

Asn Ile Ala Val Ala Val Lys Glu Pro Thr Met Glu Val Ser Lys Val
            195                 200                 205

Ile Phe Ser His Lys Asp Ile Ser Leu Leu Val Ala Thr Gly Gly Pro
        210                 215                 220

Gly Val Val Thr Thr Val Leu Ser Ser Gly Lys Arg Ala Met Gly Ala
225                 230                 235                 240

Gly Ala Gly Asn Pro Pro Val Leu Val Asp Glu Thr Ala Asn Ile Pro
                245                 250                 255

Lys Ala Ala Glu Asp Ile Ile Asn Gly Cys Thr Phe Asp Asn Asn Leu
            260                 265                 270

Pro Cys Ile Ala Glu Lys Glu Val Val Ala Val Asp Met Ile Ala Asp
        275                 280                 285

Glu Leu Ile Tyr His Met Glu Gln Val Gly Cys Tyr His Ala Asn Ala
    290                 295                 300
```

```
Glu Glu Val Gln Lys Leu Ile Gln Thr Val Phe Ile Glu Asn Asn Gly
305             310             315             320

Lys Arg Thr Leu Asn Arg Gln Cys Val Gly Arg Ser Ala Lys Val Leu
                325             330             335

Leu Gly Lys Ile Gly Val Thr Val Gly Asp Glu Ile Arg Cys Ile Ile
                340             345             350

Phe Glu Gly Glu Lys Thr Asn Pro Met Ile Trp Glu Glu Leu Met Met
            355             360             365

Pro Ile Leu Gly Ile Val Arg Val Lys Asn Val Glu Glu Gly Met Gly
    370             375             380

Ile Ala Leu Glu Leu Glu His Gly Asn Arg His Ser Ala His Met His
385             390             395             400

Ser Thr Asn Val Asn Asn Leu Thr Lys Phe Gly Lys Met Ile Asp Thr
                405             410             415

Ala Ile Phe Val Lys Asn Ala Pro Ser Tyr Ala Ala Leu Gly Phe Gly
                420             425             430

Gly Glu Gly Tyr Pro Thr Phe Thr Ile Cys Ser Arg Thr Gly Glu Gly
            435             440             445

Leu Thr Ser Ala Lys Asn Phe Thr Lys Ser Arg Arg Cys Val Met Gly
    450             455             460

Asp Ala Leu Cys Ile Arg
465             470
```

<210> SEQ ID NO 37

<400> SEQUENCE: 37

000

<210> SEQ ID NO 38
<211> LENGTH: 469
<212> TYPE: PRT
<213> ORGANISM: Caldithrix abyssi

<400> SEQUENCE: 38

```
Met His Leu Asp Asp Lys Gln Ile Ala Gln Ile Val Glu Thr Val Leu
1               5               10              15

Ser Arg Leu Glu Arg Asn Glu Ser Arg Thr Gly Arg Ser Arg His Pro
                20              25              30

Gln Gly Val Phe Glu Thr Leu Asp Glu Ala Val Glu Ala Ala Arg Gln
            35              40              45

Ala Gln Lys Lys Ile Arg Lys Leu Glu Leu Arg Ala Lys Ile Ile Gln
    50              55              60

Ala Ile Arg Gln Ala Gly Val Lys His Ala Arg Glu Leu Ala Glu Met
65              70              75              80

Ala Val Gln Glu Thr Gly Met Gly Arg Val Glu Asp Lys Ile Ala Lys
                85              90              95

Asn Ile Ser Gln Ala Glu Lys Thr Pro Gly Ile Glu Asp Leu Gln Pro
                100             105             110

Leu Ala Leu Ser Gly Asp His Gly Leu Thr Leu Ile Glu Asn Ala Ala
            115             120             125

Trp Gly Val Ile Ala Ser Val Thr Pro Ser Thr Asn Pro Gly Ala Thr
    130             135             140

Val Ile Asn Asn Ser Ile Ser Met Ile Ala Ala Gly Asn Ala Val Val
145             150             155             160

Tyr Ala Pro His Pro Ala Ala Lys Lys Val Ser Gln Arg Ala Ile Glu
```

-continued

```
                165                  170                  175

Ile Leu Asn Lys Ala Ile Glu Ala Ala Gly Gly Pro Ala Thr Leu Leu
            180                  185                  190

Thr Thr Val Ala Glu Pro Ser Ile Glu Thr Ala Gln Lys Leu Phe Val
            195                  200                  205

Tyr Pro Gly Ile Asp Leu Leu Val Val Thr Gly Gly Glu Ala Val Val
        210                  215                  220

Lys Ala Ala Arg Lys Val Thr Asp Lys Arg Leu Met Ala Ala Gly Ala
225                  230                  235                  240

Gly Asn Pro Pro Val Val Val Asp Glu Thr Ala Asp Ile Ala Lys Ala
                245                  250                  255

Ala Arg Asp Ile Val Trp Gly Ala Ser Phe Asp Asn Asn Ile Val Cys
            260                  265                  270

Ala Asp Glu Lys Glu Ile Ile Ala Val Asp Ala Ile Ala Asp Arg Leu
            275                  280                  285

Lys Glu Glu Met Lys Lys His Gln Ala Val Glu Leu Thr Pro Gln Gln
        290                  295                  300

Gly Glu Glu Leu Ala Gln Ile Ile Leu Glu Asp Tyr Pro Gly Pro Asn
305                  310                  315                  320

Ala Arg Ile Asn Arg Lys Trp Val Gly Lys Asp Ala Tyr Lys Phe Ala
                325                  330                  335

Arg Glu Ile Gly Leu Asn Val Ser Lys Glu Thr Arg Leu Leu Phe Val
            340                  345                  350

Glu Ala Asp Lys Asp His Pro Phe Ala Gln Leu Glu Leu Met Met Pro
            355                  360                  365

Val Ile Pro Leu Ile Arg Ala Ala Asp Ala Asp Lys Ala Ile Asp Leu
        370                  375                  380

Ala Ile Glu Leu Glu His Gly Tyr Arg His Thr Ala Ala Met His Ser
385                  390                  395                  400

Arg His Ile Asp His Met Asp Arg Met Ala Asn Glu Ile Asn Thr Ser
                405                  410                  415

Ile Phe Val Lys Asn Gly Pro Cys Leu Ala Gly Leu Gly Phe Gly Gly
            420                  425                  430

Glu Gly Trp Thr Ser Met Thr Ile Thr Thr Pro Thr Gly Glu Gly Val
            435                  440                  445

Thr Ser Ala Arg Ser Phe Val Arg Leu Arg Arg Cys Val Val Val Asp
        450                  455                  460

His Phe Arg Ile Val
465

<210> SEQ ID NO 39

<400> SEQUENCE: 39

000

<210> SEQ ID NO 40
<211> LENGTH: 479
<212> TYPE: PRT
<213> ORGANISM: Sporomusa sphaeroides

<400> SEQUENCE: 40

Met Thr Ile Asp Pro Asn Leu Ile Ala Lys Ile Ala Ala Glu Val Met
1               5                   10                  15

Ala Arg Val Gln Glu Arg Gln Pro Glu Thr Val Ser Ala Gly Glu Gly
            20                  25                  30
```

-continued

```
Ile Phe Pro Thr Val Asp Glu Ala Val Ala Ala Ala Arg Ala Ala Gln
        35              40              45

Lys Gln Leu Lys Lys Leu Ser Ile Glu Lys Arg Glu Glu Leu Ile Gln
    50              55              60

Ala Met Arg Gln Ala Ala Cys Asp Asn Ala Glu Leu Leu Ala Glu Met
65              70              75              80

Gly Val Ser Glu Ser Gly Met Gly Arg Val Ser Asp Lys Val Ile Lys
                85              90              95

Asn Arg Leu Ala Ala Thr Lys Thr Pro Gly Thr Glu Asp Leu Lys Ser
            100             105             110

Glu Ala Trp Ser Gly Asp Arg Gly Leu Thr Leu Ile Glu Met Gly Pro
            115             120             125

Tyr Gly Val Ile Gly Ser Ile Thr Pro Thr Thr Asn Pro Ser Glu Thr
    130             135             140

Val Ile Cys Asn Gly Ile Gly Met Ile Ala Ala Gly Asn Ala Val Val
145             150             155             160

Phe Ser Pro His Pro Thr Ala Lys Asn Thr Ser Leu Val Thr Ile Lys
                165             170             175

Leu Leu Asn Lys Ala Ile Ile Gln Ala Gly Gly Pro Pro Asn Leu Leu
            180             185             190

Thr Ala Val Ala Glu Pro Ser Leu Ala Ala Thr Asn Ala Met Met Gln
            195             200             205

His Pro Asp Ile Asn Met Leu Val Ala Thr Gly Gly Pro Ala Val Val
    210             215             220

Lys Ala Val Met Ser Cys Gly Lys Lys Ala Ile Gly Ala Gly Ala Gly
225             230             235             240

Asn Pro Pro Ala Val Val Asp Glu Thr Ala Asp Ile Glu Lys Ala Ala
            245             250             255

Lys Asp Ile Ile Asp Gly Cys Ser Phe Asp Asn Asn Leu Pro Cys Ile
            260             265             270

Ala Glu Lys Glu Val Ile Val Val Gly Ser Val Ala Asp Lys Leu Met
    275             280             285

Ala Tyr Met Gln Arg Tyr Gly Ala Tyr Leu Ile Ser Gly Pro Asp Val
    290             295             300

Asp Arg Leu Ala Lys Val Ile Leu Thr Glu Lys Ala Glu Leu Ala Ala
305             310             315             320

Ala Gly Cys Thr Glu Lys Pro Lys Lys Ser Tyr Ala Val Asn Lys Asn
            325             330             335

Tyr Val Gly Lys Asp Ala Arg Tyr Ile Leu Ser Gln Ile Gly Ile Gln
            340             345             350

Val Pro Asp Ser Ile Arg Ala Val Ile Cys Glu Thr Pro Ala Asp His
    355             360             365

Pro Phe Val Val Glu Glu Leu Met Met Pro Val Leu Pro Val Val Gln
    370             375             380

Val Lys Asp Ile Asp Ala Ala Ile Glu Leu Ala Val Lys Val Glu His
385             390             395             400

Gly Asn Arg His Thr Ala Ile Met His Ser Lys Asn Val Asp Asn Leu
            405             410             415

Thr Lys Leu Ala Lys Ala Ile Glu Thr Thr Ile Phe Val Lys Asn Ala
            420             425             430

Pro Ser Tyr Ala Gly Ile Gly Val Gly Gly Glu Gly Phe Thr Thr Phe
    435             440             445
```

-continued

```
Thr Ile Ala Gly Pro Thr Gly Glu Gly Leu Thr Ser Pro Arg Ser Phe
    450                 455                 460

Thr Arg Gln Arg Arg Cys Val Leu Val Asp Ala Leu Ser Ile Val
465                 470                 475

<210> SEQ ID NO 41
<211> LENGTH: 524
<212> TYPE: PRT
<213> ORGANISM: Bacillus sp. FJAT-25547

<400> SEQUENCE: 41

Met Gly Val Asn Met Ser Glu Gln Asp Ile Gln Lys Ile Ile Gln Ser
1               5                   10                  15

Val Leu Gln Asn Ile Glu Ala Val Ser Glu Gln Asn Ser Gly His Gln
                20                  25                  30

Val Leu His Ser Asn Asp Asn Thr Asn Pro Pro Lys Pro Leu Lys Met
            35                  40                  45

Lys Arg Val Leu Pro Leu Ser Gln Gln Ile Asn Thr Ala Glu Leu Ser
    50                  55                  60

His Gln Val Asn Glu Pro Gly Ala Asn Gly Val Phe Val Arg Ile Glu
65                  70                  75                  80

Asp Ala Ile Glu Ala Gly Tyr Ile Ala Gln Leu Asn Tyr Val Lys His
                85                  90                  95

Phe Gln Leu Lys Asp Arg Glu Lys Ile Ile Ala Ala Ile Arg Glu Ala
            100                 105                 110

Val Ile Glu Asn Lys Glu Lys Leu Ala Gln Met Val Phe Glu Glu Thr
            115                 120                 125

Lys Leu Gly Arg Tyr Glu Asp Lys Ile Ala Lys His Glu Leu Val Ala
    130                 135                 140

Ser Lys Thr Pro Gly Thr Glu Asp Ile Thr Thr Ala Ala Phe Ser Gly
145                 150                 155                 160

Asp Glu Gly Leu Thr Ile Val Glu Gln Ala Pro Phe Gly Leu Val Gly
                165                 170                 175

Ala Val Thr Pro Val Thr Asn Pro Thr Glu Thr Ile Ile Asn Asn Ser
            180                 185                 190

Ile Ser Leu Leu Ala Ala Gly Asn Ala Val Val Leu Asn Val His Pro
            195                 200                 205

Ser Ser Lys Ala Ser Cys Ala Phe Val Val Asn Leu Ile Asn Gln Ala
    210                 215                 220

Ile Gln Asp Ala Gly Gly Pro Lys Asn Leu Val Ser Met Val Lys Asp
225                 230                 235                 240

Pro Thr Leu Glu Thr Leu Asn Arg Ile Ile Glu Ser Pro Lys Val Lys
                245                 250                 255

Leu Leu Val Gly Thr Gly Gly Pro Gly Met Val Lys Thr Leu Leu Lys
            260                 265                 270

Ser Gly Lys Lys Ala Ile Gly Ala Gly Ala Gly Asn Pro Pro Val Ile
            275                 280                 285

Val Asp Glu Thr Ala Asp Leu Lys Gln Ala Ala Lys Ser Ile Ile Glu
    290                 295                 300

Gly Ala Ser Phe Asp Asn Asn Leu Leu Cys Ile Ala Glu Lys Glu Leu
305                 310                 315                 320

Phe Val Ile Asp Ser Val Ala Asp Asp Leu Ile Phe Gln Met Leu Asn
            325                 330                 335

Glu Gly Ala Tyr Met Leu Asp Gln Gln Gln Leu Ser Lys Leu Met Ser
            340                 345                 350
```

Phe Ala Leu Glu Glu Asn Val His Gln Glu Ala Gly Gly Cys Ser Leu
        355                 360                 365

Asp Asn Lys Arg Glu Tyr His Val Ser Lys Asp Trp Val Gly Lys Asp
        370                 375                 380

Ala Ala Ser Phe Leu Arg Gln Ile Gly Val Ala Cys Glu Glu Asn Ile
385                 390                 395                 400

Lys Leu Leu Ile Cys Glu Val Asp Phe Asp His Pro Phe Val Gln Leu
                405                 410                 415

Glu Gln Met Met Pro Val Phe Pro Ile Val Arg Val Gly Asp Leu Asp
                420                 425                 430

Glu Ala Ile Glu Met Ala Leu Leu Ala Glu His Gly Asn Arg His Thr
        435                 440                 445

Ala Ile Met His Ser Lys Asn Val Asp His Leu Thr Lys Phe Ala Arg
        450                 455                 460

Ala Ile Glu Thr Thr Ile Phe Val Lys Asn Ala Ser Ser Leu Ala Gly
465                 470                 475                 480

Val Gly Phe Gly Gly Glu Gly His Thr Thr Met Thr Ile Ala Gly Pro
                485                 490                 495

Thr Gly Glu Gly Ile Thr Ser Ala Lys Thr Phe Thr Arg Gln Arg Arg
                500                 505                 510

Cys Val Leu Ala Glu Gly Gly Phe Arg Ile Ile Gly
        515                 520

<210> SEQ ID NO 42
<211> LENGTH: 471
<212> TYPE: PRT
<213> ORGANISM: Dorea sp. D27

<400> SEQUENCE: 42

Met Glu Ile Ser Thr Ser Gln Ile Ser Arg Tyr Ile Leu Asp Leu Gln
1               5                   10                  15

Asn Glu Leu Lys Gly Asp Ser Pro Ser Pro Ala His Met Ser Ala Gly
                20                  25                  30

Glu His Gly Ile Phe Gln Asp Ala Glu Cys Ala Ile Met Ala Ala Ser
        35                  40                  45

Gln Ala Gln Lys Arg Leu Met Glu Tyr Ser Leu Lys Glu Arg Glu Thr
        50                  55                  60

Phe Ile Glu Ala Met Arg Ala Ala Arg Glu Asn Ala Arg Lys Leu
65                  70                  75                  80

Ala Glu Thr Ala His Asp Glu Thr Gly Tyr Gly His Val Glu Asp Lys
                85                  90                  95

Val Ala Lys Asn Val Leu Ala Ala Asp Lys Thr Pro Gly Ile Glu Asp
                100                 105                 110

Leu Asn Thr Met Ala Val Ser Gly Asp Ala Gly Leu Met Leu Thr Glu
        115                 120                 125

Met Ala Pro Tyr Gly Val Ile Gly Ala Ile Thr Pro Ser Thr Asn Pro
        130                 135                 140

Thr Ala Thr Val Ile Asn Asn Gly Ile Gly Met Ile Ala Gly Gly Asn
145                 150                 155                 160

Ala Val Val Phe Asn Pro His Pro Gly Ala Lys Lys Ala Ser Leu Leu
                165                 170                 175

Thr Ile Lys Leu Met Asn Glu Ala Ile Val Gly Ala Gly Gly Pro Asp
                180                 185                 190

Asn Leu Leu Cys Ala Pro Glu Glu Pro Thr Leu Asp Thr Ser Ser Val

-continued

```
              195                 200                 205
Ile Met Ser His Pro Leu Val Lys Leu Leu Val Val Thr Gly Gly Glu
    210                 215                 220
Ala Val Val Arg Thr Ala Met Lys Thr Gly Lys Lys Cys Ile Ala Ala
225                 230                 235                 240
Gly Pro Gly Asn Pro Pro Val Val Val Asp Gly Thr Ala Asp Ile Lys
                    245                 250                 255
Arg Ala Ala Ala Asp Ile Val Lys Gly Ala His Tyr Glu Asn Cys Ile
                260                 265                 270
Leu Cys Ile Ala Glu Lys Glu Ile Leu Val Glu Ser Cys Val Ala Asp
                275                 280                 285
Glu Leu Ile Arg Glu Met Val Lys Glu Gly Ala Tyr Leu Ala Asp Glu
    290                 295                 300
Lys Glu Leu Ser Ala Ile Val Gly Lys Val Met Ile Thr Ala Lys Asp
305                 310                 315                 320
Gly Ser Tyr Ala Pro Asn Lys Lys Tyr Val Gly Arg Asp Ala Thr Tyr
                325                 330                 335
Ile Leu Lys Glu Ala Gly Ile Cys Val Asp Arg Glu Ala Lys Ile Ile
                340                 345                 350
Ile Ala Glu Val Pro Phe Gly His Pro Leu Val Met Thr Glu Met Leu
                355                 360                 365
Met Pro Val Ile Pro Val Thr Arg Val Ala Thr Val Glu Glu Ala Ile
    370                 375                 380
Glu Lys Ala Val Ile Ala Glu Asn Gly Cys His His Thr Ala Met Met
385                 390                 395                 400
His Ser Glu Asn Val Ser Asn Leu Thr Lys Met Ala Arg Ala Ala Asp
                405                 410                 415
Thr Thr Ile Phe Val Lys Asn Ala Pro Ser Tyr Ala Gly Leu Gly Ile
                420                 425                 430
Asp Gly Glu Gly Tyr Thr Thr Leu Thr Ile Ala Thr Pro Thr Gly Glu
                435                 440                 445
Gly Leu Thr Ser Ala Arg Asn Phe Thr Arg Ser Arg Arg Cys Thr Leu
    450                 455                 460
His Gly Ser Phe Arg Ile Val
465                 470
```

<210> SEQ ID NO 43

<400> SEQUENCE: 43

000

<210> SEQ ID NO 44
<211> LENGTH: 448
<212> TYPE: PRT
<213> ORGANISM: Enterococcus phoeniculicola

<400> SEQUENCE: 44

```
Ile Met Asn Thr Leu Ser Asp Lys Ile Leu Arg Gly Arg Gln Ala Met
1                   5                   10                  15
Gln Ser Ile Ser Asn Tyr Thr Gln Glu Gln Val Asp Glu Met Leu Ser
                20                  25                  30
Val Ile Ser Lys Thr Ile Phe Asp His Ala Glu Glu Leu Ala Lys Glu
        35                  40                  45
Ala Val Glu Glu Thr Gly Leu Gly Asn Tyr Glu His Lys Ile Gly Lys
    50                  55                  60
```

-continued

```
Asn Gln Asn Met Ala Ile Asn Ile Phe Ser His Leu Lys Gly Lys Lys
65                  70                  75                  80

Ser Val Gly Ile Ile Gln Thr Leu Lys Glu Glu Gly Val Val Glu Ile
                85                  90                  95

Ala His Pro Val Gly Val Ile Gly Ser Val Thr Pro Thr Thr Asn Pro
            100                 105                 110

Thr Ile Thr Pro Leu Gly Asn Gly Leu Met Ala Leu Lys Gly Lys Asn
            115                 120                 125

Ala Met Ile Val Ser Pro His Pro Arg Ala Lys Lys Thr Thr Lys His
        130                 135                 140

Thr Ile Asp Leu Met Arg Ser Ala Leu Glu Ser Ile His Ala Pro Lys
145                 150                 155                 160

Asp Leu Leu Gln Val Ile Glu Glu Pro Ser Leu Glu Leu Ser Gln Gln
                165                 170                 175

Leu Met Arg Glu Ser Asp Val Ile Val Ala Thr Gly Gly Pro Gly Leu
            180                 185                 190

Val Arg Ala Ala Tyr Ser Ser Gly Lys Pro Ala Phe Gly Val Gly Pro
        195                 200                 205

Gly Asn Val Gln Ala Ile Leu Asp Asp Asp Phe Asp Ile Asn Leu Ala
        210                 215                 220

Ala Glu Leu Thr Val Ile Gly Arg Ser Phe Asp Asn Gly Ile Val Cys
225                 230                 235                 240

Ala Cys Gln Gln Ser Leu Leu Tyr Pro Glu Lys Lys Glu Glu Glu Leu
                245                 250                 255

Phe Gln Ala Leu Glu Asn Asn Lys Ala Tyr Ile Ile Lys Glu Glu Ile
            260                 265                 270

Asp Val Gln Lys Met Arg Glu Leu Leu Phe Pro Gly Gly Lys Ser Asn
            275                 280                 285

Pro Asp Leu Val Gly Gln Thr Ala Thr Phe Ile Ala Glu Lys Ala Gly
    290                 295                 300

Ile Lys Val Pro Glu Asp Thr Ile Ile Leu Ala Val Lys Val Thr Thr
305                 310                 315                 320

Ser Gly Gln Glu Glu Leu Leu Val Lys Glu Lys Met Asn Pro Val Leu
                325                 330                 335

Val Val Lys Gly Cys Glu Ser Phe Glu Glu Ala Leu Leu Asp Ala Lys
            340                 345                 350

Asn Asn Leu Trp Val Glu Gly Ala Gly His Ser Thr Gly Ile Phe Ser
            355                 360                 365

Asn Asn Glu Gln His Ile Leu Ser Ala Gly Glu Thr Leu Pro Val Ser
        370                 375                 380

Arg Val Val Val Asn Gln Pro Thr Ile Asp Ala Gly Gly Ser Pro Thr
385                 390                 395                 400

Asn Gly Leu Asn Pro Thr Val Ser Leu Gly Cys Gly Ser Trp Gly Asn
            405                 410                 415

Asn Ser Ile Ser Glu Asn Leu Ser Tyr His His Leu Ile Asn Ile Ser
            420                 425                 430

Arg Ile Ala Tyr Pro Ile Ser Pro Lys His Thr Glu Thr Pro Trp Asn
            435                 440                 445
```

<210> SEQ ID NO 45
<211> LENGTH: 462
<212> TYPE: PRT
<213> ORGANISM: Blautia schinkii -continued

```
<400> SEQUENCE: 45

Met Pro Ile Ser Asp Ser Met Val Gln Glu Ile Val Gln Glu Val Met
1               5                   10                  15

Ala Lys Met Gln Ile Ala Asp Ala Pro Ala Gly Lys His Gly Val Phe
                20                  25                  30

Lys Asp Met Asn Glu Ala Ile Glu Ala Ala Lys Lys Thr Glu Asn Ile
            35                  40                  45

Val Lys Arg Met Ser Met Asp Gln Arg Glu Lys Ile Ile Thr Cys Ile
    50                  55                  60

Arg Lys Ser Ile Lys Lys Asn Ala Glu Ile Met Ala Arg Met Gly Val
65                  70                  75                  80

Asp Glu Thr Gly Met Gly Asn Val Gly Asp Lys Ile Leu Lys His His
                85                  90                  95

Leu Val Ala Asp Lys Thr Pro Gly Thr Glu Asp Ile Thr Thr Thr Ala
                100                 105                 110

Trp Ser Gly Asp Arg Gly Leu Thr Leu Val Glu Met Gly Pro Phe Gly
            115                 120                 125

Val Ile Gly Ala Ile Thr Pro Cys Thr Asn Pro Ser Glu Thr Ile Leu
    130                 135                 140

Cys Asn Thr Met Gly Met Leu Ala Gly Gly Asn Thr Val Val Phe Asn
145                 150                 155                 160

Pro His Pro Ala Ala Ile Lys Thr Ser Ile Tyr Ala Val Asn Leu Leu
                165                 170                 175

Asn Glu Ala Ser Leu Glu Ala Gly Gly Pro Asp Asn Ile Ala Val Thr
            180                 185                 190

Val Glu Gln Pro Thr Leu Glu Thr Ser Asn Ile Met Met Lys His Lys
            195                 200                 205

Asp Ile Pro Leu Ile Ala Ala Thr Gly Gly Pro Gly Val Val Thr Ala
    210                 215                 220

Val Leu Ser Ser Gly Lys Arg Gly Ile Gly Ala Gly Ala Gly Asn Pro
225                 230                 235                 240

Pro Ala Leu Val Asp Glu Thr Ala Asp Val Arg Lys Ala Ala Gln Asp
                245                 250                 255

Ile Val Asn Gly Cys Thr Phe Asp Asn Asn Leu Pro Cys Ile Ala Glu
            260                 265                 270

Lys Glu Ile Val Ala Val Ser Pro Ile Val Asp Glu Leu Met His Tyr
            275                 280                 285

Leu Val Ser Glu Asn Asp Cys Tyr Leu Ala Ser Lys Glu Glu Gln Asp
    290                 295                 300

Lys Leu Thr Glu Val Val Leu Ala Gly Gly Arg Leu Asn Arg Lys Cys
305                 310                 315                 320

Val Gly Arg Asp Ala Arg Thr Leu Leu Ser Met Ile Gly Val Asn Val
                325                 330                 335

Pro Ala Asn Ile Arg Cys Ile Val Phe Glu Gly Pro Lys Glu His Pro
            340                 345                 350

Leu Ile Ala Thr Glu Leu Met Met Pro Ile Leu Gly Val Val Arg Ala
            355                 360                 365

Lys Asp Phe Asp Asp Ala Val Glu Gln Ala Val Trp Leu Glu His Gly
    370                 375                 380

Asn Arg His Ser Ala His Ile His Ser Lys Asn Ile Asp Asn Ile Thr
385                 390                 395                 400

Lys Tyr Ala Lys Ala Ile Asp Thr Ala Ile Leu Val Lys Asn Ala Pro
                405                 410                 415
```

-continued

```
Ser Tyr Ala Ala Leu Gly Phe Gly Gly Glu Gly Tyr Cys Thr Phe Thr
            420                 425                 430

Ile Ala Ser Arg Thr Gly Glu Gly Leu Thr Ser Ala Ser Thr Phe Thr
            435                 440                 445

Lys Arg Arg Arg Cys Val Met Ser Asp Ser Leu Cys Ile Arg
        450                 455                 460

<210> SEQ ID NO 46

<400> SEQUENCE: 46

000

<210> SEQ ID NO 47
<211> LENGTH: 472
<212> TYPE: PRT
<213> ORGANISM: Clostridium intestinale

<400> SEQUENCE: 47

Met Ser Ile Asp Ala Thr Leu Val Glu Lys Leu Val Arg Gln Ala Ile
1               5                   10                  15

Glu Glu Ala Lys Ser Lys Asn Leu Ile Ser Phe Asn Lys Val Glu Thr
            20                  25                  30

Leu Asn Asn Tyr Gly Ile Phe Asn Thr Met Asp Glu Ala Ile Glu Ala
        35                  40                  45

Ser Asp Val Ala Gln Lys Glu Leu Leu Asn Thr Ser Met Ala Asn Arg
    50                  55                  60

Gln Lys Tyr Ile Asn Ile Ile Lys Ser Thr Val Leu Lys Arg Glu Asn
65                  70                  75                  80

Leu Glu Leu Ile Ser Arg Met Ala Val Glu Glu Thr Glu Ile Gly Arg
            85                  90                  95

Tyr Glu His Lys Leu Ile Lys Asn Arg Val Ala Ala Glu Lys Thr Pro
            100                 105                 110

Gly Thr Glu Asp Leu Val Thr Glu Ala Ile Thr Gly Asp Asn Gly Ile
        115                 120                 125

Thr Leu Ile Glu Tyr Cys Pro Phe Gly Val Ile Gly Ser Ile Thr Pro
    130                 135                 140

Thr Thr Asn Pro Thr Glu Thr Ile Ile Cys Asn Ser Met Ser Met Ile
145                 150                 155                 160

Ala Gly Gly Asn Thr Val Val Phe Ser Pro His Pro Arg Ala Lys Asn
            165                 170                 175

Val Ser Ile Lys Leu Ile Thr Met Leu Asn Lys Ala Leu Glu Glu Ala
            180                 185                 190

Gly Ala Pro Lys Asn Leu Ile Val Thr Val Lys Glu Pro Ser Ile Glu
        195                 200                 205

Asn Thr Asn Ala Met Met Asp His Pro Lys Val Arg Val Leu Val Ala
    210                 215                 220

Thr Gly Gly Pro Ala Ile Val Lys Lys Val Met Ser Thr Gly Lys Lys
225                 230                 235                 240

Ala Ile Gly Ala Gly Ala Gly Asn Pro Pro Val Val Val Asp Glu Thr
            245                 250                 255

Ala Asn Val Glu Lys Ala Ala Ile Asp Ile Val Asn Gly Cys Ser Phe
            260                 265                 270

Asp Asn Asn Val Pro Cys Val Ala Glu Lys Glu Val Phe Ala Val Asp
            275                 280                 285
```

-continued

```
Gln Ile Cys Asp Tyr Leu Ile His Tyr Met Lys Leu Asn Gly Ala Tyr
    290             295             300

Glu Ile Lys Asp Arg Asn Thr Ile Gln Lys Leu Leu Glu Leu Val Thr
305             310             315             320

Asn Glu Asn Gly Gly Pro Lys Val Ser Phe Val Gly Lys Asn Ala Ser
                325             330             335

Tyr Ile Leu Ser Lys Leu Gly Ile Asn Val Asp Asp Asn Ile Lys Ile
            340             345             350

Ile Ile Met Glu Val Asp Lys Asp His His Phe Val Lys Glu Glu Met
        355             360             365

Met Met Pro Ile Leu Pro Ile Val Arg Thr Arg Asp Val Asp Glu Ala
    370             375             380

Ile Glu Tyr Ala Tyr Val Ala Glu Asn Gly Asn Arg His Thr Ala Ile
385             390             395             400

Met His Ser Lys Asn Val Asp Lys Leu Thr Lys Met Ala Arg Leu Leu
                405             410             415

Glu Thr Thr Ile Phe Val Lys Asn Ala Pro Ser Phe Ala Gly Leu Gly
            420             425             430

Val Gly Gly Glu Gly Asn Thr Thr Phe Thr Ile Ala Gly Pro Thr Gly
            435             440             445

Glu Gly Leu Thr Thr Ala Lys Ser Phe Cys Arg Lys Arg Arg Cys Ile
    450             455             460

Met Val Asp Ala Phe Asn Ile Arg
465             470

<210> SEQ ID NO 48
<211> LENGTH: 483
<212> TYPE: PRT
<213> ORGANISM: Massilioclostridium coli

<400> SEQUENCE: 48

Met Val Phe Ser Gln Asn Gln Ile Asp Ser Ile Val Gln Ser Val Val
1               5               10              15

Ala Gln Met Gln Gly Thr Thr Pro Thr Ser Ala Pro Ala Tyr Asp Ser
            20              25              30

Thr Gln Tyr Asn Gly Arg Gln Tyr Leu Gly Val Tyr Ala Thr Met Glu
        35              40              45

Glu Gly Ile Asp Ala Ala Ala Asp Ser Tyr Lys Val Ile Arg Asn Met
    50              55              60

Ser Val Glu Gln Arg Glu Lys Ile Ile Thr Glu Ile Arg Lys Leu Thr
65              70              75              80

Arg Ala Glu Ala Glu Ile Met Ala Lys Leu Gly Val Glu Glu Thr Lys
            85              90              95

Met Gly Arg Val Glu His Lys Thr Leu Lys His Ile Leu Val Ala Asp
            100             105             110

Lys Thr Pro Gly Thr Glu Asp Ile Gln Thr Glu Ala Gln Ser Gly Asp
            115             120             125

Gly Gly Leu Thr Leu Val Glu Met Ala Pro Phe Gly Ile Ile Gly Ala
    130             135             140

Ile Thr Pro Ser Thr Asn Pro Ser Glu Thr Val Ile Cys Asn Ser Ile
145             150             155             160

Ala Met Ile Ala Ala Gly Asn Ala Val Val Phe Asn Pro His Pro Gly
            165             170             175

Ala Ile Lys Val Ser Asn Tyr Ala Val Asp Leu Val Asn Arg Ala Ser
            180             185             190
```

-continued

```
Leu Ala Ala Gly Gly Pro Ala Ser Leu Val Cys Ser Met Val Lys Pro
        195             200             205

Thr Met Gln Thr Ala Asp Val Met Tyr Lys Asp Pro Arg Val Arg Met
    210             215             220

Leu Val Cys Thr Gly Gly Pro Gly Val Val Lys Ser Val Leu Ser Ser
225             230             235             240

Gly Lys Lys Ala Ile Gly Ala Gly Ala Gly Asn Pro Pro Val Ile Val
            245             250             255

Asp Asp Thr Ala Asp Ile Lys Lys Ala Ala Lys Asp Ile Ile Asp Gly
            260             265             270

Cys Thr Phe Asp Asn Asn Leu Pro Cys Ile Ala Glu Lys Glu Val Phe
        275             280             285

Ala Phe Ser Asn Ile Ala Asp Glu Leu Met Tyr Asn Met Gln Gln Asn
    290             295             300

Gly Ala Tyr Phe Ile Thr Ala Ala Gln Ala Asp Glu Leu Ala Lys Ile
305             310             315             320

Val Leu Val Glu Lys Lys Asn Glu Lys Thr Gly Lys Ile Thr Tyr Ser
            325             330             335

Val Ser Arg Asp Trp Val Gly Arg Asp Ala Lys Lys Phe Ala Ala Ala
            340             345             350

Leu Gly Ile Glu Val Asp Asp Ser Val Arg Cys Leu Ile Cys Glu Val
        355             360             365

Glu Glu Asp His Leu Phe Val Gln Thr Glu Leu Met Met Pro Ile Leu
    370             375             380

Ala Val Val Arg Val Lys Asp Ile Asp Glu Ala Ile Glu Lys Ala Val
385             390             395             400

Arg Ala Glu His Gly Asn Arg His Ser Ala His Met His Ser Lys Asn
            405             410             415

Ile Glu Asn Leu Ser Lys Phe Ala Lys Ala Ile Glu Thr Thr Ile Phe
        420             425             430

Val Lys Asn Ala Pro Ser Tyr Ala Gly Ile Gly Phe Gly Ala Glu Gly
        435             440             445

His Thr Thr Phe Thr Ile Ala Gly Pro Thr Gly Glu Gly Leu Thr Ser
    450             455             460

Ala Arg Ser Phe Thr Arg Lys Arg Arg Cys Val Met Lys Asp Met Phe
465             470             475             480

His Ile Ile
```

```
<210> SEQ ID NO 49
<211> LENGTH: 466
<212> TYPE: PRT
<213> ORGANISM: Cloacibacillus porcorum

<400> SEQUENCE: 49
```

```
Met Asn Ile Asp Ala Ala Leu Ile Glu Gly Ile Val Lys Gly Val Met
1               5               10              15

Arg Lys Ile Asp Glu Ser Glu Asn Asn Ser Ala Gly Ser Cys Gly Ile
            20              25              30

Phe Ala Asp Met Asn Asp Ala Ile Glu Ala Ala Ala Ala Gln Arg
        35              40              45

Arg Tyr Leu Asp Cys Ser Met Ala Asp Arg Ala Arg Phe Val Glu Ala
    50              55              60

Ile Arg Gly Thr Val Leu Asn Glu Glu Asn Leu Lys Phe Met Ser Leu
65              70              75              80
```

-continued

```
Ser Thr Ile Glu Glu Thr Gly Met Gly Asn Tyr Glu His Lys Leu Val
                85              90              95

Lys Asn Arg Leu Ala Ala Thr Lys Thr Pro Gly Ile Glu Asp Leu Thr
            100             105             110

Thr Asp Ala Ile Thr Gly Asp Asp Gly Leu Thr Ile Val Glu Tyr Ser
            115             120             125

Pro Phe Gly Val Ile Gly Ala Ile Thr Pro Thr Thr Asn Pro Thr Glu
    130             135             140

Thr Ile Ile Cys Asn Ser Ile Gly Met Leu Ala Ala Gly Asn Thr Val
145             150             155             160

Val Phe Ser Pro His Pro Arg Ala Lys Lys Val Ser Leu Trp Leu Val
            165             170             175

Ser Glu Leu Asn Arg Ala Leu Ala Ala Ala Gly Ala Pro Ala Asn Leu
            180             185             190

Ile Val Thr Val Ser Glu Pro Ser Ile Glu Asn Thr Asn Leu Met Met
            195             200             205

Ala His Pro Lys Val Arg Met Leu Val Ala Thr Gly Gly Pro Ala Ile
    210             215             220

Val Lys Thr Val Leu Ser Ser Gly Lys Lys Ala Ile Gly Ala Gly Ala
225             230             235             240

Gly Asn Pro Pro Ala Val Val Asp Glu Ser Ala Asn Ile Glu Lys Ala
            245             250             255

Ala Lys Asp Ile Val Asp Gly Cys Ser Phe Asp Asn Asn Leu Pro Cys
            260             265             270

Ile Ala Glu Lys Glu Val Ile Val Val Asp Ser Ala Ala Asp Tyr Leu
            275             280             285

Ile Phe Asn Met Lys Lys Asn Gly Ala Phe Glu Val Lys Asp Pro Ala
    290             295             300

Val Ile Glu Arg Leu Val Gly Leu Val Thr Lys Glu Gly Lys Ser Pro
305             310             315             320

Lys Thr Glu Phe Val Gly Lys Ser Ala Lys Tyr Ile Leu Glu Lys Ala
            325             330             335

Gly Val Glu Ala Pro Glu Asp Thr Arg Val Ile Ile Met Glu Ala Arg
            340             345             350

Glu Glu His Pro Phe Val Gln Val Glu Leu Met Met Pro Ile Leu Pro
            355             360             365

Ile Val Arg Ala Asp Asn Val Asn Glu Ala Ile Glu Met Ala Val Arg
    370             375             380

Val Glu His Gly Asn Arg His Thr Ala Met Met His Ser Arg Asn Val
385             390             395             400

Asp Ser Leu Thr Lys Met Ala Lys Leu Ile Gln Thr Thr Ile Phe Val
            405             410             415

Lys Asn Gly Pro Ser Tyr Ala Gly Ile Gly Val Gly Gly Met Gly His
            420             425             430

Thr Thr Phe Thr Ile Ala Gly Pro Thr Gly Glu Gly Leu Thr Ser Ala
            435             440             445

Lys Thr Phe Ala Arg Arg Arg Cys Val Leu Val Gly Gly Met Asp
    450             455             460

Ile Arg
465
```

<210> SEQ ID NO 50

```
<400> SEQUENCE: 50

000

<210> SEQ ID NO 51

<400> SEQUENCE: 51

000

<210> SEQ ID NO 52

<400> SEQUENCE: 52

000

<210> SEQ ID NO 53
<211> LENGTH: 500
<212> TYPE: PRT
<213> ORGANISM: Sporosarcina globispora

<400> SEQUENCE: 53

Met Gln Glu Met Arg Asp Ala Val Lys Arg Ala Lys Glu Ala Gln Leu
1               5                   10                  15

Glu Tyr Met Ala Phe Thr Gln Glu Gln Val Asp Glu Ile Val Lys Asn
            20                  25                  30

Ala Ala Asp Ala Ala Tyr Ala Lys Ser Leu Tyr Leu Ala Gln Met Ala
        35                  40                  45

Val Glu Glu Thr Gly Met Gly Ile Val Glu His Lys Lys Ile Lys Asn
    50                  55                  60

Glu Val Gly Ser Lys Ala Val Tyr Glu Ser Ile Lys Asp Glu Lys Thr
65                  70                  75                  80

Val Gly Ile Ile Arg Glu Asp Arg Val Asn Lys Val Thr Glu Ile Ala
                85                  90                  95

Tyr Pro Tyr Gly Val Val Ala Gly Ile Ile Pro Thr Thr Asn Pro Thr
            100                 105                 110

Ser Thr Ala Ile Phe Lys Ala Leu Ile Ser Leu Lys Thr Arg Asn Ala
            115                 120                 125

Ile Val Val Ser Pro His Pro Arg Ala Val Lys Cys Thr Val Glu Ala
    130                 135                 140

Leu Lys Ile Val Asn Glu Ala Ala Ile Gln Ala Gly Ala Pro Glu Gly
145                 150                 155                 160

Leu Ile Gly Trp Ile Ser Lys Pro Ser Met Gly Ala Thr Asn Glu Leu
                165                 170                 175

Met Lys His Arg Asp Ile Ser Leu Ile Leu Ala Thr Gly Gly Gly Gly
            180                 185                 190

Leu Val Arg Ala Ala Tyr Ser Ser Gly Lys Pro Ala Tyr Gly Val Gly
            195                 200                 205

Pro Gly Asn Val Pro Cys Tyr Ile Glu Lys Thr Ala Lys Val Ala Gln
    210                 215                 220

Ser Val Lys Met Ile Ile Asp Ser Lys Ser Phe Asp Asn Gly Thr Ile
225                 230                 235                 240

Cys Ala Thr Glu Gln Ser Ile Val Ala Asp Arg Asn Ile Lys Glu Met
                245                 250                 255

Ala Met Arg Glu Leu Lys Asn Asn Gly Ala Tyr Ile Leu Asn Ser Asp
            260                 265                 270

Glu Lys Ala Ala Leu Glu Lys Ile Ile Ser Pro Ser Pro Gly Lys Leu
            275                 280                 285
```

-continued

```
Asn Pro Asp Ile Val Gly Gln Ser Ala Val Lys Ile Ala Ala Met Ala
    290             295             300

Gly Ile Gln Val Pro Asn Asp Thr Arg Val Leu Ile Ala Glu Glu Thr
305             310             315             320

Lys Val Gly Lys Asp Ile Pro Phe Ser Ile Glu Lys Leu Ser Pro Ile
            325             330             335

Phe Ala Phe Tyr Thr Ala Glu Ser Tyr Gln Asp Ala Lys Glu Ile Cys
            340             345             350

Leu Gln Leu Leu Asn Leu Gly Gly Arg Gly His Ser Leu Ser Leu His
        355             360             365

Thr Asn Asp Asp Ala Val Ala Lys Asp Phe Ala Leu Glu Met Pro Val
    370             375             380

Ser Arg Ile Leu Val Asn Thr Leu Ser Ser Ile Gly Ala Val Gly Ala
385             390             395             400

Thr Thr Gly Leu Met Pro Ser Leu Thr Leu Gly Cys Gly Ser Phe Gly
            405             410             415

Gly Asn Ile Thr Ser Asp Asn Val Thr Ala Arg His Leu Ile Asn Thr
            420             425             430

Lys Arg Met Ala Tyr Gly Thr Lys Glu Val Thr Val Pro Lys Pro Ala
        435             440             445

Ala Ser Ser Ser Ile Ala Glu Lys Glu Gln Ala Gly Ser Gln Asp Val
    450             455             460

Asp His Ile Val Ser Gln Val Leu Gln Gln Val Ser Pro Gly Gly Glu
465             470             475             480

Val Asp Ala Lys Met Ile Ala Asp Met Val Asn Gln Val Met Lys Lys
            485             490             495

Tyr Gln Thr Asn
            500

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58
<211> LENGTH: 528
<212> TYPE: PRT
<213> ORGANISM: Rhodobacter aestuarii

<400> SEQUENCE: 58
```

-continued

```
Met Lys Asp Ile Asp Ile Glu Asn Ala Val Ala Arg Val Leu Ser Gly
1               5                   10                  15

Tyr Thr Gly Pro Ala Glu Thr Pro Ala Pro Ala Pro Thr Ser Lys Pro
            20                  25                  30

Gly Thr Thr Gly Cys Val Trp Glu Pro Val Lys Ala Val Asp Pro Val
            35                  40                  45

Asp Asp Ile Ile Gly Gly Met Leu Thr Arg Ala Leu Gly Glu Arg Asn
        50                  55                  60

Cys Ser Asn Cys Lys Ala Gly Asp Cys Gln Gly Lys Ala Gly Cys Leu
65                  70                  75                  80

Ser Ile Ser Asp Ala Glu Ala Leu Glu Leu Gly Asp Gly Val Phe Ala
                85                  90                  95

Thr Met Asp Glu Ala Val Asn Ala Ala Ala Glu Ala Gln Arg Lys Tyr
            100                 105                 110

Leu Phe Cys Thr Met Gly Asp Arg Lys Arg Phe Val Glu Gly Ile Arg
            115                 120                 125

Ala Ile Phe Thr Asp Glu Ala Val Leu Glu Arg Ile Ser Arg Leu Thr
        130                 135                 140

Val Glu Gln Thr Gly Met Gly Asn Leu Ala His Lys Ile Ile Lys Asn
145                 150                 155                 160

Arg Leu Ala Ala Glu Lys Thr Pro Gly Val Glu Asp Leu Thr Thr Glu
                165                 170                 175

Ala Gln Ser Gly Asp Asp Gly Leu Thr Leu Val Glu Leu Ser Pro Phe
            180                 185                 190

Gly Val Ile Gly Ala Ile Thr Pro Thr Thr Asn Pro Thr Glu Thr Val
            195                 200                 205

Ile Cys Asn Ser Ile Gly Met Leu Ala Ala Gly Asn Ala Ala Val Phe
        210                 215                 220

Ser Pro His Pro Arg Ala Lys Gly Val Ser Leu Leu Ala Ile Lys Leu
225                 230                 235                 240

Ile Asn Arg Lys Leu Ala Ala Leu Gly Ala Pro Ala Asn Leu Val Val
                245                 250                 255

Thr Val Gln Ala Pro Ser Ile Asp Asn Thr Asn Ala Met Met Ala His
            260                 265                 270

Pro Gln Val Arg Met Leu Val Ala Thr Gly Gly Pro Gly Ile Val Arg
            275                 280                 285

Thr Val Met Ser Thr Gly Lys Lys Ala Ile Gly Ala Gly Ala Gly Asn
            290                 295                 300

Pro Pro Val Val Val Asp Glu Thr Ala Asp Ile Pro Lys Ala Ala Gln
305                 310                 315                 320

Asp Ile Val Asn Gly Ala Ser Phe Asp Asn Asn Met Pro Cys Ile Ala
            325                 330                 335

Glu Lys Glu Val Ile Val Val Asp Gln Val Ala Asp Phe Leu Ile Ser
            340                 345                 350

Glu Met Gln Arg Asn Gly Ala Trp Leu Ala Ser Asp Pro Ser Val Val
            355                 360                 365

Glu Arg Leu Ala Gln Leu Val Leu Thr Glu Lys Gly Gly Pro Gln Thr
            370                 375                 380

Gly Cys Val Gly Lys Ser Ala Ala Trp Leu Leu Gly Gln Ile Gly Ile
385                 390                 395                 400

Gln Val Gly Pro Asp Val Arg Leu Ile Ile Leu Glu Thr Thr Lys Asp
            405                 410                 415

His Pro Phe Val Gln Glu Glu Leu Met Met Pro Ile Leu Pro Val Val
```

-continued

```
                  420              425              430

Arg Val Pro Asp Val Asp Thr Ala Ile Asp Leu Ala Val Asp Leu Glu
          435              440              445

His Gly Asn Arg His Thr Ala Met Met His Ser Thr Asn Val Arg Lys
      450              455              460

Leu Thr Lys Met Ala Lys Leu Ile Gln Thr Thr Ile Phe Val Lys Asn
465              470              475              480

Gly Pro Ser Tyr Ala Gly Ile Gly Val Gly Gly Glu Gly Tyr Thr Thr
              485              490              495

Phe Thr Ile Ala Gly Pro Thr Gly Glu Gly Leu Thr Ser Pro Arg Ser
              500              505              510

Phe Ala Arg Arg Arg Lys Cys Val Met Val Glu Ala Leu Asn Val Arg
          515              520              525
```

<210> SEQ ID NO 59
<211> LENGTH: 468
<212> TYPE: PRT
<213> ORGANISM: Clostridium grantii

<400> SEQUENCE: 59

```
Met Ala Ile Asn Glu Ser Gln Ile Glu Glu Ile Val Lys Gln Val Leu
1               5               10              15

Leu Asn Val Ser Gly Thr Thr Lys Val Lys Asn Glu Asn Lys Ala Ile
          20              25              30

Gly Ile Phe Glu Asp Ile Glu Glu Ala Ile Asp Ala Ala Lys Ile Ala
          35              40              45

Gln Lys Lys Ile Lys Lys Met Ser Met Glu Gln Arg Glu Lys Ile Ile
      50              55              60

Thr Arg Ile Arg Glu Lys Thr Arg Glu Asn Ala Lys Ile Met Ser Glu
65              70              75              80

Met Ala Val Glu Glu Thr Gly Met Gly Arg Val Asp His Lys Ile Leu
              85              90              95

Lys His Leu Leu Val Ala Asp Lys Thr Pro Gly Thr Glu Asp Ile Thr
          100             105             110

Thr Thr Ala Trp Ser Gly Asp Asn Gly Leu Thr Leu Ile Glu Met Gly
          115             120             125

Ala Phe Gly Val Ile Gly Gly Ile Thr Pro Ser Thr Asn Pro Ser Cys
          130             135             140

Thr Val Leu Cys Asn Ser Ile Gly Met Ile Ala Gly Gly Asn Thr Val
145             150             155             160

Val Phe Asn Pro His Pro Gly Ala Val Lys Val Ser Asn Tyr Ala Val
              165             170             175

Thr Leu Val Asn Glu Ala Ser Val Glu Cys Gly Gly Pro Glu Asn Ile
              180             185             190

Ala Cys Ser Val Thr Lys Pro Thr Leu Asp Ser Gly Lys Ile Leu Met
          195             200             205

Thr His Lys Asp Ile Ala Leu Leu Ala Val Thr Gly Gly Pro Gly Val
      210             215             220

Val Thr Ala Ala Leu Lys Ser Gly Lys Arg Ala Leu Gly Ala Gly Ala
225             230             235             240

Gly Asn Pro Pro Val Val Val Asp Glu Thr Ala Asp Leu Gln Ser Ala
              245             250             255

Ala Lys His Ile Val Asp Gly Ala Thr Phe Asp Asn Asn Leu Pro Cys
          260             265             270
```

-continued

```
Ile Ala Glu Lys Glu Val Val Ala Val Glu Ser Ile Val Glu Glu Leu
        275                 280                 285

Lys Tyr His Met Ile Asn Asn Gly Cys Tyr Glu Leu Lys Gly Ser Asp
        290                 295                 300

Ile Asp Lys Leu Val Asn Thr Val Leu Ile Asn Asn Asn Gly Ile Ile
305                 310                 315                 320

Gly Leu Asn Arg Asp Cys Val Gly Lys Asp Ala Lys Val Ile Leu Lys
                325                 330                 335

Lys Leu Gly Ile Glu Val Asp Asp Ser Ile Arg Cys Ile Ile Phe Asp
                340                 345                 350

Ala Asp Glu Asp His Ile Leu Val Leu Glu Glu Leu Met Met Pro Ile
        355                 360                 365

Leu Gly Ile Val Lys Val Glu Asn Val Asp Glu Ala Ile Lys Leu Ala
        370                 375                 380

Val Arg Tyr Glu His Gly Asn Arg His Ser Ala His Met His Ser Lys
385                 390                 395                 400

Asn Ile Asp Asn Leu Thr Lys Tyr Gly Arg Glu Ile Asp Thr Ala Ile
                405                 410                 415

Phe Val Lys Asn Ala Pro Ser Tyr Ser Ala Leu Gly Phe Asn Gly Glu
                420                 425                 430

Gly Tyr Cys Thr Phe Thr Ile Ala Ser Arg Thr Gly Glu Gly Leu Thr
                435                 440                 445

Ser Gly Lys Thr Phe Thr Lys Ser Arg Arg Cys Val Leu Ser Asp Gly
        450                 455                 460

Leu Ser Ile Arg
465

<210> SEQ ID NO 60
<211> LENGTH: 449
<212> TYPE: PRT
<213> ORGANISM: Collinsella sp. GD7

<400> SEQUENCE: 60

Val Ala Glu Phe Ile Glu Arg Ala Arg Val Ala Gln Ala Glu Phe Glu
1               5                   10                  15

Thr Tyr Ser Gln Glu Glu Val Asp Arg Ala Val Arg Ala Ile Gly Lys
                20                  25                  30

Ala Val Phe Asp Ala Ala Glu Pro Leu Ala Lys Leu Ala Val Glu Glu
        35                  40                  45

Thr Arg Met Gly Arg Tyr Glu Asp Lys Ile Ala Lys Asn Ser Gly Lys
        50                  55                  60

Thr Lys Ile Thr Trp Asp Arg Leu Lys Gly Val Lys Ser Arg Gly Ile
65                  70                  75                  80

Ile Ala Arg His Glu Asp Glu Gly Ile Val Glu Val Ala Lys Pro Met
                85                  90                  95

Gly Val Ile Gly Cys Ile Pro Pro Thr Thr Asn Pro Thr Met Thr Pro
                100                 105                 110

Ala His Asn Ala Met Cys Ala Leu Lys Gly Gly Asn Ala Leu Leu Ile
        115                 120                 125

Ser Pro His Pro Arg Ala Lys Lys Thr Gly Val Glu Thr Val Arg Ile
        130                 135                 140

Met Arg Glu Ala Leu Glu Ala Met Gly Ala Pro Ala Asp Leu Ile Gln
145                 150                 155                 160

Ile Ile Pro Asp Pro Thr Leu Glu Ile Ser Ser Leu Val Met Ser Met
                165                 170                 175
```

-continued

```
Cys Asp Cys Thr Ile Ala Thr Gly Gly Pro Gly Met Val Lys Ala Val
            180                 185                 190

Tyr Ser Ser Gly Lys Pro Ala Phe Gly Val Gly Ala Gly Asn Val Gln
            195                 200                 205

Thr Ile Val Asp Thr Asp Ala Asp Leu Glu Leu Ser Ala Gln Gln Ile
            210                 215                 220

Val Arg Ser Arg Thr Tyr Asp Asn Gly Val Leu Cys Thr Cys Glu Gln
225                 230                 235                 240

Cys Ile His Val Gln Glu Asp Ile Tyr Gly Glu Met Val Arg Leu Phe
                245                 250                 255

Gln Gln Glu Gly Ala Phe Tyr Ile Ser Glu Gln Ala Asp Val Asp Ala
            260                 265                 270

Leu Arg Ala Ala Leu Phe Pro Asn Gly Ala Ile Asn Lys Asp Ala Val
            275                 280                 285

Gly Ala Ser Pro Gln Phe Ile Gly Ser Leu Ala Gly Leu Asp Val Pro
            290                 295                 300

Glu Asp Ala Lys Leu Leu Met Val Lys Val Asp Ala Tyr Gly Ala Asp
305                 310                 315                 320

Glu Leu Leu Cys Lys Glu Lys Leu Cys Pro Val Met Cys Val Ala Ser
                325                 330                 335

Tyr Gly Thr Trp Glu Glu Gly Val Ala Asn Ala Lys Thr Asn Leu Leu
            340                 345                 350

His Glu Gly Ala Gly His Ser Ala Ile Val Arg Ser His Thr Ala Glu
            355                 360                 365

His Val Asp Tyr Ala Gly Glu Gln Leu Pro Val Ser Arg Ile Gly Val
            370                 375                 380

Asn Met Ile Gly Ser Ser Gly Leu Gly Gly Ala Phe Asp Asn Gly Leu
385                 390                 395                 400

Asn Pro Thr Ala Thr Leu Gly Cys Gly Ser Trp Gly Asn Asn Ser Ile
                405                 410                 415

Ser Glu Asn Leu Trp Trp His His Leu Val Asn Ile Ala Arg Ile Ala
            420                 425                 430

Val Ala Leu Pro Asp Val Gln Val Pro Ser Asp Glu Glu Val Trp Gly
            435                 440                 445

Glu
```

<210> SEQ ID NO 61
<211> LENGTH: 471
<212> TYPE: PRT
<213> ORGANISM: Clostridium estertheticum

<400> SEQUENCE: 61

```
Met Glu Ile Lys Asn Asp Glu Ile Ser Ala Met Val Glu Lys Val Leu
1               5                   10                  15

Gln Glu Met Asn Arg Arg Asp Leu Asn Val Ser Glu Ser Asp Gly Val
            20                  25                  30

Phe Asp Asp Met Asp Glu Ala Ile Glu Ala Ala Ser Ile Ala Gln Lys
            35                  40                  45

Glu Leu Ile Cys Met Ser Ile Ser Gln Arg Glu Glu Leu Ile Ser Ala
            50                  55                  60

Met Arg Lys Ala Ile Leu Asp Asn Ala Thr Lys Ile Ala Asp Ile Cys
65                  70                  75                  80

Val Glu Asp Thr Gly Met Gly Arg Lys Asp His Lys Tyr Leu Lys Leu
                85                  90                  95
```

-continued

```
Lys Leu Val Ala Asn Lys Thr Pro Gly Thr Glu Val Leu Lys Thr Met
            100                 105                 110

Ala Ile Ser Gly Asp Lys Gly Leu Thr Leu Ile Glu Met Gly Pro Phe
            115                 120                 125

Gly Val Ile Gly Gly Ile Thr Pro Ser Thr Asn Pro Ser Ala Thr Val
            130                 135                 140

Met Cys Asn Ser Ile Gly Met Ile Ala Ser Gly Asn Ala Ala Val Phe
145                 150                 155                 160

Ser Pro His Pro Gly Ala Ile Glu Ser Cys Leu Ile Ser Val Arg Val
                165                 170                 175

Leu Asn Lys Ala Ile Thr Asp Ala Gly Gly Pro Arg Asn Leu Ile Thr
            180                 185                 190

Thr Leu Arg Lys Pro Ser Leu Glu Ser Thr Asp Thr Met Ile Asn Asn
            195                 200                 205

Pro Lys Ile Arg Leu Val Val Ala Thr Gly Gly Pro Phe Ile Val Lys
    210                 215                 220

Lys Val Leu Ser Ser Gly Lys Lys Ala Ile Gly Ala Gly Ala Gly Asn
225                 230                 235                 240

Pro Pro Val Val Val Asp Glu Thr Ala Asp Ile Val Lys Ala Ala Arg
                245                 250                 255

Asp Ile Ile Ala Gly Cys Cys Phe Asp Asn Asn Leu Pro Cys Ile Ala
                260                 265                 270

Glu Lys Glu Ala Ile Val Val Glu Ser Val Tyr Glu Lys Leu Ile Ala
            275                 280                 285

Glu Met Leu Lys Asn Gly Asn Val Tyr Glu Leu Asp Glu Gln Gln Lys
    290                 295                 300

Gln Lys Val Leu Asp Val Val Met Asn Lys Thr Glu Lys Gly Gly Lys
305                 310                 315                 320

Ile Lys Tyr Gly Val Asn Lys Asn Phe Val Gly Lys Asp Ala Ser Val
            325                 330                 335

Ile Leu Ala Ala Ala Gly Ile Glu Ala Pro Lys Gly Val Glu Cys Leu
            340                 345                 350

Ile Cys Arg Ala Glu Asn Leu His Pro Phe Val Gln Glu Glu Leu Met
            355                 360                 365

Met Pro Ile Leu Ala Ile Val Lys Val Lys Asp Val Asp Glu Ala Ile
    370                 375                 380

Asn Thr Ala Val Leu Asp Glu His Gly Asn Arg His Thr Ala Met Met
385                 390                 395                 400

His Ser Lys Asn Ile Asp Asn Leu Thr Lys Met Ser Arg Leu Ile Asp
                405                 410                 415

Thr Thr Ile Phe Val Lys Asn Ala Pro Ser Tyr Ala Gly Ile Gly Phe
                420                 425                 430

Gly Gly Glu Gly Trp Thr Thr Phe Thr Ile Ala Gly Pro Thr Gly Glu
            435                 440                 445

Gly Ile Thr Asn Ala Thr Ser Phe Thr Arg Gln Arg Arg Cys Thr Met
    450                 455                 460

Val Asp Ser Phe Arg Ile Ile
465                 470
```

```
<210> SEQ ID NO 62
<211> LENGTH: 483
<212> TYPE: PRT
<213> ORGANISM: bacterium MS4
```

-continued

```
<400> SEQUENCE: 62

Met Asp Ile Asp Ala Asn Leu Ile Glu Lys Met Val Lys Gln Val Leu
1               5                   10                  15

Asn Glu Ile Asp Ala Gly Lys Ala Glu Lys Thr Ala Ala Glu Ile
            20                  25                  30

Lys Lys Glu Glu Lys Gly Gly Ala Tyr Gly Ile Phe Asn Thr Met Glu
        35                  40                  45

Glu Ala Ile Asp Ala Cys Asp Ile Ala Gln Lys Gln Tyr Leu Phe Cys
    50                  55                  60

Ser Met Ala Glu Arg Gln Lys Tyr Val Gln Thr Leu Arg Asp Val Val
65                  70                  75                  80

Leu Lys Gln Glu Asn Leu Glu Leu Ile Ser Arg Leu Ala Val Glu Glu
                85                  90                  95

Thr Gly Met Gly Asn Tyr Pro His Lys Leu Ile Lys Asn Arg Leu Ala
            100                 105                 110

Ala Glu Lys Ser Pro Gly Ile Glu Asp Leu Glu Thr Thr Ala Leu Ser
            115                 120                 125

Gly Asp Asp Gly Leu Thr Leu Val Glu Tyr Cys Pro Phe Gly Val Ile
        130                 135                 140

Gly Ala Ile Thr Pro Ala Thr Asn Pro Thr Glu Thr Ile Ile Cys Asn
145                 150                 155                 160

Ser Ile Gly Met Leu Ala Ala Gly Asn Ser Ile Val Phe Ser Pro His
            165                 170                 175

Pro Arg Ala Lys Asp Val Thr Ile Arg Leu Val Thr Met Ile Asn Arg
            180                 185                 190

Ala Leu Glu Glu Thr Gly Ala Pro Lys Asn Leu Ile Val Thr Val Met
        195                 200                 205

Glu Pro Ser Ile Glu Asn Thr Asn Val Met Met Lys His Pro Lys Ile
    210                 215                 220

Arg Met Leu Val Ala Thr Gly Gly Pro Gly Ile Val Lys Leu Val Met
225                 230                 235                 240

Ser Thr Gly Lys Lys Ala Ile Gly Ala Gly Ala Gly Asn Pro Pro Val
            245                 250                 255

Val Val Asp Glu Thr Ala Asp Ile Lys Lys Ala Ala Ile Asp Ile Val
            260                 265                 270

Asn Gly Cys Ser Phe Asp Asn Asn Leu Pro Cys Ile Ala Glu Lys Glu
            275                 280                 285

Val Ile Ala Val Asp Arg Ile Thr Asp Glu Leu Ile Arg Ser Met Arg
    290                 295                 300

Glu Asn Gly Ala Tyr Gln Val Thr Asp Pro Ala Val Ile Gln Lys Leu
305                 310                 315                 320

Ala Asp Leu Val Arg Lys Glu Gly Gly Gly Pro Lys Thr Ser Phe Val
            325                 330                 335

Gly Lys Ser Ala Ile Tyr Ile Leu Asp Lys Ile Gly Ile Gln Ala Gly
            340                 345                 350

Pro Glu Val Lys Val Ile Ile Met Glu Thr Pro Lys Asp His Pro Phe
            355                 360                 365

Val Met Glu Glu Leu Met Met Pro Ile Leu Pro Ile Val Arg Thr Arg
    370                 375                 380

Asn Val Asp Glu Ala Ile Asp Leu Ala Leu Ile Ala Glu Arg Gly Asn
385                 390                 395                 400

Arg His Thr Ala Met Met His Ser Lys Asn Val Asp Lys Leu Thr Lys
            405                 410                 415
```

```
Met Ala Lys Leu Leu Gln Thr Thr Ile Phe Val Lys Asn Ala Pro Ser
            420             425             430

Tyr Ala Gly Ile Gly Val Gly Gly Glu Gly His Thr Thr Phe Thr Ile
            435             440             445

Ala Gly Pro Thr Gly Glu Gly Leu Thr Ser Ala Lys Ser Phe Cys Arg
        450             455             460

Lys Arg Arg Cys Val Leu Ser Asp Ala Phe His Ile Arg Asp Phe Ser
465             470             475             480

Lys Gly Leu
```

<210> SEQ ID NO 63
<211> LENGTH: 462
<212> TYPE: PRT
<213> ORGANISM: Clostridium glycyrrhizinilyticum

<400> SEQUENCE: 63

```
Val Ser Val Asn Glu Gln Met Val Gln Asp Ile Val Gln Glu Val Met
1               5               10              15

Ala Lys Met Gln Ile Thr Ser Asp Val Ser Gly Ser His Gly Val Phe
            20              25              30

Lys Asp Met Asn Glu Ala Ile Ala Ala Ala Lys Lys Thr Gln Lys Ile
        35              40              45

Val Gly Lys Met Ser Met Asp Gln Arg Glu Lys Ile Ile Ser Asn Ile
    50              55              60

Arg Thr Lys Ile Lys Glu Asn Ala Glu Ile Met Ala Arg Met Gly Val
65              70              75              80

Gln Glu Thr Gly Met Gly Asn Val Gly His Lys Ile Leu Lys His Val
            85              90              95

Leu Val Ala Glu Lys Thr Pro Gly Thr Glu Asp Ile Thr Thr Thr Ala
            100             105             110

Trp Ser Gly Asp Arg Gly Leu Thr Leu Ile Glu Met Gly Pro Phe Gly
            115             120             125

Val Ile Gly Ala Ile Thr Pro Cys Thr Asn Pro Ser Glu Thr Val Leu
    130             135             140

Cys Asn Thr Ile Gly Met Leu Ala Gly Gly Asn Thr Val Val Phe Asn
145             150             155             160

Pro His Pro Ala Ala Ile Lys Thr Ser Ile Phe Ala Ile Asn Leu Leu
            165             170             175

Asn Glu Ala Ser Leu Glu Ala Gly Gly Pro Asp Asn Ile Ala Cys Thr
            180             185             190

Val Glu Lys Pro Thr Leu Ala Ser Ser Asp Ile Met Met Lys His Lys
            195             200             205

Asp Ile Pro Leu Ile Ala Ala Thr Gly Gly Pro Gly Val Val Thr Ala
    210             215             220

Val Leu Ser Ser Gly Lys Arg Gly Ile Gly Ala Gly Ala Gly Asn Pro
225             230             235             240

Pro Ala Leu Val Asp Glu Thr Ala Asp Ile Arg Lys Ala Ala Glu Asp
            245             250             255

Ile Val Asn Gly Cys Thr Phe Asp Asn Asn Leu Pro Cys Ile Ala Glu
            260             265             270

Lys Glu Ile Val Ala Val Asp Ser Ile Ala Asp Glu Leu Met Tyr Tyr
            275             280             285

Met Val Ser Glu Gln Gly Cys Tyr Lys Ile Thr Lys Glu Glu Gln Asp
    290             295             300
```

-continued

```
Ala Leu Thr Ala Val Val Leu Lys Asp Gly Lys Leu Asn Arg Lys Cys
305                 310                 315                 320

Val Gly Arg Asp Ala Lys Thr Leu Leu Gly Met Ile Gly Val Thr Val
                325                 330                 335

Pro Asp Asn Ile Arg Cys Ile Thr Phe Glu Gly Pro Lys Glu His Pro
            340                 345                 350

Leu Ile Ala Glu Glu Leu Met Met Pro Ile Leu Gly Val Val Arg Ala
            355                 360                 365

Lys Asp Phe Asp Asp Ala Val Glu Gln Ala Val Trp Leu Glu His Gly
        370                 375                 380

Asn Arg His Ser Ala His Ile His Ser Lys Asn Val Asp Asn Ile Thr
385                 390                 395                 400

Thr Tyr Ala Lys Ala Ile Asp Thr Ala Ile Leu Val Lys Asn Gly Pro
                405                 410                 415

Ser Tyr Ala Ala Leu Gly Phe Gly Gly Glu Gly Tyr Cys Thr Phe Thr
            420                 425                 430

Ile Ala Ser Arg Thr Gly Glu Gly Leu Thr Ser Ala Ser Thr Phe Thr
            435                 440                 445

Lys Arg Arg Arg Cys Val Met Thr Asp Ser Leu Cys Ile Arg
    450                 455                 460
```

<210> SEQ ID NO 64

<400> SEQUENCE: 64

000

<210> SEQ ID NO 65
<211> LENGTH: 482
<212> TYPE: PRT
<213> ORGANISM: Thermincola ferriacetica

<400> SEQUENCE: 65

```
Met Ala Ile Glu Ala Tyr Gln Ile Glu Lys Ile Val Glu Glu Val Met
1               5                   10                  15

Lys Lys Met Val Ser Gly Gly Ser Gly Asp Ser Phe Ala Gly Lys Ala
            20                  25                  30

Lys Gly Ile Phe Glu Ser Val Asp Glu Ala Val Lys Ala Ala Lys Ala
        35                  40                  45

Ala Gln Lys Glu Leu Val Ala Met Arg Ile Glu Lys Arg Glu Met Leu
    50                  55                  60

Leu Lys Ala Met Arg Glu Ala Ala Ile Ala His Ala Glu Glu Leu Ala
65                  70                  75                  80

Arg Leu Ala Val Glu Glu Thr Gly Met Gly Arg Val Thr Asp Lys Ile
                85                  90                  95

Ile Lys Asn Arg Val Ala Ala Glu Lys Thr Pro Gly Thr Glu Asn Leu
            100                 105                 110

Gln Pro Ser Ala Val Thr Gly Asp Arg Gly Leu Thr Leu Ile Glu Arg
        115                 120                 125

Ala Pro Tyr Gly Val Ile Gly Ala Ile Thr Pro Ser Thr Asn Pro Cys
    130                 135                 140

Ala Thr Val Ile Asn Asn Ser Ile Ser Met Val Ala Ala Gly Asn Ser
145                 150                 155                 160

Val Val Phe Ser Val His Pro Gly Ala Lys Lys Ala Ser Leu Leu Thr
                165                 170                 175
```

-continued

```
Val Glu Ile Leu Asn Glu Ala Ile Glu Lys Ala Gly Gly Pro Ala Asn
            180             185             190

Val Leu Thr Ala Val Ala Ser Pro Ser Leu Glu Asn Thr Asn Ala Leu
            195             200             205

Met Lys His Pro Asp Ile Lys Leu Leu Val Ala Thr Gly Gly Pro Gly
            210             215             220

Leu Val Lys Ala Val Leu Ser Ser Gly Lys Lys Ala Ile Gly Ala Gly
225             230             235             240

Ala Gly Asn Pro Pro Ala Leu Val Asp Glu Thr Ala Asp Leu Glu Arg
                245             250             255

Ala Ala Lys Ser Ile Val Ala Gly Ala Ser Phe Asp Asn Asn Leu Pro
            260             265             270

Cys Ile Ala Glu Lys Glu Val Ile Val Val Asp Tyr Val Ala Asn Gln
            275             280             285

Leu Ile Ser Tyr Met Lys Gln Asn Gly Ala Tyr Leu Ala Asn Asp Arg
            290             295             300

Glu Ile Lys Ala Leu Met Asp Leu Val Leu Thr Lys Asn Glu Asn Leu
305             310             315             320

Lys Ala Glu Gly Cys Thr Val Lys Pro Glu Lys Leu Tyr Gly Gly Ile
                325             330             335

Asn Lys Glu Tyr Val Gly Lys Asp Ala Ala Tyr Ile Met Lys Lys Ile
                340             345             350

Gly Val Asp Ile Pro Glu Asp Thr Lys Leu Ile Ile Cys Glu Val Asp
                355             360             365

Glu Asp His Pro Phe Val Leu Glu Glu Leu Met Met Pro Ile Leu Pro
            370             375             380

Ile Val Arg Val Pro Asn Val Gln Lys Ala Ile Glu Val Gly Val Arg
385             390             395             400

Val Glu His Gly Asn Arg His Thr Ala Val Met His Ser Gln Asn Ile
                405             410             415

Asp Asn Leu Ser Ala Phe Ala Arg Ala Ile Gln Thr Thr Ile Phe Val
            420             425             430

Lys Asn Gly Pro Ser Tyr Ala Gly Ile Gly Ile Gly Gly Glu Gly Tyr
            435             440             445

Thr Thr Phe Thr Ile Ala Gly Pro Thr Gly Glu Gly Leu Thr Ala Ala
            450             455             460

Ser Ser Phe Thr Arg Gln Arg Arg Cys Val Leu Val Asp Gly Phe Ser
465             470             475             480

Ile Val
```

```
<210> SEQ ID NO 66
<211> LENGTH: 461
<212> TYPE: PRT
<213> ORGANISM: Lachnospiraceae bacterium AC3007

<400> SEQUENCE: 66

Met Asn Glu Lys Leu Val Gln Glu Ile Val Arg Arg Val Met Ala Asp
1               5               10              15

Ile Asn Asp Glu Gly Gly Ala Asp Gly Met His Gly Val Phe Ser Asp
                20              25              30

Met Asn Asp Ala Ile Glu His Ala Leu Lys Ala Gln Glu Lys Val Arg
            35              40              45

Val Met Thr Leu Asp Gln Arg Glu Lys Ile Ile Ser Ala Ile Arg Arg
            50              55              60
```

-continued

Lys Thr Asn Glu Asn Val Glu Thr Ile Ala Arg Met Gly Val Glu Glu
65                  70                      75                  80

Thr Gly Met Gly Asn Val Gly Asp Lys Ile Leu Lys His Lys Leu Thr
                85                  90                  95

Ala Asp Lys Thr Pro Gly Thr Glu Asp Ile Thr Thr Thr Ala Trp Ser
            100                 105                 110

Gly Asp Arg Gly Leu Thr Leu Val Glu Met Gly Pro Phe Gly Val Ile
            115                 120                 125

Gly Ala Ile Thr Pro Ala Thr Asn Pro Ser Glu Thr Val Ile Cys Asn
            130                 135                 140

Ser Ile Gly Met Ile Ala Gly Gly Asn Thr Val Val Phe Asn Pro His
145                 150                 155                 160

Pro Asn Ala Lys Lys Thr Thr Ile Tyr Thr Ile Asn Met Ile Asn Glu
                165                 170                 175

Ala Ser Leu Glu Ala Gly Gly Pro Asp Asn Ile Ala Cys Thr Val Gln
            180                 185                 190

Glu Pro Thr Met Glu Thr Ser Ala Ile Met Met Lys His Pro Lys Ile
            195                 200                 205

Pro Leu Leu Val Ala Thr Gly Gly Pro Gly Val Val Thr Ala Val Leu
            210                 215                 220

Ser Ser Gly Lys Arg Ala Ile Gly Ala Gly Ala Gly Asn Pro Pro Ala
225                 230                 235                 240

Leu Val Asp Glu Thr Ala Asp Ile Glu Lys Ala Ala Arg Asp Ile Ile
                245                 250                 255

Asn Gly Cys Thr Phe Asp Asn Asn Leu Pro Cys Ile Ala Glu Lys Glu
            260                 265                 270

Val Val Ala Val Asp Ala Ile Phe Asp Glu Leu Met Arg His Phe Glu
            275                 280                 285

Glu Glu Asn Gly Cys Tyr Arg Ala Ser Arg Glu Ile Gln Asp Lys Leu
            290                 295                 300

Ile Ala Thr Val Ile Thr Pro Lys Gly Ala Leu Asn Arg Lys Cys Val
305                 310                 315                 320

Gly Arg Asp Ala Lys Thr Leu Leu Lys Met Val Gly Val Asp Ala Pro
                325                 330                 335

Ala Asp Thr Arg Cys Ile Ile Phe Glu Gly Glu Lys Glu His Pro Leu
            340                 345                 350

Ile Ala Thr Glu Leu Met Met Pro Ile Leu Gly Val Val Arg Val Lys
            355                 360                 365

Asp Phe Arg Glu Gly Val Glu Thr Ala Val Trp Leu Glu His Gly Asn
    370                 375                 380

Arg His Ser Ala His Ile His Ser Lys Asn Val Asp Arg Ile Thr Glu
385                 390                 395                 400

Tyr Ala Arg Ala Leu Asp Thr Ala Ile Leu Val Lys Asn Gly Pro Ser
                405                 410                 415

Tyr Ala Ala Leu Gly Phe Gly Gly Glu Gly Tyr Pro Thr Phe Thr Ile
            420                 425                 430

Ala Ser Arg Thr Gly Glu Gly Leu Thr Ser Ala Ser Thr Phe Thr Lys
            435                 440                 445

Arg Arg Arg Cys Val Met Thr Asp Ser Leu Cys Ile Arg
    450                 455                 460

<210> SEQ ID NO 67
<211> LENGTH: 471
<212> TYPE: PRT

-continued

```
<213> ORGANISM: Eubacterium sp. 14-2

<400> SEQUENCE: 67

Met Asn Ile Asp Glu Arg Val Val Ala Ser Ile Val Asn Ala Val Leu
1               5                   10                  15

Gly Arg Leu Asp Asp Val Ser Ser Pro Ala Ala Glu Ala Gly Gly Gly
            20                  25                  30

Asn Trp Gly Ile Phe Glu Ser Met Asn Asp Ala Val Glu Ala Ala Ala
        35                  40                  45

Ala Ala Gln Lys Lys Tyr Ile Asn Cys Thr Met His Asp Arg Ala Ala
    50                  55                  60

Tyr Val Gln Ala Ile Arg Asp Val Val Leu Lys Gln Glu Asn Leu Glu
65                  70                  75                  80

Tyr Ile Ser Arg Gln Ser Ala Glu Glu Thr Gly Met Gly Asn Tyr Glu
                85                  90                  95

His Lys Leu Ile Lys Asn Arg Leu Ala Ala Thr Lys Thr Pro Gly Thr
            100                 105                 110

Glu Asp Leu Thr Thr Asp Ala Met Ser Gly Asp Asp Gly Leu Thr Leu
            115                 120                 125

Val Glu Tyr Ser Pro Phe Gly Val Ile Gly Ala Ile Thr Pro Thr Thr
    130                 135                 140

Asn Pro Thr Glu Thr Ile Ile Cys Asn Ser Ile Gly Met Leu Ala Ala
145                 150                 155                 160

Gly Asn Ser Val Val Phe Ser Pro His Pro Arg Ala Lys Asn Val Ser
                165                 170                 175

Leu His Leu Ile Arg Leu Ile Asn Arg Ala Leu Ala Glu Ala Gly Ala
            180                 185                 190

Pro Ala Asn Leu Val Val Thr Val Ser Gln Pro Ser Ile Glu Asn Thr
            195                 200                 205

Asn Ala Met Met Ser His Pro Met Val Arg Met Leu Val Ala Thr Gly
    210                 215                 220

Gly Pro Gly Ile Val Lys Thr Val Leu Ser Ser Gly Lys Lys Ala Ile
225                 230                 235                 240

Gly Ala Gly Ala Gly Asn Pro Pro Val Val Val Asp Glu Thr Ala Asn
                245                 250                 255

Ile Glu Lys Ala Gly Lys Asp Ile Ile Asp Gly Cys Cys Phe Asp Asn
            260                 265                 270

Asn Leu Pro Cys Ile Ala Glu Lys Glu Val Ile Val Val Asp Ser Ala
            275                 280                 285

Ala Asp Tyr Leu Ile Phe Asn Met Lys Lys Asn Gly Ala Tyr Glu Val
    290                 295                 300

Lys Asp Pro Glu Ile Ile Asp Arg Ile Val Lys Leu Val Val Gln Glu
305                 310                 315                 320

Asn Gly Lys Ser Pro Val Thr Ser Phe Val Gly Lys Ser Ala Lys Tyr
                325                 330                 335

Ile Leu Glu Gln Ala Gly Val His Val Asp Asp Asp Val Arg Val Ile
            340                 345                 350

Ile Ala Gln Thr Gly Glu Asp His Pro Phe Val Gln Val Glu Leu Met
            355                 360                 365

Met Pro Ile Leu Pro Ile Val Arg Val Pro Asp Val Asp Ala Gly Ile
    370                 375                 380

Glu Met Ala Val Arg Val Glu His Gly Asn Arg His Thr Ala Met Met
385                 390                 395                 400
```

His Ser Arg Asn Val Asp Lys Leu Thr Lys Met Ala Lys Leu Ile Gln
              405             410             415

Thr Thr Ile Phe Val Lys Asn Gly Pro Ser Tyr Ala Gly Ile Gly Val
              420             425             430

Gly Gly Glu Gly Tyr Thr Thr Phe Thr Ile Ala Gly Pro Thr Gly Glu
          435             440             445

Gly Leu Thr Ser Ala Lys Ser Phe Ala Arg Arg Arg Cys Val Leu
      450             455             460

Val Gly Gly Met Asp Val Arg
465             470

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74
<211> LENGTH: 469
<212> TYPE: PRT
<213> ORGANISM: Anaerosalibacter massiliensis

<400> SEQUENCE: 74

Met Glu Leu Asp Lys Met Asp Leu Glu Gln Ile Val Asn Leu Val Val
1               5                   10                  15

Glu Gln Leu Lys Gly Glu Asp Thr Ser Ser Tyr Cys Lys Glu Glu Ser
              20                  25                  30

Lys Asn Gly Val Phe Asn Asn Met Asn Glu Ala Ile Glu Lys Ala Tyr
          35                  40                  45

Ile Ala Gln Lys Asp Phe Phe Lys Asn Tyr Asn Leu Glu Asp Arg Arg
      50                  55                  60

Arg Ile Ile Lys Thr Ile Arg Lys Glu Leu Met Glu Asp Val Glu Leu
65                  70                  75                  80

-continued

```
Leu Ala Lys Leu Gly Val Glu Asp Thr Gly Met Gly Arg Tyr Glu Asp
                85                  90                  95

Lys Leu Lys Lys Asn Lys Leu Val Ile Glu Lys Thr Pro Gly Val Glu
                100                 105                 110

Asp Leu Asn Ser Glu Val Phe Thr Gly Asp Asn Gly Leu Thr Leu Val
                115                 120                 125

Glu Leu Ser Pro Tyr Gly Val Ile Gly Ala Ile Ala Pro Ser Thr Asn
            130                 135                 140

Pro Ser Glu Thr Val Ile Cys Asn Ser Ile Gly Met Ile Ala Ala Gly
145                 150                 155                 160

Asn Ser Val Val Phe Ser Pro His Pro Gly Ala Lys Asn Ile Ser Met
                165                 170                 175

Lys Thr Val Glu Leu Ile Asn Lys Ala Ile Glu Lys Ala Gly Gly Pro
                180                 185                 190

Lys Asn Leu Val Val Thr Thr Ser Asn Pro Ser Ile Glu Asn Ala Glu
            195                 200                 205

Ile Met Met Lys His Glu Lys Ile Lys Met Ile Val Ala Thr Gly Gly
        210                 215                 220

Pro Gly Val Val Lys Ser Ala Leu Ser Gln Gly Lys Lys Ala Ile Gly
225                 230                 235                 240

Ala Gly Ala Gly Asn Pro Pro Ala Val Ile Asp Glu Thr Ala Asp Ile
                245                 250                 255

Glu Lys Ala Ala Arg Asp Ile Ile Ala Gly Cys Ser Phe Asp Asn Asn
            260                 265                 270

Leu Pro Cys Ile Ala Glu Lys Glu Val Ile Val Val Asp Ser Val Ala
            275                 280                 285

Asp Tyr Leu Ile Phe Ser Met Asn Lys Asn Asn Val Tyr His Leu Lys
        290                 295                 300

Asp Glu Glu Lys Ile Asp Lys Leu Ala Ser Met Val Ile Asp Lys Asn
305                 310                 315                 320

Gly Arg Ile Asn Arg Lys Phe Val Gly Lys Asp Ala Lys Val Ile Leu
                325                 330                 335

Lys Ala Val Asp Ile Glu Cys Glu His Asp Val Arg Ala Ile Ile Val
            340                 345                 350

Glu Thr Glu Lys Asp His Pro Phe Val Val Thr Glu Leu Met Met Pro
        355                 360                 365

Ile Leu Pro Ile Val Arg Val Lys Asp Ile Asp Glu Ala Ile Lys Leu
    370                 375                 380

Ala Val Glu Val Glu Gln Gly Asn Arg His Thr Ala Ile Met His Ser
385                 390                 395                 400

Lys Asn Val Asp Asn Leu Ser Arg Phe Ala Arg Glu Ile Glu Thr Thr
                405                 410                 415

Ile Phe Val Lys Asn Ala Pro Ser Phe Ala Gly Leu Gly Phe Gly Gly
                420                 425                 430

Glu Gly Tyr Pro Thr Phe Thr Ile Ala Gly Pro Thr Gly Glu Gly Leu
            435                 440                 445

Thr Ser Ala Arg Ser Phe Ala Arg Lys Arg Arg Cys Ser Leu Val Gly
    450                 455                 460

Ser Phe Ser Ile Lys
465
```

<210> SEQ ID NO 75
<211> LENGTH: 473

-continued

```
<212> TYPE: PRT
<213> ORGANISM: Clostridium indolis DSM 755

<400> SEQUENCE: 75

Met Glu Ile Gly Ala Lys Glu Ile Glu Leu Ile Val Arg Glu Val Leu
1               5                   10                  15

Ala Gly Ile Glu Ser Arg Gly Ile Lys Pro Ser Tyr Thr Pro Ser Arg
            20                  25                  30

Ser Glu Asp Gly Val Phe Glu Arg Val Glu Asp Ala Ile Glu Ala Ala
        35                  40                  45

Tyr Ala Ala Gln Arg Glu Trp Val Glu His Tyr Arg Val Glu Asp Arg
    50                  55                  60

Arg Arg Ile Ile Glu Ala Ile Arg Val Thr Ala Lys Ser His Ala Glu
65                  70                  75                  80

Ser Leu Ala Lys Met Val Trp Glu Glu Thr Gly Met Gly Arg Phe Glu
                85                  90                  95

Asp Lys Ile Gln Lys His Met Ala Val Ile Glu Lys Thr Pro Gly Val
            100                 105                 110

Glu Cys Leu Thr Thr Glu Ala Ile Ser Gly Asp Gly Gly Leu Met Ile
            115                 120                 125

Glu Glu Tyr Ala Pro Phe Gly Val Ile Gly Ala Ile Thr Pro Ser Thr
        130                 135                 140

Asn Pro Thr Glu Thr Ile Ile Asn Asn Thr Ile Ser Met Ile Ala Gly
145                 150                 155                 160

Gly Asn Ser Val Val Phe Asn Val His Pro Gly Ala Lys Arg Cys Cys
                165                 170                 175

Ala His Cys Leu Lys Ile Leu His Gln Ala Ile Val Glu Asn Gly Gly
            180                 185                 190

Pro Ala Ser Leu Ile Thr Met Gln Lys Glu Pro Asp Met Glu Ala Val
            195                 200                 205

Ser Lys Leu Thr Ser Asp Pro Arg Ile Arg Leu Met Val Gly Thr Gly
        210                 215                 220

Gly Met Pro Met Val Asn Ala Leu Leu Arg Ser Gly Lys Lys Thr Ile
225                 230                 235                 240

Gly Ala Gly Ala Gly Asn Pro Pro Val Ile Val Asp Asp Thr Ala Asp
                245                 250                 255

Val Ser Leu Ala Ala Arg Glu Ile Tyr Arg Gly Ala Ser Phe Asp Asn
            260                 265                 270

Asn Ile Leu Cys Leu Ala Glu Lys Glu Val Phe Val Met Glu Arg Ala
            275                 280                 285

Ala Asp Glu Leu Val Asn Lys Leu Ile Lys Glu Gly Ala Tyr Leu Leu
        290                 295                 300

Ser Ser Leu Glu Leu Ser Glu Ile Leu Lys Phe Ala Met Val Glu Lys
305                 310                 315                 320

Asn Gly Ser Tyr Glu Val Asn Lys Lys Trp Val Gly Lys Asp Ala Gly
                325                 330                 335

Gln Phe Leu Glu Ala Ile Gly Val Ser Gly His Lys Asp Val Arg Leu
            340                 345                 350

Leu Ile Cys Glu Thr Asp Arg Ser His Pro Phe Val Met Val Glu Gln
            355                 360                 365

Leu Met Pro Ile Leu Pro Ile Val Arg Leu Arg Thr Phe Glu Glu Cys
        370                 375                 380

Val Glu Ser Ala Leu Ala Ala Glu Ser Gly Asn Arg His Thr Ala Ser
385                 390                 395                 400
```

-continued

```
Met Phe Ser Arg Asn Val Glu Asn Met Thr Lys Phe Gly Lys Ile Ile
                405                 410                 415

Glu Thr Thr Ile Phe Thr Lys Asn Gly Ser Thr Leu Lys Gly Val Gly
                420                 425                 430

Ile Gly Gly Glu Gly His Thr Thr Met Thr Ile Ala Gly Pro Thr Gly
                435                 440                 445

Glu Gly Leu Thr Cys Ala Arg Ser Phe Thr Arg Arg Arg Cys Met
    450                 455                 460

Leu Ala Glu Gly Gly Leu Arg Ile Ile
465                 470

<210> SEQ ID NO 76

<400> SEQUENCE: 76

000

<210> SEQ ID NO 77
<211> LENGTH: 467
<212> TYPE: PRT
<213> ORGANISM: Catabacter hongkongensis

<400> SEQUENCE: 77

Met Gly Leu Ser Glu Gln Gln Ile Lys Gln Ile Val Glu Glu Thr Val
1                 5                  10                  15

Arg Asn Ile Gly Thr Gly Thr Ala Gly Ala Ala Cys Ser Gly Ser Trp
                20                  25                  30

Met Cys Asp Asp Ala Asn Asp Ala Val Glu Asn Ala Lys Arg Ala Gln
                35                  40                  45

Lys Gln Leu Met Thr Met Thr Leu Glu Gln Arg Gly Arg Leu Val Ser
    50                  55                  60

Ala Met Arg Glu Ala Ala Leu Ala Asn Ser Val Lys Leu Ala Glu Met
65                  70                  75                  80

Ala His Glu Glu Thr Gly Tyr Gly Ser Val Glu His Lys Ile Met Lys
                85                  90                  95

Asn Glu Leu Ala Ala Lys Lys Thr Pro Gly Ile Glu Asp Leu His Thr
                100                 105                 110

Gln Ala Phe Ser Gly Asp Asp Gly Leu Thr Ile Val Glu Gln Ala Pro
                115                 120                 125

Phe Gly Val Ile Gly Ser Ile Thr Pro Ser Thr Asn Pro Thr Ser Thr
    130                 135                 140

Val Ile Asn Asn Ser Ile Ser Met Val Ala Ala Gly Asn Ala Val Val
145                 150                 155                 160

Tyr Asn Pro His Pro Ala Ala Lys Arg Ala Ser Gln Glu Ala Met Arg
                165                 170                 175

Ile Leu Asn Glu Ala Ile Val Ser Ala Gly Gly Pro Ala Thr Leu Ile
                180                 185                 190

Thr Thr Val Lys Glu Pro Thr Leu Glu Ser Gly Gln Val Ile Met Asn
                195                 200                 205

His Arg Asp Ile Lys Met Leu Ser Ile Thr Gly Gly Glu Ala Val Val
    210                 215                 220

Ala Val Ala Met Lys Thr Gly Lys Lys Val Val Ala Ala Gly Pro Gly
225                 230                 235                 240

Asn Pro Pro Val Ile Val Asp Asp Thr Ala Val Ile Pro Lys Ala Ala
                245                 250                 255
```

```
Lys Asp Ile Val Asp Gly Ala Ser Phe Asp Asn Asn Val Leu Cys Val
            260             265             270

Ala Glu Lys Glu Val Phe Ala Phe Asp Asn Ile Thr Asp Gln Leu Met
            275             280             285

Ser Glu Met Glu Lys Asn Gly Ala Tyr Arg Val Ser Gly Glu Asp Ile
            290             295             300

Asn Lys Ile Val Asn Thr Val Leu Val Leu Lys Asp Gly His Tyr Val
305             310             315             320

Ile Asn Arg Lys Phe Val Gly Arg Asp Ala Thr Tyr Ile Met Gln Glu
                325             330             335

Ser Gly Val Ser Tyr Thr Gly Asn Pro Arg Leu Val Ile Ala Glu Val
            340             345             350

Ser Ala Asn His Pro Phe Val Thr Val Glu Met Leu Met Pro Val Leu
            355             360             365

Gly Val Val Arg Val Arg Asn Ile Asp Glu Ala Val Asp Glu Ala Phe
            370             375             380

Arg Ala Glu Arg Gly Cys Gln His Ser Ala Leu Ile His Ser Thr Asn
385             390             395             400

Ile Arg Asn Met Ser Lys Ala Ala Ser Thr Met Asn Thr Thr Ile Phe
                405             410             415

Val Lys Asn Ala Pro Ser Tyr Ser Gly Leu Gly Phe Gly Gly Glu Gly
            420             425             430

Tyr Ala Thr Leu Thr Ile Ala Thr Pro Thr Gly Glu Gly Leu Thr Ser
            435             440             445

Ala Lys Thr Phe Thr Arg Ala Arg Arg Cys Val Leu Lys Gly Asp Leu
            450             455             460

Arg Ile Ile
465

<210> SEQ ID NO 78

<400> SEQUENCE: 78

000

<210> SEQ ID NO 79

<400> SEQUENCE: 79

000

<210> SEQ ID NO 80
<211> LENGTH: 463
<212> TYPE: PRT
<213> ORGANISM: Bacillus thermotolerans

<400> SEQUENCE: 80

Met Ala Val Gln Glu Arg Asp Leu Glu Ser Ile Val Lys Lys Val Leu
1               5               10              15

Glu Glu Leu Ser Arg Lys Glu Glu Thr Pro Glu Ala Gly Gln Gly Val
            20              25              30

Phe Glu Asp Met Asn Asp Ala Ile Glu Ala Ala Glu Gln Ala Gln Lys
            35              40              45

Glu Leu Ile Lys Leu Ser Leu Glu Glu Arg Gly Ala Ile Ile Glu Ala
    50              55              60

Ile Arg Glu Ala Ser Arg Lys His Val Glu Thr Phe Ala Arg Met Ala
65              70              75              80
```

-continued

```
Val Glu Glu Thr Gly Met Gly Asn Tyr Glu Asp Lys Val Arg Lys Asn
                85                  90                  95

Val Leu Val Ile Asp Lys Thr Pro Gly Ile Glu Asp Leu Lys Thr Glu
            100                 105                 110

Ala Val Ser Gly Asp Asn Gly Leu Thr Val Val Glu Leu Ser Pro Tyr
            115                 120                 125

Gly Val Ile Gly Ser Ile Thr Pro Thr Thr Asn Pro Thr Glu Thr Ile
        130                 135                 140

Ile Cys Asn Ser Ile Gly Met Ile Ala Ala Gly Asn Ser Val Val Phe
145                 150                 155                 160

Ser Pro His Pro Gly Ala Lys Asp Thr Ser Leu Lys Ala Val Glu Ile
                165                 170                 175

Ile Asn Gln Ala Ile Val Glu Ala Gly Gly Pro Lys Asn Leu Ile Thr
            180                 185                 190

Ser Ile Ala Glu Pro Ser Ile Asp Gln Ala Asn Ile Met Met Arg His
            195                 200                 205

Lys Lys Val Arg Met Leu Val Ala Thr Gly Gly Pro Gly Val Val Lys
        210                 215                 220

Ala Val Leu Thr Ser Gly Lys Lys Ala Ile Gly Ala Gly Ala Gly Asn
225                 230                 235                 240

Pro Pro Val Val Val Asp Glu Thr Ala Asp Leu Glu Lys Ala Ala Lys
            245                 250                 255

Asp Ile Val Asp Gly Cys Ser Phe Asp Asn Asn Ile Pro Cys Val Ala
            260                 265                 270

Glu Lys Glu Leu Phe Val Val Glu Ala Val Ala Asp Tyr Leu Val Phe
        275                 280                 285

His Met Lys Lys His Gly Ala Phe Gln Leu Asn Asp Pro Lys His Val
        290                 295                 300

Glu Lys Leu Thr Glu Leu Val Val Asp Asn Gly His Ala Asn Lys Glu
305                 310                 315                 320

Phe Val Gly Lys Asp Ile Gln Tyr Ile Leu Lys Gln Ile Gly Val Asp
                325                 330                 335

Ala Pro Gln Asp Ala Arg Ile Ala Ile Met Asp Val Gly Ala Asp His
            340                 345                 350

Pro Leu Val Ser Ala Glu Leu Met Met Pro Ile Leu Pro Val Val Arg
        355                 360                 365

Thr Ala Asn Val Asp Glu Ala Ile Glu Leu Ala Val Glu Ala Glu His
        370                 375                 380

Gly Phe Arg His Thr Ser Ile Met His Ser Lys Asn Ile Asp Asn Leu
385                 390                 395                 400

Thr Lys Phe Ala Lys Ala Ile Gln Thr Thr Ile Phe Val Lys Asn Gly
            405                 410                 415

Pro Ser Tyr Ala Gly Leu Gly Val Gly Gly Glu Gly Tyr Thr Ser Phe
            420                 425                 430

Thr Ile Ala Gly Pro Thr Gly Glu Gly Leu Thr Ser Ala Lys Asp Phe
            435                 440                 445

Ala Arg Lys Arg Lys Cys Val Leu Val Asp Ser Leu Ser Val Arg
    450                 455                 460
```

<210> SEQ ID NO 81

<400> SEQUENCE: 81

000

<210> SEQ ID NO 82
<211> LENGTH: 511
<212> TYPE: PRT
<213> ORGANISM: Gracilibacillus kekensis

<400> SEQUENCE: 82

Met Gln Leu Asn Glu Lys Asp Ile Gln Thr Ile Ile Asp Ser Val Leu
1               5                   10                  15

Lys Asn Val Glu Ala Ala Val Glu Asn Arg Gln Pro Thr Gln Ala Ser
            20                  25                  30

Gly Gln Ser Ser Glu Gln Gln Pro Ile Lys Met Lys Gln Leu Ser Pro
        35                  40                  45

Ser Ala Pro Ser Asn Thr Phe Asn Met Ser Ser Asn Lys Asp Gly Val
    50                  55                  60

Phe Glu Arg Val Thr Asp Ala Ile Glu Ala Ala Ser Lys Ala Gln Glu
65                  70                  75                  80

Val Trp Met Lys Gln Tyr Thr Leu Glu Glu Lys Glu Asn Leu Ile Asn
                85                  90                  95

Ser Ile Arg Gln Ala Val Ala Gln Gln Val Asn His Phe Ala Lys Ser
            100                 105                 110

Ala Leu Glu Glu Thr Gly Leu Gly Asn Tyr Glu Asp Lys Val Leu Lys
        115                 120                 125

Leu Ser Leu Thr Val Glu Lys Thr Pro Gly Thr Glu Leu Leu Gln Thr
    130                 135                 140

Glu Thr Phe Ser Gly Asp Asp Gly Leu Ser Phe Val Glu Gln Thr Pro
145                 150                 155                 160

Phe Gly Val Ile Gly Ala Val Thr Pro Val Thr Asn Pro Ile Asp Thr
                165                 170                 175

Ile Val Asn Asn Gly Ile Gly Met Ile Ala Ala Gly Asn Ala Val Val
            180                 185                 190

Phe Asn Val His Pro Ser Ala Lys Lys Thr Ser Arg Glu Met Ile Gln
            195                 200                 205

Leu Leu Asn Gln Thr Ile Val Asn Ala Gly Gly Pro Glu Asn Leu Leu
    210                 215                 220

Thr Met Val Gln Glu Pro Thr Ile Glu Thr Val Gln Glu Ile Ala Asn
225                 230                 235                 240

His Pro Ser Val Lys Leu Leu Val Gly Thr Gly Gly Pro Gly Met Val
                245                 250                 255

Lys Ser Leu Leu Lys Ser Gly Lys Lys Ala Ile Gly Ala Gly Ala Gly
            260                 265                 270

Asn Pro Pro Val Ile Val Asp Glu Thr Ala Asp Leu Lys Gln Ala Ala
        275                 280                 285

Lys Asp Ile Ile Glu Gly Ala Ser Phe Asp Asn Asn Leu Leu Cys Ile
    290                 295                 300

Ala Glu Lys Glu Val Phe Val Leu Asp Gln Val Ala Asp Asp Leu Ile
305                 310                 315                 320

Phe Glu Leu Leu Asn Gln Gln Val His Met Leu Asp His Gln Gln Leu
            325                 330                 335

Glu Lys Val Met Lys Leu Thr Leu Lys Glu Asn Thr Glu Gly Ile Pro
            340                 345                 350

Gly Gly Cys Ser Tyr Leu Ser Arg Asp Tyr Leu Val Ser Lys Asp Trp
        355                 360                 365

Val Gly Lys Asp Ala Thr Gln Ile Leu Glu Gln Ile Gly Val Ser Asn
    370                 375                 380

-continued

```
Val Gln Thr Lys Leu Leu Ile Cys Glu Val Asp Ala Glu His Pro Tyr
385                 390                 395                 400

Val Gln Leu Glu Gln Leu Met Pro Ile Leu Pro Ile Val Arg Val Lys
                405                 410                 415

Ser Val Asp Glu Ala Ile Glu Lys Ala Val Lys Ala Glu His Gly Asn
            420                 425                 430

Arg His Thr Ala Val Met His Ser Asn His Ile Lys Asn Val Thr Lys
            435                 440                 445

Phe Ala Lys Ala Ile Gly Thr Thr Ile Phe Val Asn Asn Gly Ser Ser
        450                 455                 460

Leu Ser Gly Val Gly Tyr Arg Gly Glu Gly Phe Thr Thr Met Thr Ile
465                 470                 475                 480

Ala Gly Pro Thr Gly Glu Gly Val Thr Ser Ala Arg Thr Phe Thr Arg
                485                 490                 495

Gln Arg Arg Thr Val Ile Ala Asn Gly Gly Phe Asn Ile Arg Gly
                500                 505                 510

<210> SEQ ID NO 83

<400> SEQUENCE: 83

000

<210> SEQ ID NO 84
<211> LENGTH: 479
<212> TYPE: PRT
<213> ORGANISM: Propionispora sp. 2/2-37

<400> SEQUENCE: 84

Met Ile Gln Glu Gln Glu Leu Ile Ala Lys Ile Thr Ala Gln Val Ile
1                   5                   10                  15

Ala Gln Met Gln Gln Gly Gln Ala Ala Ala Val Pro Glu His Tyr Gly
                20                  25                  30

Val Phe Asp Ser Ile Asp Gly Ala Val Ala Ala Ala Arg Lys Ala Tyr
            35                  40                  45

Gln Ser Leu Arg Ala Leu Pro Leu Glu Lys Arg Glu Gln Leu Val Gly
        50                  55                  60

Ala Met Arg Lys Thr Ala Tyr Asp His Ala Glu Ile Met Ala Glu Met
65                  70                  75                  80

Ala Val Thr Glu Ser Gly Met Gly Arg Tyr Ser Asp Lys Val Ile Lys
                85                  90                  95

Asn Arg Thr Ala Ala Leu Lys Thr Pro Gly Thr Glu Asp Leu Lys Thr
                100                 105                 110

Arg Ala Trp Ser Gly Asp Cys Gly Leu Thr Leu Val Glu Met Gly Pro
            115                 120                 125

Tyr Gly Val Ile Gly Ala Ile Thr Pro Thr Thr Asn Pro Thr Glu Thr
        130                 135                 140

Leu Ile Cys Asn Gly Ile Gly Met Ile Ala Ala Gly Asn Ala Val Phe
145                 150                 155                 160

Phe Ser Pro His Pro Thr Ala Lys Asn Thr Ser Ile Trp Thr Ile Gln
                165                 170                 175

Leu Leu Asn Lys Ala Leu Val Glu Ala Gly Gly Pro Pro Asn Leu Leu
                180                 185                 190

Thr Thr Val Tyr Asn Pro Ser Ile Ala Val Ala Asn Ala Met Met Lys
            195                 200                 205
```

```
His Pro Asp Val Asn Met Leu Val Ala Thr Gly Gly Pro Gly Val Val
    210             215                 220

Lys Ala Val Leu Ser Ser Gly Lys Lys Ala Ile Gly Ala Gly Ala Gly
225             230                 235                 240

Asn Pro Pro Ala Val Val Asp Glu Thr Ala Asp Leu Glu Lys Ala Ala
            245                 250                 255

Lys Asp Ile Val Ala Gly Cys Ser Phe Asp Asn Asn Leu Pro Cys Ile
            260                 265                 270

Ala Glu Lys Glu Val Ile Ala Val Gly Ser Ile Ala Asp Arg Leu Met
        275                 280                 285

Asp Tyr Met Val Arg Asn Gly Ala Tyr Lys Ile Thr Pro Gln Gln Thr
    290                 295                 300

Ala Glu Leu Val Asn Leu Leu Leu Thr Val Lys Glu Glu Lys Met Ala
305             310                 315                 320

Glu Gly Cys Thr Ala Lys Thr Lys Arg Thr Tyr Gly Ile Asn Lys Asp
            325                 330                 335

Tyr Val Gly Lys Ser Ala Gln Cys Ile Leu Ser Lys Ile Gly Val Thr
        340                 345                 350

Val Lys Asp Asp Ile Arg Val Ile Leu Cys Glu Ala Glu Ala Asp His
        355                 360                 365

Pro Phe Val Leu Glu Glu Leu Met Met Pro Val Leu Pro Val Val Gln
    370                 375                 380

Val Lys Asp Val Asp Ala Ala Ile Glu Leu Ala Val Arg Val Glu His
385             390                 395                 400

Gly Asn Arg His Thr Ala Val Met His Ser Lys Asn Val Asp His Leu
            405                 410                 415

Thr Arg Met Ala Arg Ala Ile Asp Thr Thr Ile Phe Val Lys Asn Ala
        420                 425                 430

Pro Ser Tyr Ala Gly Ile Gly Val Gly Gly Glu Gly Tyr Cys Thr Phe
        435                 440                 445

Thr Ile Ala Gly Pro Thr Gly Glu Gly Leu Thr Ser Pro Arg Ser Phe
    450                 455                 460

Thr Arg Ala Arg Arg Cys Val Leu Val Asp Gly Phe Ser Ile Val
465                 470                 475
```

```
<210> SEQ ID NO 85

<400> SEQUENCE: 85

000

<210> SEQ ID NO 86
<211> LENGTH: 478
<212> TYPE: PRT
<213> ORGANISM: Clostridium chauvoei

<400> SEQUENCE: 86

Val Phe Ser Asp Glu Lys Ser Ile Glu Glu Ile Val Ile Lys Val Leu
1               5                   10                  15

Glu Glu Ile His Thr Asp Arg Lys Thr Lys Cys Asn Lys Asn Cys Asn
            20                  25                  30

Ser Asn Cys Gly Cys Asn Lys Asp Lys Phe Ile Phe Ser Ser Val Asp
        35                  40                  45

Asp Ala Val Ala Ala Ala Lys Lys Ser Phe Phe Glu Leu Lys Lys Leu
    50                  55                  60

Thr Ile Arg Glu Arg Glu Glu Ile Ile Lys Asn Ile Arg Lys Lys Cys
```

-continued

```
65                    70                   75                   80

Leu Asp Tyr Ala Asp Lys Leu Ser Ile Met Ala Val Glu Glu Thr Gly
                85                   90                   95

Met Gly Lys Val Glu Asp Lys Val Thr Lys His Ile Leu Ile Ala Glu
                100                  105                  110

Lys Thr Pro Gly Thr Glu Asp Leu Lys Thr Thr Ala Trp Ser Gly Asp
            115                  120                  125

Gly Gly Leu Thr Leu Ile Glu Gln Gly Ala Phe Gly Val Ile Ala Ala
        130                  135                  140

Ile Thr Pro Ser Thr Asn Pro Thr Ala Thr Val Leu Cys Asn Ala Ile
145                  150                  155                  160

Gly Met Ile Ser Ala Gly Asn Thr Ile Val Phe Ala Pro His Pro Asn
                165                  170                  175

Ala Val Lys Cys Ser Asn Leu Ala Val Lys Leu Ile Asn Glu Ala Ser
                180                  185                  190

Lys Glu Ala Gly Gly Pro Glu Asn Ile Ala Val Ser Phe Arg Lys Pro
            195                  200                  205

Ser Ile Asp Ile Thr Thr Glu Leu Met Lys His Lys Asp Ile Ala Leu
    210                  215                  220

Ile Ser Ala Thr Gly Gly Pro Gly Val Val Asn Gln Ala Leu Ser Ser
225                  230                  235                  240

Gly Lys Arg Ala Leu Gly Ala Gly Ala Gly Asn Pro Pro Val Ile Val
                245                  250                  255

Asp Glu Thr Ala Asn Ile Glu Lys Ala Ala Lys Asp Ile Ile Asp Gly
                260                  265                  270

Ala Thr Phe Asp Asn Asn Leu Pro Cys Ile Ala Glu Lys Glu Val Ile
            275                  280                  285

Val Ile Asp Ser Val Ser Asn Lys Leu Ile Glu Tyr Met Ile Lys Phe
    290                  295                  300

Gly Ala Tyr Leu Leu Lys Asp Lys Glu Gln Ile Lys Arg Leu Glu Asp
305                  310                  315                  320

Lys Leu Leu Ile Lys Asn Gly Lys Lys Val Thr Leu Asn Arg Asp Phe
            325                  330                  335

Val Gly Lys Asp Ala Lys Val Ile Leu Asp Ser Ile Asp Ile Leu Val
            340                  345                  350

Asp Asp Ser Ile Lys Cys Ile Ile Phe Glu Gly Asp Lys Asp Ser Leu
            355                  360                  365

Leu Ile Lys Glu Glu Leu Met Met Pro Ile Leu Gly Ile Val Lys Val
    370                  375                  380

Asn Asn Phe Asp Glu Ala Val Glu Cys Ala Leu Glu Leu Glu His Gly
385                  390                  395                  400

Asn Arg His Ser Ala His Met His Ser Lys Asn Ile Asp Asn Leu Thr
                405                  410                  415

Thr Phe Ala Arg Val Ile Asp Thr Ala Ile Phe Val Lys Asn Ala Pro
            420                  425                  430

Ser Tyr Ser Ala Leu Gly Val Asn Ala Glu Gly Phe Ala Thr Phe Thr
        435                  440                  445

Ile Ala Ser Lys Thr Gly Glu Gly Leu Ser Ser Thr Lys Thr Phe Thr
    450                  455                  460

Lys Asn Arg Arg Cys Val Leu Ser Asp Gly Leu Ser Ile Arg
465                  470                  475
```

<210> SEQ ID NO 87

<211> LENGTH: 467
<212> TYPE: PRT
<213> ORGANISM: 10500A Thermoanaerobacterium aotearoense

<400> SEQUENCE: 87

Met Lys Val Lys Glu Glu Asp Ile Glu Ala Ile Val Lys Lys Val Leu
1               5                   10                  15

Ser Glu Phe Asn Phe Glu Lys Asn Thr Lys Ser Phe Arg Asp Phe Gly
                20                  25                  30

Val Phe Gln Asp Met Asn Asp Ala Ile Arg Ala Ala Lys Asp Ala Gln
            35                  40                  45

Lys Lys Leu Arg Asn Met Ser Met Glu Ser Arg Glu Lys Ile Ile Gln
        50                  55                  60

Asn Ile Arg Lys Lys Ile Met Glu Asn Lys Lys Ile Leu Ala Glu Met
65                  70                  75                  80

Gly Val Ser Glu Thr Gly Met Gly Lys Val Glu His Lys Ile Ile Lys
                85                  90                  95

His Glu Leu Val Ala Leu Lys Thr Pro Gly Thr Glu Asp Ile Val Thr
            100                 105                 110

Thr Ala Trp Ser Gly Asp Lys Gly Leu Thr Leu Val Glu Met Gly Pro
            115                 120                 125

Phe Gly Val Ile Gly Thr Ile Thr Pro Ser Thr Asn Pro Ser Glu Thr
        130                 135                 140

Val Leu Cys Asn Ser Ile Gly Met Ile Ala Ala Gly Asn Ser Val Val
145                 150                 155                 160

Phe Asn Pro His Pro Gly Ala Val Asn Val Ser Asn Tyr Ala Val Lys
                165                 170                 175

Leu Val Asn Glu Ala Val Met Glu Ala Gly Gly Pro Glu Asn Leu Val
            180                 185                 190

Ala Ser Val Glu Lys Pro Thr Leu Glu Thr Gly Asn Ile Met Phe Lys
        195                 200                 205

Ser Pro Asp Val Ser Leu Leu Val Ala Thr Gly Gly Pro Gly Val Val
        210                 215                 220

Thr Ser Val Leu Ser Ser Gly Lys Arg Ala Ile Gly Ala Gly Ala Gly
225                 230                 235                 240

Asn Pro Pro Val Val Val Asp Glu Thr Ala Asp Ile Lys Lys Ala Ala
                245                 250                 255

Lys Asp Ile Val Asp Gly Ala Thr Phe Asp Asn Asn Leu Pro Cys Ile
            260                 265                 270

Ala Glu Lys Glu Val Val Ser Val Asp Lys Ile Thr Asp Glu Leu Ile
        275                 280                 285

Tyr Tyr Met Gln Gln Asn Gly Cys Tyr Lys Ile Glu Gly Arg Glu Ile
    290                 295                 300

Glu Lys Leu Ile Glu Leu Val Leu Asp His Lys Gly Gly Lys Ile Thr
305                 310                 315                 320

Leu Asn Arg Lys Trp Val Gly Lys Asp Ala His Leu Ile Leu Lys Ala
                325                 330                 335

Ile Gly Ile Asp Ala Asp Glu Ser Val Arg Cys Ile Ile Phe Glu Ala
            340                 345                 350

Glu Lys Asp Asn Pro Leu Val Val Glu Glu Leu Met Met Pro Ile Leu
            355                 360                 365

Gly Ile Val Arg Ala Lys Asn Val Asp Glu Ala Ile Met Ile Ala Thr
        370                 375                 380

Glu Leu Glu His Gly Asn Arg His Ser Ala His Met His Ser Lys Asn

-continued

```
385                 390                 395                 400

Val Asp Asn Leu Thr Lys Phe Gly Lys Ile Ile Asp Thr Ala Ile Phe
                405                 410                 415

Val Lys Asn Ala Pro Ser Tyr Ala Ala Leu Gly Tyr Gly Gly Glu Gly
                420                 425                 430

Tyr Cys Thr Phe Thr Ile Ala Ser Arg Thr Gly Glu Gly Leu Thr Ser
                435                 440                 445

Ala Arg Thr Phe Thr Lys Ser Arg Arg Cys Val Leu Ala Asp Gly Leu
        450                 455                 460

Ser Ile Arg
465

<210> SEQ ID NO 88
<211> LENGTH: 462
<212> TYPE: PRT
<213> ORGANISM: Ruminococcus sp. AT10

<400> SEQUENCE: 88

Val Ser Val Asn Glu Gln Met Val Gln Asp Ile Val Gln Glu Val Leu
1               5                   10                  15

Ala Lys Met Gln Ile Ala Ser Asp Val Ser Gly Asn Arg Gly Val Phe
                20                  25                  30

Ala Asp Met Asn Glu Ala Ile Ala Ala Ala Gln Lys Ala Gln Lys Val
        35                  40                  45

Val Ala Arg Met Thr Leu Asp His Arg Glu Lys Val Ile Ser Asn Ile
    50                  55                  60

Arg Lys Lys Ile Asn Glu Asn Ala Glu Ile Leu Ala Arg Met Gly Val
65                  70                  75                  80

Glu Glu Thr Gly Met Gly Asn Val Gly His Lys Ile Leu Lys His Gln
                85                  90                  95

Leu Val Ala Glu Lys Thr Pro Gly Thr Glu Asp Ile Thr Thr Thr Ala
                100                 105                 110

Trp Ser Gly Asp Arg Gly Leu Thr Leu Ile Glu Met Gly Pro Phe Gly
                115                 120                 125

Val Ile Gly Ala Ile Thr Pro Cys Thr Asn Pro Ser Glu Thr Val Leu
        130                 135                 140

Cys Asn Thr Ile Gly Met Phe Ala Gly Gly Asn Thr Val Val Phe Asn
145                 150                 155                 160

Pro His Pro Ala Ala Ile Lys Thr Ser Ile Tyr Ala Val Asn Leu Leu
                165                 170                 175

Asn Glu Ala Ser Val Glu Ala Gly Gly Pro Asp Asn Ile Ala Cys Thr
                180                 185                 190

Val Glu His Pro Thr Leu Glu Thr Ser Asn Ile Met Met Lys His Lys
        195                 200                 205

Ala Ile Gln Leu Ile Ala Ala Thr Gly Gly Pro Gly Val Val Thr Ala
        210                 215                 220

Val Leu Ser Ser Gly Arg Arg Gly Ile Gly Ala Gly Ala Gly Asn Pro
225                 230                 235                 240

Pro Ala Leu Val Asp Glu Thr Ala Asp Ile Arg Lys Ala Ala Glu Asp
                245                 250                 255

Ile Val Asn Gly Cys Thr Phe Asp Asn Asn Leu Pro Cys Ile Ala Glu
                260                 265                 270

Lys Glu Ile Val Ala Val Glu Ser Val Ala Asp Glu Leu Leu His Tyr
        275                 280                 285
```

-continued

```
Met Ile Gln Glu Gln Gly Cys Tyr Leu Ala Ser Lys Glu Glu Gln Asp
    290                 295                 300

Ala Leu Thr Ala Val Val Leu Lys Asp Gly Arg Leu Asn Arg Lys Cys
305                 310                 315                 320

Val Gly Arg Asp Ala Lys Thr Leu Leu Gly Met Ile Gly Val Thr Val
                325                 330                 335

Pro Asp Asn Ile Arg Cys Ile Thr Phe Glu Gly Pro Lys Glu His Pro
                340                 345                 350

Leu Ile Ala Thr Glu Leu Met Met Pro Ile Leu Gly Val Val Arg Ala
                355                 360                 365

Lys Asp Phe Asn Asp Ala Val Glu Gln Ala Val Trp Leu Glu His Gly
    370                 375                 380

Asn Arg His Ser Ala His Ile His Ser Lys Asn Val Asp His Ile Thr
385                 390                 395                 400

Lys Tyr Ala Lys Ala Ile Asp Thr Ala Ile Leu Val Lys Asn Gly Pro
                405                 410                 415

Ser Tyr Ala Ala Leu Gly Phe Gly Gly Glu Gly Phe Cys Thr Phe Thr
                420                 425                 430

Ile Ala Ser Arg Thr Gly Glu Gly Leu Thr Ser Ala Ser Thr Phe Thr
                435                 440                 445

Lys Arg Arg Arg Cys Val Met Ser Asp Ser Leu Cys Ile Arg
    450                 455                 460
```

<210> SEQ ID NO 89

<400> SEQUENCE: 89

000

<210> SEQ ID NO 90
<211> LENGTH: 469
<212> TYPE: PRT
<213> ORGANISM: Acetobacterium dehalogenans

<400> SEQUENCE: 90

```
Met Asn Ile Asp Thr Thr Gly Ile Glu Tyr Ile Val Lys Lys Val Met
1               5                   10                  15

Ala Glu Ile Asp Cys Ala Asp Ala Gly Gly Lys Pro Leu Lys Asp Gly
                20                  25                  30

Glu Leu Gly Val Phe Asn Asp Met Glu Asn Ala Ile Asp Ala Ala Phe
            35                  40                  45

Thr Ala Gln Lys Thr Phe Met Arg Glu Ser Leu Ala Tyr Arg Ser Lys
    50                  55                  60

Leu Ile Ala Ala Met Arg Ala Glu Met Leu Lys Lys Glu Asn Met Glu
65                  70                  75                  80

Met Ile Cys Gln Met Ala Val Glu Glu Thr Gly Met Gly Asn Tyr Glu
                85                  90                  95

His Lys Leu Leu Lys His Glu Leu Ala Thr Val Lys Thr Pro Gly Val
            100                 105                 110

Glu Asp Leu Val Ala Glu Ala Phe Thr Gly Asp Asp Gly Leu Thr Leu
            115                 120                 125

Ile Glu Gln Ser Pro Phe Gly Val Ile Gly Ser Val Ser Pro Ser Thr
    130                 135                 140

Asn Pro Ser Glu Thr Val Ile Cys Asn Ser Ile Gly Met Leu Ala Ala
145                 150                 155                 160

Gly Asn Thr Val Val Phe Ala Pro His Pro Ser Ala Lys Asn Thr Ser
```

-continued

```
                165              170              175

Ala Leu Thr Val Lys Leu Leu Asn Lys Ala Ile Leu Glu Ala Gly Gly
            180              185              190

Pro Glu Asn Leu Ile Val Thr Thr Ala Glu Pro Thr Ile Asp Ser Ala
            195              200              205

Asn Thr Met Phe Ala Ser Pro Lys Ile Thr Leu Leu Cys Ala Thr Gly
    210              215              220

Gly Pro Gly Val Val Lys Thr Val Leu Gln Ser Gly Lys Lys Ala Ile
225              230              235              240

Gly Ala Gly Ala Gly Asn Pro Pro Ala Leu Val Asp Glu Thr Ala Asp
            245              250              255

Ile Glu Lys Ala Gly Lys Asp Ile Ile Asp Gly Cys Cys Phe Asp Asn
            260              265              270

Asn Leu Pro Cys Ile Ala Glu Lys Glu Val Val Val Glu Gln Val
            275              280              285

Ala Asp Tyr Leu Ile Phe Asn Met Lys Lys Asn Gly Ala Tyr Glu Leu
    290              295              300

Lys Asp Ala Lys Lys Ile Ala Glu Leu Glu Glu Leu Val Ile Pro Gly
305              310              315              320

Gly Arg Leu Ser Arg Asp Tyr Val Gly Arg Ser Ala Lys Val Ile Leu
            325              330              335

Lys Gly Ile Gly Ile Asp Val Asp Asp Ser Ile Arg Val Ile Ile Met
            340              345              350

Glu Thr Ser Lys Asp His Ile Phe Ala Val Glu Glu Leu Met Met Pro
            355              360              365

Ile Leu Pro Ile Val Arg Val Lys Asn Ile Ala Glu Gly Ile Asp Leu
    370              375              380

Ala Val Ala Leu Glu His Gly Asn Arg His Thr Ala Ile Met His Ser
385              390              395              400

Thr Asn Ile Asn Asn Leu Thr Glu Met Ala Lys Arg Val Gln Thr Thr
            405              410              415

Ile Phe Val Lys Asn Gly Pro Ser Tyr Ala Gly Ile Gly Val Gly Gly
            420              425              430

Glu Gly Tyr Thr Thr Phe Thr Ile Ala Gly Pro Thr Gly Glu Gly Leu
            435              440              445

Thr Ser Ala Lys Thr Phe Thr Arg Lys Arg Arg Cys Val Leu Val Gly
    450              455              460

Gly Phe Thr Ile Lys
465
```

```
<210> SEQ ID NO 91
<211> LENGTH: 461
<212> TYPE: PRT
<213> ORGANISM: Spirochaeta alkalica

<400> SEQUENCE: 91

Ala Thr Leu Leu Glu Arg Ala Arg Ala Ala Gln Glu Lys Ile Ala Thr
1               5               10              15

Cys Thr Gln Arg Glu Ile Asp Asp Leu Cys Leu Ser Val Gly Trp Glu
            20              25              30

Val Tyr Thr Asp Glu Asn Ile Ala Lys Leu Ala Glu Cys Ala Val Gln
            35              40              45

Thr Thr Gly Met Gly Asn Val Pro Asp Lys Ile Thr Lys His Lys Val
    50              55              60
```

-continued

```
Lys Val Leu Gly Val Leu Lys Asp Leu Arg Lys Ala Arg Thr Val Gly
65                  70                  75                  80

Leu Ile Glu Arg Asp Glu Ala Arg Gly Leu Ser Lys Tyr Ala Lys Pro
                85                  90                  95

Val Gly Val Val Gly Ala Leu Leu Pro Val Thr Asn Pro Thr Ala Thr
            100                 105                 110

Pro Ala Ser Asn Gly Leu Ser Ile Leu Lys Gly Arg Asn Ala Val Ile
            115                 120                 125

Phe Ala Pro His Pro Arg Gly Ala Ala Ala Ser Ala Leu Ala Val Glu
        130                 135                 140

Phe Met Arg Arg Gly Leu Arg Arg Val Gly Ala Pro Glu Asp Leu Ile
145                 150                 155                 160

Gln Ile Val Glu Asp Pro Ser Leu Gly Gln Thr Gly Glu Leu Met Lys
                165                 170                 175

Gln Val Asp Leu Val Val Ala Thr Gly Gly Gly Ala Met Val Lys Ala
            180                 185                 190

Ala Tyr Ser Ser Gly Thr Pro Ala Tyr Gly Val Gly Pro Gly Asn Ser
            195                 200                 205

Val Gln Ile Ile Ala Glu Asp Ala Asp Leu Ala Asp Ala Ala Ala Lys
    210                 215                 220

Ile Ala Leu Ser Lys Ala Phe Asp His Ala Thr Ser Cys Ser Ser Glu
225                 230                 235                 240

Asn Ser Ile Ile Val Glu Asp Ser Val Tyr Glu Gly Met Ile Thr Glu
                245                 250                 255

Leu Val Gln Asn Gln Gly Cys Tyr Leu Thr Thr Pro Arg Glu Arg Ser
            260                 265                 270

Gln Leu Glu Ala Leu Leu Trp Arg Pro Gly Lys Thr Gly Gln Leu Ala
            275                 280                 285

Leu Asn Pro Gly Ile Ile Ala Arg Ser Ala Ala Thr Ile Ala Ala Glu
    290                 295                 300

Ala Gly Ile Thr Leu Pro Glu Gly Thr Arg Val Ile Leu Val Glu Gly
305                 310                 315                 320

Gln His Pro Leu Glu Gln Asp Pro Phe Ser Gln Glu Lys Leu Cys Pro
                325                 330                 335

Val Leu Thr Val Tyr Arg Tyr Thr Arg Trp Glu Glu Ala Val Asp Leu
            340                 345                 350

Leu Val Arg Leu Thr Asp Gln Ala Gly Thr Gly His Ser Cys Gly Ile
            355                 360                 365

His Thr Phe Arg Glu Asp Tyr Ile Arg His Leu Gly Glu Thr Met Arg
    370                 375                 380

Thr Ser Arg Ile Met Val Arg Gln Ala Gln Ala Pro Ala Asn Gly Gly
385                 390                 395                 400

Asn Phe Phe Asn Ala Met Pro Ser Thr Val Thr Leu Gly Cys Gly Thr
                405                 410                 415

Trp Gly Gly Asn Ile Thr Thr Glu Asn Ile His Trp Lys His Phe Ile
            420                 425                 430

Asn Val Thr Trp Val Ser Glu Pro Ile Pro Pro Asp Arg Pro Asp Asp
            435                 440                 445

Glu Glu Ile Trp Gly Ser Phe Trp Ser Arg Tyr Ala Glu
    450                 455                 460
```

<210> SEQ ID NO 92

<400> SEQUENCE: 92

000

<210> SEQ ID NO 93

<400> SEQUENCE: 93

000

<210> SEQ ID NO 94
<211> LENGTH: 494
<212> TYPE: PRT
<213> ORGANISM: Clostridium caminithermale DSM 15212

<400> SEQUENCE: 94

```
Met Gln Ile Asn Glu Leu Gln Ile Glu Lys Leu Val Ala Glu Val Leu
1               5                   10                  15

Ala Lys Thr Leu Gly Ala Glu Gly Asn Ser Ser Leu Val Asn Asn Asn
            20                  25                  30

Ser Ile Gly Asn Ser Asn Glu Tyr Glu Tyr Asn Gln Ser Leu Glu Val
        35                  40                  45

Gly Val Phe Glu Lys Met Glu Asp Ala Ile Asn Glu Ala His Arg Ala
    50                  55                  60

Tyr Gln Gln Leu Lys Asn Tyr Ser Ile Lys Asp Arg Gln Arg Phe Ile
65                  70                  75                  80

Asp Gly Ile Lys Glu Trp Thr Leu Arg Glu Lys Asn Ile Leu Ala Lys
                85                  90                  95

Lys Val Val Glu Glu Thr Gly Leu Gly Asn Tyr Glu Asp Lys Ile Ile
            100                 105                 110

Lys His Glu Leu Ala Ala Arg Thr Ala Gly Thr Glu Val Leu Ser Ser
        115                 120                 125

Lys Val Gln Ser Gly Asp Thr Gly Leu Ala Leu Ile Glu Gln Ala Pro
    130                 135                 140

Tyr Gly Val Val Gly Ala Thr Thr Pro Ser Thr Asn Pro Ser Glu Thr
145                 150                 155                 160

Val Ile Ser Asn Thr Ile Ala Met Leu Ala Ala Gly Asn Thr Val Val
                165                 170                 175

Phe Asn Val His Pro Ser Ser Lys His Val Cys Ala Tyr Thr Val Ala
            180                 185                 190

Lys Ile Asn Glu Cys Ile Met Asp Leu Gly Gly Pro Ala Asn Ile Ile
        195                 200                 205

Thr Met Val Lys Asp Pro Thr Met Glu Ser Leu Gln Val Met Ala Asn
    210                 215                 220

Cys Pro Lys Ile Asn Leu Leu Val Gly Thr Gly Gly Pro Gly Leu Val
225                 230                 235                 240

Arg Ala Leu Leu Lys Ser Gly Lys Lys Ala Ile Gly Ala Gly Ala Gly
                245                 250                 255

Asn Pro Pro Val Val Val Asp Ser Thr Ala Asn Ile Lys Lys Ala Ala
            260                 265                 270

Ala Asp Ile Ile Lys Gly His Ser Phe Asp Asn Asn Ile Val Cys Ile
        275                 280                 285

Leu Glu Lys Glu Val Phe Val Val Asp Glu Val Ala Asn Glu Leu Ile
    290                 295                 300

Glu Asn Met Lys Ser Glu Gly Ala Phe Tyr Leu Asp Ser Ser Tyr Ile
305                 310                 315                 320

Ser Ala Leu Thr Asp Leu Ile Ile Glu Ala Thr Asp Lys Lys Phe Phe
```

-continued

```
                     325                330                335
Leu Gly Asn Ser Ser Lys Thr Thr Asn Leu His Thr Lys Lys Glu Trp
                 340                345                350
Val Gly Lys Asp Ala Tyr Lys Ile Leu Asp Ala Leu Gly Ile Arg Tyr
                 355                360                365
Ser Thr Arg Pro Lys Cys Ile Ile Cys Glu Val Pro Phe Glu His Pro
             370                375                380
Phe Val Gln Leu Glu Leu Leu Met Pro Val Leu Pro Ile Val Arg Val
385                390                395                400
Glu Asn Phe Val Lys Gly Val Glu Tyr Ala Val Glu Ala Glu His Gly
                 405                410                415
Asn Arg His Thr Ala Ile Val His Ser Gln Asn Ile Asp Asn Ile Thr
                 420                425                430
Tyr Tyr Ala Lys Ala Ile Asp Thr Thr Ile Phe Val Lys Asn Ala Pro
                 435                440                445
Ser Val Ala Gly Ile Gly Val Asp Ser Glu Ser Val Val Ser Phe Ser
             450                455                460
Ile Ala Gly Pro Thr Gly Glu Gly Ile Thr Thr Ala Lys Asp Phe Thr
465                470                475                480
Arg Ala Arg His Cys Val Leu Val Asp Gly Phe Arg Ile Ile
                 485                490
```

<210> SEQ ID NO 95
<211> LENGTH: 464
<212> TYPE: PRT
<213> ORGANISM: Caldanaerobius fijiensis

<400> SEQUENCE: 95

```
Val Val Lys Glu Glu Gln Ile Glu Ala Ile Val Arg Glu Val Leu Arg
1                5                10                15
Arg Ile Asp Arg Glu Asp Ile Lys Leu Asn Glu Asp Lys His Gln Leu
                 20                25                30
Gly Val Phe Asp Lys Met Glu Asp Ala Ile Glu Ala Ala Lys Asp Ala
             35                40                45
Phe Glu Lys Phe Ser Asn Met Thr Leu Glu Asp Arg Glu Arg Phe Ile
         50                55                60
Ser Glu Ile Arg Lys Ala Thr Leu Glu Asn Ala Arg Val Leu Ala Glu
65                70                75                80
Met Gly Val Lys Glu Thr Gly Met Gly Lys Val Glu His Lys Val Leu
                 85                90                95
Lys His Gln Leu Val Ala Lys Lys Thr Pro Gly Thr Glu Asp Leu Lys
                 100                105                110
Thr Gln Ala Trp Ser Gly Asp Lys Gly Leu Thr Leu Val Glu Met Ala
             115                120                125
Pro Phe Gly Val Ile Gly Ala Ile Thr Pro Ser Thr Asn Pro Ser Glu
         130                135                140
Thr Ile Ile Cys Asn Ser Ile Gly Met Ile Ala Ala Gly Asn Ala Val
145                150                155                160
Val Phe Ser Pro His Pro Gly Ala Lys Arg Val Ser Asn Phe Ala Val
                 165                170                175
Asp Met Ile Asn Arg Ala Ile Ile Arg Ala Gly Gly Pro Glu Asn Leu
             180                185                190
Val Val Ser Ile Lys Glu Pro Ser Ile Asn Thr Thr Asn Ala Met Ile
             195                200                205
```

-continued

```
Lys His Pro Asp Val Lys Leu Leu Val Ala Thr Gly Gly Pro Glu Ile
    210                 215                 220

Val Lys Ile Val Leu Ser Ser Gly Lys Lys Ala Ile Gly Ala Gly Ala
225                 230                 235                 240

Gly Asn Pro Pro Val Val Val Asp Glu Thr Ala Asp Ile Lys Lys Ala
                245                 250                 255

Ala Lys Asp Ile Ile Asp Gly Cys Thr Phe Asp Asn Asn Leu Pro Cys
                260                 265                 270

Ile Ala Glu Lys Glu Val Ile Ala Val Glu Lys Ile Tyr Arg Asp Leu
            275                 280                 285

Leu Asp Glu Ile Leu Lys Gln Gly Val Tyr Lys Leu Asn Ala Leu Gln
    290                 295                 300

Ile Ser Lys Leu Glu Asn Leu Val Leu Met Asp Gly Lys Leu Asn Lys
305                 310                 315                 320

Lys Leu Val Gly Lys Asp Ala Lys Val Ile Leu Asp Gln Ile Gly Ile
                325                 330                 335

Asn Val Ser Asp Asp Ile Arg Cys Ile Ile Cys Glu Thr Asp Glu Asp
                340                 345                 350

His Pro Phe Val Met Glu Glu Leu Met Met Pro Ile Leu Pro Ile Val
            355                 360                 365

Lys Ala Lys Asn Ile Asp Asp Ala Ile Arg Ile Ala Val Lys Ala Glu
    370                 375                 380

Lys Asn Asn Arg His Thr Ala His Ile His Ser Lys Asn Ile Asp Asn
385                 390                 395                 400

Ile Thr Arg Tyr Ala Lys Ala Ile Asn Thr Thr Ile Leu Val Lys Asn
                405                 410                 415

Ala Pro Ser Tyr Ala Gly Ile Gly Phe Gly Gly Glu Gly Phe Thr Thr
                420                 425                 430

Phe Thr Ile Ala Gly Pro Thr Gly Glu Gly Leu Thr Ser Ala Gln Thr
            435                 440                 445

Phe Thr Arg Met Arg Arg Cys Val Leu Ala Asp Gly Leu Arg Ile Ile
    450                 455                 460
```

<210> SEQ ID NO 96

<400> SEQUENCE: 96

000

<210> SEQ ID NO 97
<211> LENGTH: 480
<212> TYPE: PRT
<213> ORGANISM: Pelosinus fermentans

<400> SEQUENCE: 97

```
Met Ser Ile Asp Gln Ala Leu Ile Glu Lys Ile Thr Leu Glu Ile Leu
1               5                   10                  15

Thr Lys Met Gln Thr Gly Ala Lys Ala Ala Pro Ala Gly Tyr Gly Asp
            20                  25                  30

Gly Ile Phe Glu Thr Val Asp Glu Ala Val Ala Ala Arg Lys Ala
        35                  40                  45

Tyr Gln Glu Leu Lys Thr Leu Ser Leu Glu Lys Arg Glu Val Leu Ile
    50                  55                  60

Lys Ala Met Arg Asp Val Ala Tyr Glu Asn Ala Thr Ile Leu Ala Gln
65                  70                  75                  80

Met Ala Val Asp Glu Ser Gly Met Gly Arg Val Ser Asp Lys Ile Ile
```

85                  90                  95

Lys Asn Gln Val Ala Ala Leu Lys Thr Pro Gly Thr Glu Asp Leu Thr
            100                 105                 110

Thr Gln Ala Trp Ser Gly Asp Asn Gly Leu Thr Leu Ile Glu Met Gly
            115                 120                 125

Pro Tyr Gly Val Ile Gly Ala Ile Thr Pro Thr Thr Asn Pro Thr Glu
    130                 135                 140

Thr Val Ile Cys Asn Gly Ile Gly Met Ile Ala Ala Gly Asn Thr Val
145                 150                 155                 160

Phe Phe Ser Pro His Pro Thr Ala Lys Asn Thr Ser Met Lys Ile Ile
            165                 170                 175

Thr Leu Leu Asn Gln Ala Ile Val Lys Ala Gly Gly Pro Asn Asn Leu
            180                 185                 190

Leu Thr Ser Val Ala Asn Pro Ser Ile Lys Ala Ala Asn Glu Met Met
            195                 200                 205

Lys His Pro Gly Ile Asn Met Leu Val Ala Thr Gly Gly Pro Gly Val
    210                 215                 220

Val Lys Ala Val Leu Ser Ser Gly Lys Lys Ala Ile Gly Ala Gly Ala
225                 230                 235                 240

Gly Asn Pro Pro Val Ile Val Asp Glu Thr Ala Asp Ile Glu Lys Ala
            245                 250                 255

Ala Arg Asp Ile Val Ala Gly Cys Ser Phe Asp Asn Asn Leu Pro Cys
            260                 265                 270

Ile Ala Glu Lys Glu Val Ile Ala Ile Gly Ser Ile Ala Asp Arg Leu
            275                 280                 285

Ile Thr Tyr Met Gln Lys Tyr Gly Ala Tyr Leu Ile Ser Gly Ser Asn
    290                 295                 300

Ile Asp Arg Leu Leu Asn Val Ile Met Thr Val Gln Glu Glu Lys Ile
305                 310                 315                 320

Ala Glu Gly Cys Thr Asp Lys Pro Lys Arg Ser Tyr Gly Ile Asn Lys
            325                 330                 335

Asp Tyr Val Gly Lys Asp Ala Lys Tyr Leu Leu Ser Lys Ile Gly Ile
            340                 345                 350

Asp Val Pro Asp Ser Val Arg Val Val Leu Cys Glu Thr Pro Ala Asp
            355                 360                 365

His Pro Phe Val Ile Glu Glu Leu Met Met Pro Val Leu Pro Val Val
    370                 375                 380

Gln Val Lys Asp Ile Asp Glu Ala Ile Glu Val Ala Val Arg Val Glu
385                 390                 395                 400

His Gly Asn Arg His Thr Ala Ala Met His Ser Lys Asn Val Asp His
            405                 410                 415

Leu Thr Arg Phe Ala Arg Ala Val Glu Thr Thr Ile Phe Val Lys Asn
            420                 425                 430

Ala Pro Ser Tyr Ala Gly Ile Gly Val Gly Gly Glu Gly Phe Thr Ser
            435                 440                 445

Phe Thr Leu Ala Gly Pro Thr Gly Glu Gly Ile Thr Ser Pro Arg Ser
    450                 455                 460

Phe Thr Arg Gln Arg Arg Cys Val Leu Val Asp Ala Phe Ser Ile Val
465                 470                 475                 480

<210> SEQ ID NO 98

<400> SEQUENCE: 98

```
000

<210> SEQ ID NO 99

<400> SEQUENCE: 99

000

<210> SEQ ID NO 100
<211> LENGTH: 463
<212> TYPE: PRT
<213> ORGANISM: Blautia wexlerae

<400> SEQUENCE: 100

Met Pro Val Ser Glu Ser Met Val Gln Glu Ile Val Gln Gln Val Met
1               5                   10                  15

Ala Lys Met Gln Ile Ala Asp Ala Pro Ala Glu Lys Gln His Gly Val
            20                  25                  30

Phe Lys Asp Met Asn Asp Ala Ile Glu Ala Ala Lys Lys Ser Gln Glu
        35                  40                  45

Ile Val His Lys Met Ser Met Asp Gln Arg Glu Lys Ile Ile Ser Cys
    50                  55                  60

Ile Arg Lys Lys Ile Lys Glu Asn Ala Glu Ile Met Ala Arg Met Gly
65                  70                  75                  80

Val Glu Glu Thr Lys Met Gly Asn Val Gly Asp Lys Ile Leu Lys His
                85                  90                  95

His Leu Val Ala Asp Lys Thr Pro Gly Thr Glu Ala Ile Thr Thr Thr
            100                 105                 110

Ala Trp Ser Gly Asp Arg Gly Leu Thr Leu Val Glu Met Gly Pro Phe
        115                 120                 125

Gly Val Ile Gly Ala Ile Thr Pro Cys Thr Asn Pro Ser Glu Thr Val
    130                 135                 140

Leu Cys Asn Thr Met Gly Met Leu Ala Gly Gly Asn Thr Val Val Phe
145                 150                 155                 160

Asn Pro His Pro Ala Ala Val Lys Thr Ser Leu Tyr Ala Val Asn Leu
                165                 170                 175

Val Asn Glu Ala Ser Leu Glu Gln Gly Gly Pro Asp Asn Ile Ala Val
            180                 185                 190

Ser Val Glu Asn Pro Thr Leu Asp Thr Ser Ser Val Met Met Lys His
        195                 200                 205

Lys Asp Ile His Leu Leu Val Ala Thr Gly Gly Pro Gly Val Val Thr
    210                 215                 220

Ala Val Leu Ser Ser Gly Lys Arg Gly Ile Gly Ala Gly Ala Gly Asn
225                 230                 235                 240

Pro Pro Ala Leu Val Asp Glu Thr Ala Asp Ile Arg Lys Ala Ala Arg
                245                 250                 255

Asp Ile Val Asn Gly Cys Thr Phe Asp Asn Asn Leu Pro Cys Ile Ala
            260                 265                 270

Glu Lys Glu Val Val Ala Val Ser Ser Ile Met Asp Glu Leu Met His
        275                 280                 285

Tyr Met Leu Thr Glu Asn Asp Cys Tyr Leu Ala Ser Lys Glu Glu Gln
    290                 295                 300

Asp Lys Leu Val Glu Val Val Leu Ala Gly Gly Lys Leu Asn Arg Lys
305                 310                 315                 320

Cys Val Gly Arg Asp Ala Arg Thr Leu Leu Ser Met Ile Gly Val Asp
                325                 330                 335
```

-continued

```
Ala Pro Ala Asn Ile Arg Cys Ile Ile Phe Glu Gly Pro Lys Glu His
        340                 345                 350

Pro Leu Ile Thr Thr Glu Leu Met Met Pro Ile Leu Gly Ile Val Arg
        355                 360                 365

Ala Arg Asp Phe Glu Asp Ala Val Glu Gln Ala Val Trp Leu Glu His
        370                 375                 380

Gly Asn Arg His Ser Ala His Ile His Ser Lys Asn Val Asp Arg Ile
385                 390                 395                 400

Thr Thr Tyr Ala Lys Ala Ile Asp Thr Ala Ile Val Val Lys Asn Gly
                405                 410                 415

Pro Ser Tyr Ala Ser Leu Gly Phe Gly Ser Glu Gly Tyr Thr Thr Phe
                420                 425                 430

Thr Ile Ala Ser Arg Thr Gly Glu Gly Leu Thr Cys Ala Ser Thr Phe
                435                 440                 445

Thr Lys Arg Arg Arg Cys Ile Met Glu Asp Ser Leu Cys Ile Arg
        450                 455                 460
```

```
<210> SEQ ID NO 101
<211> LENGTH: 500
<212> TYPE: PRT
<213> ORGANISM: Paenibacillus sp. OSY-SE

<400> SEQUENCE: 101
```

```
Ile Lys Leu Thr Glu Thr Asp Ile Gln Asn Ile Ile Gln Gly Val Leu
1               5                   10                  15

Lys Asn Ile Glu Gln Asn Leu Pro Gly Ala Gln Ala Ala Asp Asp Ala
            20                  25                  30

Ala Thr Gly Gln Ala Lys Pro Glu Ser Ala Pro Val Ala Ala Ala Pro
        35                  40                  45

Val Arg Ser Asn Gly Asp Tyr Gly Val Phe Asp Glu Ala Glu Ala Ala
        50                  55                  60

Ile Ala Ala Ala Tyr Gln Ala Gln Arg Ala Tyr Ala His His Phe Ser
65                  70                  75                  80

Met Gln Asp Arg Glu Arg Phe Ile Ala Ala Ile Arg Lys Ala Thr Leu
                85                  90                  95

Glu His Lys Glu Thr Leu Ala Ser Met Val Leu Lys Glu Thr Lys Leu
            100                 105                 110

Gly Arg Tyr Glu Asp Lys Ile Ala Lys Leu Glu Leu Thr Ala Leu Lys
            115                 120                 125

Thr Pro Gly Thr Glu Asp Leu Glu Thr Lys Ala Phe Ser Gly Asp Asn
        130                 135                 140

Gly Leu Thr Leu Val Lys Asp Gly Pro Phe Gly Val Ile Gly Ala Val
145                 150                 155                 160

Thr Pro Val Thr Asn Ser Val Glu Thr Val Ile Asn Asn Ala Ile Gly
                165                 170                 175

Met Leu Ala Ala Gly Asn Ala Val Val Tyr Asn Val His Pro Ser Ser
            180                 185                 190

Lys Ala Cys Cys Ala Tyr Ala Val Lys Met Ile Asn Arg Ala Val Gln
            195                 200                 205

Glu Ala Gly Gly Pro Glu His Leu Val Thr Met Val Lys Glu Pro Thr
        210                 215                 220

Lys Glu Thr Leu Asp Ala Ile Thr Gln Ser Pro Lys Val Gln Leu Leu
225                 230                 235                 240

Val Gly Thr Gly Gly Pro Gly Leu Val Arg Ala Leu Leu Arg Ser Gly
```

-continued

```
                   245                 250                 255
Lys Lys Ala Ile Gly Ala Gly Ala Gly Asn Pro Pro Val Ile Val Asp
            260                 265                 270

Glu Thr Ala Asn Ile Glu Arg Ala Ala Lys Glu Ile Ile Ala Gly Ala
            275                 280                 285

Ser Phe Glu Asn Asn Ile Leu Cys Ile Ala Glu Lys Glu Val Phe Val
            290                 295                 300

Val Asp Lys Val Ala Asp Asp Leu Leu Phe His Met Leu Asn His Gly
305                 310                 315                 320

Ala Tyr Arg Leu Asp Asp Arg Glu Leu Glu Gln Val Met Ser Phe Ala
                325                 330                 335

Leu Glu Ala Asn Val Asn Glu Thr Ala Gly Gly Cys Ser Leu Asp Met
            340                 345                 350

Lys Arg Glu Tyr His Thr Val Lys Glu Trp Ile Gly Lys Asp Ala Ala
            355                 360                 365

Leu Phe Leu Glu Lys Ile Gly Val Thr Pro Glu Lys Glu Val Lys Leu
            370                 375                 380

Leu Ile Cys Glu Val Asp Phe Asp His Pro Phe Val Gln Leu Glu Gln
385                 390                 395                 400

Met Met Pro Val Leu Pro Ile Val Arg Val Ser Asp Leu Asp Glu Ala
                405                 410                 415

Ile Arg Leu Ala Val Glu Ala Glu His Gly Asn Arg His Thr Ala Leu
                420                 425                 430

Met His Ser Thr Asn Val Ala Asn Phe Ala Ala Phe Glu Arg Ala Ile
            435                 440                 445

Gly Thr Thr Ile Phe Val Lys Asn Ala Ser Ser Leu Ala Gly Val Gly
            450                 455                 460

Ala Gly Gly Glu Gly Cys Thr Thr Met Thr Ile Ala Gly Pro Thr Gly
465                 470                 475                 480

Glu Gly Leu Thr Ser Ala Arg Thr Phe Thr Arg Lys Lys Arg Cys Val
                485                 490                 495

Leu Ala Glu Arg
                500
```

<210> SEQ ID NO 102

<400> SEQUENCE: 102

000

<210> SEQ ID NO 103
<211> LENGTH: 476
<212> TYPE: PRT
<213> ORGANISM: Spirochaetes bacterium GWC2_52_13

<400> SEQUENCE: 103

```
Val Ser Gln Ser Ile Glu Asp Thr Val Arg Thr Leu Val Glu Lys Leu
1               5                   10                  15

Val Leu Glu Tyr Ser Ala Ser Ser Val Gly Val Asp His Ile Ala Pro
                20                  25                  30

Ser Gln Tyr Ala Ser Gly Ile Phe Pro Thr Met Asp Leu Ala Val Lys
            35                  40                  45

Ala Ala Tyr Glu Ala Gln Arg His Leu Val Gly Leu Pro Leu Glu Lys
        50                  55                  60

Arg Lys Glu Ile Val Gln Ala Met Arg Glu Thr Ala Met Asp His Ala
65                  70                  75                  80
```

-continued

```
Gln Glu Phe Ala Glu Met Ala Val Gln Glu Ser Gly Arg Gly Asn Val
            85                  90                  95

Ala Asp Lys Ile Ala Lys Asn Ile Leu Ala Ala Lys Lys Thr Pro Gly
            100                 105                 110

Val Glu Asp Val Glu Thr Ser Ala Tyr Ser Asp Glu His Gly Leu Ser
            115                 120                 125

Leu Val Glu Arg Ala Pro Tyr Gly Val Ile Gly Ser Ile Thr Pro Val
        130                 135                 140

Thr Asn Pro Thr Ala Thr Ile Ile Asn Asn Gly Ile Ser Met Ile Ser
145                 150                 155                 160

Gly Gly Asn Ser Val Val Phe Asn Pro His Pro Gly Ala Lys Asn Val
            165                 170                 175

Ser Cys Phe Ala Ile Glu Val Leu Asn Ala Ala Ile Glu Arg Val Gly
            180                 185                 190

Gly Pro Arg Asn Leu Leu Val Ser Leu Ala Gln Pro Thr Ile Glu Ser
            195                 200                 205

Ala Asn Glu Met Met Gly His Gln Lys Ile Ser Leu Leu Val Val Thr
        210                 215                 220

Gly Gly Pro Gly Val Val Lys Ala Ala Met Asn Ser Gly Lys Lys Val
225                 230                 235                 240

Ile Ala Ala Gly Pro Gly Asn Pro Pro Cys Val Val Asp Glu Thr Ala
            245                 250                 255

Lys Ile Gln Lys Ala Ala Lys Asp Ile Val Asp Gly Ala Ser Phe Asp
            260                 265                 270

Asn Asn Leu Val Cys Ile Cys Glu Lys Glu Val Leu Val Val Lys Ser
            275                 280                 285

Val Ala Asn Glu Leu Ile Gly Glu Met Gln Lys Val Gly Ala Tyr Leu
        290                 295                 300

Leu Ser Asp Gln Gln Ala Lys Ser Leu Leu Asp Gln Ile Ile Glu Val
305                 310                 315                 320

Pro Gly Met Met Asn Ser Glu Gly Val Val Lys Arg Glu Tyr Val Gly
            325                 330                 335

Lys Ser Pro Ser Phe Leu Ala Ser Leu Ile Gly Val Thr Val Pro Glu
            340                 345                 350

Ser Thr Arg Leu Leu Ile Cys Asp Val Asp Ala Gly Asn Pro Leu Val
            355                 360                 365

Trp Thr Glu Gln Leu Met Pro Phe Leu Pro Ile Val Arg Met Glu Asn
        370                 375                 380

Val Asp Gln Cys Ile Asp Leu Ala Val Gln Cys Glu His Gly Phe Arg
385                 390                 395                 400

His Thr Ala Ile Met His Ser Leu Asn Val Glu Lys Leu Ser Lys Met
            405                 410                 415

Ala Arg Gln Met Asn Cys Ser Leu Phe Val Lys Asn Gly Pro Cys Tyr
            420                 425                 430

Ala Gly Leu Gly Asn Gly Gly Ala Gly Tyr Thr Ser Phe Thr Ile Ala
            435                 440                 445

Ser Pro Thr Gly Glu Gly Leu Thr Arg Ala Arg Thr Phe Thr Arg Glu
            450                 455                 460

Arg Arg Cys Thr Leu Val Asp Tyr Phe Arg Ile Ile
465                 470                 475
```

<210> SEQ ID NO 104

-continued

```
<400> SEQUENCE: 104

000

<210> SEQ ID NO 105

<400> SEQUENCE: 105

000

<210> SEQ ID NO 106

<400> SEQUENCE: 106

000

<210> SEQ ID NO 107
<211> LENGTH: 454
<212> TYPE: PRT
<213> ORGANISM: Romboutsia lituseburensis DSM

<400> SEQUENCE: 107

Met Glu Ala Arg Asp Tyr Val Leu Gln Leu Ile Asn Lys Ala Arg Ile
1               5                   10                  15

Ala Gln Lys Glu Phe Glu Lys Tyr Ser Gln Glu Gln Val Asp Glu Ala
            20                  25                  30

Val Arg Ala Ile Gly Lys Ser Ile Tyr Asp Asn Gly Glu Met Leu Ala
        35                  40                  45

Arg Met Ala Val Asp Glu Thr Lys Met Gly Val Tyr Glu Asp Lys Ile
    50                  55                  60

Val Lys Asn Lys Gly Lys Ser Lys Ala Val Trp Asn Lys Leu Lys Gly
65                  70                  75                  80

Val Lys Ser Arg Gly Ile Ile Lys Tyr Ile Ala Glu Glu Gly Leu Val
            85                  90                  95

Glu Val Ala Lys Pro Ile Gly Val Val Gly Ala Val Thr Pro Thr Thr
            100                 105                 110

Asn Pro Thr Met Thr Pro Met His Asn Ala Met Ile Ala Leu Lys Gly
        115                 120                 125

Gly Asn Ala Ile Ile Ile Cys Pro His Pro Arg Ala Lys Asn Thr Gly
    130                 135                 140

Val Lys Thr Val Asp Leu Met Arg Glu Ala Leu Asp Lys Val Gly Ala
145                 150                 155                 160

Pro Lys Asp Leu Ile Gln Ile Val Asn Glu Pro Thr Val Glu Ile Ser
            165                 170                 175

Asn Leu Val Met Gln Leu Ser Asp Val Cys Val Ser Thr Gly Gly Pro
            180                 185                 190

Gly Met Val Lys Val Ala Tyr Ser Ser Gly Lys Pro Ala Phe Gly Val
            195                 200                 205

Gly Ala Gly Asn Val Gln Cys Leu Ile Asp Lys Asp Ala Asn Leu Glu
    210                 215                 220

Glu Val Val Pro Lys Val Ile Lys Gly Arg Ile Tyr Asp Asn Gly Ile
225                 230                 235                 240

Leu Cys Thr Cys Glu Gln Ser Ala Ile Cys Pro Asp Glu Met Tyr Asn
            245                 250                 255

Glu Phe Ile Asp Arg Leu Val Gln Ser Gly Ala Tyr Tyr Ile Glu Lys
            260                 265                 270

Glu Glu Glu Val Lys Ser Leu Arg Lys Ala Leu Phe Pro Asp Gly Asn
        275                 280                 285
```

-continued

```
Ile Ser Lys Asp Cys Val Gly Ala Ser Pro Tyr Glu Ile Ala Lys Met
    290                 295                 300

Ala Ser Ile Ala Ile Pro Lys Asp Thr Lys Leu Leu Val Val Lys Val
305                 310                 315                 320

Glu Lys Tyr Gly Thr Glu Glu Tyr Phe Ala Lys Glu Lys Met Cys Pro
                325                 330                 335

Val Leu Ser Ala Tyr Lys Tyr Glu Lys Trp Glu Asp Ala Val Asn Ile
                340                 345                 350

Ala Asn Gln Asn Leu Glu Tyr Glu Gly Lys Gly His Ser Ala Ile Ile
                355                 360                 365

His Ser Tyr Thr Lys Glu Asn Ile Glu Tyr Ala Ala Asn Ile Leu Pro
    370                 375                 380

Val Ser Arg Phe Gly Val Asn Gln Ile Gly Ser Ser Gly Leu Gly Gly
385                 390                 395                 400

Ser Phe Leu Asn Gly Leu Asn Pro Thr Ala Thr Leu Gly Cys Gly Ser
                405                 410                 415

Trp Gly Asn Asn Ser Ile Ser Glu Asn Leu Trp Phe Asn His Leu Ile
                420                 425                 430

Asn Val Ser Lys Ile Ala Tyr Glu Val Pro Ser Lys Lys Ile Pro Thr
                435                 440                 445

Asp Asp Glu Ile Trp Asn
    450

<210> SEQ ID NO 108

<400> SEQUENCE: 108

000

<210> SEQ ID NO 109
<211> LENGTH: 485
<212> TYPE: PRT
<213> ORGANISM: Clostridium sp. CAG:448

<400> SEQUENCE: 109

Met Ala Ile Asn Trp Thr Glu Ala Gln Ile Ala Asp Ile Val Ser Lys
1                   5                   10                  15

Val Ile Ala Gly Met Gly Glu Gln Thr Leu Val Asn Asp Lys Glu Trp
                20                  25                  30

Asp Ala Thr Gln Tyr His Gly Arg Lys Leu Ile Gly Ile Phe Glu Thr
            35                  40                  45

Met Glu Glu Ala Ile Asp Ala Ala Ser Ala Gly Tyr Ala Ala Ile Arg
    50                  55                  60

Ala Met Ser Val Ala Gln Arg Glu Thr Leu Ile Ser Ser Ile Arg Thr
65                  70                  75                  80

Tyr Cys Arg Asn Glu Ala Arg Ile Met Ala Glu Leu Gly Val Ala Glu
                85                  90                  95

Thr His Met Gly Arg Val Asp His Lys Thr Ala Lys His Ile Leu Val
                100                 105                 110

Ala Asp Lys Thr Pro Gly Thr Glu Asp Ile Val Ala Glu Ala Lys Thr
            115                 120                 125

Gly Asp Cys Gly Leu Thr Leu Thr Glu Arg Ala Pro Phe Gly Val Val
    130                 135                 140

Gly Ala Ile Thr Pro Ser Thr Asn Pro Ser Glu Thr Val Ile Cys Asn
145                 150                 155                 160
```

Ser Met Gly Met Ile Ala Ala Gly Asn Gly Val Val Phe Asn Pro His
              165                 170                 175

Pro Gly Ala Ile Ala Thr Ser Asn Tyr Ala Val Asp Leu Val Asn Arg
              180                 185                 190

Ala Val Phe Ala Ala Gly Gly Pro Lys Val Leu Val Ala Ser Val Arg
              195                 200                 205

Lys Pro Thr Met Asp Thr Ala Gln Val Met Tyr Lys His Pro Ala Ile
      210                 215                 220

Arg Leu Leu Val Cys Thr Gly Gly Pro Gly Val Val Lys Ala Val Leu
225                 230                 235                 240

Ser Ser Gly Lys Lys Ala Ile Gly Ala Gly Ala Gly Asn Pro Pro Val
              245                 250                 255

Ile Val Asp Asp Thr Ala Asp Ile Glu Lys Ala Ala Lys Asp Ile Ile
              260                 265                 270

Asp Gly Cys Thr Phe Asp Asn Asn Leu Pro Cys Ile Ala Glu Lys Glu
              275                 280                 285

Val Phe Val Phe Asp Asn Val Ala Asp Arg Leu Ile Ala Gly Met Leu
      290                 295                 300

Arg Asn Gly Cys Ile Lys Leu Thr Arg Glu Gln Ala Asp Glu Leu Ala
305                 310                 315                 320

Lys Val Val Val Val Glu Lys Thr Asp Ser Lys Thr Gly Lys Val Thr
              325                 330                 335

Arg Ser Val Asn Arg Asp Cys Val Gly Arg Asp Cys Arg Val Ile Leu
              340                 345                 350

Lys Lys Ile Gly Ile Glu Val Gly Pro Glu Ile Arg Cys Ala Ile Ala
              355                 360                 365

Glu Val Pro Phe Glu His Thr Phe Val Gln Thr Glu Leu Met Met Pro
      370                 375                 380

Ile Leu Gly Ile Val Arg Val Lys Asp Ile Asp Glu Ala Ile Asp Leu
385                 390                 395                 400

Ala Val Lys Ala Glu His Gly Asn Arg His Thr Ala His Met His Ser
              405                 410                 415

Lys Asn Ile Asp Asn Leu Ser Arg Phe Ala Lys Ala Ile Glu Thr Thr
              420                 425                 430

Ile Phe Val Lys Asn Ala Pro Ser Tyr Ala Gly Ile Gly Phe Gly Gly
              435                 440                 445

Glu Gly His Thr Thr Phe Thr Ile Ala Gly Pro Thr Gly Glu Gly Ile
      450                 455                 460

Thr Ser Ala Lys Ser Tyr Thr Arg Leu Arg Arg Cys Val Met Ala Asp
465                 470                 475                 480

His Phe Arg Ile Ile
              485

<210> SEQ ID NO 110

<400> SEQUENCE: 110

000

<210> SEQ ID NO 111
<211> LENGTH: 462
<212> TYPE: PRT
<213> ORGANISM: Yersinia bercovieri ATCC 43970

<400> SEQUENCE: 111

Met Asn Thr Asn Asp Leu Glu Ser Leu Ile Arg Thr Ile Leu Thr Glu

-continued

```
1              5                   10                  15

Gln Leu Thr Pro Ala Thr Ala Ser Ala Ser Asn Ala Ile Phe Ala Ser
                20                  25                  30

Val Asp Glu Ala Val Asn Ala Ala His Ser Ala Phe Leu Arg Tyr Gln
                35                  40                  45

Gln Ser Pro Met Lys Thr Arg Ser Ala Ile Ile Ser Ala Leu Arg Gln
        50                  55                  60

Gln Leu Lys Pro Gln Leu Ala Ser Leu Ser Glu Arg Gly Ala Ser Glu
65                  70                  75                  80

Thr Gly Met Gly Asn Lys Glu Asp Lys Phe Leu Lys Asn Lys Ala Ala
                85                  90                  95

Leu Glu Asn Thr Pro Gly Ile Glu Asp Leu Ser Thr Thr Ala Leu Thr
                100                 105                 110

Gly Asp Gly Gly Met Val Leu Phe Glu Tyr Ser Pro Phe Gly Val Ile
        115                 120                 125

Gly Ser Val Ala Pro Ser Thr Asn Pro Thr Glu Thr Ile Ile Asn Asn
        130                 135                 140

Ser Ile Ser Met Leu Ala Ala Gly Asn Ala Val Tyr Phe Ser Pro His
145                 150                 155                 160

Pro Gly Ala Lys Ala Val Ser Leu Asp Leu Ile Ala Gln Ile Glu Ala
                165                 170                 175

Ile Ile Phe Asn Ser Cys Gly Ile Arg Asn Leu Val Val Thr Val Gln
                180                 185                 190

Glu Pro Ser Phe Glu Ala Thr Gln Gln Met Met Ala His Asp Lys Ile
                195                 200                 205

Ala Leu Leu Ala Ile Thr Gly Gly Pro Ala Ile Val Ala Met Gly Met
        210                 215                 220

Lys Ser Gly Lys Lys Val Ile Gly Ala Gly Ala Gly Asn Pro Pro Cys
225                 230                 235                 240

Leu Val Asp Glu Thr Ala Glu Leu Ala Lys Ala Ala Gln Asp Ile Val
                245                 250                 255

Ser Gly Ala Ser Phe Asp Tyr Asn Leu Pro Cys Ile Ala Glu Lys Ser
                260                 265                 270

Leu Ile Val Val Glu Ser Val Ala Asp Arg Leu Leu Gln Gln Met Gln
        275                 280                 285

Ala Phe Asp Ala Leu Leu Ile Ser Asn Pro Gln Asp Val Asp Ser Leu
        290                 295                 300

Arg Lys Ala Cys Leu Thr Pro Gln Gly His Ala Asn Lys Asn Leu Val
305                 310                 315                 320

Gly Lys Ser Pro Leu Glu Leu Leu Lys Ala Ala Gly Leu Thr Cys Pro
                325                 330                 335

Ala Lys Ala Pro Arg Leu Leu Leu Val Glu Val Ala Gly Asp Asp Pro
        340                 345                 350

Leu Val Thr Thr Glu Gln Leu Met Pro Leu Leu Pro Val Val Arg Val
        355                 360                 365

Lys Asp Phe Asp Ala Ala Leu Thr Leu Ala Leu Gln Val Glu Gly Gly
        370                 375                 380

Leu His His Thr Ala Thr Met His Ser Gln Asn Val Ser Arg Leu Asn
385                 390                 395                 400

Leu Ala Ala Arg Leu Leu Gln Thr Ser Ile Phe Val Lys Asn Gly Pro
                405                 410                 415

Ser Tyr Ala Gly Ile Gly Val Gly Gly Glu Gly Phe Thr Thr Phe Thr
                420                 425                 430
```

-continued

```
Ile Ala Thr Pro Thr Gly Glu Gly Thr Thr Ser Ala Arg Thr Phe Ala
        435             440             445

Arg Gln Arg Arg Cys Val Leu Thr Asn Gly Phe Ser Ile Arg
    450             455             460

<210> SEQ ID NO 112
<211> LENGTH: 511
<212> TYPE: PRT
<213> ORGANISM: Proteocatella sphenisci

<400> SEQUENCE: 112

Val Asp Ile Gly Gln Lys Asp Ile Glu Leu Ile Val Gln Gln Val Leu
1               5                   10                  15

Lys Asn Val Val Ser Gln Ser Ala Ala Ala Gln Ser Asn Ser Gln Pro
            20                  25                  30

Glu Val Lys Thr Tyr Arg Pro Gly Val Pro Val Gln Glu Phe Ser Met
        35                  40                  45

Lys Ser Gln Tyr Ala Pro Ser Ser Pro Tyr Pro Ser Ser Ser Gln Ser
    50                  55                  60

Ser Ala Gly Asp Tyr Gly Val Phe Glu Thr Met Asp Gln Ala Val Glu
65                  70                  75                  80

Ala Ala Tyr Gln Ala Gln Lys Ile Tyr Gln Ala Lys Phe Gln Leu Lys
                85                  90                  95

Asp Arg Glu Arg Leu Ile Lys Ser Ile Arg Glu Thr Gly Met Lys Asn
            100                 105                 110

Val Glu Lys Leu Ala Arg Met Ser Val Asp Glu Thr Gly Leu Gly Arg
            115                 120                 125

Tyr Glu Asp Lys Ile Leu Lys Asn Thr Leu Val Leu Glu Arg Thr Pro
    130                 135                 140

Gly Thr Glu Cys Leu Lys Thr Glu Ala Ile Ser Gly Asp Asp Gly Leu
145                 150                 155                 160

Thr Ile Ile Glu His Ala Pro Tyr Gly Val Ile Gly Ser Ile Thr Pro
                165                 170                 175

Val Thr Asn Pro Thr Glu Thr Ile Ile Asn Asn Val Ile Ser Met Ile
            180                 185                 190

Ala Gly Gly Asn Ser Val Val Phe Asn Val His Pro Ser Ala Lys Glu
            195                 200                 205

Ser Cys Arg Phe Ala Val Gln Met Ile Asn Lys Ala Ile Glu Glu Val
    210                 215                 220

Gly Gly Pro Lys Asn Leu Val Ser Met Val Lys Gln Pro Thr Leu Asp
225                 230                 235                 240

Thr Val Ser Gln Leu Ser Lys Asn Asp Lys Val Arg Leu Met Ala Gly
                245                 250                 255

Thr Gly Gly Met Pro Met Val Arg Ser Leu Leu Gln Ser Gly Lys Lys
                260                 265                 270

Val Ile Gly Ala Gly Ala Gly Asn Pro Pro Val Ile Val Asp Glu Thr
            275                 280                 285

Ala Asp Ile Lys Arg Ala Ala Ala Glu Ile Phe Lys Gly Ala Ser Phe
    290                 295                 300

Asp Asn Asn Val Leu Cys Leu Ala Glu Lys Glu Val Phe Ile Val Glu
305                 310                 315                 320

Ser Val Ala Thr Asp Phe Val Tyr Asn Met Ile Gln Glu Gly Ala Phe
                325                 330                 335

Leu Leu Asn Glu Ser Gln Leu Glu Lys Ile Met Asn Leu Val Leu Thr
```

-continued

```
              340              345              350

Tyr Glu Glu Thr Pro Asn Gly Arg Glu Tyr His Thr Ser Lys Asn Trp
         355              360              365

Val Gly Lys Asp Ala Gly Lys Met Leu Asp Ala Ile Gly Ile Asn Gly
         370              375              380

Lys Ser Asp Cys Arg Leu Leu Ile Cys Glu Val Gly Pro Asn His Pro
385              390              395              400

Phe Val Leu Leu Glu Gln Leu Met Pro Val Leu Pro Ile Val Lys Cys
              405              410              415

Lys Asn Leu Asp Glu Ala Ile Lys Phe Ala Met Ile Ala Glu His Gly
         420              425              430

Asn Arg His Thr Ala Ser Met Phe Ser Gln Ser Ile Asn Asn Leu Thr
         435              440              445

Arg Phe Ala Arg Glu Val Glu Thr Thr Ile Phe Val Lys Asn Ala Ala
         450              455              460

Thr Leu Ala Gly Val Gly Phe Gly Gly Glu Gly His Thr Thr Met Thr
465              470              475              480

Ile Ala Gly Pro Thr Gly Glu Gly Ile Thr Asn Ala Val Ser Phe Thr
              485              490              495

Arg Gln Arg Arg Cys Ala Leu Ser Glu Gly Gly Phe Arg Ile Ile
         500              505              510
```

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117
<211> LENGTH: 480
<212> TYPE: PRT
<213> ORGANISM: Pelosinus propionicus DSM

<400> SEQUENCE: 117

```
Met Ser Ile Asp Gln Ala Leu Ile Glu Lys Ile Thr Leu Glu Ile Leu
1               5               10              15

Ser Lys Met Gln Thr Gly Ala Lys Ala Ala Pro Thr Gly Tyr Gly Ser
              20              25              30

Gly Ile Phe Glu Thr Val Asp Glu Ala Val Ala Ala Ala Arg Lys Ala
         35              40              45

Tyr Gln Glu Leu Lys Thr Leu Ser Leu Glu Lys Arg Glu Val Leu Ile
         50              55              60
```

-continued

```
Lys Ala Met Arg Asp Val Ala Tyr Glu Asn Ala Thr Ile Leu Ala Gln
65                  70                  75                  80

Met Ala Val Asp Glu Ser Gly Met Gly Arg Val Ser Asp Lys Ile Ile
                85                  90                  95

Lys Asn Gln Val Ala Ala Leu Lys Thr Pro Gly Thr Glu Asp Leu Thr
            100                 105                 110

Thr Gln Ala Trp Ser Gly Asp Asn Gly Leu Thr Leu Ile Glu Met Gly
            115                 120                 125

Pro Tyr Gly Val Ile Gly Ala Ile Thr Pro Thr Thr Asn Pro Thr Glu
        130                 135                 140

Thr Val Ile Cys Asn Gly Ile Gly Met Ile Ala Ala Gly Asn Thr Val
145                 150                 155                 160

Phe Phe Ser Pro His Pro Thr Ala Lys Asn Thr Ser Ile Lys Ile Ile
                165                 170                 175

Thr Leu Leu Asn Asp Ala Ile Val Lys Ala Gly Gly Pro Asn Asn Leu
            180                 185                 190

Leu Thr Ser Val Ala Asn Pro Ser Ile Lys Ala Ala Asn Glu Met Met
        195                 200                 205

Lys His Pro Gly Ile Asn Met Leu Val Ala Thr Gly Gly Pro Gly Val
    210                 215                 220

Val Lys Ala Val Leu Ser Ser Gly Lys Lys Ala Ile Gly Ala Gly Ala
225                 230                 235                 240

Gly Asn Pro Pro Val Ile Val Asp Glu Thr Ala Asp Ile Glu Lys Ala
                245                 250                 255

Ala Arg Asp Ile Val Ala Gly Cys Ser Phe Asp Asn Asn Leu Pro Cys
            260                 265                 270

Ile Ala Glu Lys Glu Val Ile Ala Val Gly Ser Ile Ala Asp Arg Leu
            275                 280                 285

Ile Thr Tyr Met Gln Lys Tyr Gly Ala Tyr Leu Ile Ser Gly Ser Asn
        290                 295                 300

Ile Asp Arg Leu Leu Asp Val Ile Met Thr Val Gln Glu Glu Lys Ile
305                 310                 315                 320

Ala Glu Gly Cys Thr Asp Lys Pro Lys Arg Ser Tyr Gly Ile Asn Lys
                325                 330                 335

Asp Tyr Val Gly Lys Asp Ala Lys Tyr Leu Leu Ser Lys Ile Gly Ile
            340                 345                 350

Asp Val Pro Asp Ser Val Lys Val Val Leu Cys Glu Thr Pro Ala Asp
        355                 360                 365

His Pro Phe Val Ile Glu Glu Leu Met Met Pro Val Leu Pro Val Val
    370                 375                 380

Gln Val Lys Asp Ile Asp Glu Ala Ile Glu Val Ala Val Arg Val Glu
385                 390                 395                 400

His Gly Asn Arg His Thr Ala Ala Met His Ser Lys Asn Val Asp His
                405                 410                 415

Leu Thr Arg Phe Ala Arg Ala Val Glu Thr Thr Ile Phe Val Lys Asn
            420                 425                 430

Ala Pro Ser Tyr Ala Gly Ile Gly Val Gly Gly Glu Gly Phe Thr Ser
        435                 440                 445

Phe Thr Leu Ala Gly Pro Thr Gly Glu Gly Ile Thr Ser Pro Arg Ser
    450                 455                 460

Phe Thr Arg Gln Arg Arg Cys Val Leu Val Asp Ala Phe Ser Ile Val
465                 470                 475                 480
```

```
<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129
```

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134
<211> LENGTH: 457
<212> TYPE: PRT
<213> ORGANISM: Clostridium sp. KLE

<400> SEQUENCE: 134

Met Val Gln Asp Ile Val Lys Glu Val Val Ala Arg Met Gln Leu Ser
1               5                   10                  15

Gly Thr Ala Gln Ser Ala Gln His Gly Val Phe Asn Asp Met Asn Gln
            20                  25                  30

Ala Ile Glu Ala Ala Lys Glu Ala Glu Lys Thr Val Arg Arg Met Thr
        35                  40                  45

Met Asp Gln Arg Glu Gln Ile Val Ser Asn Ile Arg Lys Lys Thr His
    50                  55                  60

Glu Ala Ala Glu Ile Leu Ala Arg Met Gly Val Glu Glu Thr Gly Met
65                  70                  75                  80

Gly Asn Val Gly Asp Lys Ile Leu Lys His His Leu Leu Ala Asp Lys
                85                  90                  95

Thr Pro Gly Thr Glu Asp Ile Thr Thr Thr Ala Trp Ser Gly Asp Arg
            100                 105                 110

Gly Leu Thr Leu Ile Glu Met Gly Pro Phe Gly Val Ile Gly Ala Ile
            115                 120                 125

Thr Pro Cys Thr Asn Pro Ser Glu Thr Val Leu Cys Asn Ser Ile Gly
    130                 135                 140

Met Ile Ala Ala Gly Asn Thr Val Val Phe Asn Pro His Pro Gln Ala
145                 150                 155                 160

Ile Arg Thr Ser Ile Phe Ala Ile Asn Leu Val Asn Glu Ala Ser Leu
                165                 170                 175

Glu Ala Gly Gly Pro Asp Asn Val Ala Cys Thr Val Phe Lys Pro Thr
            180                 185                 190

Leu Glu Thr Ser Asn Ile Met Met Lys His Lys Asp Ile Pro Leu Ile
            195                 200                 205

-continued

```
Ala Ala Thr Gly Gly Pro Gly Val Val Thr Ala Val Leu Ser Ser Gly
    210                 215             220

Lys Arg Gly Ile Gly Ala Gly Ala Gly Asn Pro Pro Ala Leu Val Asp
225                 230                 235                 240

Glu Thr Ala Asp Ile Arg Lys Ala Ala Ala Asp Ile Val Asn Gly Cys
                245                 250                 255

Thr Phe Asp Asn Asn Leu Pro Cys Ile Ala Glu Lys Glu Ile Val Ala
                260                 265                 270

Val Asp Ser Ile Ala Asp Glu Leu Met Asn Tyr Met Ile Ser Glu Gln
                275                 280                 285

Gly Cys Tyr Leu Ile Ser Lys Glu Glu Gln Asp Lys Leu Thr Ala Thr
    290                 295                 300

Val Leu Thr Pro Lys Gly Leu Asn Arg Lys Cys Val Gly Arg Asp Ala
305                 310                 315                 320

Arg Thr Leu Leu Ser Met Ile Gly Ile Gln Ala Pro Glu Asn Ile Arg
                325                 330                 335

Cys Ile Val Phe Glu Gly Glu Lys Glu His Pro Leu Ile Ser Glu Glu
                340                 345                 350

Leu Met Met Pro Ile Leu Gly Leu Val Arg Ala Lys Asp Phe Asp Asp
                355                 360                 365

Ala Val Glu Lys Ala Val Trp Leu Glu His Gly Asn Arg His Ser Ala
    370                 375                 380

His Ile His Ser Lys Asn Ile Asp Asn Ile Thr Lys Tyr Ala Arg Ala
385                 390                 395                 400

Ile Asp Thr Ala Ile Leu Val Lys Asn Ala Pro Ser Tyr Ala Ala Leu
                405                 410                 415

Gly Phe Gly Gly Glu Gly Phe Cys Thr Phe Thr Ile Ala Ser Arg Thr
                420                 425                 430

Gly Glu Gly Leu Thr Ser Thr Ser Thr Phe Thr Lys Arg Arg Arg Cys
    435                 440                 445

Val Met Ser Asp Ser Leu Cys Ile Arg
    450                 455
```

```
<210> SEQ ID NO 135
<211> LENGTH: 527
<212> TYPE: PRT
<213> ORGANISM: Caldalkalibacillus thermarum TA2.A1

<400> SEQUENCE: 135

Met Asn Met Thr Glu Lys Asp Ile Glu Lys Ile Val Gln Ser Val Leu
1               5                   10                  15

His Asn Val Glu Ser Ala Leu Gly Lys Ser Ala Ser Ala Ser Pro Ser
                20                  25                  30

Val Ser Ala Val Ser Val Ala Ser Gly Glu Gly Ile Lys Pro Val Gln
            35                  40                  45

Phe Lys Gln Val Pro Val Phe Gln Gln Glu Thr Val Lys Ser Pro Asn
    50                  55                  60

Arg Asn Arg Asn Leu Gly Gly Ala Glu Glu Lys Trp Gly Val Phe Asn
65                  70                  75                  80

His Met Glu Asp Ala Ile Glu Ala Ser Tyr Arg Ala Gln Met Glu Phe
                85                  90                  95

Val Lys His Phe Gln Leu Lys Asp Arg Glu Lys Ile Ile Thr Ala Ile
                100                 105                 110

Arg Glu Ala Val Leu Arg Glu Lys Glu Val Leu Ala Arg Lys Val Tyr
```

-continued

```
            115                 120                 125
Glu Glu Thr Lys Ile Gly Arg Tyr Glu Asp Lys Val Ala Lys His Glu
    130                 135                 140

Leu Ala Ala Leu Lys Thr Pro Gly Thr Glu Asp Leu Lys Thr Glu Ala
145                 150                 155                 160

Phe Ser Gly Asp Asn Gly Leu Thr Ile Val Glu Arg Ala Pro Tyr Gly
                165                 170                 175

Leu Ile Gly Ala Val Thr Pro Val Thr Asn Pro Thr Glu Thr Ile Ile
                180                 185                 190

Asn Asn Ala Ile Gly Met Leu Ala Ala Gly Asn Ala Val Val Phe Asn
                195                 200                 205

Val His Pro Ser Ser Lys Arg Ser Cys Ala Tyr Ala Val Gln Leu Ile
    210                 215                 220

Asn Lys Ala Ile Thr Glu Ala Gly Gly Pro His His Leu Val Thr Met
225                 230                 235                 240

Val Lys Glu Pro Thr Leu Asp Thr Leu Gln Thr Leu Ile Asp Ser Pro
                245                 250                 255

Lys Val Lys Leu Leu Val Gly Thr Gly Gly Pro Gly Leu Val Gln Thr
                260                 265                 270

Leu Leu Lys Ser Gly Lys Lys Ala Ile Gly Ala Gly Ala Gly Asn Pro
                275                 280                 285

Pro Val Ile Val Asp Asp Thr Ala Asp Leu Glu His Ala Ala Arg Ser
    290                 295                 300

Ile Ile Glu Gly Ala Ala Phe Asp Asn Asn Leu Leu Cys Ile Ala Glu
305                 310                 315                 320

Lys Glu Val Phe Val Leu Glu Ser Val Ala Asp Asp Leu Ile Phe His
                325                 330                 335

Met Leu Asn His Gly Ala Tyr Met Leu Gly Gln His Glu Val Glu Gln
                340                 345                 350

Val Met Ala Phe Ala Leu Glu Glu Gln Gly Asn Glu Gln Asn Arg Gly
                355                 360                 365

Cys Gly Phe Asn Pro Gln Arg His Tyr Gln Val Ser Lys Asp Trp Ile
    370                 375                 380

Gly Gln Asp Ala Arg Leu Phe Leu Glu His Ile Gly Val Gln Pro Pro
385                 390                 395                 400

Thr Glu Val Lys Leu Leu Ile Cys Asp Val Glu Phe Asp His Pro Phe
                405                 410                 415

Val Gln Leu Glu Gln Met Met Pro Val Leu Pro Ile Val Arg Val Lys
                420                 425                 430

Thr Leu Asp Glu Ala Ile Glu Lys Ala Val Met Ala Glu His Gly Asn
                435                 440                 445

Arg His Thr Ala Ile Met His Ser Lys Asn Val Asp His Leu Thr Lys
    450                 455                 460

Phe Ala Arg Ala Ile Gln Thr Thr Leu Phe Val Lys Asn Ala Ser Ser
465                 470                 475                 480

Leu Ala Gly Val Gly Tyr Gly Gly Glu Gly His Thr Thr Met Thr Ile
                485                 490                 495

Ala Gly Pro Thr Gly Glu Gly Val Thr Ser Ala Lys Thr Phe Thr Arg
                500                 505                 510

Glu Arg Arg Cys Val Leu Ala Glu Gly Gly Phe Arg Ile Ile Gly
    515                 520                 525
```

<210> SEQ ID NO 136

-continued

<400> SEQUENCE: 136

000

<210> SEQ ID NO 137
<211> LENGTH: 476
<212> TYPE: PRT
<213> ORGANISM: Caldalkalibacillus thermarum TA2.A1

<400> SEQUENCE: 137

```
Val Pro Val Phe Gln Gln Glu Thr Val Lys Ser Pro Asn Arg Asn Arg
1               5                   10                  15

Asn Leu Gly Gly Ala Glu Glu Lys Trp Gly Val Phe Asn His Met Glu
            20                  25                  30

Asp Ala Ile Glu Ala Ser Tyr Arg Ala Gln Met Glu Phe Val Lys His
        35                  40                  45

Phe Gln Leu Lys Asp Arg Glu Lys Ile Ile Thr Ala Ile Arg Glu Ala
    50                  55                  60

Val Leu Arg Glu Lys Glu Val Leu Ala Arg Lys Val Tyr Glu Glu Thr
65                  70                  75                  80

Lys Ile Gly Arg Tyr Glu Asp Lys Val Ala Lys His Glu Leu Ala Ala
                85                  90                  95

Leu Lys Thr Pro Gly Thr Glu Asp Leu Lys Thr Glu Ala Phe Ser Gly
            100                 105                 110

Asp Asn Gly Leu Thr Ile Val Glu Arg Ala Pro Tyr Gly Leu Ile Gly
        115                 120                 125

Ala Val Thr Pro Val Thr Asn Pro Thr Glu Thr Ile Ile Asn Asn Ala
    130                 135                 140

Ile Gly Met Leu Ala Ala Gly Asn Ala Val Val Phe Asn Val His Pro
145                 150                 155                 160

Ser Ser Lys Arg Ser Cys Ala Tyr Ala Val Gln Leu Ile Asn Lys Ala
                165                 170                 175

Ile Thr Glu Ala Gly Gly Pro His His Leu Val Thr Met Val Lys Glu
            180                 185                 190

Pro Thr Leu Asp Thr Leu Gln Thr Leu Ile Asp Ser Pro Lys Val Lys
            195                 200                 205

Leu Leu Val Gly Thr Gly Gly Pro Gly Leu Val Gln Thr Leu Leu Lys
    210                 215                 220

Ser Gly Lys Lys Ala Ile Gly Ala Gly Ala Gly Asn Pro Pro Val Ile
225                 230                 235                 240

Val Asp Asp Thr Ala Asp Leu Glu His Ala Ala Arg Ser Ile Ile Glu
                245                 250                 255

Gly Ala Ala Phe Asp Asn Asn Leu Leu Cys Ile Ala Glu Lys Glu Val
                260                 265                 270

Phe Val Leu Glu Ser Val Ala Asp Asp Leu Ile Phe His Met Leu Asn
            275                 280                 285

His Gly Ala Tyr Met Leu Gly Gln His Glu Val Glu Gln Val Met Ala
            290                 295                 300

Phe Ala Leu Glu Glu Gln Gly Asn Glu Gln Asn Arg Gly Cys Gly Phe
305                 310                 315                 320

Asn Pro Gln Arg His Tyr Gln Val Ser Lys Asp Trp Ile Gly Gln Asp
                325                 330                 335

Ala Arg Leu Phe Leu Glu His Ile Gly Val Gln Pro Pro Thr Glu Val
            340                 345                 350
```

-continued

```
Lys Leu Leu Ile Cys Asp Val Glu Phe Asp His Pro Phe Val Gln Leu
        355             360             365

Glu Gln Met Met Pro Val Leu Pro Ile Val Arg Val Lys Thr Leu Asp
    370             375             380

Glu Ala Ile Glu Lys Ala Val Met Ala Glu His Gly Asn Arg His Thr
385             390             395             400

Ala Ile Met His Ser Lys Asn Val Asp His Leu Thr Lys Phe Ala Arg
            405             410             415

Ala Ile Gln Thr Thr Leu Phe Val Lys Asn Ala Ser Ser Leu Ala Gly
            420             425             430

Val Gly Tyr Gly Gly Glu Gly His Thr Thr Met Thr Ile Ala Gly Pro
            435             440             445

Thr Gly Glu Gly Val Thr Ser Ala Lys Thr Phe Thr Arg Glu Arg Arg
    450             455             460

Cys Val Leu Ala Glu Gly Gly Phe Arg Ile Ile Gly
465             470             475
```

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145
<211> LENGTH: 462
<212> TYPE: PRT
<213> ORGANISM: Blautia sp. CAG:257

-continued

<400> SEQUENCE: 145

```
Met Pro Ile Ser Glu Asn Met Val Gln Glu Ile Val Gln Glu Val Met
1               5                   10                  15

Ala Lys Met Gln Ile Ala Glu Ala Pro Ala Gly Lys His Gly Ile Phe
            20                  25                  30

Lys Asp Met Asn Asp Ala Ile Glu Ala Ala Lys Lys Ala Glu Leu Ile
        35                  40                  45

Val Lys Arg Met Ser Met Asp Gln Arg Glu Lys Ile Ile Thr Cys Ile
    50                  55                  60

Arg Lys Lys Ile Lys Glu Asn Ala Glu Val Leu Ala Arg Met Gly Val
65                  70                  75                  80

Glu Glu Thr Gly Met Gly Asn Val Gly Asp Lys Ile Leu Lys His His
            85                  90                  95

Leu Val Ala Asp Lys Thr Pro Gly Thr Glu Asp Ile Thr Thr Thr Ala
            100                 105                 110

Trp Ser Gly Asp Arg Gly Leu Thr Leu Ile Glu Met Gly Pro Phe Gly
            115                 120                 125

Val Ile Gly Ala Ile Thr Pro Cys Thr Asn Pro Ser Glu Thr Val Leu
    130                 135                 140

Cys Asn Thr Met Gly Met Leu Ala Gly Gly Asn Thr Val Val Phe Asn
145                 150                 155                 160

Pro His Pro Ala Ala Ile Lys Thr Ser Ile Tyr Ala Ile Asn Leu Leu
            165                 170                 175

Asn Glu Ala Ser Leu Glu Ser Gly Gly Pro Asp Asn Ile Ala Val Thr
            180                 185                 190

Val Glu Lys Pro Thr Leu Glu Thr Ser Asp Ile Met Met Lys His Lys
            195                 200                 205

Asp Ile His Leu Ile Ala Ala Thr Gly Gly Pro Gly Val Val Thr Ala
    210                 215                 220

Val Leu Ser Ser Gly Lys Arg Gly Ile Gly Ala Gly Ala Gly Asn Pro
225                 230                 235                 240

Pro Ala Leu Val Asp Glu Thr Ala Asp Ile Arg Lys Ala Ala Gln Asp
            245                 250                 255

Ile Val Asn Gly Cys Thr Phe Asp Asn Asn Leu Pro Cys Ile Ala Glu
            260                 265                 270

Lys Glu Ile Val Ala Val Ser Ser Ile Ala Asp Glu Leu Met His Tyr
            275                 280                 285

Leu Ile Thr Glu Asn Asp Cys Tyr Leu Ala Ser Lys Glu Glu Gln Asp
    290                 295                 300

Lys Leu Thr Glu Val Val Leu Ala Gly Gly Lys Leu Asn Arg Lys Cys
305                 310                 315                 320

Val Gly Arg Asp Ala Arg Thr Leu Leu Ser Met Ile Gly Val Asp Ala
            325                 330                 335

Pro Ala Asn Ile Arg Cys Ile Val Phe Glu Gly Pro Lys Glu His Pro
            340                 345                 350

Leu Ile Ala Glu Glu Leu Met Met Pro Ile Leu Gly Met Val Arg Ala
            355                 360                 365

Arg Asp Phe Asp Asp Ala Val Glu Gln Ala Val Trp Leu Glu His Gly
            370                 375                 380

Asn Arg His Ser Ala His Ile His Ser Lys Asn Val Asp Asn Ile Thr
385                 390                 395                 400

Lys Tyr Ala Arg Ala Ile Asp Thr Ala Ile Leu Val Lys Asn Gly Pro
            405                 410                 415
```

-continued

```
Ser Tyr Ser Ala Leu Gly Phe Gly Gly Glu Gly Phe Cys Thr Phe Thr
            420             425             430

Ile Ala Ser Arg Thr Gly Glu Gly Leu Thr Ser Ala Ser Thr Phe Thr
            435             440             445

Lys Arg Arg Arg Cys Val Met Ser Asp Ser Leu Cys Ile Arg
    450             455             460

<210> SEQ ID NO 146
<211> LENGTH: 469
<212> TYPE: PRT
<213> ORGANISM: Listeria marthii FSL

<400> SEQUENCE: 146

Met Glu Ser Leu Glu Leu Glu Gln Leu Val Lys Lys Val Leu Leu Glu
1               5                   10                  15

Lys Leu Ala Glu Gln Lys Glu Ala Pro Ala Lys Pro Ile Thr Gln Gly
            20                  25                  30

Ala Lys Ser Gly Ile Phe Asp Thr Val Asp Glu Ala Val Gln Ala Ala
            35                  40                  45

Val Ile Ala Gln Asn Cys Tyr Lys Glu Lys Ser Leu Glu Glu Arg Arg
        50                  55                  60

Asn Val Val Lys Ala Ile Arg Glu Thr Leu Tyr Pro Glu Ile Glu Thr
65                  70                  75                  80

Ile Ala Thr Lys Ala Val Ala Glu Thr Gly Met Gly Asn Val Ala Asp
                85                  90                  95

Lys Ile Leu Lys Asn Thr Leu Ala Ile Glu Lys Thr Pro Gly Val Glu
            100                 105                 110

Asp Leu Tyr Thr Glu Val Ala Thr Gly Asp Asn Gly Met Thr Leu Tyr
            115                 120                 125

Glu Leu Ser Pro Tyr Gly Val Ile Gly Ala Val Ala Pro Ser Thr Asn
            130                 135                 140

Pro Thr Glu Thr Leu Ile Cys Asn Thr Ile Gly Met Leu Ala Ala Gly
145                 150                 155                 160

Asn Ala Val Phe Tyr Ser Pro His Pro Gly Ala Lys Asn Ile Ser Leu
                165                 170                 175

Trp Leu Ile Glu Lys Leu Asn Thr Ile Val Arg Glu Ser Cys Gly Ile
            180                 185                 190

Asp Asn Leu Val Val Thr Val Glu Lys Pro Ser Ile Gln Ala Ala Gln
            195                 200                 205

Glu Met Met Asn His Pro Lys Val Pro Leu Leu Val Ile Thr Gly Gly
            210                 215                 220

Pro Gly Val Val Leu Gln Ala Met Gln Ser Gly Lys Lys Val Ile Gly
225                 230                 235                 240

Ala Gly Ala Gly Asn Pro Pro Ser Ile Val Asp Glu Thr Ala Asn Ile
                245                 250                 255

Glu Lys Ala Ala Ala Asp Ile Val Asp Gly Ala Ser Phe Asp His Asn
            260                 265                 270

Ile Leu Cys Ile Ala Glu Lys Ser Ile Val Ala Val Glu Ser Ile Ala
            275                 280                 285

Asp Phe Leu Leu Phe Gln Met Glu Lys Asn Gly Ala Leu His Val Thr
        290                 295                 300

Asn Pro Ser Asp Ile Gln Lys Leu Glu Lys Val Ala Val Thr Asp Lys
305                 310                 315                 320

Gly Val Thr Asn Lys Lys Leu Val Gly Lys Ser Ala Ala Glu Ile Leu
```

-continued

```
                        325              330              335
Lys Glu Ala Gly Ile Thr Cys Asp Phe Thr Pro Arg Leu Ile Ile Val
             340              345              350

Glu Thr Thr Lys Thr His Pro Phe Ala Thr Val Glu Leu Leu Met Pro
             355              360              365

Ile Val Pro Leu Val Arg Val Pro Asp Phe Asp Glu Ala Leu Glu Val
             370              375              380

Ala Ile Glu Leu Glu Gln Gly Leu His His Thr Ala Thr Met His Ser
385              390              395              400

Gln Asn Ile Ser Arg Leu Asn Lys Ala Ala Arg Asp Met Gln Thr Ser
             405              410              415

Ile Phe Val Lys Asn Gly Pro Ser Phe Ala Gly Leu Gly Phe Arg Gly
             420              425              430

Glu Gly Ser Thr Thr Phe Thr Ile Ala Thr Pro Thr Gly Glu Gly Thr
             435              440              445

Thr Thr Ala Arg His Phe Ala Arg Arg Arg Cys Val Leu Thr Asp
             450              455              460

Gly Phe Ser Ile Arg
465

<210> SEQ ID NO 147

<400> SEQUENCE: 147

000

<210> SEQ ID NO 148
<211> LENGTH: 473
<212> TYPE: PRT
<213> ORGANISM: Clostridium methoxybenzovorans

<400> SEQUENCE: 148

Met Glu Ile Gly Ala Lys Glu Ile Glu Leu Ile Val Arg Glu Val Leu
1               5                10               15

Ala Gly Ile Glu Ser Arg Gly Ile Lys Pro Ser Tyr Thr Pro Ser Arg
             20               25               30

Ser Glu Asp Gly Val Phe Glu Arg Val Glu Asp Ala Ile Glu Ala Ala
             35               40               45

Tyr Ala Ala Gln Arg Glu Trp Val Glu His Tyr Arg Val Glu Asp Arg
     50               55               60

Arg Arg Ile Ile Glu Ala Ile Arg Val Thr Ala Lys Ser His Ala Glu
65               70               75               80

Ser Leu Ala Lys Met Val Trp Glu Glu Thr Gly Met Gly Arg Phe Glu
             85               90               95

Asp Lys Ile Gln Lys His Met Ala Val Ile Glu Lys Thr Pro Gly Val
             100              105              110

Glu Cys Leu Thr Thr Glu Ala Ile Ser Gly Asp Gly Gly Leu Met Ile
             115              120              125

Glu Glu Tyr Ala Pro Phe Gly Val Ile Gly Ala Ile Thr Pro Ser Thr
             130              135              140

Asn Pro Thr Glu Thr Ile Ile Asn Asn Thr Ile Ser Met Ile Ala Gly
145              150              155              160

Gly Asn Ser Val Val Phe Asn Val His Pro Gly Ala Lys Arg Cys Cys
             165              170              175

Ala His Cys Leu Lys Ile Leu His Gln Ala Ile Val Glu Asn Gly Gly
             180              185              190
```

```
Pro Ala Ser Leu Ile Thr Met Gln Lys Glu Pro Asp Met Glu Ala Val
        195                 200                 205

Ser Lys Leu Thr Ser Asp Pro Arg Ile Arg Leu Met Val Gly Thr Gly
        210                 215                 220

Gly Met Pro Met Val Asn Ala Leu Leu Arg Ser Gly Lys Lys Thr Ile
225                 230                 235                 240

Gly Ala Gly Ala Gly Asn Pro Pro Val Ile Val Asp Asp Thr Ala Asp
                245                 250                 255

Val Ser Leu Ala Ala Arg Glu Ile Tyr Arg Gly Ala Ser Phe Asp Asn
                260                 265                 270

Asn Ile Leu Cys Leu Ala Glu Lys Glu Val Phe Val Met Glu Arg Ala
        275                 280                 285

Ala Asp Glu Leu Val Asn Lys Leu Ile Lys Glu Gly Ala Tyr Leu Leu
        290                 295                 300

Ser Ser Met Glu Leu Ser Glu Ile Leu Lys Phe Ala Met Val Glu Lys
305                 310                 315                 320

Asn Gly Ser Tyr Glu Val Asn Lys Lys Trp Val Gly Lys Asp Ala Gly
                325                 330                 335

Gln Phe Leu Glu Ala Ile Gly Val Ser Gly His Lys Asp Val Arg Leu
        340                 345                 350

Leu Ile Cys Glu Thr Asp Arg Ser His Pro Phe Val Met Val Glu Gln
        355                 360                 365

Leu Met Pro Ile Leu Pro Ile Val Arg Leu Arg Thr Phe Glu Glu Cys
        370                 375                 380

Val Glu Ser Ala Leu Ala Ala Glu Ser Gly Asn Arg His Thr Ala Ser
385                 390                 395                 400

Met Phe Ser Arg Asn Val Glu Asn Met Thr Lys Phe Gly Lys Ile Ile
                405                 410                 415

Glu Thr Thr Ile Phe Thr Lys Asn Gly Ser Thr Leu Lys Gly Val Gly
                420                 425                 430

Ile Gly Gly Glu Gly His Thr Thr Met Thr Ile Ala Gly Pro Thr Gly
                435                 440                 445

Glu Gly Leu Thr Cys Ala Arg Ser Phe Thr Arg Arg Arg Cys Met
        450                 455                 460

Leu Ala Glu Gly Gly Leu Arg Ile Ile
465                 470

<210> SEQ ID NO 149
<211> LENGTH: 477
<212> TYPE: PRT
<213> ORGANISM: Bacillus sp. m3-13

<400> SEQUENCE: 149

Val Gln Ile Lys Glu Ser Asp Ile Lys Glu Met Val Ala Gln Val Leu
1               5                   10                  15

Ala Gln Leu Gly Asp Glu Ser Lys Gln Pro Ser Pro Ala Ser Glu Gln
        20                  25                  30

Gly Ser Asn Glu Val Pro Leu Gly Asn Gly Val Phe Thr Thr Val Asp
        35                  40                  45

Gln Ala Thr Glu Ala Ala Thr Glu Ala Trp Asp Lys Leu Arg Ala Thr
        50                  55                  60

Ser Leu Glu Thr Arg Lys Asn Met Ile Glu Lys Met Arg Glu Val Ser
65                  70                  75                  80

Arg Glu His Ala Lys Ala Leu Ala Glu Leu Ala Val Lys Glu Thr Gly
```

-continued

```
                    85              90              95

Leu Gly Arg Val Glu Asp Lys Val Ala Lys Asn Leu Leu Ala Ala Asp
            100             105             110

Lys Thr Pro Gly Val Glu Asp Ile Val Ala Thr Thr Tyr Ser Gly Asp
            115             120             125

Gly Gly Leu Thr Leu Val Glu Tyr Ser Pro Val Gly Val Tyr Gly Ala
            130             135             140

Ile Thr Pro Ser Thr Asn Pro Ala Ala Thr Ile Ile Asn Asn Ser Ile
145             150             155             160

Ser Leu Val Ala Ala Gly Asn Ala Val Val Phe Asn Pro His Pro Ser
            165             170             175

Ala Lys Gln Val Ser Ile Lys Thr Met Gln Leu Leu Asn Glu Ala Ile
            180             185             190

Val Ala Ala Gly Gly Pro Ala Asn Thr Leu Thr Ser Val Ala Ser Pro
            195             200             205

Asn Ile Glu Thr Ser Asn Glu Val Met Lys His Pro Lys Val Arg Ala
            210             215             220

Leu Val Val Thr Gly Gly Gly Ile Val Val Gln Ala Ala Met Ser Ala
225             230             235             240

Gly Lys Lys Val Ile Ala Ala Gly Pro Gly Asn Pro Pro Val Val Val
            245             250             255

Asp Glu Thr Ala Ile Ile Ser Lys Ala Ala Lys Asp Ile Val Thr Gly
            260             265             270

Ala Ser Phe Asp Asn Asn Val Leu Cys Thr Ala Glu Lys Glu Val Phe
            275             280             285

Val Val Glu Lys Val Ala Asn Thr Leu Lys Ser Glu Met Thr Lys Asn
            290             295             300

Gly Ala Val Glu Leu Lys Gly Tyr Gln Leu Glu Lys Leu Leu Gly Lys
305             310             315             320

Ile Leu Val Lys Lys Gly Glu Lys Tyr Tyr Pro Asn Arg Asp Phe Ile
            325             330             335

Gly Lys Asp Ala Ser Val Leu Leu Glu Ala Ala Gly Ile Arg Ser Asp
            340             345             350

Ser Asn Val Lys Leu Ile Ile Ala Glu Thr Lys Glu Asp His Pro Leu
            355             360             365

Val His Thr Glu Met Leu Met Pro Ile Leu Pro Ile Val Arg Val Ser
            370             375             380

Asp Val Asp Lys Ala Ile Ser Leu Ala Val Lys Ala Glu Lys Gly Asn
385             390             395             400

Arg His Thr Ala Ile Met His Ser Gln Asn Val Thr Asn Leu Thr Lys
            405             410             415

Met Ala Lys Glu Ile Gln Ala Thr Ile Phe Val Lys Asn Gly Pro Ser
            420             425             430

Val Ala Gly Leu Gly Tyr Gln Ser Glu Gly Phe Thr Thr Leu Thr Ile
            435             440             445

Ala Gly Pro Thr Gly Glu Gly Leu Thr Ser Ala Lys Thr Phe Thr Arg
            450             455             460

Gln Arg Arg Cys Val Leu Val Asp Gly Phe Arg Ile Ile
465             470             475
```

<210> SEQ ID NO 150
<211> LENGTH: 472
<212> TYPE: PRT
<213> ORGANISM: bacterium CG2_30_54_10

-continued

<400> SEQUENCE: 150

Met Ser Val Ser Lys Asp Glu Ile Asn Val Ile Val Gln Glu Val Leu
1               5                   10                  15

Lys Ala Ile Glu Thr Ser Gly Gly Leu Pro Ser Ala Ala Ser Ser Val
                20                  25                  30

Gly Arg Ile Ser Gln Lys Gly Val Phe Glu Asn Leu Asp Asp Ala Ile
            35                  40                  45

Lys Ala Ala Gly Gln Ala Gln Lys Lys Leu Val Glu Leu Pro Leu Lys
        50                  55                  60

Thr Arg Gly Glu Ile Ile Ala Asn Met Arg Arg Arg Ala Ala Glu Asn
65                  70                  75                  80

Val Glu Glu Ile Ser Arg Leu Gly His Glu Glu Thr Gly Tyr Gly Arg
                85                  90                  95

Ile Ala Asp Lys Ile Gln Lys Asn Met Leu Ala Ile Thr Lys Thr Pro
            100                 105                 110

Gly Ile Glu Asp Leu Gln Pro Val Ala Tyr Ser Gly Asp His Gly Leu
            115                 120                 125

Thr Ile Val Glu Gln Ala Pro Tyr Gly Val Ile Gly Ala Ile Thr Pro
            130                 135                 140

Ser Thr Asn Pro Ser Glu Thr Val Ile Cys Asn Ser Ile Gly Met Ile
145                 150                 155                 160

Ala Ala Gly Asn Ala Val Val Phe Gly Pro His Pro Ser Ala Ala Gln
                165                 170                 175

Val Cys Leu Leu Ala Ile Ser Val Leu Asn Asp Ala Val Val Glu Ala
            180                 185                 190

Gly Gly Pro Glu Asn Leu Met Val Ser Val Ser Lys Pro Ser Ile Gln
            195                 200                 205

Thr Ala Gln Ala Leu Met Ala His Pro Asp Ile Arg Leu Leu Val Val
            210                 215                 220

Thr Gly Gly Pro Ala Val Val Ala Ala Ala Lys Ser Gly Lys Lys
225                 230                 235                 240

Phe Ile Ala Ala Gly Pro Gly Asn Pro Pro Ala Val Val Asp Glu Thr
                245                 250                 255

Ala Asp Leu Lys Lys Ala Ala Arg Asp Ile Ile Ser Gly Ala Thr Leu
            260                 265                 270

Asp Asn Asn Ile Leu Cys Ile Ala Glu Lys Glu Ile Ile Val Val Glu
            275                 280                 285

Ser Val Ala Asp Glu Leu Lys Arg His Leu Cys Asn Ser Gly Ala Tyr
            290                 295                 300

Glu Ala Ser Ala Arg Glu Ile Leu Gln Leu Glu Lys Leu Val Ile Asp
305                 310                 315                 320

Pro Arg Thr His Gly Pro Asn Arg Ser Phe Ile Gly Lys Asn Ala Ser
                325                 330                 335

Val Ile Leu Asp Ala Ile Gly Val Lys Val Ser Asp Glu Val Arg Met
            340                 345                 350

Val Leu Cys Glu Val Gly Pro Asp His Pro Phe Val Val Glu Glu Met
            355                 360                 365

Met Met Pro Val Val Pro Leu Val Arg Val Arg Asp Val His Thr Ala
            370                 375                 380

Val Asp Phe Ala Val Lys Ile Glu His Gly Cys Arg His Thr Ala Ile
385                 390                 395                 400

Met His Ser Lys Asn Leu Asp Asn Leu His Leu Met Ala Thr Arg Cys

```
                405                 410                 415

Asn Cys Ser Ile Phe Val Lys Asn Gly Pro Ser Tyr Ala Gly Leu Gly
            420                 425                 430

Leu Gly Gly Glu Gly Phe Thr Thr Phe Thr Ile Ala Ser Pro Thr Gly
        435                 440                 445

Glu Gly Leu Thr Ser Ala Arg Thr Phe Thr Arg Gln Arg Arg Cys Val
    450                 455                 460

Leu Val Asp Tyr Phe Arg Ile Val
465                 470

<210> SEQ ID NO 151

<400> SEQUENCE: 151

000

<210> SEQ ID NO 152
<211> LENGTH: 475
<212> TYPE: PRT
<213> ORGANISM: Candidatus Izimaplasma sp

<400> SEQUENCE: 152

Met Ser Thr Asn Asp Leu Ile Lys Gln Leu Thr Glu Glu Met Glu Arg
1               5                   10                  15

Lys Tyr Gly Asn Asp Val Val Thr Lys Pro Asn Thr Pro Thr Asn Ser
            20                  25                  30

Tyr Asn Thr Gly Tyr Val Gly Ile Phe Glu Asn Val Glu Asp Ala Ile
        35                  40                  45

Leu Ala Ala Lys Glu Ser Gln Lys Gln Leu Met Glu Leu Ser Met Lys
    50                  55                  60

Lys Arg Lys Glu Ile Ile Glu Ala Met Arg Lys Ala Ser Leu Glu Asn
65                  70                  75                  80

Ala Glu Lys Leu Ala Ile Met Ala His Glu Glu Thr Gly Phe Gly Arg
                85                  90                  95

Val Ala Asp Lys Ile Ile Lys Asn Val Leu Ala Ala Glu Lys Thr Pro
            100                 105                 110

Gly Thr Glu Asp Leu Ser Ser Ser Thr Phe Thr Gly Asp Asp Gly Met
        115                 120                 125

Thr Leu Val Glu Leu Ala Pro Tyr Gly Val Ile Gly Ser Ile Thr Pro
    130                 135                 140

Ser Thr Asn Pro Ser Ser Thr Ile Ile Asn Asn Ser Ile Ser Met Val
145                 150                 155                 160

Ala Ala Gly Asn Gly Val Val Tyr Asn Pro His Pro Ser Ala Lys Lys
                165                 170                 175

Val Thr Ser Glu Thr Ile Ser Ile Leu Asn Lys Ala Ile Ser Ser Val
            180                 185                 190

Gly Gly Pro Arg Glu Leu Leu Thr Ala Pro Leu Thr Pro Thr Met Asp
        195                 200                 205

Thr Ser Lys Val Ile Met Thr His Lys Asp Val Arg Ile Leu Val Val
    210                 215                 220

Thr Gly Gly Glu Ala Val Val Gly Val Ala Met Lys Ser Gly Lys Lys
225                 230                 235                 240

Val Ile Ala Ala Gly Pro Gly Asn Pro Pro Val Ile Val Asp Glu Thr
                245                 250                 255

Ala Asn Ile Lys Lys Ala Ala Asn Asp Val Phe Arg Gly Ala Ser Phe
            260                 265                 270
```

```
Asp Asn Asn Ile Leu Cys Ile Ala Glu Lys Glu Ala Phe Val Ile Asn
        275                 280                 285

Ser Val Ile Asn Glu Phe Lys Gln Glu Met Val Ser Asn Gly Ala Tyr
        290                 295                 300

Glu Leu Lys Arg His Glu Ile Asp Leu Val Thr Glu Glu Val Phe Thr
305                 310                 315                 320

Lys Asn Lys Asn Gly Asp Thr Val Val Asn Arg Lys His Val Gly Lys
                325                 330                 335

Ser Ala Val Glu Ile Leu Lys Ala Cys Asn Ile Met Val His Gln Asp
                340                 345                 350

Ile Arg Leu Ile Thr Ala Glu Val Ser Glu Asn His Pro Phe Ile Thr
        355                 360                 365

Val Glu Met Leu Met Pro Val Leu Gly Ile Val Arg Val Tyr Ser Ile
        370                 375                 380

Asp Glu Ala Ile Glu Lys Ala Val Ile Ala Glu Asp Gly Cys Leu His
385                 390                 395                 400

Thr Ala Ile Met His Ser Glu Ser Val Ser Asn Leu Thr Lys Ala Ala
                405                 410                 415

Arg Ala Leu Asn Thr Ser Ile Phe Val Lys Asn Ala Pro Ser Phe Ala
                420                 425                 430

Gly Leu Gly Ile Glu Gly Glu Gly Phe Thr Thr Leu Thr Ile Ala Thr
                435                 440                 445

Pro Thr Gly Glu Gly Leu Thr Ser Ala Arg Ser Phe Thr Arg Ile Arg
        450                 455                 460

Arg Cys Thr Leu Ser Gly Gly Phe Arg Ile Val
465                 470                 475

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157
<211> LENGTH: 462
<212> TYPE: PRT
<213> ORGANISM: Firmicutes bacterium CAG:41

<400> SEQUENCE: 157

Val Pro Ile Asn Glu Asn Met Val Gln Asp Ile Val Gln Glu Val Leu
1               5                   10                  15
```

-continued

```
Ala Lys Met Gln Ile Gln Glu Ala Pro Thr Gly Lys His Gly Val Phe
            20                  25                  30

Lys Asp Met Asn Glu Ala Ile Glu Ala Ala Lys Lys Ala Gln Gln Thr
            35                  40                  45

Val Lys Lys Met Ser Met Asp Gln Arg Glu Lys Ile Leu Ser Ile Ile
    50                  55                  60

Arg Lys Lys Ile Cys Glu Asn Ala Glu Thr Met Ala Arg Met Gly Val
65                  70                  75                  80

Glu Glu Thr Gly Met Gly Asn Val Gly Asp Lys Ile Leu Lys His Arg
                85                  90                  95

Leu Val Ala Glu Lys Thr Pro Gly Thr Glu Asp Ile Thr Thr Thr Ala
            100                 105                 110

Trp Ser Gly Asp Arg Gly Leu Thr Leu Val Glu Met Gly Pro Phe Gly
            115                 120                 125

Val Ile Gly Ala Ile Thr Pro Cys Thr Asn Pro Ser Glu Thr Val Leu
    130                 135                 140

Cys Asn Thr Met Gly Met Leu Ala Gly Gly Asn Thr Val Val Phe Asn
145                 150                 155                 160

Pro His Pro Ala Ala Ile Lys Thr Ser Ile Phe Ala Ile Asn Leu Leu
                165                 170                 175

Asn Glu Ala Ser Leu Glu Gly Gly Gly Pro Asp Asn Ile Ala Cys Thr
            180                 185                 190

Val Glu Asn Pro Thr Leu Glu Thr Ser Asn Ile Met Met Lys His Lys
            195                 200                 205

Asp Ile Pro Leu Ile Ala Ala Thr Gly Gly Pro Gly Val Val Thr Ala
    210                 215                 220

Val Leu Ser Ser Gly Lys Arg Gly Ile Gly Ala Gly Ala Gly Asn Pro
225                 230                 235                 240

Pro Ala Leu Val Asp Glu Thr Ala Asp Ile Arg Lys Ala Ala Gln Asp
            245                 250                 255

Ile Val Asn Gly Cys Val Phe Asp Asn Asn Leu Pro Cys Ile Ala Glu
            260                 265                 270

Lys Glu Ile Val Ala Val Ser Ser Val Val Asp Glu Leu Met His Tyr
            275                 280                 285

Met Val Thr Glu Gln Gly Cys Tyr Leu Ala Ser Lys Glu Glu Gln Asp
    290                 295                 300

Ala Leu Thr Ala Val Val Leu Ala Gly Gly Arg Leu Asn Arg Lys Cys
305                 310                 315                 320

Val Gly Arg Asp Ala Arg Thr Leu Leu Ser Met Ile Gly Val Asp Ala
            325                 330                 335

Pro Ala Asn Ile Arg Cys Ile Thr Phe Glu Gly Pro Lys Glu His Pro
            340                 345                 350

Leu Ile Ala Glu Glu Leu Met Met Pro Ile Leu Gly Val Val Arg Ala
            355                 360                 365

Lys Asp Phe Glu Asp Ala Val Glu Gln Ala Val Trp Leu Glu His Gly
    370                 375                 380

Asn Arg His Ser Ala His Ile His Ser Lys Asn Ile Asp Asn Ile Thr
385                 390                 395                 400

Thr Tyr Ala Lys Ala Ile Asp Thr Ala Ile Leu Val Lys Asn Ala Pro
                405                 410                 415

Ser Tyr Ala Ala Leu Gly Phe Gly Gly Glu Gly Tyr Cys Thr Phe Thr
            420                 425                 430

Ile Ala Ser Arg Thr Gly Glu Gly Leu Thr Ser Ala Ser Thr Phe Thr
```

-continued

_____

```
                435                 440                 445

Lys Arg Arg Arg Cys Val Met Ser Asp Ser Leu Cys Ile Arg
    450                 455                 460

<210> SEQ ID NO 158
<211> LENGTH: 465
<212> TYPE: PRT
<213> ORGANISM: Fusobacterium nucleatum subsp.

<400> SEQUENCE: 158

Met Glu Phe Glu Val Asn Asn Ile Glu Glu Ile Val Glu Leu Ile Met
1               5                   10                  15

Lys Lys Met Ala Glu Ser Asn Ile Ser Thr Ala Gly Asn Ser Lys Asn
            20                  25                  30

Gly Val Phe Asp Asn Val Asp Gly Ala Ile Glu Glu Ala Lys Lys Ala
            35                  40                  45

Gln Ala Ile Leu Phe Ser Ser Lys Leu Glu Leu Arg Glu Lys Ile Ile
        50                  55                  60

Ala Ser Ile Arg Asp Thr Leu Lys Asn His Val Thr Glu Leu Ala Glu
65                  70                  75                  80

Leu Ala Val Lys Glu Thr Gly Met Gly Arg Val Ala Asp Lys Glu Leu
                85                  90                  95

Lys Asn Lys Ile Ala Ile Glu Lys Thr Pro Gly Leu Glu Asp Leu Lys
            100                 105                 110

Ala Phe Ala Phe Ser Gly Asp Asp Gly Leu Thr Val Met Glu Leu Ser
            115                 120                 125

Pro Tyr Gly Val Ile Gly Ala Ile Thr Pro Ser Thr Asn Pro Ser Glu
    130                 135                 140

Thr Val Ile Cys Asn Ser Ile Gly Met Ile Ala Ala Gly Asn Ala Val
145                 150                 155                 160

Ile Phe Ala Pro His Pro Gly Ala Lys Arg Thr Ser Ile Arg Thr Val
            165                 170                 175

Glu Leu Ile Asn Glu Ala Ile Arg Lys Val Gly Gly Pro Asp Asn Leu
            180                 185                 190

Ile Val Thr Ile Arg Glu Pro Ser Ile Glu Asn Thr Glu Lys Ile Ile
            195                 200                 205

Ala Asn Pro Asn Ile Lys Met Leu Val Ala Thr Gly Gly Pro Gly Val
    210                 215                 220

Val Lys Thr Val Met Ser Ser Gly Lys Lys Ala Ile Gly Ala Gly Ala
225                 230                 235                 240

Gly Asn Pro Pro Val Leu Val Asp Glu Thr Ala Asp Ile Glu Lys Ala
            245                 250                 255

Ala Lys Asp Ile Ile Ala Gly Cys Ser Phe Asp Asn Asn Leu Pro Cys
            260                 265                 270

Thr Ala Glu Lys Glu Val Val Ala Val Asp Ser Ile Val Asn Tyr Leu
            275                 280                 285

Ile Phe Glu Met Gln Lys Asn Gly Ala Tyr Leu Leu Lys Asp Lys Glu
    290                 295                 300

Leu Ile Glu Lys Leu Leu Ser Leu Val Leu Lys Asn Asn Ser Pro Asp
305                 310                 315                 320

Arg Lys Tyr Val Gly Arg Asp Ala Lys Tyr Leu Leu Lys Gln Ile Gly
            325                 330                 335

Ile Glu Val Gly Asp Glu Ile Lys Val Ile Ile Val Glu Thr Asp Lys
            340                 345                 350
```

```
Asn His Pro Phe Ala Val Glu Glu Leu Leu Met Pro Ile Leu Pro Ile
    355                 360             365

Val Lys Val Lys Asp Ala Leu Glu Gly Ile Lys Val Ala Lys Glu Leu
    370             375             380

Glu Arg Gly Leu Arg His Thr Ala Val Ile His Ser Lys Asn Ile Asp
385             390             395             400

Ile Leu Thr Lys Tyr Ala Arg Glu Met Glu Thr Thr Ile Leu Val Lys
            405             410             415

Asn Gly Pro Ser Tyr Ala Gly Ile Gly Ile Gly Gly Glu Gly His Val
            420             425             430

Thr Phe Thr Ile Ala Gly Pro Thr Gly Glu Gly Leu Thr Ser Ala Lys
            435             440             445

Ser Phe Ala Arg Asn Arg Arg Cys Val Leu Val Gly Gly Phe Ser Ile
    450             455             460

Lys
465
```

<210> SEQ ID NO 159
<211> LENGTH: 467
<212> TYPE: PRT
<213> ORGANISM: Thermoanaerobacterium xylanolyticum LX-11

<400> SEQUENCE: 159

```
Met Lys Val Lys Glu Glu Asp Ile Glu Ala Ile Val Lys Lys Val Leu
1               5               10              15

Ser Glu Phe Asn Leu Glu Lys Thr Thr Ser Lys Tyr Gly Asp Val Gly
            20              25              30

Ile Phe Gln Asp Met Asn Asp Ala Ile Ser Ala Ala Lys Asp Ala Gln
        35              40              45

Lys Lys Leu Arg Asn Met Pro Met Glu Ser Arg Glu Lys Ile Ile Gln
    50              55              60

Asn Ile Arg Lys Lys Ile Met Glu Asn Lys Lys Ile Leu Ala Glu Met
65              70              75              80

Gly Val Arg Glu Thr Gly Met Gly Arg Val Glu His Lys Ile Val Lys
                85              90              95

His Glu Leu Val Ala Leu Lys Thr Pro Gly Thr Glu Asp Ile Thr Thr
            100             105             110

Thr Ala Trp Ser Gly Asp Lys Gly Leu Thr Leu Val Glu Met Gly Pro
            115             120             125

Phe Gly Val Ile Gly Ala Ile Thr Pro Ser Thr Asn Pro Ser Glu Thr
    130             135             140

Val Leu Cys Asn Ser Ile Gly Met Ile Ala Ala Gly Asn Ser Val Val
145             150             155             160

Phe Asn Pro His Pro Gly Ala Val Asn Val Ser Asn Tyr Ala Val Lys
            165             170             175

Leu Val Asn Glu Ala Ala Met Glu Ala Gly Gly Pro Glu Asn Leu Val
            180             185             190

Val Ser Val Glu Lys Pro Thr Leu Glu Thr Gly Asn Val Met Phe Lys
            195             200             205

Ser Ser Asp Val Ser Leu Leu Val Ala Thr Gly Gly Pro Gly Val Val
    210             215             220

Thr Ala Val Leu Ser Ser Gly Lys Arg Ala Ile Gly Ala Gly Ala Gly
225             230             235             240

Asn Pro Pro Val Val Val Asp Glu Thr Ala Asp Ile Lys Lys Ala Ala
            245             250             255
```

```
Lys Asp Ile Ile Asp Gly Ala Thr Phe Asp Asn Asn Leu Pro Cys Ile
            260                 265                 270

Ala Glu Lys Glu Val Val Ser Val Asp Lys Ile Thr Asp Glu Leu Ile
            275                 280                 285

Tyr Tyr Met Gln Lys Asn Gly Cys Tyr Lys Ile Glu Gly Arg Glu Ile
            290                 295                 300

Glu Lys Leu Ile Glu Leu Val Leu Asp His Glu Gly Gly Lys Thr Thr
305                 310                 315                 320

Leu Asn Arg Lys Trp Val Gly Lys Asp Ala His Leu Ile Leu Lys Ala
            325                 330                 335

Ile Gly Ile Asp Ala Asp Glu Ser Val Arg Cys Ile Ile Phe Glu Ala
            340                 345                 350

Glu Lys Asp Asn Pro Leu Val Val Glu Glu Leu Met Met Pro Ile Leu
            355                 360                 365

Gly Ile Val Arg Ala Lys Asn Val Asp Glu Ala Ile Met Ile Ala Thr
            370                 375                 380

Glu Leu Glu His Gly Asn Arg His Ser Ala His Met His Ser Lys Asn
385                 390                 395                 400

Ile Asp Asn Leu Thr Lys Phe Gly Lys Ile Ile Asp Thr Ala Ile Phe
            405                 410                 415

Val Lys Asn Ala Pro Ser Tyr Ala Ala Leu Gly Tyr Gly Gly Glu Gly
            420                 425                 430

Tyr Cys Thr Phe Thr Ile Ala Ser Arg Thr Gly Glu Gly Leu Thr Ser
            435                 440                 445

Ala Arg Thr Phe Thr Lys Ser Arg Arg Cys Val Leu Ala Asp Gly Leu
            450                 455                 460

Ser Ile Arg
465

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164
<211> LENGTH: 441
<212> TYPE: PRT
<213> ORGANISM: Listeria monocytogenes

<400> SEQUENCE: 164
```

-continued

```
Met Thr Lys Gly Ala Lys Ser Gly Val Phe Asp Thr Val Asp Glu Ala
1               5               10              15

Val Gln Ala Ala Val Ile Ala Gln Asn Ser Tyr Lys Glu Lys Ser Leu
            20              25              30

Glu Glu Arg Arg Asn Val Val Lys Ala Ile Arg Glu Ala Leu Tyr Pro
        35              40              45

Glu Ile Glu Ser Ile Ala Ala Arg Ala Val Ala Glu Thr Gly Met Gly
    50              55              60

Asn Val Ala Asp Lys Ile Leu Lys Asn Thr Leu Ala Ile Glu Lys Thr
65              70              75              80

Pro Gly Val Glu Asp Leu Tyr Thr Glu Val Ala Thr Gly Asp Asn Gly
            85              90              95

Met Thr Leu Tyr Glu Leu Ser Pro Tyr Gly Val Ile Gly Ala Val Ala
            100             105             110

Pro Ser Thr Asn Pro Thr Glu Thr Leu Ile Cys Asn Thr Ile Gly Met
        115             120             125

Leu Ala Ala Gly Asn Ala Val Phe Tyr Ser Pro His Pro Gly Ala Lys
        130             135             140

Asn Ile Ser Leu Trp Leu Ile Glu Lys Leu Asn Thr Ile Val Arg Glu
145             150             155             160

Ser Cys Gly Val Asp Asn Leu Val Val Thr Val Glu Lys Pro Ser Ile
            165             170             175

Gln Ala Ala Gln Glu Met Met Asn His Pro Lys Val Pro Leu Leu Val
            180             185             190

Ile Thr Gly Gly Pro Gly Val Val Leu Gln Ala Met Gln Ser Gly Lys
            195             200             205

Lys Val Ile Gly Ala Gly Ala Gly Asn Pro Pro Ser Ile Val Asp Glu
        210             215             220

Thr Ala Asn Ile Glu Lys Ala Ala Ala Asp Ile Val Asp Gly Ala Ser
225             230             235             240

Phe Asp His Asn Ile Leu Cys Ile Ala Glu Lys Ser Val Val Ala Val
            245             250             255

Asp Ser Ile Ala Asp Phe Leu Met Phe Gln Met Glu Lys Asn Gly Ala
            260             265             270

Leu His Val Thr Asn Pro Ser Asp Ile Gln Lys Leu Glu Lys Val Ala
        275             280             285

Val Thr Asp Lys Gly Val Thr Asn Lys Lys Leu Val Gly Lys Ser Ala
    290             295             300

Ser Glu Ile Leu Lys Glu Ala Gly Ile Ala Cys Asp Phe Ser Pro Arg
305             310             315             320

Leu Ile Ile Val Glu Thr Glu Lys Thr His Pro Phe Ala Thr Val Glu
            325             330             335

Leu Leu Met Pro Ile Val Pro Val Val Arg Val Pro Asn Phe Glu Glu
        340             345             350

Ala Leu Glu Val Ala Ile Glu Leu Glu Gln Gly Leu His His Thr Ala
        355             360             365

Thr Met His Ser Gln Asn Ile Ser Arg Leu Asn Lys Ala Ala Arg Asp
    370             375             380

Met Gln Thr Ser Ile Phe Val Lys Asn Gly Pro Ser Phe Ala Gly Leu
385             390             395             400

Gly Phe Arg Gly Glu Gly Ser Thr Thr Phe Thr Ile Ala Thr Pro Thr
            405             410             415

Gly Glu Gly Thr Thr Thr Ala Arg His Phe Ala Arg Arg Arg Arg Cys
```

-continued

```
              420               425               430

Val Leu Thr Asp Gly Phe Ser Ile Arg
        435               440

<210> SEQ ID NO 165
<211> LENGTH: 481
<212> TYPE: PRT
<213> ORGANISM: Clostridium lavalense

<400> SEQUENCE: 165

Met Glu Ile Glu Thr Arg Asp Ile Glu Arg Ile Val Arg Gln Val Met
1               5                   10                  15

Ala Val Met Glu Gln Gln Gly Thr Ile Ala Gly Gly Ala Tyr Pro Pro
            20                  25                  30

Ala Pro Gly Thr Pro Ala Pro Arg Gly Asp Asn Gly Val Phe Glu Arg
        35                  40                  45

Val Glu Asp Ala Ile Asp Ala Ala Tyr Ala Ala Gly Arg Glu Trp Ala
    50                  55                  60

Phe His Tyr Lys Val Glu Asp Arg Arg Arg Val Ile Glu Ala Ile Arg
65                  70                  75                  80

Val Met Ala Arg Glu Asn Ala Arg Thr Leu Ala Gln Met Val Arg Asp
                85                  90                  95

Glu Thr Gly Met Gly Arg Met Glu Asp Lys Val Glu Lys His Leu Ala
            100                 105                 110

Val Ala Asp Lys Thr Pro Gly Val Glu Cys Leu Thr Thr Asp Ala Ile
            115                 120                 125

Ser Gly Asp Gly Gly Leu Met Ile Glu Glu Tyr Ala Pro Phe Gly Val
        130                 135                 140

Ile Gly Ala Ile Thr Pro Ser Thr Asn Pro Thr Glu Thr Val Ile His
145                 150                 155                 160

Asn Thr Ile Ser Met Ile Ala Gly Gly Asn Ser Val Val Phe Asn Val
                165                 170                 175

His Pro Gly Ala Lys Lys Cys Cys Ala Phe Cys Leu Gln Leu Leu His
            180                 185                 190

Lys Thr Ile Val Glu Asn Gly Gly Pro Ala Asn Leu Ile Thr Met Gln
            195                 200                 205

Arg Glu Pro Thr Met Asp Ala Val Asn Lys Met Thr Ser Ser Pro Lys
        210                 215                 220

Ile Arg Leu Met Val Gly Thr Gly Gly Met Gly Met Val Asn Ala Leu
225                 230                 235                 240

Leu Arg Ser Gly Lys Lys Thr Ile Gly Ala Gly Ala Gly Asn Pro Pro
                245                 250                 255

Val Ile Val Asp Asp Thr Ala Asp Val Lys Leu Ala Ala Arg Glu Leu
            260                 265                 270

Tyr Trp Gly Ala Ser Phe Asp Asn Asn Leu Phe Cys Phe Ala Glu Lys
        275                 280                 285

Glu Val Phe Val Met Glu Ala Ser Ala Asp Gly Leu Ile Arg Gly Leu
        290                 295                 300

Val Glu Gln Gly Ala Tyr Leu Leu Thr Pro Ala Glu Thr Glu Ala Ile
305                 310                 315                 320

Val Lys Leu Ala Leu Ile Gln Lys Asp Gly Lys Tyr Glu Val Asn Lys
                325                 330                 335

Lys Trp Val Gly Lys Asp Ala Gly Leu Phe Leu Lys Ala Ile Gly Val
            340                 345                 350
```

-continued

```
Ser Gly His Glu Asn Thr Arg Leu Leu Ile Cys Asp Val Pro Lys Cys
        355                 360                 365

His Pro Tyr Val Met Val Glu Gln Leu Met Pro Val Leu Pro Ile Val
        370                 375                 380

Arg Cys Arg Thr Phe Asp Glu Cys Ile Gln Cys Ser Val Glu Ala Glu
385                 390                 395                 400

Gln Gly Asn Arg His Thr Ser Ser Ile Phe Ser Thr Asn Val Tyr Asn
                405                 410                 415

Met Thr Lys Phe Gly Lys Glu Ile Glu Thr Thr Ile Tyr Val Lys Asn
                420                 425                 430

Gly Ala Thr Leu Arg Gly Leu Gly Ile Gly Gly Glu Gly His Thr Thr
                435                 440                 445

Met Thr Ile Ala Gly Pro Thr Gly Glu Gly Leu Thr Cys Ala Arg Ser
        450                 455                 460

Phe Thr Arg Arg Arg Arg Cys Met Leu Ala Glu Gly Gly Leu Arg Ile
465                 470                 475                 480

Ile
```

```
<210> SEQ ID NO 166
<211> LENGTH: 474
<212> TYPE: PRT
<213> ORGANISM: Acetanaerobacterium elongatum

<400> SEQUENCE: 166

Met Glu Phe Ala Val Asn Glu Ile Ser Met Ile Val Glu Gln Val Leu
1               5                   10                  15

Lys Asn Leu Asp Leu Ser Lys Val Ser Ala Gly Asn Ala Pro Ala Ser
            20                  25                  30

Pro Lys Gly Asp Tyr Gly Val Phe Glu Asn Val Glu Asp Ala Ile Glu
            35                  40                  45

Ala Ala Tyr Gln Ala Gln Lys Ile Tyr Leu Asp Lys Phe Gln Val Lys
        50                  55                  60

Asp Arg Gln Arg Ile Ile Ala Ala Ile Arg Lys Val Cys Arg Glu Asn
65                  70                  75                  80

Ala Glu Thr Leu Ala Arg Met Val Arg Glu Glu Ser Lys Met Gly Arg
                85                  90                  95

Tyr Glu Asp Lys Ile Gln Lys His Leu Ala Val Ile Asp Asn Thr Pro
            100                 105                 110

Gly Pro Glu Cys Leu Thr Thr Asp Ala Ile Ser Gly Asp Ser Gly Leu
            115                 120                 125

Met Leu Glu Glu Tyr Ala Pro Phe Gly Leu Ile Gly Ala Ile Thr Pro
        130                 135                 140

Val Thr Asn Pro Thr Glu Thr Ile Ile Asn Asn Thr Ile Ser Met Ile
145                 150                 155                 160

Ser Gly Gly Asn Ser Val Val Phe Asn Val His Pro Ser Ala Lys Asn
                165                 170                 175

Val Cys Ala Tyr Cys Leu Arg Leu Ile Asn Lys Thr Ile Ile Asp Asn
            180                 185                 190

Gly Gly Pro Ala Asn Leu Ile Thr Met Ala Lys Glu Pro Thr Met Asp
            195                 200                 205

Thr Val Lys Ala Ile Ser Ser Ser Pro Lys Val Arg Leu Met Val Gly
        210                 215                 220

Thr Gly Gly Met Pro Met Val Asn Ala Leu Leu Arg Ser Gly Lys Lys
225                 230                 235                 240
```

-continued

```
Val Ile Gly Ala Gly Ala Gly Asn Pro Pro Val Ile Val Asp Asn Thr
            245             250             255

Ala Asp Ile Lys Lys Ala Ala Lys Asp Ile Tyr Tyr Gly Ala Ser Phe
            260             265             270

Asp Asn Asn Leu Leu Cys Leu Ala Glu Lys Glu Val Phe Val Leu Asp
            275             280             285

Glu Val Ala Asn Gln Phe Ile Tyr Asn Met Val Glu Glu Gly Ala Tyr
        290             295             300

Leu Leu Asn Gly Val Gln Leu Glu Lys Ile Leu Asn Leu Val Phe Lys
305             310             315             320

Phe Asp Gly Lys Tyr Asp Val Asn Lys Lys Trp Val Gly Gln Asp Ala
            325             330             335

Gly Lys Met Leu Asp Ala Ile Gly Val Glu Gly Lys Ser Asp Thr Arg
            340             345             350

Leu Leu Ile Cys Glu Val Pro His Asp His Pro Phe Val Met Val Glu
            355             360             365

Gln Leu Met Pro Val Leu Pro Ile Val Arg Cys Arg Asn Leu Asp Glu
        370             375             380

Ala Ile Glu Tyr Ala Tyr Ile Ala Glu Ser Gly Asn Arg His Thr Ala
385             390             395             400

Ser Met Phe Ser Lys Asn Val Asp Asn Met Thr Arg Phe Ala Arg Lys
            405             410             415

Ile Glu Thr Thr Ile Phe Val Lys Asn Gly Pro Thr Leu Asn Gly Val
            420             425             430

Gly Ile Gly Gly Glu Gly Tyr Ala Thr Met Thr Ile Ala Gly Pro Thr
            435             440             445

Gly Glu Gly Leu Thr Cys Ala Lys Ser Phe Thr Arg Arg Arg Arg Cys
        450             455             460

Met Leu Ser Asp Gly Gly Leu Arg Val Ile
465             470
```

<210> SEQ ID NO 167
<211> LENGTH: 464
<212> TYPE: PRT
<213> ORGANISM: Alkaliphilus peptidifermentans DSM

<400> SEQUENCE: 167

```
Met Val Glu Glu Leu Lys Ile Glu Glu Ile Ile Arg Arg Val Met Lys
1               5               10              15

Glu Ile Ser Ser Lys Asn Glu Thr Gly Glu Glu Gly Ala Tyr Gly Ile
            20              25              30

Phe Gln Asp Met Asn Asp Ala Val Asp Ala Ala Tyr Ile Ala Gln Lys
        35              40              45

Glu Leu Ile Gly Phe Asn Leu Glu Thr Arg Gly Lys Phe Ile Glu Ala
        50              55              60

Met Arg Gln Ala Ala Arg Gln Asn Val Glu Leu Leu Ser Lys Met Ala
65              70              75              80

His Glu Glu Thr Asp Met Gly Arg Tyr Glu Asp Lys Ile Leu Lys Asn
            85              90              95

Arg Leu Ala Ile Glu Lys Thr Pro Gly Ile Glu Asp Leu Gly Ser Glu
            100             105             110

Val Phe Thr Gly Asp Asp Gly Leu Thr Leu Ile Glu Leu Ser Pro Tyr
        115             120             125

Gly Val Ile Gly Ser Ile Ser Pro Val Thr Asn Pro Ser Glu Thr Ile
        130             135             140
```

-continued

```
Ile Cys Asn Ala Ile Gly Met Ile Ala Ala Gly Asn Ala Val Ala Phe
145              150              155              160

Ser Pro His Pro Ser Ala Lys Lys Thr Ser Leu Lys Thr Ile Glu Ile
                165              170              175

Leu Asn Lys Gly Ile Ile Glu Ala Gly Gly Pro Lys Asn Leu Ile Val
            180              185              190

Ala Val Glu Asn Pro Ser Ile Glu Gln Ala Glu Ala Met Met Lys His
            195              200              205

Lys Lys Ile Asn Met Leu Val Ala Thr Gly Gly Pro Gly Val Val Lys
        210              215              220

Ser Val Leu Ser Ser Gly Lys Lys Ala Ile Gly Ala Gly Ala Gly Asn
225              230              235              240

Pro Pro Ala Val Val Asp Glu Thr Ala Asp Ile Glu Lys Ala Ala Arg
            245              250              255

Asp Ile Ile Ala Gly Cys Ser Phe Asp Asn Asn Leu Pro Cys Val Ala
            260              265              270

Glu Lys Glu Val Ile Val Val Asp Ser Val Ala Asp Tyr Leu Ile Phe
        275              280              285

Asn Met Lys Lys Asn Gly Ala Tyr Glu Leu Lys Glu Lys Asp Leu Ile
        290              295              300

Glu Gln Leu Glu Lys Leu Val Val Asn Glu Lys Gly Tyr Pro Val Lys
305              310              315              320

Glu Phe Val Gly Lys Asn Ala Asp Tyr Ile Leu Ser Lys Met Gly Ile
            325              330              335

Lys Cys Asp Asp Ser Ile Arg Ala Ile Ile Val Glu Val Pro Lys Ser
        340              345              350

His Pro Phe Val Val Gly Glu Leu Met Met Pro Val Leu Pro Ile Val
        355              360              365

Arg Val Asn Asp Val Glu Glu Ala Ile Lys Leu Ala Val Glu Val Glu
    370              375              380

His Gly Phe Lys His Thr Ala Ile Met His Ser Lys Asn Ile Asp Arg
385              390              395              400

Leu Ser Lys Phe Ala Lys Glu Ile Gln Thr Thr Ile Phe Val Lys Asn
            405              410              415

Gly Pro Ser Phe Ala Gly Ile Gly Val Gly Gly Glu Gly Tyr Ala Thr
            420              425              430

Phe Thr Ile Ala Gly Pro Thr Gly Glu Gly Leu Thr Ser Ala Lys Ser
        435              440              445

Phe Ala Arg Arg Arg Cys Thr Leu Val Gly Gly Phe Ser Ile Lys
    450              455              460
```

<210> SEQ ID NO 168

<400> SEQUENCE: 168

000

<210> SEQ ID NO 169

<400> SEQUENCE: 169

000

<210> SEQ ID NO 170

<400> SEQUENCE: 170

-continued

```
000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176
<211> LENGTH: 481
<212> TYPE: PRT
<213> ORGANISM: Clostridium populeti

<400> SEQUENCE: 176

Met Asp Ile Ser Ser Gln Glu Ile Glu Ala Ile Val Arg Lys Val Ile
1               5                   10                  15

Ala Gly Ile Asn Pro Ala Thr Asn Val Thr Pro Asp Ile Pro Ala Ile
            20                  25                  30

Lys Ser Pro Lys Tyr Thr Gly Asp Asn Gly Val Phe Glu Arg Val Glu
        35                  40                  45

Glu Ala Val Glu Ala Ala Trp Lys Ala Gln Arg Asp Trp Val Thr Asn
    50                  55                  60

Tyr Lys Val Glu Asp Arg His Arg Ile Val Glu Ala Ile Arg Arg Cys
65                  70                  75                  80

Gly Arg Asp His Val Glu Glu Trp Ser His Leu Ile Val Glu Glu Thr
                85                  90                  95

Gln Met Gly Arg Tyr Glu Asp Lys Val Glu Lys His Leu Ala Val Ile
            100                 105                 110

Asn Lys Thr Pro Gly Pro Glu Cys Leu Thr Thr Glu Ala Ile Ser Gly
        115                 120                 125

Asp Ala Gly Leu Met Ile Glu Glu Tyr Ala Pro Phe Gly Val Ile Gly
    130                 135                 140

Ser Ile Thr Pro Thr Thr Asn Pro Thr Glu Thr Met Ile His Asn Thr
145                 150                 155                 160

Ile Ser Met Ile Ser Gly Gly Asn Ser Ile Val Phe Asn Val His Pro
                165                 170                 175
```

-continued

```
Arg Ala Lys Arg Val Cys Ala Glu Cys Leu Gln Ala Leu His Lys Ala
            180                 185                 190

Ile Val Asp Ala Gly Gly Pro Ala Asn Leu Ile Thr Met Leu Arg Glu
            195                 200                 205

Pro Thr Met Asp Thr Val Asp Met Leu Thr Ser Asn Pro Lys Val Arg
    210                 215                 220

Leu Met Thr Gly Thr Gly Gly Met Gly Met Val Asn Ala Leu Leu Arg
225                 230                 235                 240

Ser Gly Lys Lys Cys Ile Gly Ala Gly Ala Gly Asn Pro Pro Val Ile
            245                 250                 255

Val Asp Glu Thr Ala Asp Val Glu Leu Ala Ala Arg Lys Ile Tyr Glu
            260                 265                 270

Gly Ala Ser Phe Asp Asn Asn Ile Leu Cys Phe Ala Glu Lys Glu Val
            275                 280                 285

Phe Val Val Ser Pro Asn Tyr Glu Gly Phe Ile His Asn Ile Gln Lys
    290                 295                 300

Gln Gly Ala Tyr Leu Leu Asn Asn Ser Gln Val Glu Ala Leu Val Lys
305                 310                 315                 320

Ile Cys Leu Glu Pro Asn Lys Asn Gln Ser Gly Tyr Glu Val Asn Lys
            325                 330                 335

Lys Trp Val Gly Lys Asn Ala Ala Leu Ile Leu Ala Gln Ile Gly Val
            340                 345                 350

Gln Val Glu Asp Ser Cys Arg Leu Ala Val Cys Glu Val Pro Ala Asp
            355                 360                 365

His Pro Phe Val Leu Val Glu Gln Met Met Pro Val Leu Pro Ile Val
    370                 375                 380

Arg Cys Ser Thr Phe Glu Glu Ala Met Glu Lys Ala Val Ile Ala Glu
385                 390                 395                 400

Gln Gly Asn Arg His Thr Ser Ser Ile Phe Ser Lys Asp Val Asp His
            405                 410                 415

Met Thr Arg Phe Ala Arg Leu Ile Glu Thr Thr Ile Tyr Val Lys Asn
            420                 425                 430

Ser Cys Thr Lys Ala Gly Val Gly Ile Gly Gly Glu Gly His Cys Thr
            435                 440                 445

Met Thr Ile Ala Gly Pro Thr Gly Glu Gly Ile Thr Asn Ala Lys Ser
    450                 455                 460

Phe Cys Arg Arg Arg Arg Cys Met Leu Ala Glu Gly Gly Leu Arg Ile
465                 470                 475                 480

Ile
```

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

```
<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187
<211> LENGTH: 450
<212> TYPE: PRT
<213> ORGANISM: Candidatus Bacteroides periocalifornicus

<400> SEQUENCE: 187

Met Thr Ile Ala Glu Met Val Ala Lys Ala Arg Val Ala Gln Ala Glu
1               5                   10                  15

Phe Glu Lys Asn Phe Asp Gln Ala Lys Thr Asp Ala Val Val Arg Glu
            20                  25                  30

Ile Gly Lys Thr Val Phe Asp Asn Ala Glu Met Leu Ala Lys Met Ala
        35                  40                  45

Val Glu Glu Thr Arg Met Gly Val Tyr Glu Asp Lys Val Ala Lys Asn
    50                  55                  60

Lys Gly Lys Ala Arg Gly Val Trp Tyr Asp Leu Lys Gly Lys Lys Ser
65                  70                  75                  80

Met Gly Val Leu Ser Val Asp Pro Glu Thr Asp Leu Ile Thr Met Leu
                85                  90                  95

Lys Pro Val Gly Val Val Ala Ala Ile Thr Pro Thr Thr Asn Pro Ile
            100                 105                 110
```

Val Thr Pro Met Ser Lys Ser Met Phe Ala Val Lys Gly Lys Asn Ala
        115                 120                 125

Ile Ile Val Ala Pro His Pro Arg Ser Lys Lys Cys Thr Ala Lys Thr
    130                 135                 140

Ile Glu Leu Ile Asn Lys Ala Ile Ala Lys Phe Gly Val Pro Lys Asp
145                 150                 155                 160

Leu Ile Gln Val Ile Glu Glu Pro Ser Ile Pro Leu Thr Gln Glu Leu
                165                 170                 175

Met Ala Ser Cys Asp Val Val Leu Ala Thr Gly Gly Met Gly Met Val
            180                 185                 190

Lys Ala Ala Tyr Ser Ser Gly Lys Pro Ser Tyr Gly Val Gly Ala Gly
            195                 200                 205

Asn Val Gln Val Ile Ile Asp Arg Gly Val Asp Tyr Asp Lys Ala Ala
    210                 215                 220

Ala Thr Ile Ile Lys Gly Arg Ile Phe Asp Asn Gly Ile Ile Cys Ser
225                 230                 235                 240

Gly Glu Gln Ser Phe Ile Tyr Pro Lys Asp Glu Lys Ala Lys Val Phe
                245                 250                 255

Asp Ala Phe Lys Lys Asn Gly Ala Tyr Ile Val Ala Asp Ala Asp His
            260                 265                 270

Asp Lys Val Val Asn Ala Leu Phe Glu Asp Gly His Ile Ala Gly Asp
            275                 280                 285

Val Val Gly Gln Ser Val Gln Phe Val Ala Lys Lys Ala Gly Leu Asn
    290                 295                 300

Val Pro Ala Asp Ala Arg Val Ile Val Val Glu Ala Lys Gly Val Gly
305                 310                 315                 320

Ala Gln Asp Pro Ile Cys Lys Glu Lys Met Cys Pro Val Leu Ala Ala
                325                 330                 335

Phe Gly Tyr Asp Lys Phe Glu Glu Ala Ile Gln Ile Ala Lys Thr Asn
            340                 345                 350

Leu Leu Asn Glu Gly Asn Gly His Ser Ala Gly Ile His Ser Asn Asn
            355                 360                 365

Glu Glu His Ile Arg Met Val Gly Glu Gly Leu Thr Val Ser Arg Val
    370                 375                 380

Val Val Asn Ala Pro Val Ser Thr Thr Ala Gly Gly Ala Ile Gly Ser
385                 390                 395                 400

Gly Leu Ala Val Thr Asn Thr Leu Gly Cys Gly Thr Trp Gly Asn Asn
                405                 410                 415

Thr Leu Ser Glu Asn Leu Thr Tyr Lys His Leu Leu Asn Thr Thr Arg
            420                 425                 430

Val Ala Arg Ile Ser Pro Lys Val His Gln Pro Thr Asp Glu Glu Leu
            435                 440                 445

Trp Gly
    450

<210> SEQ ID NO 188
<211> LENGTH: 480
<212> TYPE: PRT
<213> ORGANISM: Anaerocolumna aminovalerica

<400> SEQUENCE: 188

Met Glu Phe Gly Thr Lys Glu Ile Ser Met Ile Val Glu Gln Val Leu
1               5                   10                  15

Lys Asn Leu Glu Glu Asn Asn Leu Ile Ser Thr Lys Lys Thr Ser Asn
        20                  25                  30

-continued

```
Ser Gly Leu Tyr Ser Asp Lys Gly Asp Tyr Gly Val Phe Glu Arg Val
        35              40              45

Glu Asp Ala Ile Asp Ala Ala Tyr Glu Ala Gln Lys Ile Tyr Leu Asp
    50              55              60

Asn Phe Lys Ile Lys Asp Arg Gln Arg Leu Ile Ala Ala Ile Arg Lys
65              70              75              80

Val Ser Ile Glu Asn Ala Glu Thr Leu Ala Arg Met Ile Val Glu Glu
                85              90              95

Ser Lys Met Gly Arg Val Glu Asp Lys Val Lys Lys His Leu Ala Val
                100             105             110

Ile Glu Asn Thr Pro Gly Pro Glu Cys Leu Thr Thr Asp Ala Ile Thr
        115             120             125

Gly Asp Gly Gly Leu Met Ile Glu Glu Tyr Ala Pro Phe Gly Leu Ile
    130             135             140

Gly Ala Ile Thr Pro Val Thr Asn Pro Thr Glu Thr Ile Ile Asn Asn
145             150             155             160

Thr Ile Ser Met Ile Ser Gly Gly Asn Gly Ile Val Phe Asn Val His
                165             170             175

Pro Ser Ala Lys Lys Val Cys Ala Tyr Cys Leu Gln Phe Ile Asn Lys
            180             185             190

Thr Ile Ile Glu Asn Gly Gly Pro Ala Asn Leu Ile Thr Met Val Lys
            195             200             205

Glu Pro Thr Met Glu Thr Cys Asn Ile Ile Thr Gln Ser Pro Lys Val
    210             215             220

Arg Leu Met Val Gly Thr Gly Gly Met Gly Met Val Asn Ser Leu Leu
225             230             235             240

Arg Ser Gly Lys Lys Thr Ile Gly Ala Gly Ala Gly Asn Pro Pro Val
            245             250             255

Ile Val Asp Glu Thr Ala Asp Ile Lys Lys Ala Ala Lys Asp Ile Tyr
            260             265             270

Tyr Gly Ala Ser Phe Asp Asn Asn Leu Leu Cys Leu Ala Glu Lys Glu
            275             280             285

Val Phe Val Leu Glu Glu Val Ala Asn Asp Phe Ile Tyr Asn Met Val
    290             295             300

Asp Glu Gly Ala Phe Leu Leu Asn Gly Ala Gln Leu Glu Ala Ile Thr
305             310             315             320

Asn Leu Val Leu Lys Tyr Glu Asn Gly Lys Tyr Asp Ile Asn Lys Lys
            325             330             335

Trp Val Gly Gln Asp Ala Gly Lys Met Leu Glu Ala Ile Gly Ile Thr
            340             345             350

Gly Lys Ser Asp Thr Arg Leu Leu Ile Cys Asp Val Pro Tyr Asp Asn
            355             360             365

Pro Phe Val Leu Leu Glu Gln Leu Met Pro Val Leu Pro Ile Val Arg
    370             375             380

Cys Lys Asn Leu Asn Gln Ala Ile Asp Tyr Ala Met Ile Ala Glu Ser
385             390             395             400

Gly Asn Arg His Thr Ala Ser Met Phe Ser Lys Asn Val Asp Asn Met
            405             410             415

Thr Arg Phe Ala Arg Lys Ile Glu Thr Thr Ile Phe Val Lys Asn Gly
            420             425             430

Cys Thr Leu Glu Gly Val Gly Ile Gly Gly Glu Gly Tyr Thr Thr Met
            435             440             445
```

```
Thr Ile Ala Gly Pro Thr Gly Glu Gly Ile Thr Cys Ala Lys Ser Phe
    450                 455                 460

Thr Arg Arg Arg Cys Met Leu Ala Asp Gly Gly Leu Arg Ile Ile
465                 470                 475                 480

<210> SEQ ID NO 189
<211> LENGTH: 364
<212> TYPE: PRT
<213> ORGANISM: Candida tropicalis

<400> SEQUENCE: 189

Met Ile Thr Ala Gln Ala Val Leu Tyr Thr Gln His Gly Glu Pro Lys
1               5                   10                  15

Asp Val Leu Phe Thr Gln Ser Phe Glu Ile Asp Asp Asp Asn Leu Ala
                20                  25                  30

Pro Asn Glu Val Ile Val Lys Thr Leu Gly Ser Pro Val Asn Pro Ser
                35                  40                  45

Asp Ile Asn Gln Ile Gln Gly Val Tyr Pro Ser Lys Pro Ala Lys Thr
    50                  55                  60

Thr Gly Phe Gly Thr Thr Glu Pro Ala Ala Pro Cys Gly Asn Glu Gly
65                  70                  75                  80

Leu Phe Glu Val Ile Lys Val Gly Ser Asn Val Leu Ser Leu Glu Ala
                85                  90                  95

Gly Asp Trp Val Ile Pro Ser His Val Asn Phe Gly Thr Trp Arg Thr
                100                 105                 110

His Ala Leu Gly Asn Asp Asp Asp Phe Ile Lys Leu Pro Asn Pro Ala
            115                 120                 125

Gln Ser Lys Ala Asn Gly Lys Pro Asn Gly Leu Thr Ile Asn Gln Gly
        130                 135                 140

Ala Thr Ile Ser Val Asn Pro Leu Thr Ala Tyr Leu Met Leu Thr His
145                 150                 155                 160

Tyr Val Lys Leu Thr Pro Gly Lys Asp Trp Phe Ile Gln Asn Gly Gly
                165                 170                 175

Thr Ser Ala Val Gly Lys Tyr Ala Ser Gln Ile Gly Lys Leu Leu Asn
                180                 185                 190

Phe Asn Ser Ile Ser Val Ile Arg Asp Arg Pro Asn Leu Asp Glu Val
            195                 200                 205

Val Ala Ser Leu Lys Glu Leu Gly Ala Thr Gln Val Ile Thr Glu Asp
        210                 215                 220

Gln Asn Asn Ser Arg Glu Phe Gly Pro Thr Ile Lys Glu Trp Ile Lys
225                 230                 235                 240

Gln Ser Gly Gly Glu Ala Lys Leu Ala Leu Asn Cys Val Gly Gly Lys
                245                 250                 255

Ser Ser Thr Gly Ile Ala Arg Lys Leu Asn Asn Asn Gly Leu Met Leu
            260                 265                 270

Thr Tyr Gly Gly Met Ser Phe Gln Pro Val Thr Ile Pro Thr Ser Leu
            275                 280                 285

Tyr Ile Phe Lys Asn Phe Thr Ser Ala Gly Phe Trp Val Thr Glu Leu
    290                 295                 300

Leu Lys Asn Asn Lys Glu Leu Lys Thr Leu Thr Leu Asn Gln Ile Ile
305                 310                 315                 320

Ala Trp Tyr Glu Glu Gly Lys Leu Thr Asp Ala Lys Ser Ile Glu Thr
                325                 330                 335

Leu Tyr Asp Gly Thr Lys Pro Leu His Glu Leu Tyr Gln Asp Gly Val
            340                 345                 350
```

-continued

```
Ala Asn Ser Lys Asp Gly Lys Gln Leu Ile Thr Tyr
        355                 360

<210> SEQ ID NO 190
<211> LENGTH: 405
<212> TYPE: PRT
<213> ORGANISM: Euglena gracilis

<400> SEQUENCE: 190

Met Ala Met Phe Thr Thr Thr Ala Lys Val Ile Gln Pro Lys Ile Arg
1               5                   10                  15

Gly Phe Ile Cys Thr Thr Thr His Pro Ile Gly Cys Glu Lys Arg Val
                20                  25                  30

Gln Glu Glu Ile Ala Tyr Ala Arg Ala His Pro Pro Thr Ser Pro Gly
            35                  40                  45

Pro Lys Arg Val Leu Val Ile Gly Cys Ser Thr Gly Tyr Gly Leu Ser
        50                  55                  60

Thr Arg Ile Thr Ala Ala Phe Gly Tyr Gln Ala Ala Thr Leu Gly Val
65                  70                  75                  80

Phe Leu Ala Gly Pro Pro Thr Lys Gly Arg Pro Ala Ala Ala Gly Trp
                85                  90                  95

Tyr Asn Thr Val Ala Phe Glu Lys Ala Ala Leu Glu Ala Gly Leu Tyr
                100                 105                 110

Ala Arg Ser Leu Asn Gly Asp Ala Phe Asp Ser Thr Thr Lys Ala Arg
            115                 120                 125

Thr Val Glu Ala Ile Lys Arg Asp Leu Gly Thr Val Asp Leu Val Val
        130                 135                 140

Tyr Ser Ile Ala Ala Pro Lys Arg Thr Asp Pro Ala Thr Gly Val Leu
145                 150                 155                 160

His Lys Ala Cys Leu Lys Pro Ile Gly Ala Thr Tyr Thr Asn Arg Thr
                165                 170                 175

Val Asn Thr Asp Lys Ala Glu Val Thr Asp Val Ser Ile Glu Pro Ala
                180                 185                 190

Ser Pro Glu Glu Ile Ala Asp Thr Val Lys Val Met Gly Gly Glu Asp
            195                 200                 205

Trp Glu Leu Trp Ile Gln Ala Leu Ser Glu Ala Gly Val Leu Ala Glu
        210                 215                 220

Gly Ala Lys Thr Val Ala Tyr Ser Tyr Ile Gly Pro Glu Met Thr Trp
225                 230                 235                 240

Pro Val Tyr Trp Ser Gly Thr Ile Gly Glu Ala Lys Lys Asp Val Glu
                245                 250                 255

Lys Ala Ala Lys Arg Ile Thr Gln Gln Tyr Gly Cys Pro Ala Tyr Pro
            260                 265                 270

Val Val Ala Lys Ala Leu Val Thr Gln Ala Ser Ser Ala Ile Pro Val
        275                 280                 285

Val Pro Leu Tyr Ile Cys Leu Leu Tyr Arg Val Met Lys Glu Lys Gly
        290                 295                 300

Thr His Glu Gly Cys Ile Glu Gln Met Val Arg Leu Leu Thr Thr Lys
305                 310                 315                 320

Leu Tyr Pro Glu Asn Gly Ala Pro Ile Val Asp Glu Ala Gly Arg Val
                325                 330                 335

Arg Val Asp Asp Trp Glu Met Ala Glu Asp Val Gln Gln Ala Val Lys
                340                 345                 350

Asp Leu Trp Ser Gln Val Ser Thr Ala Asn Leu Lys Asp Ile Ser Asp
```

-continued

```
        355             360             365
Phe Ala Gly Tyr Gln Thr Glu Phe Leu Arg Leu Phe Gly Phe Gly Ile
    370             375             380

Asp Gly Val Asp Tyr Asp Gln Pro Val Asp Val Glu Ala Asp Leu Pro
385             390             395             400

Ser Ala Ala Gln Gln
            405
```